US012595486B2

(12) United States Patent
Velasquez et al.

(10) Patent No.: US 12,595,486 B2
(45) Date of Patent: *Apr. 7, 2026

(54) APTAMERS FOR PERSONAL HEALTH CARE APPLICATIONS

(71) Applicant: The Procter & Gamble Company, Cincinnati, OH (US)

(72) Inventors: Juan Esteban Velasquez, Cincinnati, OH (US); Spencer Christopher Rupard, Morrow, OH (US); Amy Violet Trejo, Mason, OH (US); Adam Michael Pitz, Morrow, OH (US); Kelly Lee Schmeichel, Cincinnati, OH (US); Erin Nicole Swigart, Cincinnati, OH (US); Gregory Allen Penner, London (CA); Hilda Andamiche Namanja-Magliano, Loveland, OH (US); Matthew Scott Wagner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 644 days.

This patent is subject to a terminal disclaimer.

(21) Appl. No.: 18/065,739

(22) Filed: Dec. 14, 2022

(65) Prior Publication Data

US 2023/0287434 A1 Sep. 14, 2023

(30) Foreign Application Priority Data

Dec. 14, 2021 (EP) .................................... 21214416

(51) Int. Cl.
| | |
|---|---|
| *C12N 15/115* | (2010.01) |
| *A61P 31/16* | (2006.01) |
| *C12Q 1/68* | (2018.01) |

(52) U.S. Cl.
CPC ............ *C12N 15/115* (2013.01); *A61P 31/16* (2018.01); *C12N 2310/16* (2013.01); *C12N 2310/32* (2013.01); *C12N 2310/344* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2004/0253243 A1* | 12/2004 | Epstein ................ | C12N 15/115 424/145.1 |
| 2009/0054362 A1* | 2/2009 | James ..................... | A61P 31/18 435/5 |
| 2021/0403919 A1 | 12/2021 | Velasquez et al. | |

FOREIGN PATENT DOCUMENTS

| | | |
|---|---|---|
| WO | 9119813 A1 | 12/1991 |
| WO | 2017035666 A1 | 3/2017 |
| WO | 2020020947 A1 | 1/2020 |
| WO | 2021262911 A1 | 12/2021 |

OTHER PUBLICATIONS

Ellington, A.D. and Szostak J. W., "In vitro selection of RNA molecules that bind specific ligands", Department of Molecular Biology, vol. 346, Aug. 30, 1990, pp. 818-822.
Ellington, A.D. and Szostak J. W., "Selection in vitro of Single-stranded DNA molecules that fold into specific ligand-binding structures", Department of Molecular Biology, vol. 355, Feb. 27, 1992, pp. 850-852.
Green et al., "Nuclease-resistant nucleic acid ligands to vascular permeability factor/vascular endothelial growth factor", NeXstar Pharmaceuticals, Chemistry & Biology, Oct. 1995, pp. 683-695.
Gruber AR et al; "The Vienna RNA Websuite", Nucleic Acids Research, vol. 36, Issue suppl_2, URL: (http://rna.tbi.univie.ac.at//cgi-bin/RNAWebSuite/RNAfold.cgi), dated Apr. 19, 2008, pp. 70-74.
Hermanson G. T., "Bioconjugate Techniques", 2nd Edition, Academic Press, San Diego, 2008, 34 pages.
Kim, Y. S. and M. B. Gu, "Advances in Aptamer Screening and Small Molecule Aptasensors", Adv. Biochem Eng Biotechnol, vol. 140, Jul. 13, 2013, pp. 29-67.
Stoltenburg, R. et al., "SELEX—A (r)evolutionary method to generate high-affinity nucleic acid ligands", Science Direct, Biomolecular Engineering, vol. 24(4), Jun. 1, 2007, pp. 381-403.
The Apta-Index, Aptagen, Aptamer database, URL: http://www.aptagen.com/aptamer-index/aptamer-list.aspx;, 1 page.
ViennaRNA Web Services, created by the Theoretical Biology Group at the Institute for Theoretical Chemistry at the University of Vienna; 4 pages.
PCT Search Report and Written Opinion for PCT/US2022/081491 dated Apr. 20, 2023,15 pages.
PCT Search Report and Written Opinion for PCT/US2022/081492 dated Apr. 26, 2023,14 pages.
PCT Search Report and Written Opinion for PCT/US2022/081493 dated Apr. 20, 2023,15 pages.
PCT Search Report and Written Opinion for PCT/US2022/081494 dated Apr. 20, 2023,15 pages.
All Office Actions; U.S. Appl. No. 18/065,652, filed Dec. 14, 2022.
All Office Actions; U.S. Appl. No. 18/065,655, filed Dec. 14, 2022.
All Office Actions; U.S. Appl. No. 18/065,723, filed Dec. 14, 2022.

(Continued)

*Primary Examiner* — Sean McGarry
(74) *Attorney, Agent, or Firm* — Jay A. Krebs

(57) ABSTRACT

An aptamer composition is disclosed which has one or more oligonucleotides that include at least one of deoxyribonucleotides, ribonucleotides, derivatives of deoxyribonucleotides, derivatives of ribonucleotides, or mixtures thereof. The aptamer composition has a binding affinity for one or more cellular membrane glycoproteins selected from the group consisting of: intercellular adhesion molecule 1 (ICAM-1), low-density lipoprotein receptor (LDLR) family members, and cadherin-related family member 3 (CDHR3), preferably intercellular adhesion molecule 1 (ICAM-1), and is configured to reduce the binding of one or more human rhinoviruses to the intercellular adhesion molecule 1 (ICAM-1).

22 Claims, 24 Drawing Sheets

Specification includes a Sequence Listing.

(56)            References Cited

OTHER PUBLICATIONS

Extended EP Search Report and Written Opinion for 21214416.6 dated Jun. 3, 2022, 09 pages.

Lineberger D W et al; "Domains 1 and 2 of ICAM-1 are sufficient to bind human rhinoviruses" Virus Research, brvol. 24, No. 2, Dated Jul. 1, 1992 (Jul. 1, 1992), brpp. 173-186, XP023706540, ISSN: 0168-1702, DOI: br10.1016/0168-1702 (92) 90005-T [retrieved on Jul. 1, 1992].

Newton P. et al; "Development of a homogeneous high-throughput screening assay for biological inhibitors of human rhinovirus infection" Journal of Biomolecular Screening Society for Laboratory Automation and Screening, vol. 18, Year 2012, pp. 237-246, XP055844039, Retrieved from the Internet: URL :https :1/journals. sagepub. com/doi/pdf/10.1177/1087057112469047.

Sener Berke Bilgentjr et al; "Inhibition of cell migration and invasion by ICAM-1 binding DNA aptamers" Analytical Biochemistry, vol. 628, 114262, Dated May 24, 2021 (May 24, 2021) pp. 1-9, XP086706552, brISSN: 0003-2697, DOI: 10. 1016/J.AB. 2021. 114262 [retrieved on May 24, 2021].

Unpublished U.S. Appl. No. 18/065,652, filed Dec. 14, 2022, to Juan Esteban Velasquez et al.

Unpublished U.S. Appl. No. 18/065,655, filed Dec. 14, 2022, to Juan Esteban Velasquez et al.

Unpublished U.S. Appl. No. 18/065,723, filed Dec. 14, 2022, to Juan Esteban Velasquez et al.

* cited by examiner

Sense primer          Random sequence          Antisense primer
FIG. 1
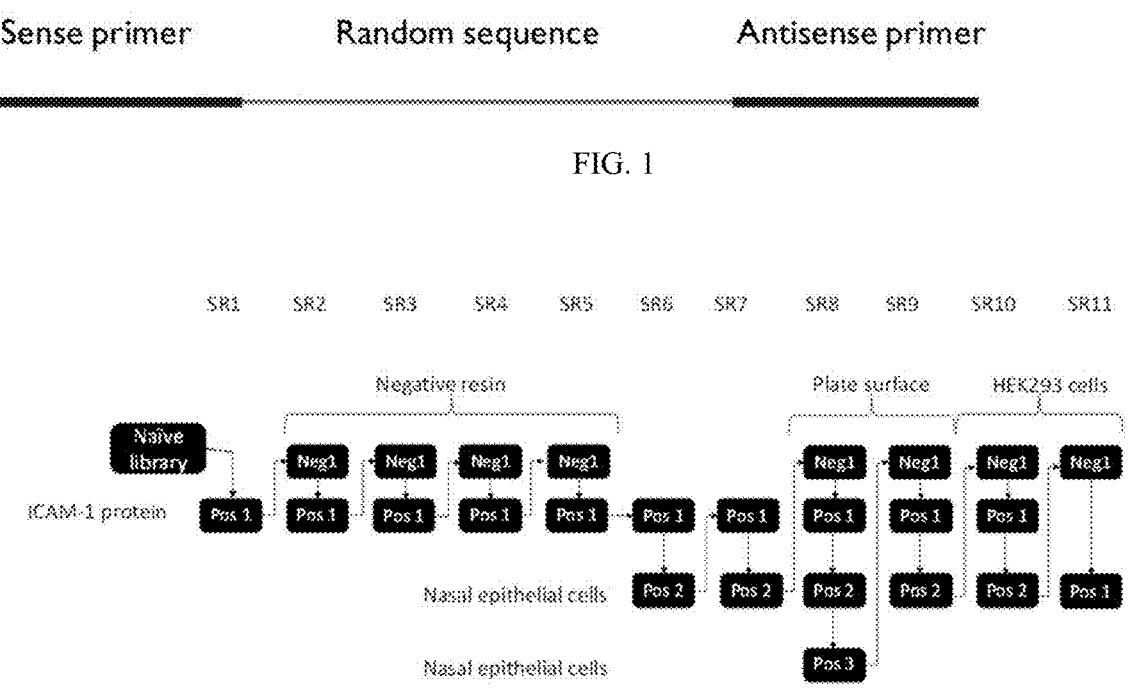
FIG. 2
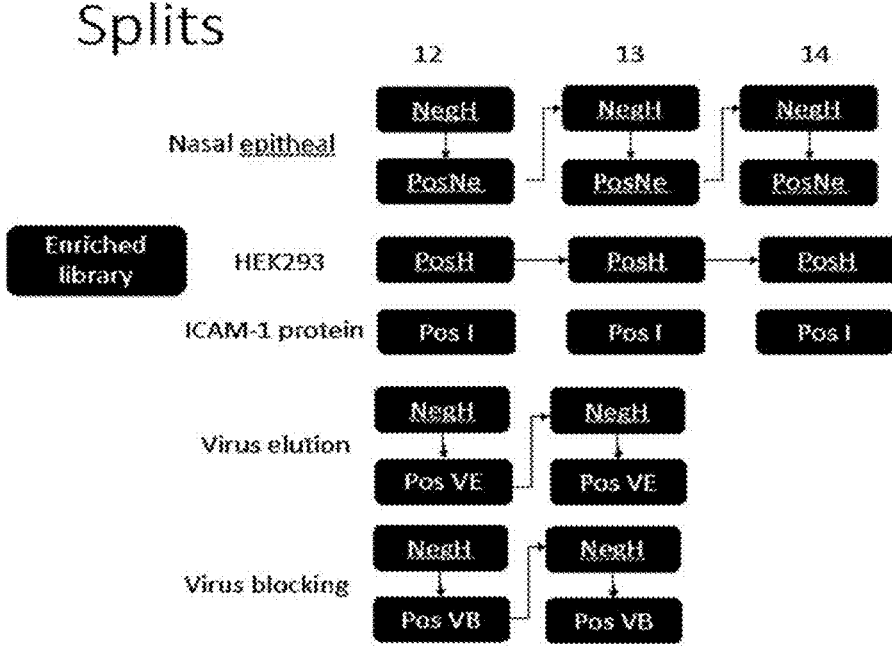
FIG. 3

FIG. 7A
FIG. 7B
FIG. 7C
FIG. 7D
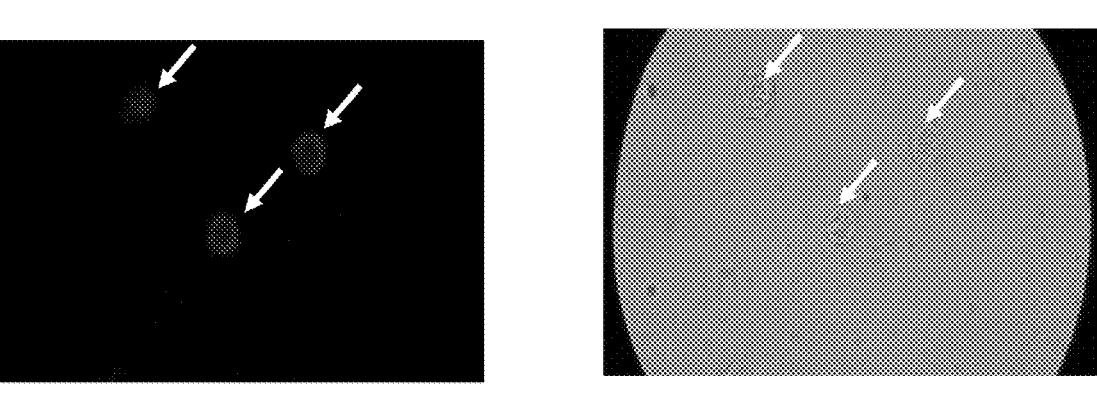
FIG. 7E
FIG. 7F
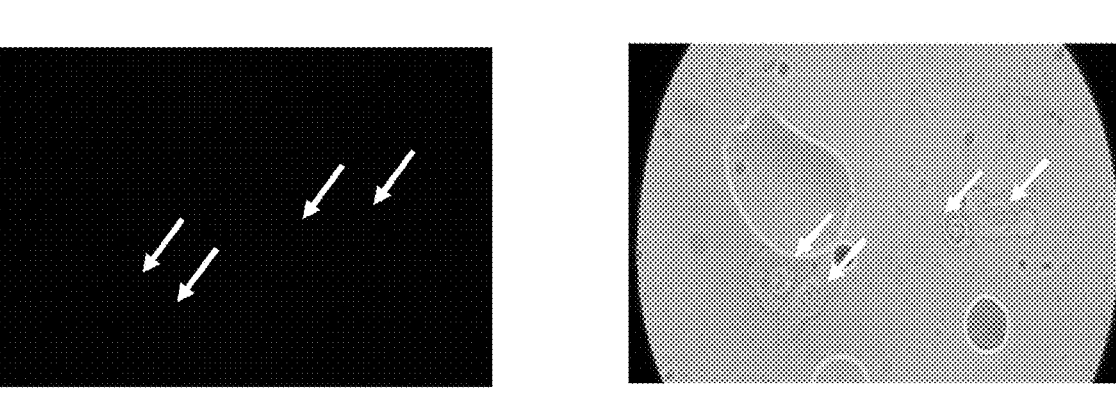
FIG. 7G
FIG. 7H

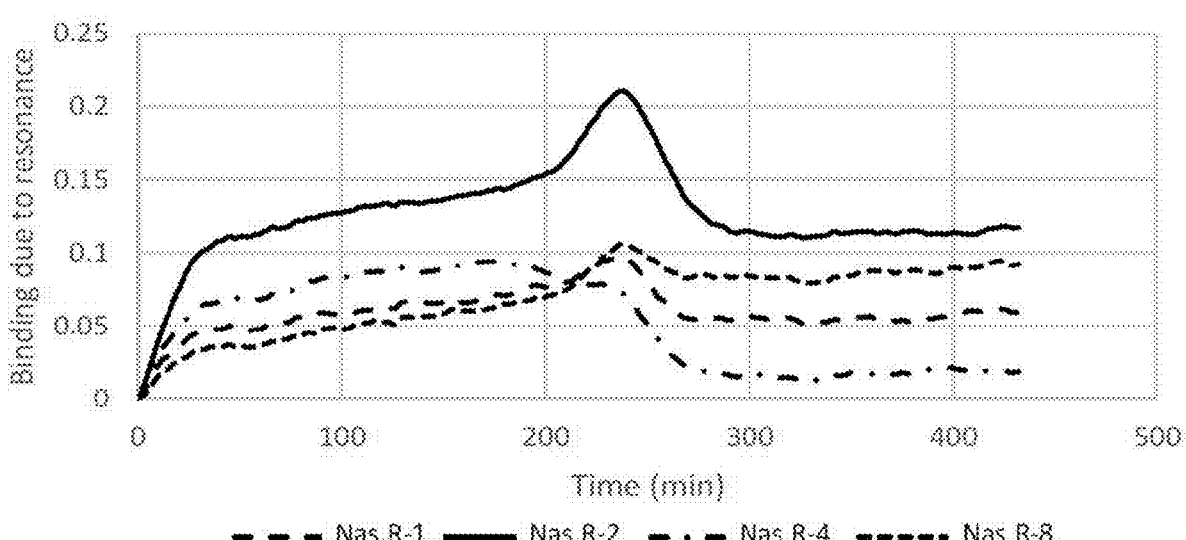
FIG. 8
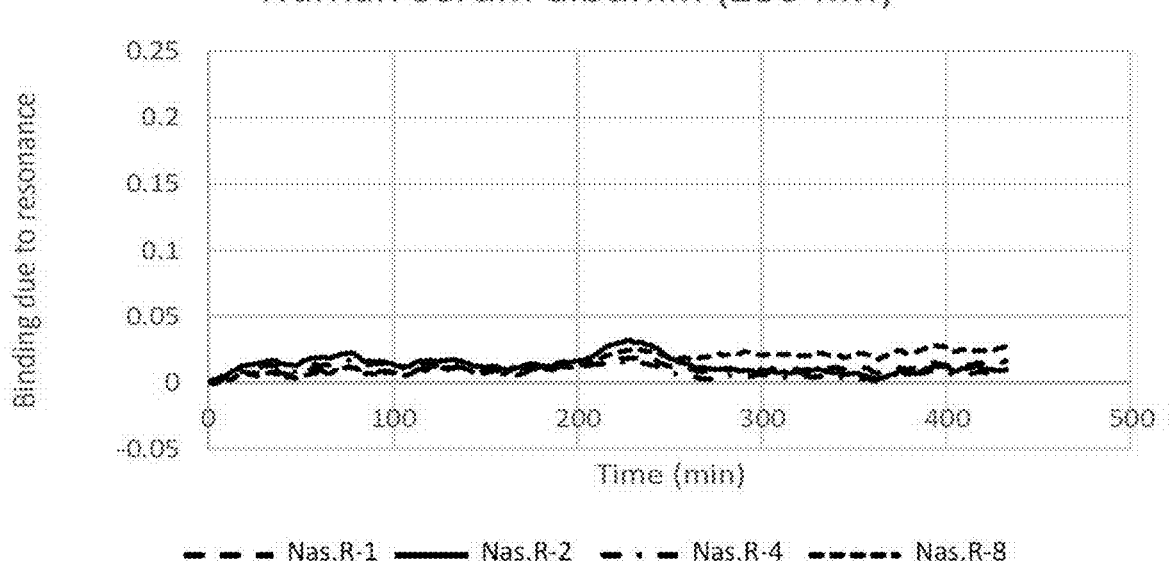
FIG. 9

```
ICAM-1   ----QTSVSPSKVILPRGGSVLVTCSTSCDQPKLLGIETPLPKKELLLPGNNRKVYELSNV   57
ICAM-3   QEFLLRVEPQNPVLSAGGSLFVNCSTDCPSSEKIALETSLSKE-LVASGMGWAAFNLSNV   59
ICAM-5   RPFWADLQPRVAFVERGGSLWLNCSTNCPRPERGGLETSLRRR-GTQRGLRWLARQLVDI   59
               :.*    .:   ***: :.***.*    :   .:*** * :: .     *  . :* ::

ICAM-1   QE-DSQPMCYSNCPDGQSTAKTFLTVYWTPERVELAPLPSWQPVGKNLTLRCQVEGGAPR   116
ICAM-3   TG-NSRILCSVYCNGSQITGSSNITVYRLPERVELAPLPPWQPVGQNFTLRCQVEDGSPR   118
ICAM-5   REPETQPVCFFRCARRTLQARGLIRTFQRPDRVELMPLPPWQPVGENFTLSCRVPGAGPR   119
             :::  :*   *        .    :  .: *:**** *** *****:*;:** *;* ..:.**

ICAM-1   ANLTVVLLRGEKELKREPAVGEP------AEVTTTVLVRRDHHGANFSCRTELDLRPQGLE   171
ICAM-3   TSLTVVLLRWEEELSRQPAVEEP------AEVTATVLASRDDHGAPFSCRTELDWQPQGLG   173
ICAM-5   ASLTLTLLNGAQELIRRSFAGEPPRARGAVLEATVLARREDHGANFSCRAKLDLAPRGLG   179
           :.**:.***   :** *.   .  **      * :*;****. *;.*** ****;***;;*;**

ICAM-1   LFENTSAPYQLQTFVLPATPPQLVSPRVLEVDTQGTVVCSLDGLFPVSEAQVHLALGDQR   231
ICAM-3   LFVNTSAPRQLRTFVLPVTPPRLVAPRFLEVETGWPVDCTLDGLFPASEAQVYLALGDQN   233
ICAM-5   LFENSSAPRELRTFGLSPDAPRLAAPRLLEVGSERPVSCTLDGLFPASEARVYLALGDQN   239
           ** *;*** ;*;;** *   *;:.;**.*** ;.   * *;******.***;*;******

ICAM-1   LRPTVTYGNDSFSAKASVSVTAEDEGTQRLTCAVILGNQSQETLQTVTIYSFPAPNVILT   291
ICAM-3   LRATVMNHRGDTLTATATATARAIQEGARKIVCNVTLGGERRRARKNLTVFSFLGPIVNLS   293
ICAM-5   LSPDVTLEGDAFVATATATASAEQEGARQLVCNVTLGGENRETRENVTIYSFPAPLLTLS   299
           *;. *    .:*;: *.*:;.:. *;;**;:;.;.* * **.: ;*: ::(*):;** .* ; *;

ICAM-1   KPEVSEGTEVTVKCEAHPRAKVTLNGVPAQPLGPRAQLLLKATPEDNGRSFSCSATLEVA   351
ICAM-3   RPTAHKGSTVIVSCMAGARVQVTLDGVPAAAPGQPAQLQLNATESSIDGRSFFCSATLEVD   353
ICAM-5   RPSVSKGQMVTVTCAAGAQALVTLRGVPAAVPGQPAQLQLNATENDDRKSFTCDATLDVD   359
           ;*. ;.** ***.;* * ;. ***;****   *   *** *;** .*; *** *;.***;*

ICAM-1   GQLIHKNQTRELRVLYGPRLDERICPGNWTWPENSQQTPMCQAWGNPLPELKCLKDG-TF   410
ICAM-3   GEFLHRRSSVQLRVLYGPKIDRATCPQHLAWKDKTBRVLQCQARGNFYPELRCLKEGSSR   413
ICAM-5   GETLIKNRSAELRVLYAPRLDDSDCPRSWTWPEGPEQTLRCEARGNFEPSVHCARSDGGA   419
           *:; ;:*  ;******.*;:*   **  .*  : .;.  *;*  *** *.;::* .;..

ICAM-1   PLFIGESVTVTRDLEGTYLCKARSTQGEVTRKVTVNVLSPRYE------------------   453
ICAM-3   RVPVGIPFFVNVTHRGTYQCQASSSRGKYTLVVVMDIEAGSSR----------------   456
ICAM-5   VLALGLLGPVTRALSGTYRCKAANDQGEAVKDVTLTVEYAPALDSVGCPERITWLEGTEA   479
           : ;*   *;. .;*** *;* . ;*; . *;; :
```

FIG. 10

```
         (1)   1        10         20         30         40
Nas-3    (1)  ATTTTCGTTTTATTTCAGTTTAATTGCGTTTAGTATCTGG
Nas-88   (1)  ATTTTCGTTTTATTTTAGTTTAATTGCGTTTAGTATCTGG
```

FIG: 13

```
         (1)   1        10         20         30          43
Nas-45   (1)  GTAAAAATTAGAGAT-TAAAATAGTTCCTTT--CAGTTTTGTC
Nas-8    (1)  GTAAAAATTAAAGAGATTAA---GGT-CCTTAAGCAGTTTTGTC
```

```
         (1)   1        10         20         30          42
Nas-47   (1)  GTAAATAACCAGTTA-TA-CAGAAAGATCTCAGCAATTTATC
Nas-78   (1)  GTAATTAATCAAACAATAGCAGCAA-ATCTCAGCAATTT-TC
```

FIG. 14

```
         (1)   1        10         20         30          44
Nas-13   (1)  GTAAAAATTTTCAT--CTCAGCAAT--TAAATCCAAAGAATCCA
Nas-97   (1)  GTAAAAATTTAAATAACTCAGCAATCATAGATCCGACTGA----
```

```
         (1)   1        10         20         30          43
Nas-31   (1)  GTAAAAAGATAAAACTTAG---TTGCAGAATTTGCCTTCATT
Nas-93   (1)  GTAAATAACAAAAATCTCAGCTTTTGCAGAATTTATCCAC----
```

```
         (1)   1        10         20         30          43
Nas-39   (1)  GTAAAATAAAAGTTTTCCTATCAGCAAA-CTCACAAATTC--
Nas-82   (1)  GTAAA-TAAAAAGCAGATCT---CAGCAAAACTCGTAAATTCAA
```

```
         (1)   1        10         20         30          44
Nas-61   (1)  GTAAAATAAAGAGGATAACTACAATCA-TCAGCA-ATCAT-AT-
Nas-91   (1)  GTAAAAATAA-----ATAACTACGAGATCTCAGCAGATCATTATC
```

```
         (1)   1        10         20         30          45
Nas-87   (1)  GTAATTAAAAAACCTTCACA-CAGAAAACATTCCT-CAATTT---
Nas-94   (1)  ----GTAAATAAACT-CACAGCAGAAAAAATTCCTTCAACTTGTA
```

Nas-5/5.1

Nas-8/8.1

E = End
H = Hairpin Loop
I = Internal Loop
S = Stem

| Motif | Symbol | Motif Consensus |
|---|---|---|
| 1. | | IISSSEEEEE |
| 2 | | HHHHHHHSSSSSSSS |
| 3 | | EEEEEEEEEEEE |

SEQUENCE LISTING

```
Sequence total quantity: 270
SEQ ID NO: 1              moltype = RNA  length = 80
FEATURE                   Location/Qualifiers
misc_feature              1..80
                          note = Synthetic aptamer sequences
source                    1..80
                          mol_type = other RNA
                          organism = synthetic construct
SEQUENCE: 1
gggtgcatcg tttacgcgat tagtctgata aacaaaaga tttcgctaaa aatcaatctg  60
ctgctgagga aggatatgag                                             80

SEQ ID NO: 2              moltype = RNA  length = 80
FEATURE                   Location/Qualifiers
misc_feature              1..80
                          note = N/A
source                    1..80
                          mol_type = other RNA
                          organism = synthetic construct
SEQUENCE: 2
gggtgcatcg tttacgcaga tagcagcagg aatcaagcgg taggagtcta gcagaagctg  60
ctgctgagga aggatatgag                                             80

SEQ ID NO: 3              moltype = RNA  length = 80
FEATURE                   Location/Qualifiers
misc_feature              1..80
                          note = Synthetic aptamer sequences
source                    1..80
                          mol_type = other RNA
                          organism = synthetic construct
SEQUENCE: 3
gggtgcatcg tttacgcatt ttcgttttat ttcagtttaa ttgcgtttag tatctggctg  60
ctgctgagga aggatatgag                                             80

SEQ ID NO: 4              moltype = RNA  length = 80
FEATURE                   Location/Qualifiers
misc_feature              1..80
                          note = Synthetic aptamer sequences
source                    1..80
                          mol_type = other RNA
                          organism = synthetic construct
SEQUENCE: 4
gggtgcatcg tttacgcgca acataaaaat ttaaagtgct cagttgtcaa tctatgactg  60
ctgctgagga aggatatgag                                             80

SEQ ID NO: 5              moltype = RNA  length = 80
FEATURE                   Location/Qualifiers
misc_feature              1..80
                          note = Synthetic aptamer sequences
source                    1..80
                          mol_type = other RNA
                          organism = synthetic construct
SEQUENCE: 5
gggtgcatcg tttacgcgta aatggtccgc tattaaaaga aaagaatgaa gtctcagctg  60
ctgctgagga aggatatgag                                             80

SEQ ID NO: 6              moltype = RNA  length = 80
FEATURE                   Location/Qualifiers
misc_feature              1..80
                          note = Synthetic aptamer sequences
source                    1..80
                          mol_type = other RNA
                          organism = synthetic construct
SEQUENCE: 6
gggtgcatcg tttacgctat tttcatttgt ttttttaatt tactagtgta aacaatcctg  60
```

-continued

```
ctgctgagga aggatatgag                                            80

SEQ ID NO: 7              moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 7
gggtgcatcg tttacgcgta aataagtaga taaagtggca gtttgttttc cttggaactg   60
ctgctgagga aggatatgag                                            80

SEQ ID NO: 8              moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 8
gggtgcatcg tttacgcgta aaaattaaag agattaaggt ccttaagcag ttttgtcctg   60
ctgctgagga aggatatgag                                            80

SEQ ID NO: 9              moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 9
gggtgcatcg tttacgcgta aaaaaatcaa aacttcagca aattatttat caacgtcctg   60
ctgctgagga aggatatgag                                            80

SEQ ID NO: 10             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 10
gggtgcatcg tttacgcgta aaataaatta aaaagaactt cttcagcaat caatatcctg   60
ctgctgagga aggatatgag                                            80

SEQ ID NO: 11             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 11
gggtgcatcg tttacgcgta aataaaaatg aaaaattgtc tctcagcttt caaagtcctg   60
ctgctgagga aggatatgag                                            80

SEQ ID NO: 12             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 12
gggtgcatcg tttacgcgta aaaaaaaaat atcttcggag aattcagcaa ttttatcctg   60
ctgctgagga aggatatgag                                            80

SEQ ID NO: 13             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 13
gggtgcatcg tttacgcgta aaaattttca tctcagcaat taaatccaaa gaatccactg   60
ctgctgagga aggatatgag                                            80
```

-continued

```
SEQ ID NO: 14            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 14
gggtgcatcg tttacgcgta aaatatatca gcaaagtagt ttaagcctcc tcagtttctg    60
ctgctgagga aggatatgag                                                80

SEQ ID NO: 15            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 15
gggtgcatcg tttacgcgta aattatgaaa aatacagcaa ggatttaacc tcagtttctg    60
ctgctgagga aggatatgag                                                80

SEQ ID NO: 16            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 16
gggtgcatcg tttacgcgta aaataaataa atcttcaaag tacagacctc gatttttctg    60
ctgctgagga aggatatgag                                                80

SEQ ID NO: 17            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 17
gggtgcatcg tttacgctta taggtattag acattttcaa ttaaagtgaa ttagtgtctg    60
ctgctgagga aggatatgag                                                80

SEQ ID NO: 18            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 18
gggtgcatcg tttacgcgta aaatgtgaca gcaggataat aaaataagta ctcagtactg    60
ctgctgagga aggatatgag                                                80

SEQ ID NO: 19            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 19
gggtgcatcg tttacgcgta attaagaaaa ataaaagtac tctgcagttt ttatccactg    60
ctgctgagga aggatatgag                                                80

SEQ ID NO: 20            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 20
gggtgcatcg tttacgcgta aaaataaaat tttcccagac cagttatctg ccttaaactg    60
ctgctgagga aggatatgag                                                80

SEQ ID NO: 21            moltype = RNA   length = 80
FEATURE                  Location/Qualifiers
```

-continued

```
misc_feature          1..80
                      note = Synthetic aptamer sequences
source                1..80
                      mol_type = other RNA
                      organism = synthetic construct
SEQUENCE: 21
gggtgcatcg tttacgcgta aagaaaaaaa tcagctttta gtcgccttcc attttgactg    60
ctgctgagga aggatatgag                                               80

SEQ ID NO: 22         moltype = RNA   length = 80
FEATURE               Location/Qualifiers
misc_feature          1..80
                      note = Synthetic aptamer sequences
source                1..80
                      mol_type = other RNA
                      organism = synthetic construct
SEQUENCE: 22
gggtgcatcg tttacgcgta aataaataat caaaattaca ctcagtggca atttcctctg    60
ctgctgagga aggatatgag                                               80

SEQ ID NO: 23         moltype = RNA   length = 80
FEATURE               Location/Qualifiers
misc_feature          1..80
                      note = Synthetic aptamer sequences
source                1..80
                      mol_type = other RNA
                      organism = synthetic construct
SEQUENCE: 23
gggtgcatcg tttacgcgta aaatacagga tacgacaata actcagcaga ttttatcctg    60
ctgctgagga aggatatgag                                               80

SEQ ID NO: 24         moltype = RNA   length = 80
FEATURE               Location/Qualifiers
misc_feature          1..80
                      note = Synthetic aptamer sequences
source                1..80
                      mol_type = other RNA
                      organism = synthetic construct
SEQUENCE: 24
gggtgcatcg tttacgcgtt aaaaattgtg cactgagatg acgcagcatt aactacactg    60
ctgctgagga aggatatgag                                               80

SEQ ID NO: 25         moltype = RNA   length = 80
FEATURE               Location/Qualifiers
misc_feature          1..80
                      note = Synthetic aptamer sequences
source                1..80
                      mol_type = other RNA
                      organism = synthetic construct
SEQUENCE: 25
gggtgcatcg tttacgcgta aataaaaatt aatcagcaat tttccactca gttgtacctg    60
ctgctgagga aggatatgag                                               80

SEQ ID NO: 26         moltype = RNA   length = 80
FEATURE               Location/Qualifiers
misc_feature          1..80
                      note = Synthetic aptamer sequences
source                1..80
                      mol_type = other RNA
                      organism = synthetic construct
SEQUENCE: 26
gggtgcatcg tttacgcgta aaaataaaaa atctcgatca ctgcagtttt attccggctg    60
ctgctgagga aggatatgag                                               80

SEQ ID NO: 27         moltype = RNA   length = 80
FEATURE               Location/Qualifiers
misc_feature          1..80
                      note = Synthetic aptamer sequences
source                1..80
                      mol_type = other RNA
                      organism = synthetic construct
SEQUENCE: 27
gggtgcatcg tttacgcgta aacaaatatc gattaaaata aaatctcagc aagaatcctg    60
ctgctgagga aggatatgag                                               80

SEQ ID NO: 28         moltype = RNA   length = 80
FEATURE               Location/Qualifiers
misc_feature          1..80
                      note = Synthetic aptamer sequences
```

-continued

```
source                  1..80
                        mol_type = other RNA
                        organism = synthetic construct
SEQUENCE: 28
gggtgcatcg tttacgcgta aaataaataa aattatccca ggagcaaatt ttcttcgctg   60
ctgctgagga aggatatgag                                               80

SEQ ID NO: 29           moltype = RNA   length = 80
FEATURE                 Location/Qualifiers
misc_feature            1..80
                        note = Synthetic aptamer sequences
source                  1..80
                        mol_type = other RNA
                        organism = synthetic construct
SEQUENCE: 29
gggtgcatcg tttacgcgta gaagaattaa tagtggacat atcaatagca gtttatcctg   60
ctgctgagga aggatatgag                                               80

SEQ ID NO: 30           moltype = RNA   length = 80
FEATURE                 Location/Qualifiers
misc_feature            1..80
                        note = Synthetic aptamer sequences
source                  1..80
                        mol_type = other RNA
                        organism = synthetic construct
SEQUENCE: 30
gggtgcatcg tttacgcgta aacatattca gcagttaaaa tttagtaggt tcagtagctg   60
ctgctgagga aggatatgag                                               80

SEQ ID NO: 31           moltype = RNA   length = 80
FEATURE                 Location/Qualifiers
misc_feature            1..80
                        note = Synthetic aptamer sequences
source                  1..80
                        mol_type = other RNA
                        organism = synthetic construct
SEQUENCE: 31
gggtgcatcg tttacgcgta aaaaagataa aacttagttg cagaatttgc cttcattctg   60
ctgctgagga aggatatgag                                               80

SEQ ID NO: 32           moltype = RNA   length = 80
FEATURE                 Location/Qualifiers
misc_feature            1..80
                        note = Synthetic aptamer sequences
source                  1..80
                        mol_type = other RNA
                        organism = synthetic construct
SEQUENCE: 32
gggtgcatcg tttacgcgta aaaagtttga tggaagcaga ttagtttagt caaatttctg   60
ctgctgagga aggatatgag                                               80

SEQ ID NO: 33           moltype = RNA   length = 80
FEATURE                 Location/Qualifiers
misc_feature            1..80
                        note = Synthetic aptamer sequences
source                  1..80
                        mol_type = other RNA
                        organism = synthetic construct
SEQUENCE: 33
gggtgcatcg tttacgcgta aaatgaaata aggaatcctt cagcagtatt tatccttctg   60
ctgctgagga aggatatgag                                               80

SEQ ID NO: 34           moltype = RNA   length = 80
FEATURE                 Location/Qualifiers
misc_feature            1..80
                        note = Synthetic aptamer sequences
source                  1..80
                        mol_type = other RNA
                        organism = synthetic construct
SEQUENCE: 34
gggtgcatcg tttacgcgta aagaataaaa atgacaaaat tctcagcttt tgtcaacctg   60
ctgctgagga aggatatgag                                               80

SEQ ID NO: 35           moltype = RNA   length = 80
FEATURE                 Location/Qualifiers
misc_feature            1..80
                        note = Synthetic aptamer sequences
source                  1..80
                        mol_type = other RNA
```

```
                        organism = synthetic construct
SEQUENCE: 35
gggtgcatcg tttacgcgta aaaaatgaaa tgaaaaaatt ctcagctgtc tatcttcctg    60
ctgctgagga aggatatgag                                                 80

SEQ ID NO: 36           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 36
gggtgcatcg tttacgcgta aataagtaaa aaactcagtt ttcagttaag tatccaactg    60
ctgctgagga aggatatgag                                                 80

SEQ ID NO: 37           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 37
gggtgcatcg tttacgcgta aatttcagca gagtaataat aacacttctt cagtttgctg    60
ctgctgagga aggatatgag                                                 80

SEQ ID NO: 38           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 38
gggtgcatcg tttacgcgta aaattaagaa gtattatcag ttagcttttt cttccaactg    60
ctgctgagga aggatatgag                                                 80

SEQ ID NO: 39           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 39
gggtgcatcg tttacgcgta aaataaaaag ttttcctatc agcaaactca caaattcctg    60
ctgctgagga aggatatgag                                                 80

SEQ ID NO: 40           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 40
gggtgcatcg tttacgcgta aaatgaaatg taaaagaatt gaacttggca gattttcctg    60
ctgctgagga aggatatgag                                                 80

SEQ ID NO: 41           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 41
gggtgcatcg tttacgcgta aattaaagta gcagtaattt cagcagtttt tacctctctg    60
ctgctgagga aggatatgag                                                 80

SEQ ID NO: 42           moltype = RNA  length = 80
FEATURE                 Location/Qualifiers
misc_feature            1..80
                        note = Synthetic aptamer sequences
source                  1..80
                        mol_type = other RNA
                        organism = synthetic construct
SEQUENCE: 42
```

```
gggtgcatcg tttacgcgta aataaaggat aaaataattt cagggcagtt tctcatcctg  60
ctgctgagga aggatatgag                                              80

SEQ ID NO: 43              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 43
gggtgcatcg tttacgcagg atcgttttaa gtaaataaa agatttcctt ggtaatcctg   60
ctgctgagga aggatatgag                                              80

SEQ ID NO: 44              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 44
gggtgcatcg tttacgcgta aaataaagat caattaaagg ctttgatcga ttttcctctg  60
ctgctgagga aggatatgag                                              80

SEQ ID NO: 45              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 45
gggtgcatcg tttacgcgta aaaattagag attaaaatag ttcctttcag ttttgtcctg  60
ctgctgagga aggatatgag                                              80

SEQ ID NO: 46              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 46
gggtgcatcg tttacgcgta aaattgacaa tgtgaaaagc agacagcaaa tattcctctg  60
ctgctgagga aggatatgag                                              80

SEQ ID NO: 47              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 47
gggtgcatcg tttacgcgta aataaccagt tatacagaaa gatctcagca atttatcctg  60
ctgctgagga aggatatgag                                              80

SEQ ID NO: 48              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 48
gggtgcatcg tttacgctta cagaaggatt gcaccacatg cgtactcgat gaaacacctg  60
ctgctgagga aggatatgag                                              80

SEQ ID NO: 49              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 49
gggtgcatcg tttacgcgta aaataataat taaactcagc aaattcaatc caactttctg  60
ctgctgagga aggatatgag                                              80
```

-continued

```
SEQ ID NO: 50              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 50
gggtgcatcg tttacgcgta aacaagaata aattcagcag tggttttgat cctttgactg   60
ctgctgagga aggatatgag                                               80

SEQ ID NO: 51              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 51
gggtgcatcg tttacgcgta aattaatcag attgaacaaa agttttccct cagttttctg   60
ctgctgagga aggatatgag                                               80

SEQ ID NO: 52              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 52
gggtgcatcg tttacgcgta aagaaaaaca tcagagcagt tataatagtc cttttttcctg  60
ctgctgagga aggatatgag                                               80

SEQ ID NO: 53              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 53
gggtgcatcg tttacgcgta aagaaaataa acttgatcaa acttagcagt ttttatcctg   60
ctgctgagga aggatatgag                                               80

SEQ ID NO: 54              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 54
gggtgcatcg tttacgcatt ttcgttatat ttctggtttt tatgcgtgag aatcctgctg   60
ctgctgagga aggatatgag                                               80

SEQ ID NO: 55              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 55
gggtgcatcg tttacgcgta aaaataagat ctcacagcga caaatttttc ttccagtctg   60
ctgctgagga aggatatgag                                               80

SEQ ID NO: 56              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 56
gggtgcatcg tttacgcgta aatttaagac atgacagcag acattttatc ttcagacctg   60
ctgctgagga aggatatgag                                               80

SEQ ID NO: 57              moltype = RNA   length = 80
```

```
FEATURE              Location/Qualifiers
misc_feature         1..80
                     note = Synthetic aptamer sequences
source               1..80
                     mol_type = other RNA
                     organism = synthetic construct
SEQUENCE: 57
gggtgcatcg tttacgcgta ataacagaaa tataactcag ctgaattaat ttttccgctg   60
ctgctgagga aggatatgag                                               80

SEQ ID NO: 58        moltype = RNA   length = 80
FEATURE              Location/Qualifiers
misc_feature         1..80
                     note = Synthetic aptamer sequences
source               1..80
                     mol_type = other RNA
                     organism = synthetic construct
SEQUENCE: 58
gggtgcatcg tttacgcgta aaaataaatt ccaaaatatt cagcagaaat cctcgaactg   60
ctgctgagga aggatatgag                                               80

SEQ ID NO: 59        moltype = RNA   length = 80
FEATURE              Location/Qualifiers
misc_feature         1..80
                     note = Synthetic aptamer sequences
source               1..80
                     mol_type = other RNA
                     organism = synthetic construct
SEQUENCE: 59
gggtgcatcg tttacgcgta aaaataatag gttccaatca agcagtacaa aattcctctg   60
ctgctgagga aggatatgag                                               80

SEQ ID NO: 60        moltype = RNA   length = 80
FEATURE              Location/Qualifiers
misc_feature         1..80
                     note = Synthetic aptamer sequences
source               1..80
                     mol_type = other RNA
                     organism = synthetic construct
SEQUENCE: 60
gggtgcatcg tttacgcgta aaaaatctaa aaagatatca gcaggcaaat tttccttctg   60
ctgctgagga aggatatgag                                               80

SEQ ID NO: 61        moltype = RNA   length = 80
FEATURE              Location/Qualifiers
misc_feature         1..80
                     note = Synthetic aptamer sequences
source               1..80
                     mol_type = other RNA
                     organism = synthetic construct
SEQUENCE: 61
gggtgcatcg tttacgcgta aaataaagag gataactaca atcatcagca atcatatctg   60
ctgctgagga aggatatgag                                               80

SEQ ID NO: 62        moltype = RNA   length = 80
FEATURE              Location/Qualifiers
misc_feature         1..80
                     note = Synthetic aptamer sequences
source               1..80
                     mol_type = other RNA
                     organism = synthetic construct
SEQUENCE: 62
gggtgcatcg tttacgcgta aatttagtag aaaggaaaga cgaagtttcc tcagtttctg   60
ctgctgagga aggatatgag                                               80

SEQ ID NO: 63        moltype = RNA   length = 80
FEATURE              Location/Qualifiers
misc_feature         1..80
                     note = Synthetic aptamer sequences
source               1..80
                     mol_type = other RNA
                     organism = synthetic construct
SEQUENCE: 63
gggtgcatcg tttacgcgta aaaataatag atctcagaat atgaaagcag ttctttcctg   60
ctgctgagga aggatatgag                                               80

SEQ ID NO: 64        moltype = RNA   length = 80
FEATURE              Location/Qualifiers
misc_feature         1..80
```

-continued

```
                          note = Synthetic aptamer sequences
source                    1..80
                          mol_type = other RNA
                          organism = synthetic construct
SEQUENCE: 64
gggtgcatcg tttacgcgta acaagatatt cacagcagat tttaaaaaat tcctcgtctg    60
ctgctgagga aggatatgag                                                80

SEQ ID NO: 65             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 65
gggtgcatcg tttacgcgta aaaagttgac aattaataaa atcttcttag cattttcctg    60
ctgctgagga aggatatgag                                                80

SEQ ID NO: 66             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 66
gggtgcatcg tttacgcgta aaacaaaatg aaacttatag ctcagcatat tttgatcctg    60
ctgctgagga aggatatgag                                                80

SEQ ID NO: 67             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 67
gggtgcatcg tttacgcgta aattatcaaa aaagcagatt taagtatacc tcagttactg    60
ctgctgagga aggatatgag                                                80

SEQ ID NO: 68             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 68
gggtgcatcg tttacgcgta aataaaatag ctcagcaagg aagtttttt cctcaaactg      60
ctgctgagga aggatatgag                                                80

SEQ ID NO: 69             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 69
gggtgcatcg tttacgcgta aatttgagaa aagaacagca gactcaaatc tttttaactg    60
ctgctgagga aggatatgag                                                80

SEQ ID NO: 70             moltype = RNA   length = 80
FEATURE                   Location/Qualifiers
misc_feature              1..80
                          note = Synthetic aptamer sequences
source                    1..80
                          mol_type = other RNA
                          organism = synthetic construct
SEQUENCE: 70
gggtgcatcg tttacgcgta acagaaaatt aagctcagca atagtaatta tcctagtctg    60
ctgctgagga aggatatgag                                                80

SEQ ID NO: 71             moltype = RNA   length = 80
FEATURE                   Location/Qualifiers
misc_feature              1..80
                          note = Synthetic aptamer sequences
source                    1..80
```

-continued

```
                              mol_type = other RNA
                              organism = synthetic construct
SEQUENCE: 71
gggtgcatcg tttacgcgta atgaaaataa atcagtctca cagcatttta aaacttcctg    60
ctgctgagga aggatatgag                                                80

SEQ ID NO: 72                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
SEQUENCE: 72
gggtgcatcg tttacgcgta tttacaagca acaaagttac aatcagcaga atttatcctg    60
ctgctgagga aggatatgag                                                80

SEQ ID NO: 73                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
SEQUENCE: 73
gggtgcatcg tttacgcgta aaaaattgtc tatagcactt ttagattccc aaactaactg    60
ctgctgagga aggatatgag                                                80

SEQ ID NO: 74                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
SEQUENCE: 74
gggtgcatcg tttacgcgta aaaaaatcag caaaatcgaa aactcatgca gtttgtcctg    60
ctgctgagga aggatatgag                                                80

SEQ ID NO: 75                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
SEQUENCE: 75
gggtgcatcg tttacgcgta aaaaattcct taaaaattta actaactgga taggtctctg    60
ctgctgagga aggatatgag                                                80

SEQ ID NO: 76                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
SEQUENCE: 76
gggtgcatcg tttacgcgta aaacaaaatt tctgacagca attccttcgt taaaaatctg    60
ctgctgagga aggatatgag                                                80

SEQ ID NO: 77                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
SEQUENCE: 77
gggtgcatcg tttacgcgta aattattaaa aaaatcagca aagtttattt cccacggctg    60
ctgctgagga aggatatgag                                                80

SEQ ID NO: 78                 moltype = RNA   length = 80
FEATURE                       Location/Qualifiers
misc_feature                  1..80
                              note = Synthetic aptamer sequences
source                        1..80
                              mol_type = other RNA
                              organism = synthetic construct
```

```
SEQUENCE: 78
gggtgcatcg tttacgcgta attaatcaaa caatagcagc aaatctcagc aattttcctg   60
ctgctgagga aggatatgag                                                80

SEQ ID NO: 79            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 79
gggtgcatcg tttacgcgta atttgaaagt ctcataaatt tttttttttt tttcaatctg   60
ctgctgagga aggatatgag                                                80

SEQ ID NO: 80            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 80
gggtgcatcg tttacgcgta aaaattcagc atgatttcaa ttactccttt cattgatctg   60
ctgctgagga aggatatgag                                                80

SEQ ID NO: 81            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 81
gggtgcatcg tttacgcgta aaataaataa aaatcagtag caatctttct cacagtgctg   60
ctgctgagga aggatatgag                                                80

SEQ ID NO: 82            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 82
gggtgcatcg tttacgcgta aataaaaagc agatctcagc aaaactcgta aattcaactg   60
ctgctgagga aggatatgag                                                80

SEQ ID NO: 83            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 83
gggtgcatcg tttacgcgta aataatgaag gactcagaca gttaaaagat gcattaactg   60
ctgctgagga aggatatgag                                                80

SEQ ID NO: 84            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 84
gggtgcatcg tttacgcgta aaaaagatca atatgaaaat cagcagttaa tatcttcctg   60
ctgctgagga aggatatgag                                                80

SEQ ID NO: 85            moltype = RNA   length = 80
FEATURE                  Location/Qualifiers
misc_feature             1..80
                         note = Synthetic aptamer sequences
source                   1..80
                         mol_type = other RNA
                         organism = synthetic construct
SEQUENCE: 85
gggtgcatcg tttacgcgta aaaataacaa acttctcagc tgtttaatat ctcctgactg   60
```

-continued

```
ctgctgagga aggatatgag                                                80

SEQ ID NO: 86              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 86
gggtgcatcg tttacgcgta aaattaaaca aatagctcag cacgaaaatt tgcgtaactg   60
ctgctgagga aggatatgag                                                80

SEQ ID NO: 87              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 87
gggtgcatcg tttacgcgta attaaaaaac cttcacacag aaaacattcc tcaatttctg   60
ctgctgagga aggatatgag                                                80

SEQ ID NO: 88              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 88
gggtgcatcg tttacgcatt ttcgttttat tttagtttaa ttgcgtttag tatctggctg   60
ctgctgagga aggatatgag                                                80

SEQ ID NO: 89              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 89
gggtgcatcg tttacgcgta aaaagtataa aggttagaaa ttcagcagtt tgatatcctg   60
ctgctgagga aggatatgag                                                80

SEQ ID NO: 90              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 90
gggtgcatcg tttacgcgta aaaaggagaa ttagtactca ccagtcgttt aaaatttctg   60
ctgctgagga aggatatgag                                                80

SEQ ID NO: 91              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 91
gggtgcatcg tttacgcgta aaaataaata actacgagat ctcagcagat cattatcctg   60
ctgctgagga aggatatgag                                                80

SEQ ID NO: 92              moltype = RNA   length = 80
FEATURE                    Location/Qualifiers
misc_feature               1..80
                           note = Synthetic aptamer sequences
source                     1..80
                           mol_type = other RNA
                           organism = synthetic construct
SEQUENCE: 92
gggtgcatcg tttacgcgta aaatggtttt tcagcagtta acataatgcc tcagtttctg   60
ctgctgagga aggatatgag                                                80
```

```
SEQ ID NO: 93          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 93
gggtgcatcg tttacgcgta aataacaaaa atctcagctt ttgcagaatt tatccacctg   60
ctgctgagga aggatatgag                                                80

SEQ ID NO: 94          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 94
gggtgcatcg tttacgcgta aataaactca cagcagaaaa aattccttca acttgtactg   60
ctgctgagga aggatatgag                                                80

SEQ ID NO: 95          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 95
gggtgcatcg tttacgcagt agttaataac aaatagtcag cagttttgtc cttcattctg   60
ctgctgagga aggatatgag                                                80

SEQ ID NO: 96          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 96
gggtgcatcg tttacgcgta aaaatagcag tagatagcgg cagttttgta tttgttactg   60
ctgctgagga aggatatgag                                                80

SEQ ID NO: 97          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 97
gggtgcatcg tttacgcgta aaaatttaaa taactcagca atcatagatc cgactgactg   60
ctgctgagga aggatatgag                                                80

SEQ ID NO: 98          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 98
gggtgcatcg tttacgcgta aagaacagct gacaagaaat tcaaaccttc agattttctg   60
ctgctgagga aggatatgag                                                80

SEQ ID NO: 99          moltype = RNA   length = 80
FEATURE                Location/Qualifiers
misc_feature           1..80
                       note = Synthetic aptamer sequences
source                 1..80
                       mol_type = other RNA
                       organism = synthetic construct
SEQUENCE: 99
gggtgcatcg tttacgcgta aagataataa gcagtattca gcagatttgt aaggtttctg   60
ctgctgagga aggatatgag                                                80

SEQ ID NO: 100         moltype = RNA   length = 80
FEATURE                Location/Qualifiers
```

```
misc_feature             1..80
                         note = Synthetic aptamer sequences
source                   1..80
                         mol_type = other RNA
                         organism = synthetic construct
SEQUENCE: 100
gggtgcatcg tttacgcgta aataagaggc agacagtatt acaaatatcc taaaatactg    60
ctgctgagga aggatatgag                                                80

SEQ ID NO: 101           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 101
gggtgcatcg tttacgcgat tagtctgata aacaaaaaga tttcgctaaa aatcaatctg    60
ctgctgagga aggatatgag                                                80

SEQ ID NO: 102           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 102
gggtgcatcg tttacgcaga tagcagcagg aatcaagcgg taggagtcta gcagaagctg    60
ctgctgagga aggatatgag                                                80

SEQ ID NO: 103           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 103
gggtgcatcg tttacgcatt ttcgttttat ttcagtttaa ttgcgtttag tatctggctg    60
ctgctgagga aggatatgag                                                80

SEQ ID NO: 104           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 104
gggtgcatcg tttacgcgca acataaaaat ttaaagtgct cagttgtcaa tctatgactg    60
ctgctgagga aggatatgag                                                80

SEQ ID NO: 105           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 105
gggtgcatcg tttacgcgta aatggtccgc tattaaaaga aaagaatgaa gtctcagctg    60
ctgctgagga aggatatgag                                                80

SEQ ID NO: 106           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 106
gggtgcatcg tttacgctat tttcatttgt tttttttaatt tactagtgta aacaatcctg   60
ctgctgagga aggatatgag                                                80

SEQ ID NO: 107           moltype = DNA   length = 80
FEATURE                  Location/Qualifiers
misc_feature             1..80
                         note = Synthetic aptamer sequences
```

-continued

```
source                   1..80
                         mol_type = other DNA
                         organism = synthetic construct
SEQUENCE: 107
gggtgcatcg tttacgcgta aataagtaga taaagtggca gtttgttttc cttggaactg    60
ctgctgagga aggatatgag                                                 80

SEQ ID NO: 108           moltype = DNA  length = 80
FEATURE                  Location/Qualifiers
misc_feature             1..80
                         note = Synthetic aptamer sequences
source                   1..80
                         mol_type = other DNA
                         organism = synthetic construct
SEQUENCE: 108
gggtgcatcg tttacgcgta aaaattaaag agattaaggt ccttaagcag ttttgtcctg    60
ctgctgagga aggatatgag                                                 80

SEQ ID NO: 109           moltype = DNA  length = 80
FEATURE                  Location/Qualifiers
misc_feature             1..80
                         note = Synthetic aptamer sequences
source                   1..80
                         mol_type = other DNA
                         organism = synthetic construct
SEQUENCE: 109
gggtgcatcg tttacgcgta aaaaaatcaa aacttcagca aattatttat caacgtcctg    60
ctgctgagga aggatatgag                                                 80

SEQ ID NO: 110           moltype = DNA  length = 80
FEATURE                  Location/Qualifiers
misc_feature             1..80
                         note = Synthetic aptamer sequences
source                   1..80
                         mol_type = other DNA
                         organism = synthetic construct
SEQUENCE: 110
gggtgcatcg tttacgcgta aaataaatta aaaagaactt cttcagcaat caatatcctg    60
ctgctgagga aggatatgag                                                 80

SEQ ID NO: 111           moltype = DNA  length = 80
FEATURE                  Location/Qualifiers
misc_feature             1..80
                         note = Synthetic aptamer sequences
source                   1..80
                         mol_type = other DNA
                         organism = synthetic construct
SEQUENCE: 111
gggtgcatcg tttacgcgta aataaaaatg aaaaattgtc tctcagcttt caaagtcctg    60
ctgctgagga aggatatgag                                                 80

SEQ ID NO: 112           moltype = DNA  length = 80
FEATURE                  Location/Qualifiers
misc_feature             1..80
                         note = Synthetic aptamer sequences
source                   1..80
                         mol_type = other DNA
                         organism = synthetic construct
SEQUENCE: 112
gggtgcatcg tttacgcgta aaaaaaaaat atcttcggag aattcagcaa ttttatcctg    60
ctgctgagga aggatatgag                                                 80

SEQ ID NO: 113           moltype = DNA  length = 80
FEATURE                  Location/Qualifiers
misc_feature             1..80
                         note = Synthetic aptamer sequences
source                   1..80
                         mol_type = other DNA
                         organism = synthetic construct
SEQUENCE: 113
gggtgcatcg tttacgcgta aaaattttca tctcagcaat taaatccaaa gaatccactg    60
ctgctgagga aggatatgag                                                 80

SEQ ID NO: 114           moltype = DNA  length = 80
FEATURE                  Location/Qualifiers
misc_feature             1..80
                         note = Synthetic aptamer sequences
source                   1..80
                         mol_type = other DNA
```

-continued

```
                          organism = synthetic construct
SEQUENCE: 114
gggtgcatcg tttacgcgta aaatatatca gcaaagtagt ttaagcctcc tcagtttctg   60
ctgctgagga aggatatgag                                                80

SEQ ID NO: 115           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 115
gggtgcatcg tttacgcgta aattatgaaa aatacagcaa ggatttaacc tcagtttctg   60
ctgctgagga aggatatgag                                                80

SEQ ID NO: 116           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 116
gggtgcatcg tttacgcgta aaataaataa atcttcaaag tacagacctc gatttttctg   60
ctgctgagga aggatatgag                                                80

SEQ ID NO: 117           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 117
gggtgcatcg tttacgctta taggtattag acattttcaa ttaaagtgaa ttagtgtctg   60
ctgctgagga aggatatgag                                                80

SEQ ID NO: 118           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 118
gggtgcatcg tttacgcgta aaatgtgaca gcaggataat aaaataagta ctcagtactg   60
ctgctgagga aggatatgag                                                80

SEQ ID NO: 119           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 119
gggtgcatcg tttacgcgta attaagaaaa ataaaagtac tctgcagttt ttatccactg   60
ctgctgagga aggatatgag                                                80

SEQ ID NO: 120           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 120
gggtgcatcg tttacgcgta aaaataaaat tttcccagac cagttatctg ccttaaactg   60
ctgctgagga aggatatgag                                                80

SEQ ID NO: 121           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 121
```

-continued

```
gggtgcatcg tttacgcgta aagaaaaaaa tcagctttta gtcgccttcc attttgactg   60
ctgctgagga aggatatgag                                                80

SEQ ID NO: 122              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 122
gggtgcatcg tttacgcgta aataaataat caaaattaca ctcagtggca atttcctctg   60
ctgctgagga aggatatgag                                                80

SEQ ID NO: 123              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 123
gggtgcatcg tttacgcgta aaatacagga tacgacaata actcagcaga ttttatcctg   60
ctgctgagga aggatatgag                                                80

SEQ ID NO: 124              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 124
gggtgcatcg tttacgcgtt aaaaattgtg cactgagatg acgcagcatt aactacactg   60
ctgctgagga aggatatgag                                                80

SEQ ID NO: 125              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 125
gggtgcatcg tttacgcgta aataaaaatt aatcagcaat tttccactca gttgtacctg   60
ctgctgagga aggatatgag                                                80

SEQ ID NO: 126              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 126
gggtgcatcg tttacgcgta aaaataaaaa atctcgatca ctgcagtttt attccggctg   60
ctgctgagga aggatatgag                                                80

SEQ ID NO: 127              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 127
gggtgcatcg tttacgcgta aacaaatatc gattaaaata aaatctcagc aagaatcctg   60
ctgctgagga aggatatgag                                                80

SEQ ID NO: 128              moltype = DNA  length = 80
FEATURE                     Location/Qualifiers
misc_feature               1..80
                            note = Synthetic aptamer sequences
source                      1..80
                            mol_type = other DNA
                            organism = synthetic construct
SEQUENCE: 128
gggtgcatcg tttacgcgta aaataaataa aattatccca ggagcaaatt ttcttcgctg   60
ctgctgagga aggatatgag                                                80
```

-continued

```
SEQ ID NO: 129          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 129
gggtgcatcg tttacgcgta gaagaattaa tagtggacat atcaatagca gtttatcctg   60
ctgctgagga aggatatgag                                               80

SEQ ID NO: 130          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 130
gggtgcatcg tttacgcgta aacatattca gcagttaaaa tttagtaggt tcagtagctg   60
ctgctgagga aggatatgag                                               80

SEQ ID NO: 131          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 131
gggtgcatcg tttacgcgta aaaaagataa aacttagttg cagaatttgc cttcattctg   60
ctgctgagga aggatatgag                                               80

SEQ ID NO: 132          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 132
gggtgcatcg tttacgcgta aaaagtttga tggaagcaga ttagtttagt caaatttctg   60
ctgctgagga aggatatgag                                               80

SEQ ID NO: 133          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 133
gggtgcatcg tttacgcgta aaatgaaata aggaatcctt cagcagtatt tatccttctg   60
ctgctgagga aggatatgag                                               80

SEQ ID NO: 134          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 134
gggtgcatcg tttacgcgta aagaataaaa atgacaaaat tctcagcttt tgtcaacctg   60
ctgctgagga aggatatgag                                               80

SEQ ID NO: 135          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 135
gggtgcatcg tttacgcgta aaaaatgaaa tgaaaaaatt ctcagctgtc tatcttcctg   60
ctgctgagga aggatatgag                                               80

SEQ ID NO: 136          moltype = DNA   length = 80
```

```
FEATURE              Location/Qualifiers
misc_feature         1..80
                     note = Synthetic aptamer sequences
source               1..80
                     mol_type = other DNA
                     organism = synthetic construct
SEQUENCE: 136
gggtgcatcg tttacgcgta aataagtaaa aaactcagtt ttcagttaag tatccaactg   60
ctgctgagga aggatatgag                                                80

SEQ ID NO: 137       moltype = DNA   length = 80
FEATURE              Location/Qualifiers
misc_feature         1..80
                     note = Synthetic aptamer sequences
source               1..80
                     mol_type = other DNA
                     organism = synthetic construct
SEQUENCE: 137
gggtgcatcg tttacgcgta aatttcagca gagtaataat aacacttctt cagtttgctg   60
ctgctgagga aggatatgag                                                80

SEQ ID NO: 138       moltype = DNA   length = 80
FEATURE              Location/Qualifiers
misc_feature         1..80
                     note = Synthetic aptamer sequences
source               1..80
                     mol_type = other DNA
                     organism = synthetic construct
SEQUENCE: 138
gggtgcatcg tttacgcgta aaattaagaa gtattatcag ttagcttttt cttccaactg   60
ctgctgagga aggatatgag                                                80

SEQ ID NO: 139       moltype = DNA   length = 80
FEATURE              Location/Qualifiers
misc_feature         1..80
                     note = Synthetic aptamer sequences
source               1..80
                     mol_type = other DNA
                     organism = synthetic construct
SEQUENCE: 139
gggtgcatcg tttacgcgta aaataaaaag ttttcctatc agcaaactca caaattcctg   60
ctgctgagga aggatatgag                                                80

SEQ ID NO: 140       moltype = DNA   length = 80
FEATURE              Location/Qualifiers
misc_feature         1..80
                     note = Synthetic aptamer sequences
source               1..80
                     mol_type = other DNA
                     organism = synthetic construct
SEQUENCE: 140
gggtgcatcg tttacgcgta aaatgaaatg taaaagaatt gaacttggca gattttcctg   60
ctgctgagga aggatatgag                                                80

SEQ ID NO: 141       moltype = DNA   length = 80
FEATURE              Location/Qualifiers
misc_feature         1..80
                     note = Synthetic aptamer sequences
source               1..80
                     mol_type = other DNA
                     organism = synthetic construct
SEQUENCE: 141
gggtgcatcg tttacgcgta aattaaagta gcagtaattt cagcagtttt tacctctctg   60
ctgctgagga aggatatgag                                                80

SEQ ID NO: 142       moltype = DNA   length = 80
FEATURE              Location/Qualifiers
misc_feature         1..80
                     note = Synthetic aptamer sequences
source               1..80
                     mol_type = other DNA
                     organism = synthetic construct
SEQUENCE: 142
gggtgcatcg tttacgcgta aataaaggat aaaataattt cagggcagtt tctcatcctg   60
ctgctgagga aggatatgag                                                80

SEQ ID NO: 143       moltype = DNA   length = 80
FEATURE              Location/Qualifiers
misc_feature         1..80
```

-continued

```
                            note = Synthetic aptamer sequences
source                      1..80
                            mol_type = other DNA
                            organism = synthetic construct
SEQUENCE: 143
gggtgcatcg tttacgcagg atcgttttaa gtaaaataaa agatttcctt ggtaatcctg     60
ctgctgagga aggatatgag                                                 80

SEQ ID NO: 144              moltype = DNA  length = 80
FEATURE                     Location/Qualifiers
misc_feature                1..80
                            note = Synthetic aptamer sequences
source                      1..80
                            mol_type = other DNA
                            organism = synthetic construct
SEQUENCE: 144
gggtgcatcg tttacgcgta aaataaagat caattaaagg ctttgatcga ttttcctctg     60
ctgctgagga aggatatgag                                                 80

SEQ ID NO: 145              moltype = DNA  length = 80
FEATURE                     Location/Qualifiers
misc_feature                1..80
                            note = Synthetic aptamer sequences
source                      1..80
                            mol_type = other DNA
                            organism = synthetic construct
SEQUENCE: 145
gggtgcatcg tttacgcgta aaaattagag attaaaatag ttcctttcag ttttgtcctg     60
ctgctgagga aggatatgag                                                 80

SEQ ID NO: 146              moltype = DNA  length = 80
FEATURE                     Location/Qualifiers
misc_feature                1..80
                            note = Synthetic aptamer sequences
source                      1..80
                            mol_type = other DNA
                            organism = synthetic construct
SEQUENCE: 146
gggtgcatcg tttacgcgta aaattgacaa tgtgaaaagc agacagcaaa tattcctctg     60
ctgctgagga aggatatgag                                                 80

SEQ ID NO: 147              moltype = DNA  length = 80
FEATURE                     Location/Qualifiers
misc_feature                1..80
                            note = Synthetic aptamer sequences
source                      1..80
                            mol_type = other DNA
                            organism = synthetic construct
SEQUENCE: 147
gggtgcatcg tttacgcgta aataaccagt tatacagaaa gatctcagca atttatcctg     60
ctgctgagga aggatatgag                                                 80

SEQ ID NO: 148              moltype = DNA  length = 80
FEATURE                     Location/Qualifiers
misc_feature                1..80
                            note = Synthetic aptamer sequences
source                      1..80
                            mol_type = other DNA
                            organism = synthetic construct
SEQUENCE: 148
gggtgcatcg tttacgctta cagaaggatt gcaccacatg cgtactcgat gaaacacctg     60
ctgctgagga aggatatgag                                                 80

SEQ ID NO: 149              moltype = DNA  length = 80
FEATURE                     Location/Qualifiers
misc_feature                1..80
                            note = Synthetic aptamer sequences
source                      1..80
                            mol_type = other DNA
                            organism = synthetic construct
SEQUENCE: 149
gggtgcatcg tttacgcgta aaataataat taaactcagc aaattcaatc caactttctg     60
ctgctgagga aggatatgag                                                 80

SEQ ID NO: 150              moltype = DNA  length = 80
FEATURE                     Location/Qualifiers
misc_feature                1..80
                            note = Synthetic aptamer sequences
source                      1..80
```

```
                         mol_type = other DNA
                         organism = synthetic construct
SEQUENCE: 150
gggtgcatcg tttacgcgta aacaagaata aattcagcag tggttttgat cctttgactg    60
ctgctgagga aggatatgag                                                80

SEQ ID NO: 151           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 151
gggtgcatcg tttacgcgta aattaatcag attgaacaaa agttttccct cagttttctg    60
ctgctgagga aggatatgag                                                80

SEQ ID NO: 152           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 152
gggtgcatcg tttacgcgta aagaaaaaca tcagagcagt tataatagtc cttttccctg    60
ctgctgagga aggatatgag                                                80

SEQ ID NO: 153           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 153
gggtgcatcg tttacgcgta aagaaaataa acttgatcaa acttagcagt ttttatcctg    60
ctgctgagga aggatatgag                                                80

SEQ ID NO: 154           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 154
gggtgcatcg tttacgcatt ttcgttatat ttctggtttt tatgcgtgag aatcctgctg    60
ctgctgagga aggatatgag                                                80

SEQ ID NO: 155           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 155
gggtgcatcg tttacgcgta aaaataagat ctcacagcga caaatttttc ttccagtctg    60
ctgctgagga aggatatgag                                                80

SEQ ID NO: 156           moltype = DNA   length = 80
FEATURE                  Location/Qualifiers
misc_feature             1..80
                         note = Synthetic aptamer sequences
source                   1..80
                         mol_type = other DNA
                         organism = synthetic construct
SEQUENCE: 156
gggtgcatcg tttacgcgta aatttaagac atgacagcag acattttatc ttcagacctg    60
ctgctgagga aggatatgag                                                80

SEQ ID NO: 157           moltype = DNA   length = 80
FEATURE                  Location/Qualifiers
misc_feature             1..80
                         note = Synthetic aptamer sequences
source                   1..80
                         mol_type = other DNA
                         organism = synthetic construct
```

-continued

```
SEQUENCE: 157
gggtgcatcg tttacgcgta ataacagaaa tataactcag ctgaattaat ttttccgctg   60
ctgctgagga aggatatgag                                               80

SEQ ID NO: 158          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 158
gggtgcatcg tttacgcgta aaaataaatt ccaaaatatt cagcagaaat cctcgaactg   60
ctgctgagga aggatatgag                                               80

SEQ ID NO: 159          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 159
gggtgcatcg tttacgcgta aaaataatag gttccaatca agcagtacaa aattcctctg   60
ctgctgagga aggatatgag                                               80

SEQ ID NO: 160          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 160
gggtgcatcg tttacgcgta aaaaatctaa aaagatatca gcaggcaaat tttccttctg   60
ctgctgagga aggatatgag                                               80

SEQ ID NO: 161          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 161
gggtgcatcg tttacgcgta aaataaagag gataactaca atcatcagca atcatatctg   60
ctgctgagga aggatatgag                                               80

SEQ ID NO: 162          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 162
gggtgcatcg tttacgcgta aatttagtag aaaggaaaga cgaagtttcc tcagtttctg   60
ctgctgagga aggatatgag                                               80

SEQ ID NO: 163          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 163
gggtgcatcg tttacgcgta aaaataatag atctcagaat atgaaagcag ttctttcctg   60
ctgctgagga aggatatgag                                               80

SEQ ID NO: 164          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 164
gggtgcatcg tttacgcgta acaagatatt cacagcagat tttaaaaaat cctcgtctg   60
```

-continued

```
ctgctgagga aggatatgag                                                  80

SEQ ID NO: 165          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 165
gggtgcatcg tttacgcgta aaaagttgac aattaataaa atcttcttag cattttcctg   60
ctgctgagga aggatatgag                                                  80

SEQ ID NO: 166          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 166
gggtgcatcg tttacgcgta aaacaaatg aaacttatag ctcagcatat tttgatcctg    60
ctgctgagga aggatatgag                                                  80

SEQ ID NO: 167          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 167
gggtgcatcg tttacgcgta aattatcaaa aaagcagatt taagtatacc tcagttactg   60
ctgctgagga aggatatgag                                                  80

SEQ ID NO: 168          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 168
gggtgcatcg tttacgcgta aataaaatag ctcagcaagg aagttttttt cctcaaactg   60
ctgctgagga aggatatgag                                                  80

SEQ ID NO: 169          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 169
gggtgcatcg tttacgcgta aatttgagaa aagaacagca gactcaaatc tttttaactg   60
ctgctgagga aggatatgag                                                  80

SEQ ID NO: 170          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 170
gggtgcatcg tttacgcgta acagaaaatt aagctcagca atagtaatta tcctagtctg   60
ctgctgagga aggatatgag                                                  80

SEQ ID NO: 171          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 171
gggtgcatcg tttacgcgta atgaaaataa atcagtctca cagcatttta aaacttcctg   60
ctgctgagga aggatatgag                                                  80
```

-continued

```
SEQ ID NO: 172          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 172
gggtgcatcg tttacgcgta tttacaagca acaaagttac aatcagcaga atttatcctg   60
ctgctgagga aggatatgag                                               80

SEQ ID NO: 173          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 173
gggtgcatcg tttacgcgta aaaaattgtc tatagcactt ttagattccc aaactaactg   60
ctgctgagga aggatatgag                                               80

SEQ ID NO: 174          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 174
gggtgcatcg tttacgcgta aaaaaatcag caaaatcgaa aactcatgca gtttgtcctg   60
ctgctgagga aggatatgag                                               80

SEQ ID NO: 175          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 175
gggtgcatcg tttacgcgta aaaaattcct taaaaattta actaactgga taggtctctg   60
ctgctgagga aggatatgag                                               80

SEQ ID NO: 176          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 176
gggtgcatcg tttacgcgta aaacaaaatt tctgacagca attccttcgt taaaaatctg   60
ctgctgagga aggatatgag                                               80

SEQ ID NO: 177          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 177
gggtgcatcg tttacgcgta aattattaaa aaaatcagca aagtttattt cccacggctg   60
ctgctgagga aggatatgag                                               80

SEQ ID NO: 178          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 178
gggtgcatcg tttacgcgta attaatcaaa caatagcagc aaatctcagc aattttcctg   60
ctgctgagga aggatatgag                                               80

SEQ ID NO: 179          moltype = DNA   length = 80
FEATURE                 Location/Qualifiers
```

-continued

```
misc_feature              1..80
                          note = Synthetic aptamer sequences
source                    1..80
                          mol_type = other DNA
                          organism = synthetic construct
SEQUENCE: 179
gggtgcatcg tttacgcgta atttgaaagt ctcataaatt ttttttttttt tttcaatctg   60
ctgctgagga aggatatgag                                                80

SEQ ID NO: 180            moltype = DNA   length = 80
FEATURE                   Location/Qualifiers
misc_feature              1..80
                          note = Synthetic aptamer sequences
source                    1..80
                          mol_type = other DNA
                          organism = synthetic construct
SEQUENCE: 180
gggtgcatcg tttacgcgta aaaattcagc atgatttcaa ttactccttt cattgatctg   60
ctgctgagga aggatatgag                                                80

SEQ ID NO: 181            moltype = DNA   length = 80
FEATURE                   Location/Qualifiers
misc_feature              1..80
                          note = Synthetic aptamer sequences
source                    1..80
                          mol_type = other DNA
                          organism = synthetic construct
SEQUENCE: 181
gggtgcatcg tttacgcgta aaataaataa aaatcagtag caatctttct cacagtgctg   60
ctgctgagga aggatatgag                                                80

SEQ ID NO: 182            moltype = DNA   length = 80
FEATURE                   Location/Qualifiers
misc_feature              1..80
                          note = Synthetic aptamer sequences
source                    1..80
                          mol_type = other DNA
                          organism = synthetic construct
SEQUENCE: 182
gggtgcatcg tttacgcgta aataaaaagc agatctcagc aaaactcgta aattcaactg   60
ctgctgagga aggatatgag                                                80

SEQ ID NO: 183            moltype = DNA   length = 80
FEATURE                   Location/Qualifiers
misc_feature              1..80
                          note = Synthetic aptamer sequences
source                    1..80
                          mol_type = other DNA
                          organism = synthetic construct
SEQUENCE: 183
gggtgcatcg tttacgcgta aataatgaag gactcagaca gttaaaagat gcattaactg   60
ctgctgagga aggatatgag                                                80

SEQ ID NO: 184            moltype = DNA   length = 80
FEATURE                   Location/Qualifiers
misc_feature              1..80
                          note = Synthetic aptamer sequences
source                    1..80
                          mol_type = other DNA
                          organism = synthetic construct
SEQUENCE: 184
gggtgcatcg tttacgcgta aaaaagatca atatgaaaat cagcagttaa tatcttcctg   60
ctgctgagga aggatatgag                                                80

SEQ ID NO: 185            moltype = DNA   length = 80
FEATURE                   Location/Qualifiers
misc_feature              1..80
                          note = Synthetic aptamer sequences
source                    1..80
                          mol_type = other DNA
                          organism = synthetic construct
SEQUENCE: 185
gggtgcatcg tttacgcgta aaaataacaa acttctcagc tgtttaatat ctcctgactg   60
ctgctgagga aggatatgag                                                80

SEQ ID NO: 186            moltype = DNA   length = 80
FEATURE                   Location/Qualifiers
misc_feature              1..80
                          note = Synthetic aptamer sequences
```

-continued

```
source                  1..80
                        mol_type = other DNA
                        organism = synthetic construct
SEQUENCE: 186
gggtgcatcg tttacgcgta aaattaaaca aatagctcag cacgaaaatt tgcgtaactg    60
ctgctgagga aggatatgag                                               80

SEQ ID NO: 187          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 187
gggtgcatcg tttacgcgta attaaaaaac cttcacacag aaaacattcc tcaatttctg    60
ctgctgagga aggatatgag                                               80

SEQ ID NO: 188          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 188
gggtgcatcg tttacgcatt ttcgttttat tttagtttaa ttgcgtttag tatctggctg    60
ctgctgagga aggatatgag                                               80

SEQ ID NO: 189          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 189
gggtgcatcg tttacgcgta aaaagtataa aggttagaaa ttcagcagtt tgatatcctg    60
ctgctgagga aggatatgag                                               80

SEQ ID NO: 190          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 190
gggtgcatcg tttacgcgta aaaaggagaa ttagtactca ccagtcgttt aaaatttctg    60
ctgctgagga aggatatgag                                               80

SEQ ID NO: 191          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 191
gggtgcatcg tttacgcgta aaaataaata actacgagat ctcagcagat cattatcctg    60
ctgctgagga aggatatgag                                               80

SEQ ID NO: 192          moltype = DNA   length = 80
FEATURE                 Location/Qualifiers
misc_feature            1..80
                        note = Synthetic aptamer sequences
source                  1..80
                        mol_type = other DNA
                        organism = synthetic construct
SEQUENCE: 192
gggtgcatcg tttacgcgta aaatggtttt tcagcagtta acataatgcc tcagtttctg    60
ctgctgagga aggatatgag                                               80

SEQ ID NO: 193          moltype = DNA   length = 80
FEATURE                 Location/Qualifiers
misc_feature            1..80
                        note = Synthetic aptamer sequences
source                  1..80
                        mol_type = other DNA
```

-continued

```
                           organism = synthetic construct
SEQUENCE: 193
gggtgcatcg tttacgcgta aataacaaaa atctcagctt ttgcagaatt tatccacctg    60
ctgctgagga aggatatgag                                                80

SEQ ID NO: 194          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 194
gggtgcatcg tttacgcgta aataaactca cagcagaaaa aattccttca acttgtactg    60
ctgctgagga aggatatgag                                                80

SEQ ID NO: 195          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 195
gggtgcatcg tttacgcagt agttaataac aaatagtcag cagttttgtc cttcattctg    60
ctgctgagga aggatatgag                                                80

SEQ ID NO: 196          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 196
gggtgcatcg tttacgcgta aaaatagcag tagatagcgg cagttttgta tttgttactg    60
ctgctgagga aggatatgag                                                80

SEQ ID NO: 197          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 197
gggtgcatcg tttacgcgta aaaatttaaa taactcagca atcatagatc cgactgactg    60
ctgctgagga aggatatgag                                                80

SEQ ID NO: 198          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 198
gggtgcatcg tttacgcgta aagaacagct gacaagaaat tcaaaccttc agattttctg    60
ctgctgagga aggatatgag                                                80

SEQ ID NO: 199          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 199
gggtgcatcg tttacgcgta aagataataa gcagtattca gcagatttgt aaggtttctg    60
ctgctgagga aggatatgag                                                80

SEQ ID NO: 200          moltype = DNA  length = 80
FEATURE                 Location/Qualifiers
misc_feature            1..80
                        note = Synthetic aptamer sequences
source                  1..80
                        mol_type = other DNA
                        organism = synthetic construct
SEQUENCE: 200
```

-continued

```
gggtgcatcg tttacgcgta aataagaggc agacagtatt acaaatatcc taaaatactg  60
ctgctgagga aggatatgag                                              80

SEQ ID NO: 201          moltype = RNA  length = 11
FEATURE                 Location/Qualifiers
misc_feature            1..11
                        note = Synthetic aptamer sequences
source                  1..11
                        mol_type = other RNA
                        organism = synthetic construct
SEQUENCE: 201
aaacaaaaag a                                                        11

SEQ ID NO: 202          moltype =   length =
SEQUENCE: 202
000

SEQ ID NO: 203          moltype = DNA  length = 11
FEATURE                 Location/Qualifiers
misc_feature            1..11
                        note = Synthetic aptamer sequences
source                  1..11
                        mol_type = other DNA
                        organism = synthetic construct
SEQUENCE: 203
aaacaaaaag a                                                        11

SEQ ID NO: 204          moltype =   length =
SEQUENCE: 204
000

SEQ ID NO: 205          moltype = RNA  length = 13
FEATURE                 Location/Qualifiers
misc_feature            1..13
                        note = Synthetic aptamer sequences
source                  1..13
                        mol_type = other RNA
                        organism = synthetic construct
SEQUENCE: 205
ataaaaattt aaa                                                      13

SEQ ID NO: 206          moltype = DNA  length = 13
FEATURE                 Location/Qualifiers
misc_feature            1..13
                        note = Synthetic aptamer sequences
source                  1..13
                        mol_type = other DNA
                        organism = synthetic construct
SEQUENCE: 206
ataaaaattt aaa                                                      13

SEQ ID NO: 207          moltype = RNA  length = 12
FEATURE                 Location/Qualifiers
misc_feature            1..12
                        note = Artificial Sequence
source                  1..12
                        mol_type = other RNA
                        organism = synthetic construct
SEQUENCE: 207
gtaaaaatta aa                                                       12

SEQ ID NO: 208          moltype = DNA  length = 12
FEATURE                 Location/Qualifiers
misc_feature            1..12
                        note = Synthetic aptamer sequences
source                  1..12
                        mol_type = other DNA
                        organism = synthetic construct
SEQUENCE: 208
gtaaaaatta aa                                                       12

SEQ ID NO: 209          moltype =   length =
SEQUENCE: 209
000

SEQ ID NO: 210          moltype =   length =
SEQUENCE: 210
000
```

-continued

```
SEQ ID NO: 211            moltype =    length =
SEQUENCE: 211
000

SEQ ID NO: 212            moltype =    length =
SEQUENCE: 212
000

SEQ ID NO: 213            moltype = AA   length = 532
FEATURE                   Location/Qualifiers
source                    1..532
                          mol_type = protein
                          organism = Homo sapiens
SEQUENCE: 213
MAPSSPRPAL PALLVLLGAL FPGPGNAQTS VSPSKVILPR GGSVLVTCST SCDQPKLLGI   60
ETPLPKKELL LPGNNRKVYE LSNVQEDSQP MCYSNCPDGQ STAKTFLTVY WTPERVELAP  120
LPSWQPVGKN LTLRCQVEGG APRANLTVVL LRGEKELKRE PAVGEPAEVT TTVLVRRDHH  180
GANFSCRTEL DLRPQGLELF ENTSAPYQLQ TFVLPATPPQ LVSPRVLEVD TQGTVVCSLD  240
GLFPVSEAQV HLALGDQRLN PTVTYGNDSF SAKASVSVTA EDEGTQRLTC AVILGNQSQE  300
TLQTVTIYSF PAPNVILTKP EVSEGTEVTV KCEAHPRAKV TLNGVPAQPL GPRAQLLLKA  360
TPEDNGRSFS CSATLEVAGQ LIHKNQTREL RVLYGPRLDE RDCPGNWTWP ENSQQTPMCQ  420
AWGNPLPELK CLKDGTFPLP IGESVTVTRD LEGTYLCRAR STQGEVTRKV TVNVLSPRYE  480
IVIITVVAAA VIMGTAGLST YLYNRQRKIK KYRLQQAQKG TPMKPNTQAT PP          532

SEQ ID NO: 214            moltype = AA   length = 453
FEATURE                   Location/Qualifiers
source                    1..453
                          mol_type = protein
                          organism = Homo sapiens
SEQUENCE: 214
QTSVSPSKVI LPRGGSVLVT CSTSCDQPKL LGIETPLPKK ELLLPGNNRK VYELSNVQED   60
SQPMCYSNCP DGQSTAKTFL TVYWTPERVE LAPLPSWQPV GKNLTLRCQV EGGAPRANLT  120
VVLLRGEKEL KREPAVGEPA EVTTTVLVRR DHHGANFSCR TELDLRPQGL ELFENTSAPY  180
QLQTFVLPAT PPQLVSPRVL EVDTQGTVVC SLDGLFPVSE AQVHLALGDQ RLNPTVTYGN  240
DSFSAKASVS VTAEDEGTQR LTCAVILGNQ SQETLQTVTI YSFPAPNVIL TKPEVSEGTE  300
VTVKCEAHPR AKVTLNGVPA QPLGPRAQLL LKATPEDNGR SFSCSATLEV AGQLIHKNQT  360
RELRVLYGPR LDERDCPGNW TWPENSQQTP MCQAWGNPLP ELKCLKDGTF PLPIGESVTV  420
TRDLEGTYLC RARSTQGEVT RKVTVNVLSP RYE                               453

SEQ ID NO: 215            moltype = AA   length = 63
FEATURE                   Location/Qualifiers
source                    1..63
                          mol_type = protein
                          organism = Homo sapiens
SEQUENCE: 215
GGSVLVTCST SCDQPKLLGI ETPLPKKELL LPGNNRKVYE LSNVQEDSQP MCYSNCPDGQ   60
STA                                                                63

SEQ ID NO: 216            moltype = AA   length = 66
FEATURE                   Location/Qualifiers
source                    1..66
                          mol_type = protein
                          organism = Homo sapiens
SEQUENCE: 216
GKNLTLRCQV EGGAPRANLT VVLLRGEKEL KREPAVGEPA EVTTTVLVRR DHHGANFSCR   60
TELDLR                                                             66

SEQ ID NO: 217            moltype = AA   length = 68
FEATURE                   Location/Qualifiers
source                    1..68
                          mol_type = protein
                          organism = Homo sapiens
SEQUENCE: 217
DTQGTVVCSL DGLFPVSEAQ VHLALGDQRL NPTVTYGNDS FSAKASVSVT AEDEGTQRLT   60
CAVILGNQ                                                           68

SEQ ID NO: 218            moltype = AA   length = 54
FEATURE                   Location/Qualifiers
source                    1..54
                          mol_type = protein
                          organism = Homo sapiens
SEQUENCE: 218
GTEVTVKCEA HPRAKVTLNG VPAQPLGPRA QLLLKATPED NGRSFSCSAT LEVA         54

SEQ ID NO: 219            moltype = AA   length = 53
FEATURE                   Location/Qualifiers
source                    1..53
                          mol_type = protein
                          organism = Homo sapiens
```

-continued

```
SEQUENCE: 219
NSQQTPMCQA WGNPLPELKC LKDGTFPLPI GESVTVTRDL EGTYLCRARS TQG        53

SEQ ID NO: 220        moltype = AA   length = 13
FEATURE               Location/Qualifiers
source                1..13
                      mol_type = protein
                      organism = Homo sapiens
SEQUENCE: 220
QTSVSPSKVI LPR                                                    13

SEQ ID NO: 221        moltype = AA   length = 10
FEATURE               Location/Qualifiers
source                1..10
                      mol_type = protein
                      organism = Homo sapiens
SEQUENCE: 221
SCDQPKLLGI                                                        10

SEQ ID NO: 222        moltype = AA   length = 16
FEATURE               Location/Qualifiers
source                1..16
                      mol_type = protein
                      organism = Homo sapiens
SEQUENCE: 222
PKKELLLPGN NRKVYE                                                 16

SEQ ID NO: 223        moltype = AA   length = 15
FEATURE               Location/Qualifiers
source                1..15
                      mol_type = protein
                      organism = Homo sapiens
SEQUENCE: 223
YSNCPDGQST AKTFL                                                  15

SEQ ID NO: 224        moltype = DNA   length = 17
FEATURE               Location/Qualifiers
misc_feature          1..17
                      note = Primer
source                1..17
                      mol_type = other DNA
                      organism = synthetic construct
SEQUENCE: 224
gggtgcatcg tttacgc                                                17

SEQ ID NO: 225        moltype = DNA   length = 23
FEATURE               Location/Qualifiers
misc_feature          1..23
                      note = Primer
source                1..23
                      mol_type = other DNA
                      organism = synthetic construct
SEQUENCE: 225
ctgctgctga ggaaggatat gag                                         23

SEQ ID NO: 226        moltype = DNA   length = 34
FEATURE               Location/Qualifiers
misc_feature          1..34
                      note = Primer
source                1..34
                      mol_type = other DNA
                      organism = synthetic construct
SEQUENCE: 226
taatacgact cactataggg tgcatcgttt acgc                             34

SEQ ID NO: 227        moltype = DNA   length = 23
FEATURE               Location/Qualifiers
misc_feature          1..23
                      note = Primer
source                1..23
                      mol_type = other DNA
                      organism = synthetic construct
SEQUENCE: 227
ctcatatcct tcctcagcag cag                                         23

SEQ ID NO: 228        moltype = AA   length = 461
FEATURE               Location/Qualifiers
source                1..461
                      mol_type = protein
```

-continued

```
                              organism = Homo sapiens
SEQUENCE: 228
QTSVSPSKVI LPRGGSVLVT CSTSCDQPKL LGIETPLPKK ELLLPGNNRK VYELSNVQED    60
SQPMCYSNCP DGQSTAKTFL TVYWTPERVE LAPLPSWQPV GKNLTLRCQV EGGAPRANLT   120
VVLLRGEKEL KREPAVGEPA EVTTTVLVRR DHHGANFSCR TELDLRPQGL ELFENTSAPY   180
QLQTFVLPAT PPQLVSPRVL EVDTQGTVVC SLDGLFPVSE AQVHLALGDQ RLNPTVTYGN   240
DSFSAKASVS VTAEDEGTQR LTCAVILGNQ SQETLQTVTI YSFPAPNVIL TKPEVSEGTE   300
VTVKCEAHPR AKVTLNGVPA QPLGPRAQLL LKATPEDNGR SFSCSATLEV AGQLIHKNQT   360
RELRVLYGPR LDERDCPGNW TWPENSQQTP MCQAWGNPLP ELKCLKDGTF PLPIGESVTV   420
TRDLEGTYLC RARSTQGEVT RKVTVNVLSP RYEVDHHHHH H                       461

SEQ ID NO: 229             moltype = RNA   length = 112
FEATURE                    Location/Qualifiers
misc_feature               1..112
                           note = Aptamer
source                     1..112
                           mol_type = other RNA
                           organism = synthetic construct
SEQUENCE: 229
gggtgcatcg tttacgcgca acataaaaat ttaaagtgct cagttgtcaa tctatgactg    60
ctgctgagga aggatatgag aaacaaacaa acgtatggcg gtctccaaca gg           112

SEQ ID NO: 230             moltype = DNA   length = 20
FEATURE                    Location/Qualifiers
misc_feature               1..20
                           note = Antisense Oligo
source                     1..20
                           mol_type = other DNA
                           organism = synthetic construct
SEQUENCE: 230
cctgttggag accgccatac                                                20

SEQ ID NO: 231             moltype = AA   length = 547
FEATURE                    Location/Qualifiers
source                     1..547
                           mol_type = protein
                           organism = Homo sapiens
SEQUENCE: 231
MATMVPSVLW PRACWTLLVC CLLTPGVQGQ EFLLRVEPQN PVLSAGGSLF VNCSTDCPSS    60
EKIALETSLS KELVASGMGW AAFNLSNVTG NSRILCSVYC NGSQITGSSN ITVYRLPERV   120
ELAPLPPWQP VGQNFTLRCQ VEDGSPRTSL TVVLLRWEEE LSRQPAVEEP AEVTATVLAS   180
RDDHGAPFSC RTELDMQPQG LGLFVNTSAP RQLRTFVLPV TPPRLVAPRF LEVETSWPVD   240
CTLDGLFPAS EAQVYLALGD QMLNATVMNH GDTLTATATA TARADQEGAR EIVCNVTLGG   300
ERREARENLT VFSFLGPIVN LSEPTAHEGS TVTVSCMAGA RVQVTLDGVP AAAPGQPAQL   360
QLNATESDDG RSFFCSATLE VDGEFLHRNS SVQLRVLYGP KIDRATCPQH LKWKDKTRHV   420
LQCQARGNPY PELRCLKEGS SREVPVGIPF FVNVTHNGTY QCQASSSRGK YTLVVVMDIE   480
AGSSHFVPVF VAVLLTLGVV TIVLALMYVF REHQRSGSYH VREESTYLPL TSMQPTEAMG   540
EEPSRAE                                                             547

SEQ ID NO: 232             moltype = AA   length = 456
FEATURE                    Location/Qualifiers
source                     1..456
                           mol_type = protein
                           organism = Homo sapiens
SEQUENCE: 232
QEFLLRVEPQ NPVLSAGGSL FVNCSTDCPS SEKIALETSL SKELVASGMG WAAFNLSNVT    60
GNSRILCSVY CNGSQITGSS NITVYRLPER VELAPLPPWQ PVGQNFTLRC QVEDGSPRTS   120
LTVVLLRWEE ELSRQPAVEE PAEVTATVLA SRDDHGAPFS CRTELDMQPQ GLGLFVNTSA   180
PRQLRTFVLP VTPPRLVAPR FLEVETSWPV DCTLDGLFPA SEAQVYLALG DQMLNATVMN   240
HGDTLTATAT ATARADQEGA REIVCNVTLG GERREARENL TVFSFLGPIV NLSEPTAHEG   300
STVTVSCMAG ARVQVTLDGV PAAAPGQPAQ LQLNATESDD GRSFFCSATL EVDGEFLHRN   360
SSVQLRVLYG PKIDRATCPQ HLKWKDKTRH VLQCQARGNP YPELRCLKEG SSREVPVGIP   420
FFVNVTHNGT YQCQASSSRG KYTLVVVMDI EAGSSH                             456

SEQ ID NO: 233             moltype = AA   length = 924
FEATURE                    Location/Qualifiers
source                     1..924
                           mol_type = protein
                           organism = Homo sapiens
SEQUENCE: 233
MPGPSPGLRR ALLGLWAALG LGLFGLSAVS QEPFWADLQP RVAFVERGGS LWLNCSTNCP    60
RPERGGLETS LRRNGTQRGL RWLARQLVDI REPETQPVCF FRCARRTLQA RGLIRTFQRP   120
DRVELMPLPP WQPVGENFTL SCRVPGAGPR ASLTLTLLRG AQELIRRSFA GEPPRARGAV   180
LTATVLARRE DHGANFSCRA ELDLRPHGLG LFENSSAPRE LRTFSLSPDA PRLAAPRLLE   240
VGSERPVSCT LDGLFPASEA RVYLALGDQN LSPDVTLEGD AFVATATATA SAEQEGARQL   300
VCNVTLGGEN RETRENVTIY SFPAPLLTLS EPSVSEGQMV TVTCAAGAQA LVTLEGVPAA   360
VPGQPAQLQL NATENDDRRS FFCDATLDVD GETLIKNRSA ELRVLYAPRL DDSDCPRSWT   420
WPEGPEPQTLR CEARGNPEPS VHCARSDGGA VLALGLLGPV TRALSGTYRC KAANDQGEAV   480
KDVTLTVEYA PALDSVGCPE RITWLEGTEA SLSCVAHGVP PPDVICVRSG ELGAVIEGLL   540
```

```
RVAREHAGTY RCEATNPRGS AAKNVAVTVE YGPRFEEPSC PSNWTWVEGS GRLFSCEVDG    600
KPQPSVKCVG SGGATEGVLL PLAPPDPSPR APRIPRVLAP GIYVCNATNR HGSVAKTVVV    660
SAESPPEMDE STCPSHQTWL EGAEASALAC AARGRPSPGV RCSREGIPWP EQQRVSREDA    720
GTYHCVATNA HGTDSRTVTV GVEYRPVVAE LAASPPGGVR PGGNFTLTCR AEAWPPAQIS    780
WRAPPGALNI GLSSNNSTLS VAGAMGSHGG EYECAATNAH GRHARRITVR VAGPWLWVAV    840
GGAAGGAALL AAGAGLAFYV QSTACKKGEY NVQEAESSGE AVCLNGAGGG AGGAAGAEGG    900
PEAAGGAAES PAEGEVFAIQ LTSA                                          924

SEQ ID NO: 234          moltype = AA  length = 804
FEATURE                 Location/Qualifiers
source                  1..804
                        mol_type = protein
                        organism = Homo sapiens
SEQUENCE: 234
EPFWADLQPR VAFVERGGSL WLNCSTNCPR PERGGLETSL RRNGTQRGLR WLARQLVDIR    60
EPETQPVCFF RCARRTLQAR GLIRTFQRPD RVELMPLPPW QPVGENFTLS CRVPGAGPRA    120
SLTLTLLRGA QELIRRSFAG EPPRARGAVL TATVLARRED HGANFSCRAE LDLRPHGLGL    180
FENSSAPREL RTFSLSPDAP RLAAPRLLEV GSERPVSCTL DGLFPASEAR VYLALGDQNL    240
SPDVTLEGDA FVATATATAS AEQEGARQLV CNVTLGGENR ETRENVTIYS FPAPLLTLSE    300
PSVSEGQMVT VTCAAGAQAL VTLEGVPAAV PGQPAQLQLN ATENDDRRSF FCDATLDVDG    360
ETLIKNRSAE LRVLYAPRLD DSDCPRSWTW PEGPEQTLRC EARGNPEPSV HCARSDGGAV    420
LALGLLGPVT RALSGTYRCK AANDQGEAVK DVTLTVEYAP ALDSVGCPER ITWLEGTEAS    480
LSCVAHGVPP PDVICVRSGE LGAVIEGLLR VAREHAGTYR CEATNPRGSA AKNVAVTVEY    540
GPRFEEPSCP SNWTWVEGSG RLFSCEVDGK PQPSVKCVGS GGATEGVLLP LAPPDPSPRA    600
PRIPRVLAPG IYVCNATNRH GSVAKTVVVS AESPPEMDES TCPSHQTWLE GAEASALACA    660
ARGRPSPGVR CSREGIPWPE QQRVSREDAG TYHCVATNAH GTDSRTVTVG VEYRPVVAEL    720
AASPPGGVRP GGNFTLTCRA EAWPPAQISW RAPPGALNIG LSSNNSTLSV AGAMGSHGGE    780
YECAATNAHG RHARRITVRV AGPW                                          804

SEQ ID NO: 235          moltype = RNA  length = 12
FEATURE                 Location/Qualifiers
misc_feature            1..12
                        note = Synthetic Spacer Sequence
source                  1..12
                        mol_type = other RNA
                        organism = synthetic construct
SEQUENCE: 235
aaacaaacaa ac                                                      12

SEQ ID NO: 236          moltype = RNA  length = 20
FEATURE                 Location/Qualifiers
misc_feature            1..20
                        note = Synthetic Sense Binding Sequence
source                  1..20
                        mol_type = other RNA
                        organism = synthetic construct
SEQUENCE: 236
gtatggcggt ctccaacagg                                              20

SEQ ID NO: 237          moltype = RNA  length = 52
FEATURE                 Location/Qualifiers
misc_feature            1..52
                        note = Synthetic aptamer sequences
source                  1..52
                        mol_type = other RNA
                        organism = synthetic construct
SEQUENCE: 237
agacagcagc aggaatcaag ccgtaggagt ctagcagaag ctgctgctga gg           52

SEQ ID NO: 238          moltype = RNA  length = 50
FEATURE                 Location/Qualifiers
misc_feature            1..50
                        note = Synthetic aptamer sequences
source                  1..50
                        mol_type = other RNA
                        organism = synthetic construct
SEQUENCE: 238
agacagcagc aggaaccagc gcaggagtct ggcaggagct gctgctgagg             50

SEQ ID NO: 239          moltype = RNA  length = 37
FEATURE                 Location/Qualifiers
misc_feature            1..37
                        note = Synthetic aptamer sequences
source                  1..37
                        mol_type = other RNA
                        organism = synthetic construct
SEQUENCE: 239
gtgctcagtt gtcaatctat gactgctgct gaggaag                           37
```

-continued

```
SEQ ID NO: 240          moltype = RNA   length = 35
FEATURE                 Location/Qualifiers
misc_feature            1..35
                        note = Synthetic aptamer sequences
source                  1..35
                        mol_type = other RNA
                        organism = synthetic construct
SEQUENCE: 240
gggcgcaccg tttacgcgta aatcggtccg ctatt                              35

SEQ ID NO: 241          moltype = RNA   length = 37
FEATURE                 Location/Qualifiers
misc_feature            1..37
                        note = Synthetic aptamer sequences
source                  1..37
                        mol_type = other RNA
                        organism = synthetic construct
SEQUENCE: 241
aggtcctcaa gcagctttgt cctgctgctg aggaagg                            37

SEQ ID NO: 242          moltype = DNA   length = 52
FEATURE                 Location/Qualifiers
misc_feature            1..52
                        note = Synthetic aptamer sequences
source                  1..52
                        mol_type = other DNA
                        organism = synthetic construct
SEQUENCE: 242
agacagcagc aggaatcaag ccgtaggagt ctagcagaag ctgctgctga gg           52

SEQ ID NO: 243          moltype = DNA   length = 50
FEATURE                 Location/Qualifiers
misc_feature            1..50
                        note = Synthetic aptamer sequences
source                  1..50
                        mol_type = other DNA
                        organism = synthetic construct
SEQUENCE: 243
agacagcagc aggaaccagc gcaggagtct ggcaggagct gctgctgagg              50

SEQ ID NO: 244          moltype = DNA   length = 37
FEATURE                 Location/Qualifiers
misc_feature            1..37
                        note = Synthetic aptamer sequences
source                  1..37
                        mol_type = other DNA
                        organism = synthetic construct
SEQUENCE: 244
gtgctcagtt gtcaatctat gactgctgct gaggaag                            37

SEQ ID NO: 245          moltype = DNA   length = 35
FEATURE                 Location/Qualifiers
misc_feature            1..35
                        note = Synthetic aptamer sequences
source                  1..35
                        mol_type = other DNA
                        organism = synthetic construct
SEQUENCE: 245
gggcgcaccg tttacgcgta aatcggtccg ctatt                              35

SEQ ID NO: 246          moltype = DNA   length = 37
FEATURE                 Location/Qualifiers
misc_feature            1..37
                        note = Synthetic aptamer sequences
source                  1..37
                        mol_type = other DNA
                        organism = synthetic construct
SEQUENCE: 246
aggtcctcaa gcagctttgt cctgctgctg aggaagg                            37

SEQ ID NO: 247          moltype = DNA   length = 40
FEATURE                 Location/Qualifiers
misc_feature            1..40
                        note = Synthetic aptamer sequence
source                  1..40
                        mol_type = other DNA
                        organism = synthetic construct
SEQUENCE: 247
attttcgttt tatttcagtt taattgcgtt tagtatctgg                         40
```

```
SEQ ID NO: 248          moltype = DNA  length = 40
FEATURE                 Location/Qualifiers
misc_feature            1..40
                        note = Synthetic aptamer sequences
source                  1..40
                        mol_type = other DNA
                        organism = synthetic construct
SEQUENCE: 248
attttcgttt tattttagtt taattgcgtt tagtatctgg                            40

SEQ ID NO: 249          moltype = DNA  length = 40
FEATURE                 Location/Qualifiers
misc_feature            1..40
                        note = Synthetic aptamer sequences
source                  1..40
                        mol_type = other DNA
                        organism = synthetic construct
SEQUENCE: 249
gtaaaaatta gagattaaaa tagttccttt cagttttgtc                            40

SEQ ID NO: 250          moltype = DNA  length = 41
FEATURE                 Location/Qualifiers
misc_feature            1..41
                        note = Synthetic aptamer sequences
source                  1..41
                        mol_type = other DNA
                        organism = synthetic construct
SEQUENCE: 250
gtaaaaatta aagagattaa ggtcctttaa gcagttttgt c                          41

SEQ ID NO: 251          moltype = DNA  length = 40
FEATURE                 Location/Qualifiers
misc_feature            1..40
                        note = Synthetic aptamer sequences
source                  1..40
                        mol_type = other DNA
                        organism = synthetic construct
SEQUENCE: 251
gtaaataacc agttatacag aaagatctca gcaatttatc                            40

SEQ ID NO: 252          moltype = DNA  length = 39
FEATURE                 Location/Qualifiers
misc_feature            1..39
                        note = Synthetic aptamer sequences
source                  1..39
                        mol_type = other DNA
                        organism = synthetic construct
SEQUENCE: 252
gtaattaatc aaacaatagc agaaatctca gcaattttc                             39

SEQ ID NO: 253          moltype = DNA  length = 40
FEATURE                 Location/Qualifiers
misc_feature            1..40
                        note = Synthetic aptamer sequence
source                  1..40
                        mol_type = other DNA
                        organism = synthetic construct
SEQUENCE: 253
gtaaaaattt tcatctcagc aattaaatcc aaagaatcca                            40

SEQ ID NO: 254          moltype = DNA  length = 40
FEATURE                 Location/Qualifiers
misc_feature            1..40
                        note = Synthetic aptamer sequences
source                  1..40
                        mol_type = other DNA
                        organism = synthetic construct
SEQUENCE: 254
gtaaaaattt aaataactca gcaatcatag atccgactga                            40

SEQ ID NO: 255          moltype = DNA  length = 40
FEATURE                 Location/Qualifiers
misc_feature            1..40
                        note = Synthetic aptamer sequence
source                  1..40
                        mol_type = other DNA
                        organism = synthetic construct
SEQUENCE: 255
```

-continued

```
gtaaaaaaga taaaacttag ttgcagaatt tgccttcatt                              40

SEQ ID NO: 256          moltype = DNA   length = 40
FEATURE                 Location/Qualifiers
misc_feature            1..40
                        note = Synthetic aptamer sequence
source                  1..40
                        mol_type = other DNA
                        organism = synthetic construct
SEQUENCE: 256
gtaaataaca aaaatctcag cttttgcaga atttatccac                              40

SEQ ID NO: 257          moltype = DNA   length = 40
FEATURE                 Location/Qualifiers
misc_feature            1..40
                        note = Synthetic aptamer sequence
source                  1..40
                        mol_type = other DNA
                        organism = synthetic construct
SEQUENCE: 257
gtaaaataaa aagttttcct atcagcaaac tcacaaattc                              40

SEQ ID NO: 258          moltype = DNA   length = 40
FEATURE                 Location/Qualifiers
misc_feature            1..40
                        note = Synthetic apatmer sequence
source                  1..40
                        mol_type = other DNA
                        organism = synthetic construct
SEQUENCE: 258
gtaaataaaa agcagatctc agcaaaactc gtaaattcaa                              40

SEQ ID NO: 259          moltype = DNA   length = 40
FEATURE                 Location/Qualifiers
misc_feature            1..40
                        note = Synthetic apatamer sequences
source                  1..40
                        mol_type = other DNA
                        organism = synthetic construct
SEQUENCE: 259
gtaaaataaa gaggataact acaatcatca gcaatcatat                              40

SEQ ID NO: 260          moltype = DNA   length = 40
FEATURE                 Location/Qualifiers
misc_feature            1..40
                        note = Synthetic aptamer sequences
source                  1..40
                        mol_type = other DNA
                        organism = synthetic construct
SEQUENCE: 260
gtaaaaataa ataactacga gatctcagca gatcattatc                              40

SEQ ID NO: 261          moltype = DNA   length = 40
FEATURE                 Location/Qualifiers
misc_feature            1..40
                        note = Synthetic aptamer sequences
source                  1..40
                        mol_type = other DNA
                        organism = synthetic construct
SEQUENCE: 261
gtaattaaaa aaccttcaca cagaaaacat tcctcaattt                              40

SEQ ID NO: 262          moltype = DNA   length = 40
FEATURE                 Location/Qualifiers
misc_feature            1..40
                        note = Synthetic aptamer sequences
source                  1..40
                        mol_type = other DNA
                        organism = synthetic construct
SEQUENCE: 262
gtaaataaac tcacagcaga aaaaattcct tcaacttgta                              40

SEQ ID NO: 263          moltype = AA   length = 479
FEATURE                 Location/Qualifiers
source                  1..479
                        mol_type = protein
                        organism = Homo sapiens
SEQUENCE: 263
EPFWADLQPR VAFVERGGSL WLNCSTNCPR PERGGLETSL RRNGTQRGLR WLARQLVDIR        60
```

-continued

```
EPETQPVCFF RCARRTLQAR GLIRTFQRPD RVELMPLPPW QPVGENFTLS CRVPGAGPRA   120
SLTLTLLRGA QELIRRSFAG EPPRARGAVL TATVLARRED HGANFSCRAE LDLRPHGLGL   180
FENSSAPREL RTFSLSPDAP RLAAPRLLEV GSERPVSCTL DGLFPASEAR VYLALGDQNL   240
SPDVTLEGDA FVATATATAS AEQEGARQLV CNVTLGGENR ETRENVTIYS FPAPLLTLSE   300
PSVSEGQMVT VTCAAGAQAL VTLEGVPAAV PGQPAQLQLN ATENDDRRSF FCDATLDVDG   360
ETLIKNRSAE LRVLYAPRLD DSDCPRSWTW PEGPEQTLRC EARGNPEPSV HCARSDGGAV   420
LALGLLGPVT RALSGTYRCK AANDQGEAVK DVTLTVEYAP ALDSVGCPER ITWLEGTEA    479

SEQ ID NO: 264          moltype = DNA  length = 37
FEATURE                 Location/Qualifiers
source                  1..37
                        mol_type = other DNA
                        organism = synthetic construct
SEQUENCE: 264
gtggtcagtt gtgaatctat gactgctgct gaggaag                              37

SEQ ID NO: 265          moltype = DNA  length = 37
FEATURE                 Location/Qualifiers
source                  1..37
                        mol_type = other DNA
                        organism = synthetic construct
SEQUENCE: 265
gagctcagtt gtcaatctat gactgctgct gaggaag                              37

SEQ ID NO: 266          moltype = DNA  length = 37
FEATURE                 Location/Qualifiers
source                  1..37
                        mol_type = other DNA
                        organism = synthetic construct
SEQUENCE: 266
gtgctcactt gtcaatctat gactgctgct caggaag                              37

SEQ ID NO: 267          moltype = DNA  length = 37
FEATURE                 Location/Qualifiers
source                  1..37
                        mol_type = other DNA
                        organism = synthetic construct
SEQUENCE: 267
gtgctcactt gtcaatctat gactgctgct gagtaag                              37

SEQ ID NO: 268          moltype = DNA  length = 37
FEATURE                 Location/Qualifiers
source                  1..37
                        mol_type = other DNA
                        organism = synthetic construct
SEQUENCE: 268
gtgctctctt gtcaatctat gactgctgga gaggaag                              37

SEQ ID NO: 269          moltype = DNA  length = 37
FEATURE                 Location/Qualifiers
source                  1..37
                        mol_type = other DNA
                        organism = synthetic construct
SEQUENCE: 269
gtgctcagtt gtcaatctaa gactgctgct gaggaag                              37

SEQ ID NO: 270          moltype = DNA  length = 37
FEATURE                 Location/Qualifiers
source                  1..37
                        mol_type = other DNA
                        organism = synthetic construct
SEQUENCE: 270
gtgctcagtt gtcaaagaat gactgctgct gaggaag                              37
```

APTAMERS FOR PERSONAL HEALTH CARE APPLICATIONS

FIELD OF THE INVENTION

Described herein are nucleic acid aptamers that have a high binding affinity and specificity for cellular membrane glycoproteins and preferably for intercellular adhesion molecule-1 ("ICAM-1"), and more particularly the use of such aptamers to inhibit human rhinovirus binding to such glycoproteins and entering into cells within the nasal cavity and throat.

INCORPORATION BY REFERENCE OF THE SEQUENCE LISTING

This application contains, as a separate part of disclosure, a Sequence Listing in computer-readable form (Filename: CM05385M.txt; Size: 337 Kbytes; Created: Dec. 1, 2022) which is incorporated by reference herein in its entirety.

BACKGROUND OF THE INVENTION

Aptamers are short single-stranded oligonucleotides, with a specific and complex three-dimensional shape, that bind to target molecules. The molecular recognition of aptamers is based on structure compatibility and intermolecular interactions, including electrostatic forces, van der Waals interactions, hydrogen bonding, and $\pi$-$\pi$ stacking interactions of aromatic rings with the target material. The targets of aptamers include, but are not limited to, peptides, proteins, nucleotides, amino acids, antibiotics, low molecular weight organic or inorganic compounds, and even whole cells. The dissociation constant of aptamers typically varies between micromolar and picomolar levels, which is comparable to the affinity of antibodies to their antigens. Aptamers can also be designed to have high specificity, enabling the discrimination of target molecules from closely related derivatives.

Aptamers are usually designed in vitro from large libraries of random nucleic acids by Systematic Evolution of Ligands by Exponential Enrichment (SELEX). The SELEX method is first introduced in 1990 when single stranded RNAs are selected against low molecular weight dyes (Ellington, A. D., Szostak, J. W., 1990. Nature 346: 818-822). A few years later, single stranded DNA aptamers and aptamers containing chemically modified nucleotides are also described (Ellington, A. D., Szostak, J. W., 1992. Nature 355: 850-852; Green, L. S., et al., 1995. Chem. Biol. 2: 683-695). Since then, aptamers for hundreds of microscopic targets, such as cations, small molecules, proteins, cells, or tissues, have been selected. A compilation of examples from the literature is included in the database at the website: http://www.aptagen.com/aptamer-index/aptamer-list.aspx.

The common cold is the most frequent illness in the U.S., with 62 million people being infected each year. Adults can be infected with a common cold 2-4 times per year, while children can be infected 8-12 times per year. This leads to morbidity, frequent absences from school and work, reduced productivity, and inappropriate use of antibiotics. This translates into costing the U.S. $60 billion annually.

Human rhinoviruses cause 50-80% of common colds. Rhinoviruses are small (30 nm), nonenveloped single-stranded RNA viruses. Although rhinovirus infections are mild and self-limiting in immunocompetent hosts, it is associated with pneumonia in immunosuppressed patients, bronchiolitis in infants, and can exacerbate pre-existing pulmonary diseases such as asthma and chronic obstructive pulmonary disease.

Rhinovirus infection predominately occurs in the nasopharynx when the virus attaches to surface receptors on the nasal epithelium and infects the host cells. Fifty-seven percent of rhinoviruses attach to ICAM-1 receptors that line the airways. Once the virus enters into the cell, it hijacks the cell's replication machinery to make copies of itself. This results in cell lysis and death, allowing the virus progeny to spread to other nearby cells to repeat the infectious cycle. Ultimately, this triggers a host immune response leading to respiratory symptoms (e.g. cough, rhinorrhea, congestion, sore throat, etc.). Despite the enormous public health burden, there are no licensed vaccines or antiviral drugs for human rhinovirus.

Aptamers against target proteins such as intercellular adhesion molecule 1 (ICAM-1) have previously been described. However, no data for the binding of such aptamers to the membrane bound protein or the capacity of these aptamers to prevent the binding of natural ligands or human rhinoviruses to ICAM-1 have been reported. Thus, a need still exists for aptamers that selectively bind to cellular membrane glycoproteins, including ICAM-1, and that prevent the binding of human rhinoviruses to such glycoproteins, mitigating symptoms for common cold or preventing (re)infection.

SUMMARY OF THE INVENTION

Described herein is the use of SELEX for the selection of parent aptamers against the intercellular adhesion molecule 1 (ICAM-1) and the use of aptamers truncated therefrom for the prevention of binding of human rhinoviruses to such glycoprotein.

Described herein is also an aptamer composition. The aptamer composition comprises at least one oligonucleotide consisting of: deoxyribonucleotides, ribonucleotides, derivatives of deoxyribonucleotides, derivatives of ribonucleotides, and mixtures thereof; wherein said aptamer composition has a binding affinity for intercellular adhesion molecule 1 (ICAM-1), and wherein the aptamer composition is configured to reduce the binding of one or more human rhinoviruses to said intercellular adhesion molecule 1 (ICAM-1) and wherein the aptamer composition comprises at least one oligonucleotide forming a secondary structure from a 5'-end to a 3'-end comprising at least a 5'-dangling end, a stem, a hairpin loop, and a 3'-dangling end, wherein the stem is formed between the hairpin loop and the dangling end(s); and wherein the secondary structure comprises at least the structural sequence 5'-EEEYYSSSSYS-SSSYHHHHYYYYYYYYYSYYYYYEEEE-3' (Structure I), wherein H represents a nucleotide located in the hairpin loop, S represents a nucleotide located in the stem, E represents a nucleotide located in a dangling end and Y represents a nucleotide being absent or H, S, E or I, wherein I represent an internal loop.

The aptamer composition may further show a binding affinity for one or more of low-density lipoprotein receptor (LDLR) family members, cadherin-related family member 3 (CDHR3), and combinations thereof.

The aptamer composition may comprise at least one oligonucleotide having at least 80% sequence identity to the oligonucleotides comprising of SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246 and mixtures thereof.

Also described herein is a personal health care composition. The personal health care composition comprises the aptamer composition as described herein. The personal health care composition comprises at least one nucleic acid aptamer; wherein the nucleic acid aptamer has a binding affinity for intercellular adhesion molecule 1 (ICAM-1), wherein the nucleic acid aptamer is configured to reduce the binding of one or more human rhinoviruses to the intercellular adhesion molecule 1 (ICAM-1) and wherein the aptamer composition comprises at least one oligonucleotide forming a secondary structure from a 5'-end to a 3'-end comprising at least a 5'-dangling end, a stem, a hairpin loop, and a 3'-dangling end, wherein the stem is formed between the hairpin loop and the dangling end(s); and wherein the secondary structure comprises at least the structural sequence 5'-EEEYYSSSSYSSSSYHHHHYYYYYYYY-SYYYYYEEEE-3' (Structure I), wherein H represents a nucleotide located in the hairpin loop, S represents a nucleotide located in the stem, E represents a nucleotide located in a dangling end and Y represents a nucleotide being absent or H, S, E or I, wherein I represent an internal loop.

The nucleic acid aptamers used in the personal health care composition may comprise at least one oligonucleotide having at least 80% sequence identity to the oligonucleotides comprising SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246 and mixtures thereof.

Further described herein is an aptamer composition comprising at least one peptide or protein, wherein the peptide or protein is translated from at least one of the truncated oligonucleotides as disclosed herein.

The personal health care composition may further show a binding affinity for one or more low-density lipoprotein receptor (LDLR) family members, cadherin-related family member 3 (CDHR3), and combinations thereof.

A method for delivering a personal health care composition as disclosed herein to the upper respiratory tract is also provided, wherein the aptamer may be delivered by spraying. The method comprises administering a personal health care composition as described herein; the personal health care composition comprising at least one nucleic acid aptamer; wherein the at least one nucleic acid aptamer has a binding affinity for intercellular adhesion molecule 1 (ICAM-1), wherein the nucleic acid aptamer is configured to reduce the binding of one or more human rhinoviruses to the intercellular adhesion molecule 1 (ICAM-1) and wherein the aptamer composition comprises at least one oligonucleotide forming a secondary structure from a 5'-end to a 3'-end comprising at least a 5'-dangling end, a stem, a hairpin loop, and a 3'-dangling end, wherein the stem is formed between the hairpin loop and the dangling end(s); and wherein the secondary structure comprises at least the structural sequence 5'-EEEYYSSSSYSSSSYHHHHYYYYYYYYS-YYYYYEEEE-3' (Structure I), wherein H represents a nucleotide located in the hairpin loop, S represents a nucleotide located in the stem, E represents a nucleotide located in a dangling end and Y represents a nucleotide being absent or H, S, E or I, wherein I represent an internal loop.

The personal health care composition can also comprise one or more additional active ingredients; wherein the at least one nucleic acid aptamer and the one or more active ingredients are covalently or non-covalently attached.

Described herein is further the use of the aptamer composition as disclosed herein and/or the use of the personal health care composition as disclosed herein for inhibiting human rhinovirus infection by inhibiting binding to the intercellular adhesion molecule 1 (ICAM-1) and thereby inhibiting entering of the virus into cells within the nasal cavity and throat. The use may include delivering the aptamer composition and/or the personal health care composition as disclosed herein to the upper respiratory tract.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1 illustrates a schematic of the DNA library.

FIG. 2 illustrates the parent aptamer selection strategy during selection rounds 1 to 11.

FIG. 3 shows a schematic of the parent aptamer splits selection strategy during selection rounds 12 to 14.

FIGS. 6A-6D show the fluorescently labelled parent aptamer Nas.R-4 (SEQ ID NO: 04) bound to HNEpC and to HEK293 cells, wherein FIG. 6A shows the fluorescence image and FIG. 6B shows the brightfield image of the HNEp cells and FIG. 6C shows the fluorescence image and FIG. 6D shows the brightfield image of the HEK293 cells.

FIGS. 7A-7H show the viral inhibition test on HeLa cells using parent aptamer Nas.R-2 (SEQ ID NO: 02), parent aptamer Nas.R-8 and a negative control aptamer, wherein FIG. 7A shows the fluorescence image and FIG. 7B shows the brightfield image using the Nas.R-2 aptamer; FIG. 7C shows the fluorescence image and FIG. 7D shows the brightfield image using the Nas.R-8 aptamer; FIG. 7E shows the fluorescence image and FIG. 7F shows the brightfield image using the control aptamer; and FIG. 7G shows the fluorescence image and FIG. 7H shows the brightfield image of cells only.

FIG. 8 illustrates the Binding Affinity determined by Surface pPplasmon Resonance (SPR) of parent aptamers Nas.R-1, Nas.R-2, Nas.R-4, and Nas.R-8 (SEQ ID NOs: 01, 02, 04 and 08) with 250 nM exogenous ICAM-1.

FIG. 9 illustrates the Binding Affinity determined by Surface Plasmon Resonance (SPR) of parent aptamers Nas.R-1, Nas.R-2, Nas.R-4, and Nas.R-8 (SEQ ID NOs: 01, 02, 04 and 08) with 250 nM human serum albumin as control.

FIG. 10 shows the amino acid sequence alignment of the extracellular domains of ICAM-1, ICAM-3, and ICAM-5 (SEQ ID NOs: 214, 232, and 263).

FIG. 13 shows alignment of exemplary sequences with at least 90% nucleotide sequence identity that are identified during the selection process (Nas-3 (SEQ ID NO:103) and Nas-88 (SEQ ID NO:188).

FIG. 14 shows alignment of exemplary sequences with at least 70% nucleotide sequence identity that are identified during the selection process (Nas-45 (SEQ ID NO:145), Nas-8 (SEQ ID NO: 108), Nas-47 (SEQ ID NO:147) and Nas-78 (SEQ ID NO:178).

FIG. 15 shows alignment of exemplary sequences with at least 50% nucleotide sequence identity that are identified during the selection process (Nas-13 (SEQ ID NO:113), Nas-97 (SEQ ID NO: 197), Nas-31 (SEQ ID NO:131), Nas-93 (SEQ ID NO:193), Nas-39 (SEQ ID NO:139), Nas-82 (SEQ ID NO:182), Nas-61 (SEQ ID NO:161), Nas-91 (SEQ ID NO:191), Nas-87 (SEQ ID NO: 187, and Nas-94 (SEQ ID NO:194).

FIG. 20B and FIG. 20C show two alternative predicted secondary structures of the aptamer (SEQ ID NO: 244) truncated from Nas.D-4 (shown within the dotted line in FIG. 20A.

FIG. 31 show three secondary structures of mutant aptamer State 2 which are formed with maximum likelihood.

FIG. 32 show the distribution of secondary structures of mutant aptamer State 2.

DETAILED DESCRIPTION OF THE INVENTION

I. Definitions

Figure 4:
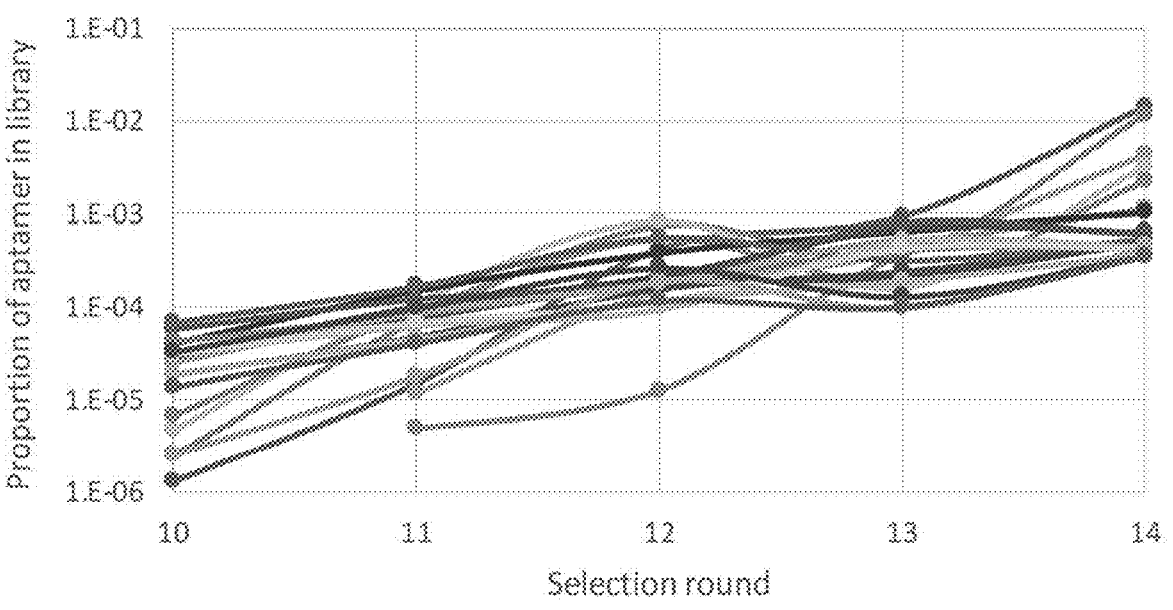
FIG. 4 illustrates the enrichment trajectories for the top twenty parent aptamers.

As used herein, the term "aptamer" refers to a single stranded oligonucleotide or a peptide that has a binding affinity for a specific target.

As used herein, the term "nucleic acid" refers to a polymer or oligomer of nucleotides. Nucleic acids are also referred as "ribonucleic acids" when the sugar moiety of the nucleotides is D-ribose and as "deoxyribonucleic acids" when the sugar moiety is 2-deoxy-D-ribose.

As used herein, the term "nucleotide" refers to a compound consisting of a nucleoside esterified to a monophosphate, polyphosphate, or phosphate-derivative group via the hydroxyl group of the 5-carbon of the sugar moiety. Nucleotides are also referred as "ribonucleotides" when the sugar moiety is D-ribose and as "deoxyribonucleotides" when the sugar moiety is 2-deoxy-D-ribose; ribonucleotides can be replaced with deoxyribonucleotides and vice versa in the composition(s), use(s), method(s) and application(s) as disclosed herein.

As used herein, the term "nucleoside" refers to a glycosylamine consisting of a nucleobase, such as a purine or pyrimidine, usually linked to a 5-carbon sugar (e.g. D-ribose or 2-deoxy-D-ribose) via a β-glycosidic linkage. Nucleosides are also referred to as "ribonucleosides" when the sugar moiety is D-ribose and as "deoxyribonucleosides" when the sugar moiety is 2-deoxy-D-ribose.

As used herein, the term "nucleobase" refers to a compound containing a nitrogen atom that has the chemical properties of a base. Non-limiting examples of nucleobases are compounds comprising pyridine, purine, or pyrimidine moieties, including but not limited to, adenine, guanine, hypoxanthine, thymine, cytosine, and uracil.

As used herein, the term "oligonucleotide" refers to an oligomer composed of nucleotides.

As used herein, the term "identical" or "sequence identity", in the context of two or more oligonucleotides, nucleic acids, or aptamers, refers to two or more sequences that are the same or have a specified percentage of nucleotides that are the same, when compared and aligned for maximum correspondence, as measured using sequence comparison algorithms or by visual inspection.

As used herein, the term "substantially homologous" or "substantially identical", in the context of two or more oligonucleotides, nucleic acids, or aptamers, generally refers to two or more sequences or subsequences that have at least 40%, 60%, 80%, 90%, 95%, 96%, 97%, 98% or 99% nucleotide identity, when compared and aligned for maximum correspondence, as measured using sequence comparison algorithms or by visual inspection.

As used herein, the term "epitope" refers to the region of a target that interacts with the aptamer. An epitope can be a contiguous stretch within the target or can be represented by multiple points that are physically proximal in a folded form of the target.

As used herein, the term "motif" refers to the sequence of contiguous, or series of contiguous, nucleotides occurring in a library of aptamers with binding affinity towards a specific target and that exhibits a statistically significant higher probability of occurrence than would be expected compared to a library of random oligonucleotides. The motif sequence is frequently the result or driver of the aptamer selection process.

As used herein, the term "personal health care compositions" refers to compositions in a form that is directly deliverable to the upper respiratory tract.

As used herein, "a pharmaceutically effective amount" refers to an amount sufficient to confer a therapeutic effect on the subject. In some aspects the therapeutic effect is reduced rhinovirus binding to cellular membrane glycoproteins such as ICAM-1, reduced severity and/or duration of a cold, or reduced incidence of respiratory illness due to rhinovirus.

As used herein the term "parent", preferably combined with sequence(s), oligonucleotide(s) and/or aptamer(s) will be used for a molecule, preferably sequence(s), oligonucleotide(s) and/or aptamer(s) which is further modified, in particular which is shortened in length or from which shorter parts are truncated.

As used herein the term "truncated", preferably combined with sequence(s), oligonucleotide(s) and/or aptamer(s) will be used for a molecule, preferably sequence(s), oligonucleotide(s) and/or aptamer(s) which is truncated from the parent molecule.

As used herein the term "hybridized" will mean what is known in the art as a Watson/Crick base-pair interaction, wherein nucleotides are paired with specific other nucleotides due to hydrogen bonds. Thereby, the base adenine is pairing with the base thymine and the base cytosine is pairing with the base guanine; in addition or alternatively the base thymine can also pair with the base guanine. The term nucleotide pair will be used to mean the same as "hybridized" in this sense.

As used herein the term "internal" will refer to structures that are separated from both ends of the aptamer (5'-end and 3'-end) by nucleotides that are hybridized to each other (a "stem" as defined below). For the maintenance of consistency, the term "external" will refer to structures that are contiguous with either end nucleotide (5'-end or 3'-end).

As used herein the term "loop" as formed in a secondary structure represent one or more internal nucleotides which are not paired. Examples for "loops" in secondary structures are hairpin loops or internal loops.

As used herein the term "hairpin loop" represents a loop formed internally in the secondary structure, wherein the loop is formed adjacent to only one "stem" region. The letter "H" will be used in structural sequences for nucleotides forming a hairpin loop.

As used herein the term "internal loop" represents a loop formed internally in the secondary structure, wherein the loop is formed adjacent to two or more "stem" regions. The letter "I" will be used in structural sequences for nucleotides forming an internal loop.

As used herein the term "stem" represents a region with paired nucleotides, wherein at least one nucleotide pair is formed, preferably two or three consecutive nucleotides pairs are formed to build a stem. The letter "S" will be used in structural sequences for nucleotides forming a stem.

As used herein the term "end" represents a region within a secondary structure comprising at least the first nucleotide of the 5'-end of the oligonucleotide or at least the last nucleotide on the 3'-end of an oligonucleotide. The letter "E" will be used in structural sequences for nucleotides forming an end of an oligonucleotide.

As used herein the term "dangling end" will be used, if the at least first nucleotide on the 5' end is unhybridized to another nucleotide, and/or at least the last nucleotide on the 3' end is unhybridized to another nucleotide. As such the respective end is said to "dangle" because it is held in space from only one point.

II. Aptamer Composition

The human rhinoviruses (RV) are the predominant cause of the common cold. They are classified in three groups (RV-A, RV-B, and RV-C), including around 160 types that express different surface proteins. Despite this diversity, rhinoviruses utilize mostly three glycoproteins of epithelial cells to cross the cellular membrane and access the host cell replication machinery: intercellular adhesion molecule 1 or ICAM-1 protein, utilized by the majority of RV-A and all RV-B types; low-density lipoprotein receptor or LDLR family members, utilized by at least twelve RV-A types; and cadherin-related family member 3 or CADHR3 proteins, utilized mostly by RV-C types.

An aptamer composition comprises at least one oligonucleotide selected from the group consisting of deoxyribonucleotides, ribonucleotides, derivatives of deoxyribonucleotides, derivatives of ribonucleotides, and mixtures thereof, wherein the aptamer composition has a binding affinity for intercellular adhesion molecule 1 (ICAM-1). Deoxyribonucleotide-based and ribonucleotide-based aptamers are included into the present invention. Deoxyribonucleotide-based aptamers may be advantageous in some examples due to lower costs and higher oligonucleotide stability. In one aspect, the aptamer composition may have a binding affinity for one or more cellular membrane glycoproteins selected from the group consisting of intercellular adhesion molecule 1 (ICAM-1), low-density lipoprotein receptor (LDLR) family members, and cadherin-related family member 3 (CDHR3) and combinations thereof. The aptamer composition is configured to reduce or inhibit the binding of one or more human rhinoviruses to the intercellular adhesion molecule 1 (ICAM-1). The aptamer composition may comprise at least one oligonucleotide, wherein the at least one oligonucleotide comprises a secondary structure providing the binding affinity to the ICAM-1 molecule. Suitable oligonucleotides forming said secondary structure comprises a length from 30 to 60 nucleotides, or from 30 to 55 nucleotides, or from 30 to 50 nucleotides, or from 30 to 45 nucleotides, or from 35 to 40 nucleotides. The secondary structure formed may comprise at least one double stranded stem region, at least one hairpin loop formed by unpaired/unhybridized nucleotides, and a 5'-end as well as a 3'-end or a combination thereof. The 5'-end and the 3'-end may be dangling ends which are not integrated into any other structural motif. One example loop formed by the secondary structure as disclosed herein is a hairpin. A stable hairpin will be formed, if at bases on either end of contiguous unhybridized bases are hybridized with each other. The secondary structure as disclosed herein may further comprise a second unpaired region which forms an internal loop comprising contiguous unhybridized bases that are flanked by different hybridized bases (stems) on either side. The unpaired loops and the double-stranded stems may vary in size and lengths. A suitable size for an example loop to be formed in the secondary structure of the sequences as disclosed herein is in the range of from 1 to 15 unpaired nucleotides or in the range of from 1 to 10 unpaired nucleotides or in the range of from 2 to 8 unpaired nucleotides. An example hairpin loop may comprise at least 3 or more unpaired nucleotides, or 4 or more unpaired nucleotides, or 5 or more unpaired nucleotides. An example internal loop may comprise at least 1 unpaired nucleotide, or from 1 to 5 unpaired nucleotides or from 1 to 10 unpaired nucleotides. A suitable size for an example double-stranded stem to be formed in the secondary structure as disclosed herein is in the range of from 1 to 15 paired nucleotides or in the range of from 1 to 10 paired nucleotides or in the range of from 2 to 8 paired nucleotides or in the range of from 3 to 6 paired nucleotides, in particular for a second stem located adjacent to the 5'-dangling end and/or the 3'-dangling end.

The length of the 5'-dangling end and/or 3'-dangling end may also vary, but a suitable length of a dangling end may comprise at least 1 unpaired/unhybridized nucleotide, or at least 3 unpaired/unhybridized nucleotides, or at least 4 unpaired/unhybridized nucleotides or at least 5 unpaired/unhybridized nucleotides. For example, the 5'-dangling end and the 3'-dangling can be elongated up to 15 unpaired/unhybridized nucleotides, but the secondary structure of the aptamer has to be conserved. A suitable length of a dangling end in the secondary structure as disclosed herein is in the range from 3 to 15 unpaired/unhybridized nucleotides.

A suitable secondary structure which shows binding affinity for ICAM-1 and is configured to inhibit binding of human rhinoviruses may comprise the structural sequence from 5'-end to 3'-end: 5'-EEEYYSSSSYSSSSYHHHH-YYYYYYYYYSYYYYYEEEE-3' (Structure I), wherein H represents a nucleotide forming the hairpin loop, S represents a nucleotide located in a stem, E represents a nucleotide located in a dangling end and Y represents a nucleotide being absent or H, S, E or I, wherein I represent an internal loop as classified herein. The structural sequence is based on P. Danaee et al.; *Nucleic Acids Research*, Volume 46, Issue 11, 20 Jun. 2018, Pages 5381-5394; incorporated herein by reference. The hairpin loop in Structure I may comprise at least one purine base, or the hairpin loop may comprise at least three pyrimidine bases or the hairpin loop may comprise a combination thereof. The length of the hairpin loop in the Structure I is at least 4 unpaired/unhybridized nucleotides, but a suitable length for a hairpin loop as disclosed herein may comprise 5 unpaired/unhybridized nucleotides or more, wherein the hairpin may be formed for example in such that the first nucleotide in the hairpin loop from the 5'-end is a purine base. For formation of a hairpin loop of unpaired/unhybridized nucleotides a stem region is formed in Structure I comprising paired nucleotides and closing the hairpin loop.

In a suitable secondary structure as disclosed herein and exemplary shown in Structure I the last nucleotide in the stem region before the hairpin loop from the 5'-end may be a purine base and/or the first nucleotide in the stem after the hairpin loop from the 5'-end may be a pyrimidine base. In addition or alternatively, the first nucleotide in the stem adjacent to the 5'-dangling end may be a pyrimidine base, wherein said stem region between the 5'-dangling end and the hairpin loop may further comprise a sequence motif of three nucleotides, namely the motif thymine-cytosine-adenine (TCA).

In a suitable secondary structure as disclosed herein and exemplary shown in Structure I suitable bases may be also present in the stem adjacent to the 3'-dangling end, wherein the last nucleotide in the stem from the 5'-end and adjacent to the 3'-dangling end may be a purine base. In addition or alternatively, the stem adjacent to the 3'-dangling end may further comprise a sequence motif of 3 nucleotides, namely the motif guanine-cytosine-thymine (GCT). The length of the stem adjacent to the dangling ends may vary and may comprise at least 3 hybridized base pairs, or at least 4 hybridized base pairs, or at least 5 hybridized base pairs.

The length of the dangling ends may also vary as shown exemplary by structure I. For example, the 5'-dangling end may comprise at least 4 unpaired nucleotides, in one example from 4 to 15 unpaired nucleotides, wherein at least two of the unpaired nucleotides may be purine bases. In addition or alternatively, the 3'-dangling end may comprise at least 3 or 4 unpaired nucleotides, in one example from 3 to 15 unpaired nucleotides, wherein the last four unpaired nucleotides of the 3'-dangling end are purine bases. Longer 3'-dangling ends are advantageous comprising 5, 6 or 7 unpaired nucleotides which may be all purine bases. In addition or alternatively, the 3'-dangling end may further comprise a sequence motif comprising from 4 to 7 unpaired nucleotides, namely the motif GAGGYYZ, wherein Y and Z are absent or selected from guanine (G), cytosine (C), adenosine (A), thymine (T) or uracil (U). In one aspect, Y may be A or G; or Y may be A in the GAGGYYZ motif. The GAGGYYZ motif may be at least partially unhybridized in advantageous aspects the motif may be completely unhybridized. In one aspect, the GAGGYYZ motif may be located near to the 3'-end and/or at the 3'-end. For example, the Y in the GAGGYYZ motif may be at least one of the last 15 nucleotides and/or the Z the GAGGYYZ motif may be at least one of the last 13 nucleotide or the last nucleotide at the 3'-end. Thereby, the 3'-end may be a dangling end and the motif may be completely located in the dangling end or may be still located partially in a stem region. For example, the GAG of the GAGGYYZ motif may be arranged paired in a stem region and/or the GYYZ of the GAGGYYZ motif may be located unpaired in the 3'-dangling end. In one aspect, the whole GAGGYYZ motif may be located unpaired in the 3'-dangling end.

The at least one oligonucleotide forming a secondary structure as disclosed herein may be truncated from the parent sequences as disclosed herein. The aptamer composition may comprise at least one oligonucleotide comprising from about 30 to about 60 consecutive nucleotides truncated from the group consisting of SEQ ID NO: 1 to SEQ ID NO: 200 as parent sequences. The aptamer composition may comprise at least one oligonucleotide comprising at least 32 consecutive nucleotides truncated from the parent sequences as disclosed herein. The aptamer composition may comprise at least one oligonucleotide comprising at least 33 consecutive nucleotides truncated from the parent sequences as disclosed herein. The aptamer composition may comprise at least one oligonucleotide comprising at least 34 consecutive nucleotides truncated from the parent sequences as disclosed herein. The aptamer composition may comprise at least one oligonucleotide comprising at least 35 consecutive nucleotides truncated from the parent sequences as disclosed herein. The aptamer composition may comprise at least one oligonucleotide comprising at least 36 consecutive nucleotides truncated from the parent sequences as disclosed herein. The aptamer composition may comprise at least one oligonucleotide comprising at least 37 consecutive nucleotides truncated from the parent sequences as disclosed herein.

In addition or alternatively, the aptamer composition may comprise at least one oligonucleotide forming the secondary structure as disclosed and being truncated from the 3'-end, from the 5'-end or from the middle of the parent sequences as disclosed herein, e.g. selected from the group consisting of SEQ ID NO: 1 to SEQ ID NO: 200 as parent sequences. The aptamer composition may comprise at least one oligonucleotide truncated from the middle of the parent sequences as disclosed herein.

The at least one truncated oligonucleotide of the present invention may start or end at nucleotide 12 counted from the 3'-end of the parent sequences as disclosed herein. The at least one truncated oligonucleotide of the present invention may start or end at nucleotide 10 counted from the 3'-end of the parent sequences as disclosed herein. The at least one truncated oligonucleotide of the present invention may start or end at any nucleotide from 9 counted from the 3'-end to the 3'-end of the parent sequences as disclosed herein.

The aptamer composition may comprise at least one oligonucleotide forming the secondary structure as disclosed herein and being truncated from the group consisting of oligonucleotides as parent sequences with at least 80% nucleotide sequence identity to sequences selected from the group consisting of SEQ ID NO: 1 to SEQ ID NO: 200, wherein the truncated oligonucleotide comprises the GAG-GYYZ motif as disclosed herein including, but not limited to all variants and further specifications. The aptamer composition may comprise at least one oligonucleotide truncated from the group consisting of oligonucleotides as parent sequences with at least 90% nucleotide sequence identity to sequences selected from the group consisting of SEQ ID NO: 1 to SEQ ID NO: 200. A non-limiting example of oligonucleotide with at least 90% nucleotide sequence identity to SEQ ID NO: 3 is for example SEQ ID NO: 88. The aptamer composition may comprise at least one oligonucleotide truncated from the group consisting of oligonucleotides as parent sequences with at least 93% nucleotide sequence identity to sequences selected from the group consisting of SEQ ID NO: 1 to SEQ ID NO: 200. The aptamer composition may comprise at least one oligonucleotide truncated from the group consisting of oligonucleotides as parent sequences with at least 96% nucleotide sequence identity to sequences selected from the group consisting of SEQ ID NO: 1 to SEQ ID NO: 200. The aptamer composition may comprise at least one oligonucleotide truncated from the group consisting of oligonucleotides as parent sequences with at least 99% nucleotide sequence identity to sequences selected from the group consisting of SEQ ID NO: 1 to SEQ ID NO: 200. The aptamer composition may comprise at least one oligonucleotide truncated from oligonucleotides as parent sequences selected from the group consisting of SEQ ID NO: 1 to SEQ ID NO: 200 showing less than 100% nucleotide sequence identity, wherein a nucleotide having pyrimidine base is replaced by another nucleotide having a pyrimidine base, a nucleotide having a purine base is replaced by another nucleotide having a purine base or a combination thereof.

The aptamer composition may comprise at least one oligonucleotide forming the secondary structure as disclosed herein and being truncated from the group consisting of SEQ ID NO: 1 to SEQ ID NO: 200 as parent sequences. The aptamer composition may comprise at least one oligonucleotide truncated from the group consisting of SEQ ID NO: 1 to SEQ ID NO: 10 as parent sequences for RNA oligonucleotides. The aptamer composition may comprise at least one oligonucleotide truncated from the group consisting of SEQ ID NO: 101 to SEQ ID NO: 110 as parent sequences, for DNA oligonucleotides. The aptamer composition may comprise at least one oligonucleotide truncated from oligonucleotides selected from the group consisting of SEQ ID NO: 1 to SEQ ID NO: 200 as parent sequences, wherein one or more nucleotides are deleted from the oligonucleotide sequence which is truncated. If one or more nucleotides are deleted from the oligonucleotide sequence which is truncated the truncated oligonucleotide(s) show less than 100% sequence identity compared to the corresponding part of the parent sequence. Suitable deletions do not alter the secondary structure of the truncated. The aptamer composition may comprise at least one oligonucleotide truncated from oligonucleotides as parent sequences selected from the group consisting of SEQ ID NO: 1 to SEQ ID NO: 200, wherein no more than 10 nucleotides are deleted from the sequence which is truncated. The aptamer composition may comprise at least one oligonucleotide truncated from oligonucleotides as parent sequences selected from the group consisting of SEQ ID NO: 1 to SEQ ID NO: 200, wherein no more than 5 nucleotides are deleted from the sequence which is truncated. The aptamer composition may comprise at least one oligonucleotide truncated from oligonucleotides as parent sequences selected from the group consisting of SEQ ID NO: 1 to SEQ ID NO: 200, wherein no more than 4 nucleotides are deleted from the sequence which is truncated. The aptamer composition may comprise at least one oligonucleotide truncated from oligonucleotides as parent sequences selected from the group consisting of SEQ ID NO: 1 to SEQ ID NO: 200, wherein no more than 3 nucleotides are deleted from the sequence which is truncated. The aptamer composition may comprise at least one oligonucleotide truncated from oligonucleotides as parent sequences selected from the group consisting of SEQ ID NO: 1 to SEQ ID NO: 200, wherein no more than 2 nucleotides are deleted from the sequence which is truncated. The aptamer composition may comprise at least one oligonucleotide truncated from oligonucleotides as parent sequences selected from the group consisting of SEQ ID NO: 1 to SEQ ID NO: 200, wherein 1 nucleotide is deleted from the oligonucleotide sequence which is truncated.

The aptamer composition may comprise at least one oligonucleotide forming the secondary structure as disclosed herein and being truncated from oligonucleotides as parent sequences selected from the group consisting of SEQ ID NO: 1 to SEQ ID NO: 200, wherein one or more nucleotides are inserted into the oligonucleotide sequence which is truncated. If one or more nucleotides are inserted into the oligonucleotide sequence which is truncated the truncated oligonucleotide(s) show less than 100% sequence identity compared to the corresponding part of the parent sequence. Suitable insertions do not alter the secondary structure of the truncated oligonucleotide. The aptamer composition may comprise at least one oligonucleotide truncated from oligonucleotides as parent sequences selected from the group consisting of SEQ ID NO: 1 to SEQ ID NO: 200, wherein no more than 10 nucleotides are inserted into the sequence which is truncated. The aptamer composition may comprise at least one oligonucleotide truncated from oligonucleotides as parent sequences selected from the group consisting of SEQ ID NO: 1 to SEQ ID NO: 200, wherein no more than 5 nucleotides are inserted into the sequence which is truncated. The aptamer composition may comprise at least one oligonucleotide truncated from oligonucleotides as parent sequences selected from the group consisting of SEQ ID NO: 1 to SEQ ID NO: 200, wherein no more than 4 nucleotides are inserted into the sequence which is truncated. The aptamer composition may comprise at least one oligonucleotide truncated from oligonucleotides as parent sequences selected from the group consisting of SEQ ID NO: 1 to SEQ ID NO: 200, wherein no more than 3 nucleotides are inserted into the sequence which is truncated. The aptamer composition may comprise at least one oligonucleotide truncated from oligonucleotides as parent sequences selected from the group consisting of SEQ ID NO: 1 to SEQ ID NO: 200, wherein no more than 2 nucleotides are inserted into the sequence which is truncated. The aptamer composition may comprise at least one oligonucleotide truncated from oligonucleotides as parent sequences selected from the group consisting of SEQ ID NO: 1 to SEQ ID NO: 200, wherein 1 nucleotide is inserted into the oligonucleotide sequence which is truncated.

The truncated oligonucleotide of the aptamer composition may comprise at least one oligonucleotide selected from the group consisting of oligonucleotides containing at least 10 contiguous nucleotides from sequences selected from the group consisting of SEQ ID NO: 201 to SEQ ID NO: 212. The truncated oligonucleotide of the aptamer composition may comprise at least one oligonucleotide containing at least 10 contiguous nucleotides from sequences selected from the group consisting of oligonucleotides nucleotides from the group consisting of SEQ ID NO: 201 to SEQ ID NO: 212. The at least one oligonucleotide can comprise one or more motifs selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212. The aptamer composition may comprise at least one oligonucleotide comprising a sequence of nucleotides with at least 80% nucleotide sequence identity to sequences selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212. The aptamer composition may comprise at least one oligonucleotide comprising a sequence of nucleotides with at least 90% nucleotide sequence identity to sequences selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212. The aptamer composition may comprise at least one oligonucleotide comprising a sequence of nucleotides with at least 95% nucleotide sequence identity to sequences selected from the group consisting of SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, and SEQ ID NO: 212.

The aptamer composition may comprise at least one oligonucleotide forming a secondary structure as disclosed and being truncated from the group consisting of SEQ ID NO: 1 to SEQ ID NO: 10 as parent sequences for RNA oligonucleotides. The aptamer composition may comprise at least one oligonucleotide truncated from the group consisting of SEQ ID NO: 2, SEQ ID NO: 4, SEQ ID NO: 5, SEQ ID NO: 7, and SEQ ID NO: 8 as parent sequences. The aptamer composition may comprise at least one oligonucleotide comprising a sequence of nucleotides with at least 80% nucleotide sequence identity to sequences selected from the group consisting of SEQ ID NO: 2, SEQ ID NO: 4, SEQ ID NO: 5, SEQ ID NO: 7, and SEQ ID NO: 8 as parent sequence. The aptamer composition may comprise at least one oligonucleotide comprising a sequence of nucleotides with at least 90% nucleotide sequence identity to sequences selected from the group consisting of SEQ ID NO: 2, SEQ ID NO: 4, SEQ ID NO: 5, SEQ ID NO: 7, and SEQ ID NO: 8 as parent sequence. The aptamer composition may comprise at least one oligonucleotide comprising a sequence of nucleotides with at least 93% nucleotide sequence identity to sequences selected from the group consisting of SEQ ID NO: 2, SEQ ID NO: 4, SEQ ID NO: 5, SEQ ID NO: 7, and SEQ ID NO: 8 as parent sequence. The aptamer composition may comprise at least one oligonucleotide comprising a sequence of nucleotides with at least 96% nucleotide sequence identity to sequences selected from the group consisting of SEQ ID NO: 2, SEQ ID NO: 4, SEQ ID NO: 5, SEQ ID NO: 7, and SEQ ID NO: 8 as parent sequence. The aptamer composition may comprise at least one oligonucleotide comprising a sequence of nucleotides with at least 99% nucleotide sequence identity to sequences selected from the group consisting of SEQ ID NO: 2, SEQ ID NO: 4, SEQ ID NO: 5, SEQ ID NO: 7, and SEQ ID NO: 8 as parent sequence.

The aptamer composition may comprise at least one oligonucleotide forming the secondary structure as disclosed and being truncated from the group consisting of SEQ ID NO: 101 to SEQ ID NO: 110 as parent sequences for DNA oligonucleotides. The aptamer composition may comprise at least one oligonucleotide truncated from the group consisting of SEQ ID NO: 102, SEQ ID NO: 104, SEQ ID NO: 105, SEQ ID NO: 107, and SEQ ID NO: 108 as parent sequence. The aptamer composition may comprise at least one oligonucleotide comprising a sequence of nucleotides with at least 80% nucleotide sequence identity to sequences selected from the group consisting of SEQ ID NO: 102, SEQ ID NO: 104, SEQ ID NO: 105, SEQ ID NO: 107, and SEQ ID NO: 108 as parent sequence. The aptamer composition may comprise at least one oligonucleotide comprising a sequence of nucleotides with at least 90% nucleotide sequence identity to sequences selected from the group consisting of SEQ ID NO: 102, SEQ ID NO: 104, SEQ ID NO: 105, SEQ ID NO: 107, and SEQ ID NO: 108 as parent sequence. The aptamer composition may comprise at least one oligonucleotide comprising a sequence of nucleotides with at least 93% nucleotide sequence identity to sequences selected from the group consisting of SEQ ID NO: 102, SEQ ID NO: 104, SEQ ID NO: 105, SEQ ID NO: 107, and SEQ ID NO: 108 as parent sequence. The aptamer composition may comprise at least one oligonucleotide comprising a sequence of nucleotides with at least 96% nucleotide sequence identity to sequences selected from the group consisting of SEQ ID NO: 102, SEQ ID NO: 104, SEQ ID NO: 105, SEQ ID NO: 107, and SEQ ID NO: 108 as parent sequence. The aptamer composition may comprise at least one oligonucleotide comprising a sequence of nucleotides with at least 99% nucleotide sequence identity to sequences selected from the group consisting of SEQ ID NO: 102, SEQ ID NO: 104, SEQ ID NO: 105, SEQ ID NO: 107, and SEQ ID NO: 108 as parent sequence.

The aptamer composition as disclosed herein may comprise at least one oligonucleotide forming the secondary structure as disclosed and being selected from the group consisting of oligonucleotides selected from the group consisting of SEQ ID NO: 237 to SEQ ID NO: 246, or at least one oligonucleotide showing at least 80% nucleotide sequence identity to sequences selected from the group consisting of SEQ ID NO: 237 to SEQ ID NO: 246. The aptamer composition may comprise at least one oligonucleotide showing at least 90% nucleotide sequence identity to sequences selected from the group consisting of SEQ ID NO: 237 to SEQ ID NO: 246. The aptamer composition may comprise at least one oligonucleotide showing at least 95% nucleotide sequence identity to sequences selected from the group consisting of SEQ ID NO: 237 to SEQ ID NO: 246. The aptamer composition may be selected from the group consisting of SEQ ID NO: 237 to SEQ ID NO: 246 and/or selected from oligonucleotide sequence(s) showing at least 80% nucleotide sequence identity, or at least 90% nucleotide sequence identity, or at least 95% nucleotide sequence identity to the sequences selected from the group consisting of SEQ ID NO: 237 to SEQ ID NO: 246.

In one aspect, the aptamer composition has a binding affinity for the human intercellular adhesion molecule 1 (ICAM-1) (SEQ ID NO: 213), its natural variants, polymorphic variants, or any post-translationally modified versions of said protein. Non-limiting examples of posttranslational modifications of ICAM-1 are disulfide bonds (e.g. between Cys48 and Cys92, Cys52 and Cys96, Cys135 and Cys186, Cys237 and Cys290, Cys332 and Cys371, Cys403 and Cys419, Cys431 and Cys457), glycosylations (e.g. at Asn130, Asn145, Asn183, Asn202, Asn267, Asn296, Asn385, and Asn406), phosphorylations (e.g. at Thr521 or Thr530), and ubiquitination.

In one aspect, the aptamer composition has a binding affinity for the extracellular domain of human intercellular adhesion molecule 1 (ICAM-1) (SEQ ID NO: 214) or any post-translationally modified versions of said domain. In one aspect, the aptamer composition has a binding affinity for one or more domains of the intercellular adhesion molecule 1 (ICAM-1) selected from the group consisting of: Ig-like C2-type 1 domain (SEQ ID NO: 215), Ig-like C2-type 2 domain (SEQ ID NO: 216), Ig-like C2-type 3 domain (SEQ ID NO: 217), Ig-like C2-type 4 domain (SEQ ID NO: 218), Ig-like C2-type 5 domain (SEQ ID NO: 219), any post-translationally modified versions of said domains, and mixtures thereof. In one aspect, the aptamer composition has a binding affinity for the Ig-like C2-type 1 domain (SEQ ID NO: 215) of the intercellular adhesion molecule 1 (ICAM-1), any post-translationally modified versions of said domain, and mixtures thereof.

In one aspect, the aptamer composition has a binding affinity for one or more regions of the human intercellular adhesion molecule 1, 2, 3 or 4 wherein said regions comprise an amino acid sequence selected from the group consisting of SEQ ID NO: 220, SEQ ID NO: 221, SEQ ID NO: 222, SEQ ID NO: 223, and fragments of said sequences.

Chemical modifications can introduce new features into the aptamers such as different molecular interactions with the target, improved binding capabilities, enhanced stability of oligonucleotide conformations, or increased resistance to nucleases. In one aspect, the at least one oligonucleotide of the aptamer composition may comprise natural or non-natural nucleobases. Natural nucleobases are adenine, cytosine, guanine, thymine, and uracil. Non-limiting examples of non-natural nucleobases can include hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, bromouracil, 5-iodouracil, and mixtures thereof.

Modifications of the phosphate backbone of the oligonucleotides can also increase the resistance against nuclease digestion. In one aspect, the nucleosides of the oligonucleotides may be linked by a chemical motif selected from the group consisting of natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In one aspect, the nucleosides of the oligonucleotides may be linked by natural phosphate diesters.

In one aspect, the sugar moiety of the nucleosides of the oligonucleotides may be selected from the group consisting of ribose, deoxyribose, 2'-fluoro deoxyribose, 2'-O-methyl ribose, 2'4)-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N, N-dimethylacetamidyl ribose, N-morpholinophosphordiamidate, α-deoxyribofuranosyl, other pentoses, hexoses, and mixtures thereof.

In one aspect, the derivatives of ribonucleotides or said derivatives of deoxyribonucleotides may be selected from the group consisting of locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

In one aspect, the nucleotides at the 5'- and 3'-ends of the at least one oligonucleotide may be inverted. In one aspect, at least one nucleotide of the at least one oligonucleotide may be fluorinated at the 2' position of the pentose group. In one aspect, the pyrimidine nucleotides of said at least one oligonucleotide may be fluorinated at the 2' position of the pentose group. In one aspect, said aptamer composition may comprise at least one polymeric material, wherein said at least one polymeric material is covalently linked to said at least one oligonucleotide. In one aspect, said at least one polymeric material may be polyethylene glycol.

In one aspect, said at least one oligonucleotide may be between about 30 and about 60 nucleotides in length. In one aspect, said at least one oligonucleotide may be less than about 50 nucleotides in length, alternatively said at least one oligonucleotide may be less than about 40 nucleotides in length.

In one aspect, said at least one oligonucleotide may be covalently or non-covalently attached to one or more additional active ingredients. In one aspect, said one or more active ingredients may be selected from the group consisting of respiratory illness treatment agents, cold-treatment agents, flu-treatment agents, antiviral agents, antimicrobial agents, cooling sensates, warming sensates, malodor absorbing agents, natural extracts, peptides, enzymes, pharmaceutical active ingredients, metal compounds, and mixtures thereof. In one aspect, said one or more active ingredients can include, but are not limited to, pharmaceutical active ingredients, menthol, levomenthol, zinc and salts thereof, eucalyptus, camphor, and combinations thereof. Suitable active ingredients include any material that is generally considered as safe and that provides health care benefits.

In one aspect, said at least one oligonucleotide may be non-covalently attached to said one or more active ingredients via molecular interactions. Examples of molecular interactions are electrostatic forces, van der Waals interactions, hydrogen bonding, and π-π stacking interactions of aromatic rings.

In one aspect, said at least one oligonucleotide may be covalently attached to said one or more active ingredients using one or more linkers or spacers. Non-limiting examples of linkers are chemically labile linkers, enzyme-labile linkers, and non-cleavable linkers. Examples of chemically labile linkers are acid-cleavable linkers and disulfide linkers. Acid-cleavable linkers take advantage of low pH to trigger hydrolysis of an acid-cleavable bond, such as a hydrazone bond, to release the active ingredient or payload. Disulfide linkers can release the active ingredients under reducing environments. Examples of enzyme-labile linkers are peptide linkers that can be cleaved in the presence of proteases and β-glucuronide linkers that are cleaved by glucuronidases releasing the payload. Non-cleavable linkers can also release the active ingredient if the aptamer is degraded by nucleases.

In one aspect, said at least one oligonucleotide may be covalently or non-covalently attached to one or more nanomaterials. In the present invention, said at least one oligonucleotide and said one or more active ingredients may be covalently or non-covalently attached to one or more nanomaterials. In one aspect, said one or more active ingredients may be carried by said one or more nanomaterials. Non-limiting examples of nanomaterials can include gold nanoparticles, nano-scale iron oxides, carbon nanomaterials (such as single-walled carbon nanotubes and graphene oxide), mesoporous silica nanoparticles, quantum dots, liposomes, poly (lactide-co-glycolic acids) nanoparticles, polymeric micelles, dendrimers, serum albumin nanoparticles, DNA-based nanomaterials, and combinations thereof. These nanomaterials can serve as carriers for large volumes of active ingredients, while the aptamers can facilitate the delivery of the nanomaterials with the actives to the expected target.

Nanomaterials can have a variety of shapes or morphologies. Non-limiting examples of shapes or morphologies can include spheres, rectangles, polygons, disks, toroids, cones, pyramids, rods/cylinders, and fibers. In the context of the present invention, nanomaterials usually have at least one spatial dimension that is less than about 100 μm and more preferably less than about 10 μm. Nanomaterials comprise materials in solid phase, semi-solid phase, or liquid phase.

Aptamers can also be peptides that bind to targets with high affinity and specificity. These peptide aptamers can be part of a scaffold protein. Peptide aptamers can be isolated from combinatorial libraries and improved by directed mutation or rounds of variable region mutagenesis and selection. In one aspect, said aptamer composition may comprise at least one peptide or protein; wherein said aptamer composition has a binding affinity for one or more cellular membrane glycoproteins, wherein said one or more cellular membrane glycoproteins can be selected from the group consisting of: intercellular adhesion molecule 1 (ICAM-1), low-density lipoprotein receptor (LDLR) family members, and cadherin-related family member 3 (CDHR3); preferably intercellular adhesion molecule 1 (ICAM-1) and wherein said aptamer is configured to reduce the binding of one or more human rhinoviruses to said cellular membrane glycoproteins, preferably the intercellular adhesion molecule 1 (ICAM-1). In particular said aptamer composition may comprise at least one peptide or protein translated from at least one oligonucleotide as disclosed herein.

III. Methods of Designing Parent Aptamer Compositions

The method of designing nucleic acid aptamers known as Systematic Evolution of Ligands by Exponential Enrichment (SELEX) has been broadly studied and improved for the selection of aptamers against small molecules and proteins (WO 91/19813). In brief, in the conventional version of SELEX, the process starts with the synthesis of a large library of oligonucleotides consisting of randomly generated sequences of fixed length flanked by constant 5'- and 3'-ends that serve as primers. The oligonucleotides in the library are then exposed to the target ligand and those that do not bind the target are removed. The bound sequences are eluted and amplified by PCR (polymerase chain reaction) to prepare for subsequent rounds of selection in which the stringency of the elution conditions is usually increased to identify the tightest-binding oligonucleotides. In addition to conventional SELEX, there are improved versions such as capillary electrophoresis-SELEX, magnetic bead-based SELEX, cell-SELEX, automated SELEX, complex-target SELEX, among others. A review of aptamer screening methods is found in (1) Kim, Y. S. and M. B. Gu, "Advances in Aptamer Screening and Small Molecule Aptasensors", Adv. Biochem. Eng. Biotechnol., 2014 140:29-67 (Biosensors based on Aptamers and Enzymes) and (2) Stoltenburg, R., et al. (2007) "SELEX-A (r)evolutionary method to generate high-affinity nucleic acid ligands" Biomol. Eng. 2007 24(4): 381-403, the contents of which are incorporated herein by reference. Although the SELEX method has been broadly applied, it is neither predictive nor standardized for every target. Instead, a method must be developed for each particular target in order for the method to lead to viable aptamers.

Despite the large number of selected aptamers, SELEX has not been routinely applied for the selection of aptamers with binding affinities towards cellular membrane glycoproteins such as intercellular adhesion molecule 1 (ICAM-1), low-density lipoprotein receptor (LDLR) family members, and cadherin-related family member 3 (CDHR3) and that prevent the binding of human rhinoviruses to such proteins. Unexpectedly, the inventors have found that SELEX can be used for the design of parent aptamers that prevent the binding of human rhinoviruses to the ICAM-1 receptor.

Selection Library

In SELEX, the initial candidate library is generally a mixture of chemically synthesized DNA oligonucleotides, each comprising a long variable region of n nucleotides flanked at the 3' and 5' ends by conserved regions or primer recognition regions for all the candidates of the library. These primer recognition regions allow the central variable region to be manipulated during SELEX in particular by means of PCR.

The length of the variable region determines the diversity of the library, which is equal to $4^n$ since each position can be occupied by one of four nucleotides A, T, G or C. For long variable regions, huge library complexities arise. For instance, when n=50, the theoretical diversity is $4^{50}$ or $10^{30}$, which is an inaccessible value in practice as it corresponds to more than 105 tons of material for a library wherein each sequence is represented once. The experimental limit is around $10^{15}$ different sequences, which is that of a library wherein all candidates having a variable region of 25 nucleotides are represented. If one chooses to manipulate a library comprising a 30-nucleotide variable region whose theoretical diversity is about $10^{18}$, only 1/1000 of the possibilities will thus be explored. In practice, that is generally sufficient to obtain aptamers having the desired properties. Additionally, since the polymerases used are unreliable and introduce errors at a rate on the order of $10^{-4}$, they contribute to significantly enrich the diversity of the sequence pool throughout the SELEX process. One candidate in 100 will be modified in each amplification cycle for a library with a random region of 100 nucleotides in length, thus leading to the appearance of $10^{13}$ new candidates for the overall library.

In one aspect, the starting mixture of oligonucleotides may comprise more than about $10^6$ different oligonucleotides and more preferably between about $10^{13}$ to about $10^{15}$ different oligonucleotides. In one aspect, the length of the variable region may be between about 10 and about 100 nucleotides. In one aspect, the length of the variable region may be between about 20 and about 60 nucleotides. In one aspect, the length of the variable region may be about 40 nucleotides. Random regions shorter than 10 nucleotides may be used but may be constrained in their ability to form secondary or tertiary structures and in their ability to bind to target molecules. Random regions longer than 100 nucleotides may also be used but may present difficulties in terms of cost of synthesis. The randomness of the variable region is not a constraint of the present invention. For instance, if previous knowledge exists regarding oligonucleotides that bind to a given target, libraries spiked with such sequences may work as well or better than completely random ones.

In the design of primer recognition sequences, care should be taken to minimize potential annealing among sequences, fold back regions within sequences, or annealing of the same sequence itself. In one aspect, the length of primer recognition sequences may be between about 10 and about 40 nucleotides. In one aspect, the length of primer recognition sequences may be between about 12 and about 30 nucleotides. In one aspect, the length of primer recognition sequences may be between about 18 and about 26 nucleotides, i.e., about 18, 19, 20, 21, 22, 23, 24, 25 or 26 nucleotides. The length and sequence of the primer recognition sequences determine their annealing temperature. In one aspect, the primer recognition sequences of said oligonucleotides may have an annealing temperature between about 60° C. and about 72° C.

Aptamers can be ribonucleotides (RNA), deoxynucleotides (DNA), or their derivatives. When aptamers are ribonucleotides, the first SELEX step may consist of transcribing the initial mixture of chemically synthesized DNA oligonucleotides via the primer recognition sequence at the 5' end. After selection, the candidates are converted back into DNA by reverse transcription before being amplified. RNA and DNA aptamers having comparable characteristics have been selected against the same target and reported in the art. Additionally, both types of aptamers can be competitive inhibitors of one another, suggesting potential overlapping of interaction sites.

New functionalities, such as hydrophobicity or photoreactivity, can be incorporated into the oligonucleotides by modifications of the nucleobases before or after selection. Modifications at the C-5 position of pyrimidines or at the C-8 or N-7 positions of purines are especially common and compatible with certain enzymes used during the amplification step in SELEX. In one aspect, said oligonucleotides may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, 5-bromouracil, 5-iodouracil, and mixtures thereof. Some non-natural nucleobases, such as 5-bromouracil or 5-iodouracil, can be used to generate photo-crosslinkable aptamers, which can be activated by UV light to form a covalent link with the target.

In one aspect, the nucleosides of said oligonucleotides may be linked by a chemical motif selected from the group consisting of natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In one aspect, the nucleosides of said oligonucleotides may be linked by natural phosphate diesters.

In one aspect, the sugar moiety of the nucleosides of said oligonucleotides may be selected from the group consisting of ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In one aspect, said derivatives of ribonucleotides or said derivatives of deoxyribonucleotides may be selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

When using modified nucleotides during the SELEX process, they should be compatible with the enzymes used during the amplification step. Non-limiting examples of modifications that are compatible with commercial enzymes include modifications at the 2' position of the sugar in RNA libraries. The ribose 2'-OH group of pyrimidine nucleotides can be replaced with 2'-amino, 2'-fluoro, 2'-methyl, or 2'-O-methyl, which protect the RNA from degradation by nucleases. Additional modifications in the phosphate linker, such as phosphorothionate and boranophosphate, are also compatible with the polymerases and confer resistance to nucleases.

In one aspect, at least one nucleotide of said oligonucleotides may be fluorinated at the 2' position of the pentose group. In one aspect, the pyrimidine nucleotides of said oligonucleotides may be at least partially fluorinated at the 2' position of the pentose group. In one aspect, all the pyrimidine nucleotides of said oligonucleotides may be fluorinated at the 2' position of the pentose group. In one aspect, at least one nucleotide of said oligonucleotides may be aminated at the 2' position of the pentose group.

Another approach, recently described as two-dimensional SELEX, simultaneously applies in vitro oligonucleotide selection and dynamic combinatorial chemistry (DCC), e.g., a reversible reaction between certain groups of the oligonucleotide (amine groups) and a library of aldehyde compounds. The reaction produces imine oligonucleotides, which are selected on the same principles as for conventional SELEX. It is thus possible to identify for a target hairpin RNA modified aptamers that differ from natural aptamers.

A very different approach relates to the use of optical isomers. Natural oligonucleotides are D-isomers. L-analogs are resistant to nucleases but cannot be synthesized by polymerases. According to the laws of optical isomerism, an L-series aptamer can form with its target (T) a complex having the same characteristics as the complex formed by the D-series isomer and the enantiomer (T') of the target (T). Consequently, if compound T' can be chemically synthesized, it can be used to perform the selection of a natural aptamer (D). Once identified, this aptamer can be chemically synthesized in an L-series. This L-aptamer is a ligand of the natural target (T).

Selection Step

Single stranded oligonucleotides can fold to generate secondary and tertiary structures, resembling the formation of base pairs. The initial sequence library is thus a library of three-dimensional shapes, each corresponding to a distribution of units that can trigger electrostatic interactions, create hydrogen bonds, etc. Selection becomes a question of identifying in the library the shape suited to the target, i.e., the shape allowing the greatest number of interactions and the formation of the most stable aptamer-target complex. For small targets (dyes, antibiotics, etc.) the aptamers identified are characterized by equilibrium dissociation constants in the micromolar range, whereas for protein targets Kd values below $10^{-9}$ M are not rare.

Selection in each round occurs by means of physical separation of oligonucleotides associated with the target from free oligonucleotides. Multiple techniques may be applied (chromatography, filter retention, electrophoresis, etc.). The selection conditions are adjusted (relative concentration of target/candidates, ion concentration, temperature, washing, etc.) so that a target-binding competition occurs between the oligonucleotides. Generally, stringency is increased as the rounds proceed in order to promote the capture of oligonucleotides with the highest affinity. In addition, counter-selections or negative selections are carried out to eliminate oligonucleotides that recognize the support or unwanted targets (e.g., filter, beads, etc.).

The SELEX process for the selection of target-specific parent aptamers is characterized by repetition of five main steps: (1) binding of oligonucleotides to the target, (2) partition or removal of oligonucleotides with low binding affinity, (3) elution of oligonucleotides with high binding affinity, (4) amplification or replication of oligonucleotides with high binding affinity, and (5) conditioning or preparation of the oligonucleotides for the next cycle. This selection process is designed to identify the oligonucleotides with the greatest affinity and specificity for the target material.

In one aspect, a method of designing a composition of parent aptamer(s) from which the aptamers forming the required secondary structure as disclosed herein may be truncated may comprise the step of contacting: a) a mixture of oligonucleotides, b) a selection buffer, and c) a target material comprising one or more cellular membrane glycoproteins selected from the group consisting of: intercellular adhesion molecule 1 (ICAM-1), low-density lipoprotein receptor (LDLR) family members, cadherin-related family member 3 (CDHR3), truncations thereof, and mixtures thereof; preferably intercellular adhesion molecule 1 (ICAM-1) and truncations thereof. In another aspect, the method of designing a composition of parent aptamer(s) as disclosed herein may comprise the step of contacting: a) a mixture of oligonucleotides, b) a selection buffer, and c) cells expressing one or more cellular membrane glycoproteins selected from the group consisting of: intercellular adhesion molecule 1 (ICAM-1), low-density lipoprotein receptor (LDLR) family members, cadherin-related family member 3 (CDHR3), truncations thereof, and mixtures thereof; preferably intercellular adhesion molecule 1 (ICAM-1) and truncations thereof. In yet another aspect, the method of designing a composition of parent aptamer(s) as disclosed herein may comprise the step of contacting: a) a mixture of oligonucleotides, b) a selection buffer, and c) human nasal epithelial cells expressing one or more cellular membrane glycoproteins selected from the group consisting of: intercellular adhesion molecule 1 (ICAM-1), low-density lipoprotein receptor (LDLR) family members, cadherin-related family member 3 (CDHR3), truncations thereof, and mixtures thereof; preferably intercellular adhesion molecule 1 (ICAM-1) and truncations thereof.

In one aspect, said mixture of oligonucleotides may comprise oligonucleotides selected from the group consisting of deoxyribonucleotides, ribonucleotides, derivatives of deoxyribonucleotides, derivatives of ribonucleotides, and mixtures thereof. Furthermore, said one or more cellular membrane glycoproteins or truncations thereof can be isolated, in mixture with other materials such as proteins or peptides, or part of a cell expressing said glycoproteins.

SELEX cycles are usually repeated several times until oligonucleotides with high binding affinity are identified. The number of cycles depends on multiple variables, including target features and concentration, design of the starting random oligonucleotide library, selection conditions, ratio of target binding sites to oligonucleotides, and the efficiency of the partitioning step. In one aspect, said contacting step may be performed at least 5 times. In one aspect, said contacting step may be performed between 6 and 30 times. In one aspect, said method further may comprise the step of removing the oligonucleotides that do not bind said target material during said contacting step.

Oligonucleotides are oligo-anions, each unit having a charge and hydrogen-bond donor/acceptor sites at a particular pH. Thus, the pH and ionic strength of the selection buffer are important and should represent the conditions of the intended aptamer application. In one aspect, the pH of said selection buffer may be between about 2 and about 9, alternatively between about 5 and about 8.

Cations do not only facilitate the proper folding of the oligonucleotides, but also can provide benefits. In one aspect, said selection buffer may comprise cations. Non-limiting examples of cations are $Na^+$, $K^+$, $Mg^+$, $Ca^{2+}$.

In order for the aptamers to maintain their structures and function during their application, the in vitro selection process can be carried out under conditions similar to those for which they are being developed. In one aspect, said selection buffer may comprise a solution or suspension of a personal health care composition selected from the group consisting of tablets, lyophilized tablets, lollipops, lozenges, liquid center-filled confectioneries, candies, powders, granular substances, films, liquids, solutions, suspensions, mouth rinses or gargles, saline washes, dispersible fluids, sprays, quick dissolving fibers, vapors, creams, ointments, powders, granular substances, films, and combinations thereof.

In one aspect, said selection buffer may comprise at least one surfactant. In one aspect, the at least one surfactant may be selected from the group consisting of anionic surfactants, amphoteric or zwitterionic surfactants, and mixtures thereof. Non-limiting examples of anionic surfactants are alkyl and alkyl ether sulfates or sulfonates, including ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and combinations thereof. Non-limiting amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate, including cocoamphoacetate, cocoamphodiacetate, lauroamphoacetate, lauroamphodiacetate, and mixtures thereof. Non-limiting examples of zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate, and betaine.

The selection buffer may comprise at least one material selected from the group comprising: aqueous carriers, gel matrixes, silicone conditioning agents, organic conditioning materials, non-ionic polymers, deposition aids, rheology modifier/suspending agents, benefit agents, and mixtures thereof. Non-limiting examples of aqueous carriers are water and water solutions of lower alkyl alcohols and polyhydric alcohols, including ethanol, isopropanol, propylene glycol, hexylene glycol, glycerin, and propane diol. Non-limiting examples of gel matrixes include water solutions of fatty alcohols, including cetyl alcohol, stearyl alcohol, behenyl alcohol, and mixtures thereof. Non-limiting examples of silicone conditioning agents include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Non-limiting examples of organic conditioning materials include hydrocarbon oils, polyolefins, fatty esters, fluorinated conditioning compounds, fatty alcohols, alkyl glucosides and alkyl glucoside derivatives, quaternary ammonium compounds, polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M, and mixtures thereof. Non-limiting examples of non-ionic polymers include polyalkylene glycols, such as polyethylene glycols. Non-limiting examples of deposition aids include copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone; vinyl esters, vinyl alcohol (made by hydrolysis of polyvinyl acetate), maleic anhydride, propylene glycol, and ethylene glycol, cationic celluloses, cationic starches, and cationic guar gums. Non-limiting examples of rheology modifier/suspending agents include homopolymers based on acrylic acid, methacrylic acid or other related derivatives, alginic acid-based materials, and cellulose derivatives. Non-limiting examples of benefit agents include brightening agents, strengthening agents, anti-fungal agents, anti-bacterial agents, anti-microbial agents, anti-dandruff agents, anti-malodor agents, perfumes, olfactory enhancement agents, anti-itch agents, cooling agents, anti-adherence agents, moisturization agents, smoothness agents, surface modification agents, antioxidants, natural extracts and essential oils, dyes, pigments, bleaches, nutrients, peptides, vitamins, enzymes, chelants, and mixtures thereof.

Negative selection or counter-selection steps can minimize the enrichment of oligonucleotides that bind to undesired targets or undesired epitopes within a target. In one aspect, said method of designing a parent aptamer composition may further comprise the step of contacting: a) a mixture of oligonucleotides, b) a selection buffer, and c) one or more undesired targets. Methods for negative selection or counter-selection of aptamers against unbound targets have been published in WO201735666, the content of which is incorporated herein by reference.

The method of designing a parent aptamer composition may comprise the steps of: a) synthesizing a mixture of oligonucleotides; b) contacting: i. said mixture of oligonucleotides, ii. a selection buffer, and iii. a target material comprising one or more cellular membrane glycoproteins; wherein said glycoproteins are selected from the group consisting of: intercellular adhesion molecule 1 (ICAM-1), its fragments, and combinations thereof, to produce a target suspension; c) removing the liquid phase from said target suspension to produce a target-oligonucleotide mixture; d) contacting said target-oligonucleotide mixture with a washing buffer and removing the liquid phase to produce a target-aptamer mixture; and e) contacting said target-aptamer mixture with an elution buffer and recovering the liquid phase to produce an aptamer mixture. In one aspect, said steps may be performed repetitively at least 5 times. In one aspect, said steps may be performed between 6 and 30 times, preferably less than 20 times.

In another aspect, a method of designing a parent aptamer composition comprising the steps of: a) synthesizing a random mixture of deoxyribonucleotides comprising oligonucleotides consisting of: i. a T7 promoter sequence at the 5'-end, ii. a variable 40-nucleotide sequence in the middle, and iii. a conserved reverse primer recognition sequence at the 3' end; b) transcribing said random mixture of deoxyribonucleotides using pyrimidine nucleotides fluorinated at the 2' position of the pentose group and natural purine nucleotides and a mutant T7 polymerase to produce a mixture of fluorinated ribonucleotides; c) contacting: i. said mixture of fluorinated ribonucleotides, ii. a selection buffer, and iii. a target material comprising one or more cellular membrane glycoproteins; wherein said glycoproteins are selected from the group consisting of: intercellular adhesion molecule 1 (ICAM-1), its fragments, and combinations thereof, to produce a target suspension; d) removing the liquid phase from said target suspension to produce a target-oligonucleotide mixture; e) contacting said target-oligonucleotide mixture with a washing buffer and removing the liquid phase to produce a target-aptamer mixture; f) contacting said target-aptamer mixture with an elution buffer and recovering the liquid phase to produce an RNA aptamer mixture; g) reserve transcribing and amplifying said RNA aptamer mixture to produce a DNA copy of said RNA aptamer mixture; and h) sequencing said DNA copy of said RNA aptamer mixture.

Post-Selection Modification

To enhance stability of the aptamers, chemical modifications can be introduced in the aptamer after the selection process. For instance, the 2'-OH groups of the ribose moieties can be replaced by 2'-fluoro, 2'-amino, or 2'-O-methyl groups. Furthermore, the 3'- and 5'-ends of the aptamers can be capped with different groups, such as streptavidin-biotin, inverted thymidine, amine, phosphate, polyethylene-glycol, cholesterol, fatty acids, proteins, enzymes, fluorophores, among others, making the oligonucleotides resistant to exonucleases or providing some additional benefits. Other modifications are described in previous sections of the present disclosure.

Unlike backbone modifications which can cause aptamer-target interaction properties to be lost, it is possible to conjugate various groups at one of the 3'- or 5'-ends of the oligonucleotide in order to convert it into a delivery vehicle, tool, probe, or sensor without disrupting its characteristics. This versatility constitutes a significant advantage of aptamers, in particular for their application in the current invention. In one aspect, one or more personal care active ingredients may be covalently attached to the 3'-end of said at least one oligonucleotide. In one aspect, one or more personal care active ingredients may be covalently attached to the 5'-end of said at least one oligonucleotide. In one aspect, one or more personal care active ingredients may be covalently attached to random positions of said at least one oligonucleotide.

Incorporation of modifications to aptamers can be performed using enzymatic or chemical methods. Non-limiting examples of enzymes used for modification of aptamers are terminal deoxynucleotidyl transferases (TdT), T4 RNA ligases, T4 polynucleotide kinases (PNK), DNA polymerases, RNA polymerases, and other enzymes known by those skilled in the art. TdTs are template-independent polymerases that can add modified deoxynucleotides to the 3' terminus of deoxyribonucleotides. T4 RNA ligases can be used to label ribonucleotides at the 3'-end by using appropriately modified nucleoside 3',5'-bisphosphates. PNK can be used to phosphorylate the 5'-end of synthetic oligonucleotides, enabling other chemical transformations (see below). DNA and RNA polymerases are commonly used for the random incorporation of modified nucleotides throughout the sequence, provided such nucleotides are compatible with the enzymes.

Non-limiting examples of chemical methods used for modification of aptamers are periodate oxidation of ribonucleotides, EDC activation of 5'-phosphate, random chemical labeling methods, and other chemical methods known by those skilled in the art, incorporated herein.

During periodate oxidation, meta- and ortho-periodates cleave the C—C bonds between vicinal diols of 3'-ribonucleotides, creating two aldehyde moieties that enable the conjugation of labels or active ingredients at the 3'-end of RNA aptamers. The resulting aldehydes can be easily reacted with hydrazine- or primary amine-containing molecules. When amines are used, the produced Schiff bases can be reduced to more stable secondary amines with sodium cyanoborohydride (NaCNBH3).

When EDC activation of 5'-phosphate is used, the 5'-phosphate of oligonucleotides is frequently activated with EDC (1-Ethyl-3-[3-dimethylaminopropyl]carbodiimide hydrochloride) and imidazole to produce a reactive imidazolide intermediate, followed by reaction with a primary amine to generate aptamers modified at the 5 'end. Because the 5' phosphate group is required for the reaction, synthetic oligonucleotides can be first treated with a kinase (e.g. PNK).

Random chemical labeling can be performed with different methods. Because they allow labeling at random sites along the aptamer, a higher degree of modification can be achieved compared to end-labeling methods. However, since the nucleobases are modified, binding of the aptamers to their target can be disrupted.

The most common random chemical modification methods involve the use of photoreactive reagents, such as phenylazide-based reagents. When the phenylazide group is exposed to UV light, it forms a labile nitrene that reacts with double bonds and C—H and N—H sites of the aptamers.

Additional information about methods for modification of aptamers is summarized in Hermanson G. T., "Bioconjugate Techniques", pp. 969-1002, 2nd Edition, Academic Press, San Diego, 2008, the content of which is incorporated herein by reference.

After selection, in addition to chemical modifications, sequence truncations can be performed to remove regions that are not essential for binding or for folding into the structure. Moreover, aptamers can be linked together to provide different features or better affinity. Thus, any truncations or combinations of the aptamers described herein can also be incorporated in the aptamer composition.

IV. Methods of Identifying Aptamers to be Truncated from the Parent Aptamers Suitable truncated sequences which form a suitable secondary structure as disclosed herein can be identified by theoretical analysis. Therefore, the main effective regions of the parent aptamers have to be determined based on stable secondary structure formation. Generally, parent aptamers are in flux among possible shapes at 37° C. and the possible shapes that a single sequence can form can be characterized by theoretical analysis, for example using online software provided by ViennaRNA Web Services, created by the Theoretical Biology Group at the Institute for Theoretical Chemistry at the University of Vienna. In addition to the theoretical possibility, the relative proportion of each shape at a given temperature can also be calculated. Accordingly, truncated aptamers may be chosen that exhibit certain of these shapes with as high a level of stability for further analysis.

V. Application of Aptamer Compositions in Personal Health Care Products

Described herein are personal health care compositions and methods for using such compositions for the prevention and treatment of cold-like symptoms due to respiratory tract viral infections. In some aspects, a personal health care composition comprises at least one aptamer as disclosed herein; wherein the at least one aptamer has a binding affinity for ICAM-1 and is configured to reduce the binding of one or more human rhinoviruses to the intercellular adhesion molecule 1 (ICAM-1). The personal health care composition can be preferably applied to areas of the upper respiratory tract, such as the nasal cavity and throat, to provide a barrier to rhinovirus binding and entrance into cells.

The personal health care composition preferably comprises a pharmaceutically effective amount of at least one aptamer as disclosed herein. In some aspects, the personal health care composition can comprise between about 0.001% to about 1% of the at least one aptamer, alternatively from about 0.005% to about 0.5%, alternatively from about 0.01% to about 0.1%, all by weight of the composition.

The personal health care compositions can be administered orally or intranasally. In one aspect, the personal health care composition can be an oral composition. An oral composition can be in liquid form, semi-solid form, suspension form, or in any solid form that is capable of quickly dissolving in the mouth. Non-limiting examples of oral dosage forms can include tablets, lyophilized tablets, lollipops, lozenges, liquid center-filled confectioneries, candies, powders, granular substances, films, liquids, solutions, suspensions, mouth rinses or gargles, saline washes, dispersible fluids, sprays, quick dissolving fibers, such as polyvinylpyrrolidone and poly(vinyl alcohol), and combinations thereof. Solid oral dosage forms can be of any desired size, shape, weight, consistency or hardness, bearing in mind that it should not be swallowed before it disintegrates and can easily fit inside the mouth. Alternatively, the personal health care composition can be a nasal composition. A nasal composition can be in any dosage form capable of quickly dispersing in the nose. Non-limiting examples of nasal dosage forms can include vapors, creams, ointments, powders, granular substances, films, liquids, dispersible fluids, sprays, and combinations thereof.

As used herein, the term "administering" with respect to a human/mammal means that the human/mammal ingests or is directed to ingest, or does ingest, or deliver, or chew, or drink, or spray, or place in mouth or nose, or inhale one or more of the personal health care compositions. Administration may be on an as-needed or as-desired basis, for example, once-weekly, or daily, including multiple times daily, for example, at least once daily, at least twice daily, at least three times daily, or at least four times daily.

The personal health care compositions may be administered to prevent and treat cold-like symptoms. As used herein "cold-like symptoms" refer to symptoms typically associated with respiratory tract viral infections. These symptoms include, but are not limited to, nasal congestion, chest congestion, sneezing, rhinorrhea, fatigue or malaise, coughing, fever, sore throat, headache, and other known cold symptoms.

As further used herein, "treat" or "treatment" with respect to respiratory illness means that administration of the referenced composition prevents, alleviates, ameliorates, inhibits, or mitigates one or more symptoms of the respiratory illness or the respiratory illness itself, or any like benefit with respect to the respiratory illness in a mammalian subject in need thereof, preferably in humans. As such, this includes, for example: preventing a respiratory illness or its associated symptoms from occurring in a mammal, for example when the mammal is predisposed to acquiring the respiratory illness, but has not yet been diagnosed with the illness; inhibiting the respiratory illness or its associated symptoms; and/or alleviating, reversing, or curing the respiratory illness or its associated symptoms. Insofar as the methods of the present invention are directed to preventing a respiratory illness, it is understood that the term "prevent" does not require that the respiratory illness be completely thwarted. Rather, as used herein, the term "preventing" or the like refers to the ability of the skilled artisan to identify susceptibility to respiratory illness (such as, for example, in humans during winter months), such that administration of the referenced compositions may occur prior to the onset of the symptoms associated with the illness.

The personal health care compositions and methods of the present invention can comprise, consist of, or consist essentially of, the essential elements and limitations of the invention described herein, as well as any additional or optional ingredients, components, or limitations described herein or otherwise useful in personal health care compositions intended for use by a subject.

All parts, percentages, and ratios herein are by weight unless otherwise specified. All such weights as they pertain to listed ingredients are based on the active level and, therefore do not include solvents or by-products that may be included in commercially available materials, unless otherwise specified. All measurements referred to herein are made at 25° C. unless otherwise specified.

The personal health care compositions of the present invention may include one or more of the following:

The personal health care composition can comprise a solvent. Non-limiting examples of solvents include water, propylene glycol, ethanol, glycerin, polyethylene glycol, and combinations thereof. Solvent can be present in an amount of from about 2% to about 99%, by weight of the composition, alternatively from about 5% to about 95%, alternatively from about 10% to about 80%, alternatively from about 12% to about 65%, alternatively from about 20% to about 50%.

The personal health care composition can comprise a thickening agent. Non-limiting examples of thickening agents can include carboxymethylcellulose (CMC), carboxymethylcellulose sodium; and mixtures thereof. When present, the composition can comprise from about 0.01% to about 60% of a thickening agent, alternatively from about 0.1% to about 40%, alternatively from about 1% to about 30%, alternatively from about 2% to about 20%, alternatively from about 3% to about 15%, all by weight of the composition. In one aspect, the thickening agent can provide a moisturizing and/or hydration benefit that relieves the cough on contact and/or provides aid in healing the mouth and/or throat.

The personal health care composition can comprise a diluent. Non-limiting examples of diluents can include microcrystalline cellulose, silicified microcrystalline cellulose, such as ProSolv® SMCC 90 (commercially available from JRS Pharma, Patterson, NY, USA), dextrose, mannitol, sorbitol, maltodextrin, maltitol, and combinations thereof. Suitable diluent levels are from about 20% to about 90% diluent, by weight of the composition, alternatively from about 30% to about 85%, alternatively from about 40% to about 83%, alternatively from about 50% to about 80%, alternatively from about 60% to about 78%.

The personal health care composition can comprise a disintegrant. A disintegrant can be included to formulate a rapid disintegration of the solid oral dosage form following administration. Non-limiting examples of disintegrants can include crospovidone, sodium starch glycolate, crosslinked sodium carboxymethyl cellulose, low substituted hydroxypropylcellulose, guar gum, sodium alginate, and mixtures thereof. Suitable disintegrant levels are from about 1% to about 20%, by weight of the composition, alternatively from about 2% to about 15%, alternatively from about 3% to about 10%, alternatively from about 5% to about 8%.

In one aspect, a composition can comprise mannitol and crospovidone to provide quick disintegration and dissolution. One advantage to using a soluble sugar, like mannitol, is that it can pick up water and dissolve quickly. One advantage to using a disintegrant, like crospovidone, is that it can absorb water and swell, thus causing the dosage form to break apart. As a dosage form breaks apart it is exposed to liquid, such as saliva in the oral cavity, and can dissolve faster. The ratio of mannitol to crospovidone can be about 15:1, alternatively about 13:1 alternatively about 10:1.

The personal health care composition can comprise a lubricant. Non-limiting examples of lubricants can include sodium stearyl fumarate, magnesium stearate, calcium stearate, zinc stearate, stearic acid, glyceryl behenate, hydrogenated vegetable oils, talc, polyethylene glycol, mineral oil, and combinations thereof. Suitable levels of lubricant are from about 0.05% to about 5% lubricant, by weight of the composition, alternatively from about 0.1% to about 3%, alternatively from about 0.25% to about 1.5%, alternatively from about 0.3% to about 1%, alternatively from about 0.4% to about 0.6%.

In one aspect, the personal health care composition can be a non-Newtonian, or thixotropic, fluid, exhibiting a reduced apparent viscosity while being subjected to shear forces, but a high apparent viscosity while at rest. One advantage to a non-Newtonian fluid is that it permits application by spraying with a pump spray device or squeeze-type spray bottle immediately following the application of a shearing force (such as those created by vigorously shaking the device) but causes the sprayed material to remain at least temporarily relatively immobile on mucosal membranes or the skin. Preferably, the composition can have a very rapid rate of viscosity recovery following withdrawal of the shearing force.

The personal health care composition can comprise a rheology-modifying agent. Non-limiting examples of rheology-modifying agents can include sodium carboxymethyl cellulose, algin, carrageenans (including iota, kappa, lambda carrageenan, and combinations thereof), carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch, microcrystalline cellulose, mixtures of microcrystalline cellulose and carboxymethylcellulose sodium (commercially available as Avicel® RC-591 from FMC Corporation, Philadelphia, Pa), xanthan gum, and combinations thereof. Suitable levels of rheology-modifying agents can be from about 0.5% to about 15%, alternatively from about 1% to about 12%, alternatively from about 2% to about 6%, all by weight of the composition. Rheology-modifying agents can not only provide viscosity benefits but can also coat the nose and throat longer to sooth and/or deliver an agent of choice.

The personal health care composition may further comprise a humectant. Humectants, which can be hygroscopic materials such as glycerin, a polyethylene or other glycol, a polysaccharide, aloe, and the like, act to inhibit water loss from the composition and may add moisturizing qualities.

The personal health care composition can comprise an acidic agent. The acidic agent can comprise organic acids, pyroglutamic acid, and combinations thereof. Suitable organic acid can include, but are not limited to, ascorbic acid, monocarboxylic acids, dicarboxylic acids, tricarboxylic acids, and mixtures thereof. Specific non-limiting examples of suitable monocarboxylic, dicarboxylic, or tricarboxylic acids include salicylic, fumaric, benzoic, glutaric, lactic, citric, malonic, acetic, glycolic, malic, adipic, succinic, aspartic, phthalic, tartaric, glutamic, gluconic, and mixtures thereof. Without being limited by theory, it is believed that incorporating acids in a nasal composition can create a hostile environment for viruses without significantly irritating specific areas of the respiratory tract such as the nasal tissues. The composition can comprise from about 0.01% to about 10% organic acid, alternatively from about 0.05% to about 5%, alternatively from about 0.10% to about 2.5%, all by weight of the composition.

The personal health care composition can comprise a surfactant spreading aid such as polyoxyethylene (20) sorbitan mono-oleate, commercially sold as Polysorbate 80, Polyoxyethylene (20) sorbitan monolaurate, commercially sold as Polysorbate 20, Polyoxyl 400 stearate, polyethylene glycol, Polyethylene-polypropylene glycol, commercially sold as Poloxamer 407, and combinations thereof. The surfactants can be included in the composition at concentrations ranging from about 0.001% to about 10%, alternatively from about 0.01% to about 5%, alternatively from about 0.1% to about 3%, by weight of the composition.

Additional Components

The personal health care composition described herein may optionally comprise one or more additional components known for use in personal health care products, provided that the additional components are physically and chemically compatible with the components described herein, or do not otherwise unduly impair product stability, aesthetics, or performance. Optional components suitable for use herein include materials such as preservatives, pH adjusting agents, chelating agents, metal compounds, pharmaceutical active ingredients, vitamins, herbal ingredients, sweeteners, sensates, flavoring agents, natural honey, volatile oils, aromatic components such as camphor, eucalyptol, menthol, fragrances and the like, antioxidants, amino acids, energy boosting ingredients, sleep aids, sodium chloride, and combinations thereof. The optional components can be included in the personal health care composition at concentrations ranging from about 0.001% to about 20%, alternatively from about 0.01% to about 10%, alternatively from about 0.1% to about 5%, all by weight of the composition.

In one aspect, the personal health care composition can comprise a preservative. Preservatives can optionally be included to prevent microbial contamination. Non-limiting examples of preservatives can include benzalkonium chloride, chlorhexidine gluconate, phenyl ethyl alcohol, phenoxyethanol, benzyl alcohol, sorbic acid, thimerosal, phenylmercuric acetate, methylparaben, propylparaben, butylparaben, chlorobutanol, and mixtures thereof.

In one aspect, the personal health care composition can comprise a pH adjusting agent. Non-limiting examples of pH adjusting agents can include sodium bicarbonate, sodium phosphate, sodium hydroxide, ammonium hydroxide, sodium stannate, triethanolamine, sodium citrate, disodium succinate, and mixtures thereof. Optional pH adjusting agents can be included in the composition to adjust the pH to a value of from about 2 to about 8, alternatively from about 2 to about 5. If present, the pH adjusting agents are generally included at concentrations ranging from about 0.01 to about 5.0%, by weight of the composition.

In one aspect, the personal health care composition can comprise a chelating agent. Non-limiting examples of suitable optional chelating agents can include phytic acid, disodium and calcium salts of ethylene diamine tetraacetic acid (EDTA), tetrasodium EDTA, sodium hexametaphosphate (SHMP), di(hydroxyethyl)glycine, 8-hydroxyquinoline, and mixtures thereof. The chelating agents can be included at concentrations ranging from about 0.001% to 10%, preferably from about 0.005% to about 5%, more preferably from about 0.01% to about 2%, by weight of the composition.

The personal health care composition can comprise a metal compound. Metal compounds suitable for use herein include those metal compounds containing a metal ion selected from the group consisting of manganese (Mn), silver (Ag), zinc (Zn), tin (Sn), iron (Fe), copper (Cu), aluminum (Al), nickel (Ni), cobalt (Co), and mixtures thereof. Non-limiting examples of a metal compound suitable for use herein include zinc acetate, zinc chloride, zinc ascorbate, zinc gluconate, zinc pidolate, zinc succinate, zinc sulphate, zinc edetate, and mixtures thereof. Zinc acetate is the most preferred metal compound.

When the personal health care composition comprises a metal compound containing a zinc ion, it is believed that the zinc ion provides for antiviral properties. Zinc ions have been shown to be both antiviral and antibacterial. They are believed to inhibit cleavage of rhinovirus polypeptides, preventing replication and formation of infective virions. Zinc ions reduce the ability of rhinoviruses to penetrate cell membranes, partly by lowering expression of intercellular adhesion molecule ICAM. Zinc ions have also been shown to stimulate T-cell lyphocytes, including production of the natural antiviral, interferon-gamma They stabilize cell plasma membranes, protecting cells from cytotoxic agents, and preventing cell leakage. Furthermore, it is known that metal ions such as iron, silver, copper, and zinc can provide antiviral properties for the prevention and treatment of cold and influenza-like symptoms. The concentration of the metal compound in the personal health care compositions can range from about 0.001% to about 20%, alternatively from about 0.01% to about 10%, alternatively from about 0.05% to about 5%, alternatively from about 0.1% to about 2%, alternatively from 0.2% to about 1%, all by weight of the composition.

Non-limiting examples of pharmaceutical active ingredients can include menthol; anesthetics such as benzocaine and lidocaine; decongestants such as phenylephrine, pseudoephedrine, xylometazoline, and oxymetazoline; antihistamines such as doxylamine, diphenhydramine, loratadine, and cetirizine; expectorants such as guaifenesin, ambroxol, and bromhexine; pain relievers such as acetaminophen (APAP), ibuprofen, ketoprofen, diclofenac, naproxen, and aspirin; antitussives such as dextromethorphan, codeine, chlophedianol, and levodropropizine; the free and addition salts thereof; and combinations thereof. Pharmaceutical active ingredients can be present at a level from about 0.01% to about 25%, alternatively from about 0.05% to about 15%, alternatively from about 0.1% to about 10%, from about 1% to about 5%, all by weight of the composition. In one aspect, the personal healthcare composition can comprise at least one aptamer as disclosed herein and one or more pharmaceutical active ingredients to provide relief of one or more symptoms and inhibit rhinovirus binding.

Non-limiting examples of vitamins can include Vitamin A, Vitamin C, Vitamin D2, Vitamin D3, Vitamin E, Vitamin K1, Vitamin K3, Vitamin B1, vitamin B3, folic acid, Vitamin B12, Vitamin B3, Vitamin B7, and combinations thereof. In some aspects, the composition can comprise from about 0.1% to about 10% vitamins, alternatively from about 1% to about 8%, alternatively from about 2% to about 6%, all by weight of the composition.

Non-limiting examples of herbal ingredients can include rosemary (leaf), ginger, lemon balm, green tea, holy basil, oregano, thyme, ashwagandha, bacopa, chamomile, valerian, rosemary, turmeric, grapeseed, blueberry, coffee, curcumin, elderberry, marshmallow root, ivy leaf, black tea, white tea, oolong tea, green tea, and combinations thereof. In some aspects, the herbal ingredient can be whole herbs or plant parts, extracts, powders, concentrates, or combinations thereof. In some aspects, the composition can comprise from about 0.1% to about 10% herbal ingredients, alternatively from about 1% to about 8%, alternatively from about 2% to about 6%, all by weight of the composition.

In one aspect, the sweetener can be selected from the group comprising sugar alcohols, synthetic sweeteners, high intensity natural sweeteners, and combinations thereof.

Non-limiting examples of nutritive sweeteners can include sucrose, dextrose, glucose, fructose, lactose, tagatose, maltose, trehalose, high fructose corn syrup, and combinations thereof. Nutritive sweeteners can be present in an amount from about 1% to about 99%, by weight of the composition, alternatively from about 4% to about 95%, alternatively from about 10% to about 70%, alternatively from about 15% to about 60%, alternatively from about 25% to about 50%, in another example about 35% to about 45%.

Non-limiting examples of sugar alcohols can include xylitol, sorbitol, mannitol, maltitol, lactitol, isomalt, erythritol, and combinations thereof. Sugar alcohols can be present in an amount from about 5% to about 70%, by weight of the composition, alternatively from about 10% to about 60%, alternatively from about 15% to about 55%, alternatively from about 25% to about 50%, alternatively from about 30% to about 45%.

Non-limiting examples of synthetic sweeteners can include aspartame, acesulfame potassium, alitame, sodium saccharin, sucralose, neotame, cyclamate, and combinations thereof. Synthetic sweeteners can be present in an amount from about 0.01% to about 10%, by weight of the composition, alternatively from about 0.05% to about 5%, alternatively about 0.1% to about 3%, alternatively from about 0.2% to about 1%, alternatively from about 0.1% to about 0.5%.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. High intensity natural sweeteners can be present in an amount from about 0.01% to about 10% by weight of the composition, alternatively about 0.05% to about 5%, alternatively from about 0.1% to about 3%, alternatively from about 0.5% to about 1%.

The personal health care composition can comprise a flavoring system comprising sensates, flavoring agents, salivating agents, and combinations thereof.

The personal health care composition can comprise a sensate. Non-limiting examples of sensates can include cooling sensates, warming sensates, tingling sensates, and combinations thereof. Sensates can deliver sensory signals to the mouth, throat, nasal, and/or sinus passages so that the personal health care composition may be perceived by the user as immediately acting to alleviate an ailment and/or to provide a soothing sensation.

Non-limiting examples of cooling sensates can include WS-23 (2-Isopropyl-N,2,3-trimethylbutyramide), WS-3 (N-ethyl-p-menthane-3-carboxamide), WS-30 (1-glyceryl-p-menthane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (ethyl 3-(p-menthane-3-carboxamido) acetate), menthol, levomenthol, 1-menthone glycerol ketal (sold as Frescolat® MGA by Symrise, Holzminden, Germany), (–)-Menthyl lactate (sold as Frescolat® ML by Symrise, Holzminden, Germany), (–)-Menthoxypropane-1,2-diol (sold as Coolact® 10 by Vantage Specialty Ingredients, Inc., Warren, NJ), 3-(1-menthoxy)-2-methylpropane-1,2-diol, (–)-Isopulegol (sold as Coolact P® by Takasago International, Tokyo, Japan), cis & trans p-Menthane-3,8-diols (sold Coolact® 38D by Takasago International), menthyl pyrrolidone carboxylate (sold as Questice® by Givaudan Active Beauty, Verbuer, Switzerland), (1R,3R,4S)-3-menthyl-3,6-dioxaheptanoate (available from Firmenich, Geneva, Switzerland), (1R,2S,5R)-3-menthyl methoxyacetate (available from Firmenich), (1R,2S,5R)-3-menthyl 3,6,9-trioxadecanoate (available from Firmenich), (1R,2S,5R)-menthyl 11-hydroxy-3,6,9-trioxaundecanoate (available from Firmenich), (1R,2S,5R)-3-menthyl (2-hydroxyethoxy)

acetate (available from Firmenich), Icilin also known as AG-3-5 (chemical name 1-(2-hydroxyphenyl)-4-(3-nitrophenyl)-3,6-dihydropyrimidin-2-one), 4-methyl-3-(1-pyrrolidinyl)-2[5H]-furanone, Peppermint oil, Spearmint oil, L-Monomenthyl succinate, L-monomenthyl glutarate, 2-1-menthoxyethanol (Coolact® 5), 3-1-Menthoxy propane-1, 2-diol (sold as TK10 by Takasago International), N-(4-cyanomethylphenyl)-p-menthanecarboxamide (sold as Evercool™ 180 by Givaudan), and combinations thereof. Cooling sensates can be present from about 0.001% to about 1%, by weight of the composition, alternatively from about 0.01% to about 0.5%, alternatively from about 0.02% to about 0.25%, alternatively from about 0.03% to about 0.10%.

Non-limiting examples of warming sensates can include vanillyl alcohol n-butyl ether (sold as TK-1000 by Takasago International), Heatenol™ (available from Sensient Pharmaceutical, St. Louis, MO), Optaheat (sold by Symrise, Holzminden, Germany), ginger extract, capsicum tincture, cinnamon, capsaicin, curry, Isobutavan, Nonivamide, vanillyl butyl ether (commercially available as Hotact® VBE), piperine, and combinations thereof. Warming sensates can be present from about 0.005% to about 2%, by weight of the composition, alternatively from about 0.01% to about 1%, and alternatively from about 0.1% to about 0.5%. Non-limiting examples of flavoring agents can include natural flavoring agents, artificial flavoring agents, artificial extracts, natural extracts and combination thereof. Non-limiting examples of flavoring agents can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, apricot, anethole, ginger, jack fruit, star fruit, blueberry, fruit punch, lemon grass, banana, strawberry banana, grape, blue raspberry, lemon lime, wintergreen mint, bubble gum, tart honey lemon, green apple, apple, tangerine, grapefruit, kiwi, pear, tangerine, tangerine lime, menthol, and combinations thereof. Flavoring agents can be present from about 0.05% to about 10%, by weight of the compo- Also described herein is a method of providing one or more health benefits comprising administering a personal health care composition as described herein comprising at least one aptamer as disclosed herein to a subject in need thereof, wherein the aptamer has a binding affinity for ICAM-1. Non-limiting examples of the one or more health benefits can include providing a physical barrier for rhinovirus to not bind and enter cells, thereby helping to stop a cold caused by rhinovirus from forming, reducing the severity and/or duration of a cold caused by rhinovirus, reducing the chances of getting a cold, and combinations thereof.

EXAMPLES

The following examples illustrate non-limiting examples of the invention described herein. The exemplified personal health care compositions can be prepared by conventional formulation and mixing techniques. It will be appreciated that other modifications of the personal health care compositions within the skill of those in the formulation art can be undertaken without departing from the spirit and scope of this invention. The following are non-limiting examples of personal health care compositions described herein.

Oral Composition Examples

| Throat Spray | | |
|---|---|---|
| | Ex. 1 (Wt %) | Ex. 2 (Wt %) |
| Benzocaine | 5.0 | 0 |
| Menthol | 1.0 | 1.0 |
| Glycerin | 17.0 | 17.0 |
| Flavoring system | 0.15 | 0.15 |
| Propylene Glycol | 65.0 | 65.0 |
| Ethyl Alcohol 95% | 7.99 | 7.99 |
| Saccharin Sodium | 0.13 | 0.13 |
| Sucralose | 0.18 | 0.18 |
| Color | 0.005 | 0.005 |
| Aptamer | 0.001-1.0 | 0.001-1.0 |
| Water | Q.S. | Q.S. |

| Orally Dissolving Tablet Formula | | | | | |
|---|---|---|---|---|---|
| | Ex. 3 (Wt %) | Ex. 4 (Wt %) | Ex. 5 (Wt %) | Ex. 6 (Wt %) | Ex. 7 (Wt %) |
| Mannitol | 59.5 | 49.5 | 39.5 | 39.5 | 39.5 |
| Sucrose | 4.0 | 4.0 | 4.0 | 4.0 | 4.0 |
| Crospovidone | 4.0 | 4.0 | 4.0 | 4.0 | 4.0 |
| ProSolv ® SMCC 90 | Q.S. | Q.S. | Q.S. | Q.S. | Q.S. |
| Diphenhydramine HCl (Active) | 0 | 12.5 | 12.5 | 12.5 | 12.5 |
| Sodium Caprate | 0 | 0 | 0 | 1.0 | 0 |
| Cetylpyridinium Chloride | 0 | 0 | 0 | 0 | 1.0 |
| Magnesium Stearate | 1.0 | 1.0 | 1.0 | 1.0 | 1.0 |
| Aptamer | 0.001-1.0 | 0.001-1.0 | 0.001-1.0 | 0.001-1.0 | 0.001-1.0 | sition, alternatively from about 0.1% to about 8%, alternatively from about 0.2% to about 6%, alternatively from about 0.4% to about 3%, alternatively from about 0.6% to about 1.5%.

Also described herein is a kit comprising the personal health care composition described herein. In one aspect, the kit can comprise a delivery device and the personal health care composition contained in the delivery device. In one aspect, the kit can optionally comprise at least one additional component, such as a supplement or a vitamin composition.

| Liquid Composition | | |
|---|---|---|
| | Ex. 8 (Wt %) | Ex. 9 (Wt %) |
| Phenylephrine HCl | 0.031 | 0 |
| Acetaminophen | 2.01 | 0 |
| Dextromethorphan | 0.06 | 0 |
| Guaifenesin | 1.24 | 0 |

-continued

Liquid Composition

| | Ex. 8 (Wt %) | Ex. 9 (Wt %) |
|---|---|---|
| Propylene glycol | 23.02 | 23.02 |
| Glycerin Solution (96%) | 8.00 | 8.00 |
| Sorbitol Solution (70%) | 13.15 | 13.15 |
| Xanthan gum | 0.15 | 0.15 |
| Sodium citrate dihydrate | 0.20 | 0.20 |
| Citric acid USP | 0.22 | 0.22 |
| Sodium benzoate | 0.10 | 0.10 |
| Saccharin sodium | 0.20 | 0.20 |
| Sucralose | 0.20 | 0.20 |
| Flavor | 0.001-0.6 | 0.001-0.6 |
| Color | 0.02 | 0.02 |
| Water | Q.S. | Q.S. |
| Aptamer | 0.001-1.0 | 0.001-1.0 |

Throat Lozenge Composition

| | Ex. 10 (Wt %) |
|---|---|
| Menthol | 0.2882 |
| Color | 0.1 |
| Ascorbic Acid | 0.26 |
| Sucrose | Q.S. |
| Liquid Glucose | 33.26 |
| Flavor | 0-0.6 |
| Aptamer | 0.001-1.0 |

Nasal Compositions

Saline Nasal Spray Composition

| | Ex. 11A (Wt %) | Ex. 11B (Wt %) |
|---|---|---|
| Water | Q.S. | Q.S. |
| Sodium Chloride | 2.0 | |
| Potassium phosphate buffer | | 1.745 |
| Aloe | 0-1.0 | |
| Sodium Bicarbonate | 0-2.0 | |
| *Eucalyptus* Oil | 0-0.3 | |
| Aptamer | 0.001-1.0 | 0.001 |

Nasal Spray Compositions

| Ingredient | Ex. 12 (Wt %) | Ex. 13 (Wt %) |
|---|---|---|
| Water | Q.S. | Q.S. |
| Avicel ™ 591 | 3 | 3 |
| Polyvinylpyrrolidone | 3 | 3 |
| Carbowax ™ PEG 1450 | 5 | 5 |
| Sodium phosphate, dibasic | 0.0975 | 0.0975 |
| Sodium phosphate, monobasic | 0.5525 | 0.5525 |
| Levomenthol | 0.027 | 0.027 |
| Eucalyptol | 0.009 | 0.009 |
| Camphor | 0.009 | 0.009 |
| Benzalkonium Chloride 50% Solution | 0.1471 | 0.1471 |
| Benzyl Alcohol | 0.35 | 0.35 |
| Disodium EDTA | 0.03 | 0.03 |
| Oxymetazoline HCl | 0.05 | 0 |
| Aptamer | 0.001-1.0 | 0.001-1.0 |

Additional Nasal Spray Compositions

| | Ex. 14 (Wt %) | Ex. 15 (Wt %) | Ex. 16 (Wt %) |
|---|---|---|---|
| Pyroglutamic Acid | 0.35 | 0.70 | 1.00 |
| Succinic Acid | 1.00 | 0.70 | 0.35 |
| Zinc Acetate Dihydrate | 0.12 | 0.012 | 0.12 |
| Polysorbate 80 | 0.05 | 0.05 | 0.05 |
| Carbopol 980 | — | — | 1.20 |
| Hydroxypropyl methyl cellulose | 1.20 | — | — |
| Poloxamer 407 | — | 15.8 | — |
| Sodium Saccharin | — | 0.025 | 0.025 |
| Sucralose | 0.025 | — | — |
| Phenyl ethyl alcohol | 0.37 | 0.37 | 0.35 |
| Sodium chloride | 0.20 | 0.20 | 0.50 |
| Camphor | — | 0.03 | — |
| Menthol | 0.02 | 0.06 | 0.02 |
| Eucalyptol | — | 0.02 | — |
| Aromatic System | 0.05 | 0.38 | 0.05 |
| Sodium Hydroxide (30%) | — | — | 0.10 |
| Disodium succinate | 1.00 | 0.50 | — |
| Water | Q.S. | Q.S. | Q.S. |
| Aptamer | 0.001-1.0 | 0.001-1.0 | 0.001-1.0 |

VI. EXAMPLES

Example 1. Aptamer Selection and Next Generation Sequence Characterization

A. Selection Strategy

One objective of this invention was to develop aptamers that would not just specifically bind to ICAM-1 receptors but would do so in a way that would inhibit the binding of virus particles to the receptor protein. The selection of aptamers against the extracellular domain of the ICAM-1 receptor alone would not necessarily be sufficient to inhibit virus binding to the same protein as aptamers are relatively small and their inhibiting footprint will be limited to the epitopes that they bind to. If the epitopes that the aptamer binds to are not involved in virus binding to the ICAM-1 receptor, they will not inhibit binding of the virus particles.

This objective was consciously incorporated into the selection strategy, first by including several rounds of positive selection against the exo-cellular domain of the ICAM-1 protein (SEQ ID NO: 214); secondly, by imposing a double positive selection such that aptamers would be enriched for binding to the ICAM-1 extra-cellular domain in the context of nasal cells; thirdly, by imposing counter selection against HEK293 cells that carry similar receptor proteins (ICAM-3 SEQ ID NO: 232 and ICAM-5 SEQ ID NO: 234; SEQ ID NO: 263); and fourthly, by performing selection channels against specific desirable and undesirable aptamer binding outcomes including, specific elution of bound aptamers from nasal cells with the addition of rhinovirus particles, inhibiting of aptamer binding to ICAM-1 cells by the pre-application of rhinovirus particles, positive selection against HEK293 cells, positive selection against the extra-cellular domain of ICAM-1, and double positive selection against the extra-cellular domain of ICAM-1 and nasal cells.

Double positive selection (extra-cellular domain of ICAM-1 and nasal cells) ensures that enriched aptamers are favored that bind to the ICAM-1 receptor as it is presented on nasal cells. If selection was only performed against the extra-cellular domain of ICAM-1, it is possible that epitopes would be present that are not present in vivo. If selection was only performed against nasal cells, it is possible that aptamers would be enriched for binding targets other than ICAM-1 on the surface of such cells.

The counter selection against HEK293 cells was implemented to drive enrichment of aptamers that bound to the N-terminus of the ICAM-1 extracellular domain HEK293 cells express other members of the ICAM receptor family, ICAM-3 and ICAM-5. These receptor proteins differ in their extracellular domain from ICAM-1 predominantly at their N-terminus. The N-terminus of the ICAM-1 receptor is the region of the extra-cellular domain that rhinovirus particles bind to. Thus, this counter selection step was included to drive aptamer selection towards those aptamers that will inhibit rhinovirus binding to nasal cells.

Finally, once the aptamer library was enriched with double positive selection against the extra-cellular domain of ICAM-1 and nasal cells, and counter selection against HEK293 cells, the enriched library was separated into aliquots and applied to several different targets, including continued double positive selection, positive selection against HEK293 cells, positive selection against the extra-cellular domain alone, selection based on rhinovirus particle elution of aptamers bound to nasal cells, and selection based on inhibiting aptamer binding to nasal cells through pre-treatment with rhinovirus particles.

Each of these selected libraries was characterized by next generation sequencing. Aptamers that exhibit higher levels of enrichment against the double positive selection, the extracellular domain selection, and either of the rhinovirus particle enabled selection processes and lower enrichment against HEK293 alone would be desirable sequences for inhibition of rhinovirus binding to nasal cells. Said aptamers were used as parent aptamers from which the aptamers as disclosed herein were truncated.

B. Growth of Human Cells

B.1. Human Nasal Epithelial Cells Growth Conditions

Primary human nasal epithelial cells (HNEpC; Promo-Cell, Catalog #C-21060) were grown in airway epithelial cell growth medium (PromoCell, Catalog #C-21160) at 37° C. and 5% $CO_2$.

B.2. Growth of HEK293 Cells

HEK293 cells purchased from ATCC (CRL-1573) were grown in Eagle's Minimum Essential Medium (EMEM)+ 10% Fetal Bovine Serum (1-BS) at 37° C. and 5% $CO_2$.

B.3. Human Rhinovirus A16 Suspension

UV inactivated HRV16 virus particles were purchased (Zeptometrix Corporation) and stored at −80° C. until use. The concentration of the virus particles (VPs) was calculated to be 98,700 vp/mL.

C. Parent Aptamer Selection

C.1. Library Preparation

In the first step, a DNA library of about $10^{15}$ different sequences (TriLink BioTechnologies), containing a random region of 40 nucleotides flanked by two conserved regions, forward primer recognition sequence (5'-GGGTG-CATCGTTTACGC-3'; SEQ ID No 224) and a 3' reverse primer recognition sequence (5'-CTGCTGCTGAG-GAAGGATATGAG-3' SEQ ID No 225) (see FIG. 1), was transcribed to RNA using a mixture of 2'-fluoro pyrimidines nucleotides (2F-UTP and 2F-CTP) and natural purine nucleotides.

In brief, about 1.66 nmoles of single stranded DNA were amplified in 390×50 jut PCR reactions for 4 cycles using the primers Lib7_T7 Fwd primer (sequence: 5'-TAATACGACTCACTATAGGGTGCATCGTTTACGC-3', (SEQ ID No 226) with transcription starting at the first G underlined) and Lib7_T7 Rvs primer (sequence 5'-CT-CATATCCTTCCTCAGCAGCAG-3' SEQ ID No 227). The amplified DNA was purified using the Genejet PCR purification kit (Fisher Scientific, Catalog #K0701). This amplification of the ssDNA library created a dsDNA library with a T7 promoter, which was used as a template to generate a modified RNA library for selection.

Post DNA amplification, 52 µg of purified dsDNA was transcribed in 26×20 µL transcription reactions by using a mutant T7 polymerase (T7 R&DNA polymerase, Lucigen, Catalog #D7P9205K) polymerase and a mixture of rATP, rGTP and the modified nucleotides 2F-UTP and 2F-CTP. The NTPs were mixed together at a ratio of 3:1 modified to non-modified. Each reaction mixture contained 4 µL 5× T7 R&D polymerase, 1 µL NTP 3:1 mix, 2 µL DTT (0.1M), 0.7 jut T7 R&D polymerase, 1.2 jut inorganic pyrophosphatase, 0.5 jut Rnase inhibitor, and 10.6 jut DNA template. The reactions were incubated at 37° C. for 16 hours.

The transcribed library was subjected to Dnase treatment by setting up reaction mixtures consisting of 10 µL 10× Dnase buffer, 4 µL Dnase I, 66 jut Rnase free water, and 20 jut transcription reaction. The reaction mixtures were then incubated at 37° C. for 30 min, 1 µL of 0.5 M EDTA was added and mixed, further incubated at 75° C. for 10 minutes and purified using Monarch RNA cleanup kit (New England Biolabs, Catalog #T2040L).

C.2. Immobilization of ICAM-1 onto his-Pur Ni-NTA Resin

Lyophilized ICAM-1 protein (50 µg Ray-Biotech, Catalog #: 228-21751-2) with a His-tag on the C-terminus region was resuspended in 100 jut of sH₂O (final concentration of 0.5 µg/µL or 9.88 µM). The solution was aliquoted and stored at −20° C. until use. The protein sequence was:

```
                                        (SEQ ID No 228)
QTSVSPSKVILPRGGSVLVTCSTSCDQPKLLGIETPLPKKELLLPGNNR

KVYELSNVQEDSQPMCYSNCPDGQSTAKTFLTVYWTPERVELAPLPSWQ

PVGKNLTLRCQVEGGAPRANLTVVLLRGEKELKREPAVGEPAEVTTTVL

VRRDHHGANFSCRTELDLRPQGLELFENTSAPYQLQTFVLPATPPQLVS

PRVLEVDTQGTVVCSLDGLFPVSEAQVHLALGDQRLNPTVTYGNDSFSA

KASVSVTAEDEGTQRLTCAVILGNQSQETLQTVTIYSFPAPNVILTKPE

VSEGTEVTVKCEAHPRAKVTLNGVPAQPLGPRAQLLLKATPEDNGRSFS

CSATLEVAGQLIHKNQTRELRVLYGPRLDERDCPGNWTWPENSQQTPMC

QAWGNPLPELKCLKDGTFPLPIGESVTVTRDLEGTYLCRARSTQGEVTR

KVTVNVLSPRYEVDHHHHHH.
```

An aliquot of His-Pur Ni-NTA (Fisher Scientific, Catalog #PI88221) resin was transferred to a 0.6 mL tube and centrifuged at 700×g for 2 minutes. The supernatant was removed, and the resin was washed 3 times with 500 µL of PBS buffer (pH 7.4). Then, aliquots of ICAM-1 protein in 1×PBS buffer (pH 7.4) were incubated with the His-Pur Ni-NTA resin overnight at 4° C. while mixing. For selection round 1, 300 pmoles of ICAM-1 protein was immobilized onto 50 µL of resin. For subsequent rounds, 50 pmoles of ICAM-1 protein was immobilized onto 25 µL of resin. After protein immobilization, the resin was transferred to a 1 mL cartridge with a fit filter and washed with 2 mL of 1×PBS buffer. Finally, aliquots of 0.5-1 mM imidazole in 1×PBS buffer were added and incubated with the resin for 30 minutes at 4° C. to block unreacted binding sites on the resin. The resin was washed three times with 1 mL aliquots of 1×PBS buffer.

For negative selections with imidazole blocked resin, aliquots of the His-Pur Ni-NTA resin were incubated with an appropriate concentration of imidazole in 1×PBS buffer for 30 minutes to block unreacted binding sites on the resin, followed by washing with 1× selection buffer. The selection buffer used for all the examples in this application was Dulbecco's PBS buffer supplemented with calcium chloride (CaCl2, 0.9 mM), magnesium chloride (MgCl2 0.49 mM), potassium chloride (KCl, 2.67 mM), potassium phosphate monobasic (KH2PO4, 1.47 mM), sodium chloride (NaCl, 137.93 mM), and sodium phosphate dibasic (Na2HPO4, 8.06 mM).

C.3. Parent Aptamer Selection Overview

The aptamer selection was performed in fourteen selection rounds ("SR"), which are illustrated in FIG. 2. The selection rounds 1 to 5 enrich the sequences in the aptamer library that bind to ICAM-1 immobilized onto the Ni-NTA Resin. In selection rounds 6 to 9, the aptamer library was subjected to the same ICAM-1 immobilized Ni-NTA Resin procedure and the eluted aptamers were further enriched towards sequences that bind to human nasal epithelial cells (HNEpC), this is referred to as double positive selection. In selection rounds 10 to 11, counter selection against HEK293 cells and positive selections against HNEpC were performed. Selection rounds 12 to 14, illustrated in FIG. 3, break out to different selection conditions and are referred to as splits. Five different splits were performed: split A: nasal epithelial cells, split B: HEK293 cells, split C: ICAM-1 protein, split D: human rhinovirus A16 (HRV16) elution, and split E: HRV16 blocking.

C.4. Parent Aptamer Selection Process

C.4.1 Selection Round 1

The aptamer selection round 1 was completed by performing a positive selection against ICAM-1 immobilized Ni-NTA resin. The RNA library (produced as described in section C.1) was heated to 45° C. for 10 minutes and allowed to cool to room temperature for 10 minutes. Then, the prepared aptamer library was added to 300 pmol of the ICAM-1 immobilized on Ni-NTA resin (prepared as described in section C.2) and incubated with rotation at room temperature for 30 minutes. Unbound RNA was washed off the resin with 500 jut of selection buffer (pH 7.4).

The bound RNA was then eluted twice by adding aliquots of 200 jut of 6 M urea to the resin and incubating the suspension at 85° C. for 5 minutes. The recovered RNA library was collected and purified using Monarch RNA cleanup kit.

The collected aptamer library was reverse transcribed following the Protoscript II Reverse Transcriptase manufacturer's protocol. The number of reverse transcription reactions varied depending on the amount of RNA going into that specific round of selection.

Then, the reverse transcribed aptamer library was amplified by polymerase chain reaction (PCR) using a standard PCR protocol and the following amplification steps:

Step 1: 95° C.—5 minutes
Step 2: 95° C.≠10 seconds
Step 3: 56° C.—15 seconds
Step 4: 72° C.—30 seconds
Repeat steps 2 to 4 for 4 cycles
Step 5: 95° C.—10 seconds
Step 6: 59° C.—15 seconds
Step 7: 72° C.—30 seconds
Repeat steps 5 to 7 for up to 26 cycles.

The PCR amplified dsDNA aptamer library was then transcribed back into RNA and subjected to Dnase treatment using the protocols described in section C.1.

C.4.2 Selection Rounds 2 to 5

Selection rounds 2 to 5 incorporate two selection strategies: negative selection against imidazole blocked Ni-NTA resin and positive selection with ICAM-1 immobilized Ni-NTA resin (see FIG. 2). The negative selection was performed to select aptamer sequences that do not bind to the imidazole blocked Ni-NTA resin (prepared as described in Section C.2). First, an aliquot of 50 μL of imidazole blocked resin was transferred to a 1 mL cartridge fitted with a 20 μm frit and washed twice with 1 mL aliquots of selection buffer. Then, the prepared RNA library from the previous selection round was heated to 45° C. for 10 minutes and allowed to cool to room temperature for 10 minutes. The RNA library was added to the cartridge and incubated at room temperature for 30 minutes with the imidazole blocked Ni-NTA resin. Following incubation, the flow through solution was collected. Then, the cartridge was washed using an aliquot of 500 jut of selection buffer and the solution was collected. The flow through solution and column wash collections were pooled together and purified with Monarch RNA cleanup kit following manufacture protocols.

The RNA library that was obtained from the negative selection was then subjected to the positive selection, which selects for sequences that bind to ICAM-1 immobilized Ni-NTA resin (prepared as described in Section C.2). In brief, the RNA library was heated to 45° C. for 10 minutes and allowed to cool to room temperature for 10 minutes. Then, the RNA library was added to 50 pmoles of the ICAM-1 immobilized on Ni-NTA resin (prepared as described in Section C.2) and incubated with rotation at room temperature for 30 minutes. Unbound RNA was washed off the resin with aliquots of 500 jut of selection buffer. The number of washes varied depending on the selection round and the number of positive selections completed and was pre-determined by selection modelling. Then, the bound RNA library was eluted twice by adding aliquots of 200 jut of 6 M urea to the resin and incubating the suspension at 85° C. for 5 minutes. The eluted RNA library was collected and purified with the Monarch RNA cleanup kit, followed by reverse transcription, PCR amplification, transcription, and DNAse treatment as described in sections C.1 and C.4.1.

C.4.3. Selection Rounds 6 to 9

The RNA aptamer library that was enriched from selection rounds 1 to 5 was further enriched in selection rounds 6 to 9, which utilizes two selection strategies: a positive selection with ICAM-1 immobilized Ni-NTA resin and another positive selection against human nasal epithelial cells (HNEpC) that express the ICAM-1 receptor. This group of selection rounds is referred to as "double positive selection". In selection round 8, two positive selections against HNEpC were performed (i.e. "triple positive selection").

In selection rounds 6 and 7, the RNA library was resuspended in 500 jut of 1× selection buffer. The first positive selection (selecting against ICAM-1 immobilized Ni-NTA resin) started by adding the resuspended RNA to the ICAM-1 immobilized on Ni-NTA resin, followed by incubation at 37° C. for 30 minutes. The unbound RNA was discarded and the resin was washed with aliquots of 500 jut of 1× selection buffer. For the elution step, an aliquot of 200 μL of 6 M urea was added to the resin and incubated at 85° C. for 5 minutes and the elution solution was collected. The elution step was repeated and the eluants were pooled together and cleaned up using a Monarch RNA clean up kit.

The second positive selection started by preparing the HNEpC cells by aspirating the medium from the 6-well plate (~3 mL) where the cells were grown, followed by washing the cells three times with 3 mL of prewarmed 1× selection buffer. A solution of 1 mL of RNA library in 1× selection buffer was immediately applied to the washed cells and incubated for 30 minutes at 37° C. and 50 revolutions per minute (rpm). After the 30-minute incubation, the supernatant containing ~50% of the cells was collected, the cells were pelleted at 500×g for 2 minutes and washed twice with 200 jut prewarmed 1× selection buffer. The cell pellet was collected, and the bound RNA was eluted from the cells by the addition of 6 M urea, followed by incubation at 85° C. and RNA purification.

The adhered cells (i.e. remaining ~50% cells) were washed twice with 1 mL of preheated 1× selection buffer. Then, an aliquot of 1 mL of 10 mM EDTA was added and allowed to incubate with the cells at 37° C. for 15 minutes at 50 rpm. The EDTA treated cells were pelleted at 500×g for 2 minutes. Then, an aliquot of 200 jut of 6 M urea was added to the pellet and the suspension was heated to 85° C. for 5 minutes, followed by centrifugation at 13,000 rpm to recover the RNA aptamers in the supernatant. The elution step was repeated one more time, the eluants were combined, and the RNA aptamers were purified. The reverse transcription, PCR amplification, and transcription following the protocol in sections C.1 and C.4.1 was performed on the purified samples.

In selection rounds 8 and 9, the EDTA lifting of the cells was removed from the protocol and the RNA bound to the cells was eluted using 6 M urea while they were still attached to the 6-well plate. Additionally, a negative selection step was included in both rounds to remove any RNA sequences that bind to the plastic of the 6-well culture plate. For the negative selection, the RNA library was resuspended in 1 mL of 1× selection buffer, followed by heating to 37° C. for at least 10 minutes. One well in a 6-well culture plate was pre-washed twice with 1 mL of 1× selection buffer. Then, the heated RNA library was added to the well and incubated at 37° C. and 50 rpm for 30 minutes. The solution in the well was collected and brought up to 1 mL volume with selection buffer. The resulting 1 mL solution of RNA library was incubated with HNEpC, grown in a 6-well plate, at 37° C. at 50 rpm for 1 hour. The unbound RNA was removed from the cells and the cells were washed twice with 1 mL of 1× selection buffer (prewarmed to 37° C.). The bound RNA was eluted by adding 1 mL of 6 M urea and incubating the cells at 85° C. for 5 minutes. The elution step was repeated. The eluants were pooled together and the RNA was purified using the Monarch RNA clean up kit. The selected RNA was reverse transcribed, PCR amplified, transcribed and DNAse treated as previously described.

C.4.4. Selection Rounds 10 and 11

In selection rounds 10 and 11, a negative selection against HEK293 cells was introduced (see FIG. 2). HEK293 cells do not express the ICAM-1 receptor, which allows for the counterselection of sequences that bind elsewhere on the cell surface that is not ICAM-1.

The HEK293 cells were grown in a 6-well culture plate and were used at 80% confluency or greater. The cells were prepared by removing and discarding all media from the well and by washing the cells three times with 3 mL of pre-warmed 1× selection buffer. Then, the prepared RNA library was added to the cells and the library and cell solution were incubated for 1 hour at 37° C. with gentle shaking (50 rpm). After incubation, the supernatant with the unbound RNA library was removed and collected. Then, the cells were washed with 1 mL of pre-warmed 1× selection buffer and the solution was also collected. The collected RNA solutions were combined and purified with a Monarch RNA Cleanup Kit. This purified RNA library was then subjected to a positive selection round against HNEpC, following the same protocol as described on selection rounds 8 and 9 (see section C.4.3). Two positive selections were performed in selection round 10, while a single positive selection was completed in selection round 11.

C.4.5. Selection Rounds 12 to 14: Nasal Epithelial Cell Split

In the nasal epithelial cell split of selection rounds 12 to 14 (see FIG. 3), the RNA library collected from selection round 11 was further subjected to the negative selection against the HEK293 cells followed by the positive selection with the HNepC, using the protocol described in section C.4.4.

C.4.6. Selection Rounds 12 to 14: HEK293 Cell Split

In the HEK293 cell split of selection rounds 12 to 14 (see FIG. 3), the RNA library collected from selection round 11 was enriched towards sequences that bind to HEK293 cells. The protocol for this selection round followed the procedure of selection rounds 10 to 11 described in section C.4.4, excluding the selection with the HNepC.

C.4.7. Selection Rounds 12 to 14: ICAM-1 Protein Split

In the ICAM-1 split of selection rounds 12 to 14 (see FIG. 3), the RNA library collected from selection round 11 was enriched towards sequences that bind to ICAM-1 immobilized onto the Ni-NTA Resin. The protocol for this selection round followed the procedure of selection round 1 described in sections C.1 and C.4.1.

C.4.8. Selection Rounds 12 to 13: Human Rhinovirus A16 (HRV16) Elution Split

The HRV16 elution split only occurred during selection rounds 12 and 13 (see FIG. 3). The RNA library collected in selection round 11 was further enriched by a negative selection against HEK293 cells followed by a positive selection on HNepC using Human Rhinovirus A16 (HRV16) particles to elute the aptamer library. The negative selection on HEK293 cells followed the same protocol of selection rounds 10 and 11 described in section C.4.4 but excluding the selection against the HNepC.

Following the negative selection with the HEK293 cells, the collected RNA was diluted in 1× selection buffer and heated to 37° C. for 15 minutes. The HNepC cells were washed three times with 1 mL of prewarmed selection buffer and the heated RNA library was added to the cells and incubated for 1 hour at 37° C. and 50 rpm. After incubation, the unbound RNA was removed and discarded. The recovered cells were washed ten times with 1 mL of preheated 1× selection buffer. Then, a suspension of 50% (v/v) virus particles (VPs) (see Section B.3) in 1× selection buffer were mixed with the cells and incubated for 1 hour at 37° C. with 50 rpm mixing. The supernatant was collected, and the RNA was purified and reverse transcribed following the protocol described in sections C.1 and C.4.1.

C.4.9. Selection Rounds 12 and 13: HRV16 Blocking Split

The HRV16 blocking split was performed during selection rounds 12 and 13 (see FIG. 3). The RNA library of selection round 11 was further enriched by a negative selection against HEK293 cells followed by a positive selection on HNepC with HRV16 bound to the ICAM-1 receptor before exposing the cells to the RNA library. The HEK293 negative selection followed the same protocol of selection rounds 10 and 11 described in section C.4.4, excluding the selection with the HNepC.

Following the negative selection on the HEK293 cells, a suspension of 50% (v/v) virus particles (VPs) in 1× selection buffer was prepared. Then, the suspension was heated to 37° C. for 15 minutes and mixed with prewashed HNepC cells, followed by incubation for 1 hour at 37° C. and 50 rpm. After incubation, all unbound VPs were removed and discarded. Then, the RNA library recovered from the negative selection was resuspended in 1× selection buffer, added to the cells, and incubated at 37° C. for 1 hour. The supernatant containing the unbound RNA was collected, purified and reverse transcribed following the protocols described in sections C.1 and C.4.1.

D. Parent Aptamers Sequencing

After 14 selection rounds, the aptamer libraries were sequenced. In summary, the selection libraries from rounds 10 to 14 were prepared for next generation sequencing (NGS) through a two-step PCR process. In the first step, a different hex code (6 base sequence) and a portion of a universal sequencing primer was added to the 5' end of each aptamer library. In the second step, complete universal sequencing primers were added to both ends. After the second PCR step, the libraries were purified through acrylamide electrophoresis and balanced for relative quantity. These libraries were then pooled and sent to the Hospital for Sick Children in Toronto for NGS with an Illumina HiSeq 2500 instrument.

The sequencing data was tabulated and analyzed. A total of 16,116,086 sequences were analyzed and each library contained more than 200,000 sequences. The sequences from selection round 14 (nasal epithelial cell split) were sorted by copy number and named in descending order with the highest copy number sequence being named Nas.R-1. These top sequences are listed in Table 4.

The copy numbers of the top sequences of selection round 14 were determined on the libraries obtained from the other selection rounds. Finally, the frequency was computed for each sequence by dividing observed copy number by the total number of sequences observed in the particular selection library. Enrichment trajectories of the top 20 sequences in terms of frequency across different selection rounds were plotted (see FIG. 4). During the selection, these sequences were enriching at a similar rate.

E: Synthesis of the Truncated Aptamers

Suitable truncated sequences which were identified by theoretical analysis as shown below in Example 4 were synthesized as disclosed below in Example 2 A.1. The synthesized truncated sequences were tested in binding assay (Example 2A.4) to confirm binding affinity for intercellular adhesion molecule 1 (ICAM-1) and being able to reduce the binding of one or more human rhinoviruses to the intercellular adhesion molecule 1 (ICAM-1).

Example 2. Aptamer Binding Specificity

It was desired to identify aptamer sequences that bind specifically to the ICAM-1 receptor and inhibit the ability of the rhinovirus from infecting human nasal epithelial cells. The previous section, Example 1, detailed the protocol on the selection process of determining sequences that enriched in the presence ICAM-1. This section will highlight the protocols that were used to determine the sequences discovered in Example 1 that have the highest affinity and specificity towards the ICAM-1 receptor target.

Multiple strategies were implemented to determine the top sequences from selection process for RNA aptamers that bind specifically and with high affinity towards human epithelial cells (HNEpC), but not towards HEK293 cells that do not express the ICAM-1 target. The first protocol included exposing HNEpC and HEK293 cells to some of the selected aptamer sequences, followed by incubation, elution, and quantification of the concentration of aptamers that bound to each cell type. Another strategy implemented included the visualization and identification of fluorescently labeled RNA aptamers that bind to HNEpC, but do not visually bind to HEK293 cells. A final strategy included immobilizing the top RNA aptamer sequences, followed by flowing the exo-cellular domain of the ICAM-1 protein and other various proteins across the aptamer and using plasmon resonance to determine binding affinity. The following section describes in detail the strategies that are summarized above.

A. Detecting Binding Specificity and Affinity Via qPCR

A.1. Synthesis of Aptamer RNA Sequences

DNA oligos that corresponded to the RNA aptamer sense and antisense sequences plus the T7 RNA polymerase promoter were purchased (Integrated DNA Technologies). Each of the oligos were mixed at equimolar concentrations in 10 mM Tris buffer (pH 8.3) containing 50 mM KCl and 1.5 mM MgCl2, followed by incubation at 95° C. for 5 minutes. Then, the modified RNA aptamers were synthesized by transcription of the dsDNA template, followed by DNAse treatment, and purification as described in Example 1 Sections C.1 and C.4.1.

A.2. RNA Aptamers, HNepC and Hek293 Cell Preparation

The modified RNA aptamers were dissolved at a concentration of 28.2 nM in 1× selection buffer. HNepC or HEK293 cells were grown in a well of a 24-well plate at densities ranging from 70-75% (HNepC) or 90-95% (HEK293 cells) following the protocol outlined in Example 1 Sections B.1 and B.2.

A.3. qPCR Analysis Procedure

For each sample, two 20 jut qPCR reactions were prepared using the Luna qPCR universal mastermix (New England Biolabs, Catalog #M3003L), 0.2 µM of each primer (forward primer: 5'-TAATACGACTCACTATAGGGTG-CATCGTTTACGC-3' (SEQ ID No 226), reverse primer: 5'-CTCATATCCTTCCTCAGCAGCAG-3' (SEQ ID No 227), and 5 µL of the cDNA sample. qPCR reactions containing known amounts of the sense DNA template were also prepared. The PCR reactions were performed using the following conditions:

Step 1: 95° C. for 3 minutes
Step 2: 95° C. for 15 seconds
Step 3: 56° C. for 15 seconds
Step 4: 60° C. for 30 seconds
Steps 2 to 4 were repeated for 40 cycles.

The Ct values of the binding assay samples were compared to the Ct values of the known amounts of DNA samples to determine the amount of RNA that bound to the cells.

A.4. Human Nasal Epithelial and HEK293 Aptamer Binding Assay

Six of the top parent aptamer sequences (Nas.R-1, Nas.R-2, Nas.R-4, Nas.R-5, Nas.R-7 and Nas.R-8) that were identified in the selection process (Example 1) were tested for their binding specificity and affinity towards HNEpC or HEK293 cells. The RNA aptamers, HNEpC, and HEK293 cells were prepared as described in Section A.2.

Figure 5:
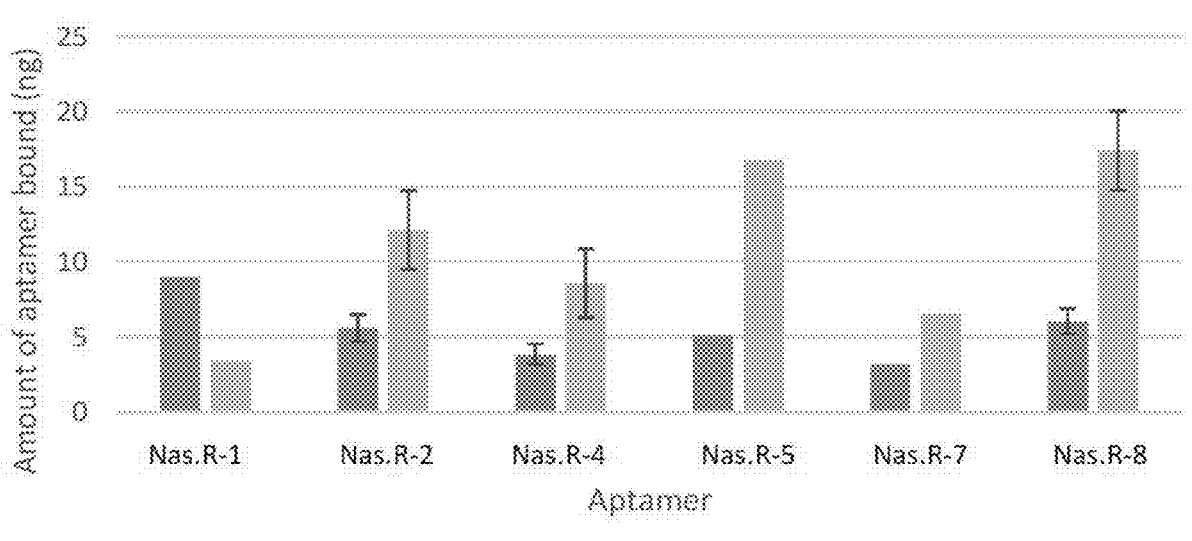
FIG. 5 illustrates the binding assay results of selected parent aptamers on Human Nasal Epithelial Cells (HNEpC) and HEK293 cells.

The aptamers were incubated with the HNEpC for 1 hour at 37° C. and 5% CO2 with gentle shaking every 15 minutes. The unbound RNA was removed and the cells were washed four times with 150 tit of 1× selection buffer prewarmed at 37° C. To elute the bound RNA aptamers, aliquots of 200 tit of 6 M urea were added to the cells, followed by incubation at 85° C. for 5 minutes. The elution step was repeated, the eluants were combined, and the RNA aptamers were purified using a Monarch RNA clean up kit following the manufacture's protocol. Each RNA sample was reverse transcribed in a 20 µL M-MµLV (New England Biolabs, M0253L) reverse transcriptase reaction following the manufacturer's protocol. The reverse transcribed sequences were quantified using qPCR analysis following the protocol described in section A.3. The same procedure was followed for the HEK293 cells. The results are illustrated in FIG. 5. For aptamers Nas.R-2, Nas.R-4, Nas.R-5, Nas.R-7, and Nas.R-8, the binding affinity towards HNepC was higher than for HEK293 cells.

A.5. HNEpC and RH-30 Aptamer Binding Assay: Truncated Vs Parent Deoxyribonucleotide Sequences The binding assay was repeated using four of the top parent deoxyribonucleotide aptamer sequences (Nas.D-2, Nas.D-4, Nas.D-5 and Nas.D-8) that were identified to be highly effective in the binding assay (Example 2, A.4). DNA was chosen for these experiments to show that both RNA and DNA example aptamers work in the present invention. Further, by changing the oligonucleotides to a DNA form stability of the oligonucleotides was improved, and costs were reduced The parent aptamers (SEQ ID NO: 102; SEQ ID NO: 104, SEQ ID NO: 105, and SEQ ID NO: 108) were tested for their binding specificity and affinity towards Human Nasal Epithelial Cells (HNEpC) or a Rhabdomyosarcoma cell line (RH-30) cells and compared to the truncated aptamer sequences (SEQ ID NO: 242, SEQ ID NO: 244, SEQ ID NO: 245 and SEQ ID NO: 246). Fluorescein amidite (FAM)-conjugated DNA aptamers were incubated at 500 nM onto cells cultured in 24-well plates for 4 hours at 37° C. in 5% $CO_2$. At specific timepoints (0.5 h, 1 h, 2 h, 4 h), the cell media was aspirated, and the wells were washed three times with 1× selection buffer. To elute and lyse the cells, 200 ul of 6M urea was applied to the well and incubated at 37° C. for 5 minutes. The urea-aptamer solution was transferred and measured in a 96-well microplate reader at 495 nm absorbance. Samples were measured in triplicate. FIGS. 23 to 26 show the results.

Figure 23:
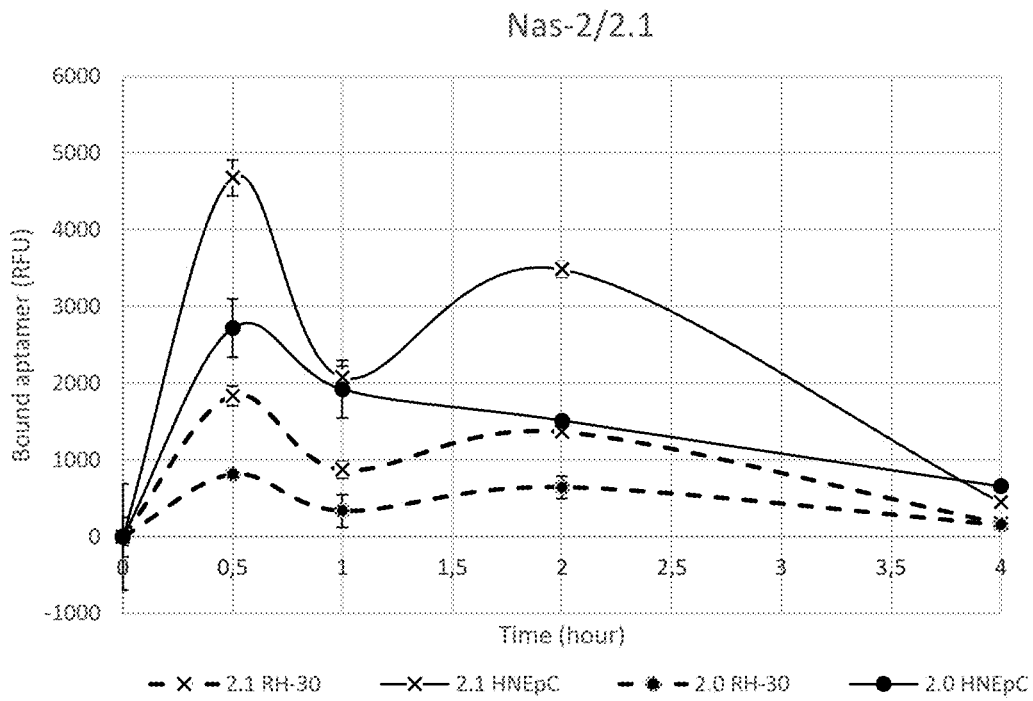
FIG. 23 shows the binding of truncated aptamer of SEQ ID NO. 242 (designated 2.1) compared to the parent aptamer sequence SEQ ID NO. 102 (designated 2.0).

As shown in FIG. 23 the binding of the truncated aptamer Nas.D-2.1a (SEQ ID NO: 242) shows a higher binding affinity (nearly 5000 RFU) compared to the parent aptamer Nas.D-2 (SEQ ID NO:102) showing nearly 3000 RFU on HNEpC after 0.5 hours. Binding to RH-30 cells shows the same result, namely a higher binding affinity of the truncated aptamer compared to the parent oligonucleotide, wherein the absolute numbers of aptamers bound to HNEpC is higher than those bound to RH-30 cells. It can be further seen that the truncated aptamer Nas.D-2.1a (SEQ ID NO: 242) shows a second binding peak after 2 hours.

Figure 24:
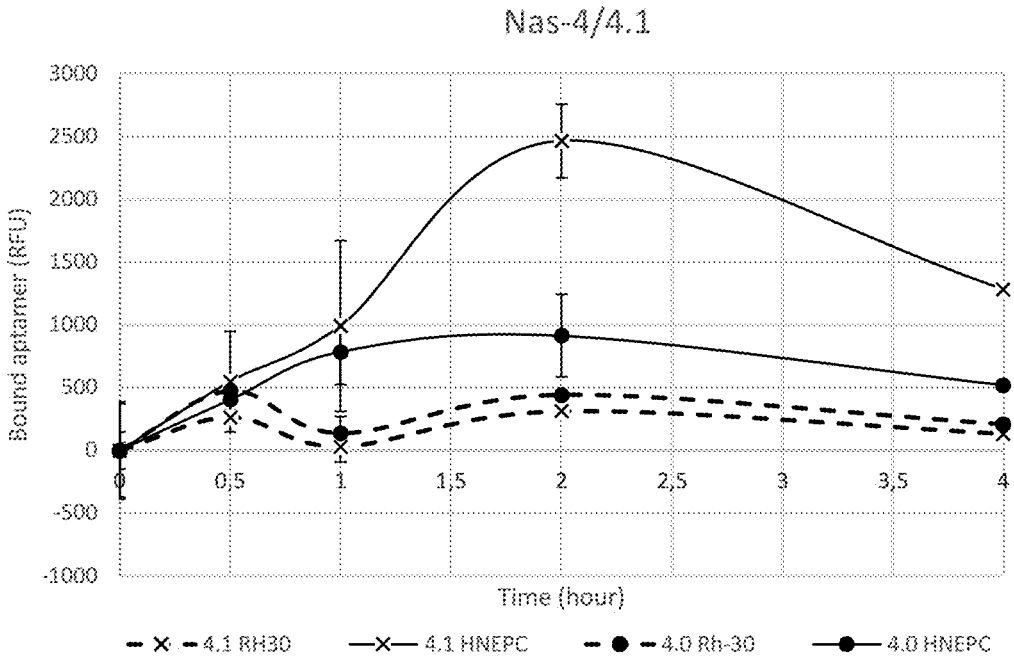
FIG. 24 shows the binding of truncated aptamer of SEQ ID NO. 244 (designated 4.1) compared to the parent aptamer sequence SEQ ID NO. 104 (designated 4.0).

FIG. 24 shows the binding of the truncated aptamer Nas.D-4.1 (SEQ ID NO: 244) compared to the parent aptamer Nas.D-4 (SEQ ID NO:104) on HNEpC and RH-30 cells. Maximal binding can be seen after 2 hours, wherein the absolute number of the truncated sequence bound to HNEpC is 2.5 times of the number of the parent aptamer bound. Binding to RH-30 cells is similar for both aptamers, truncated sequence (SEQ ID NO: 244) and parent sequence (SEQ ID NO: 104) and below 500 RFU.

Figure 25:
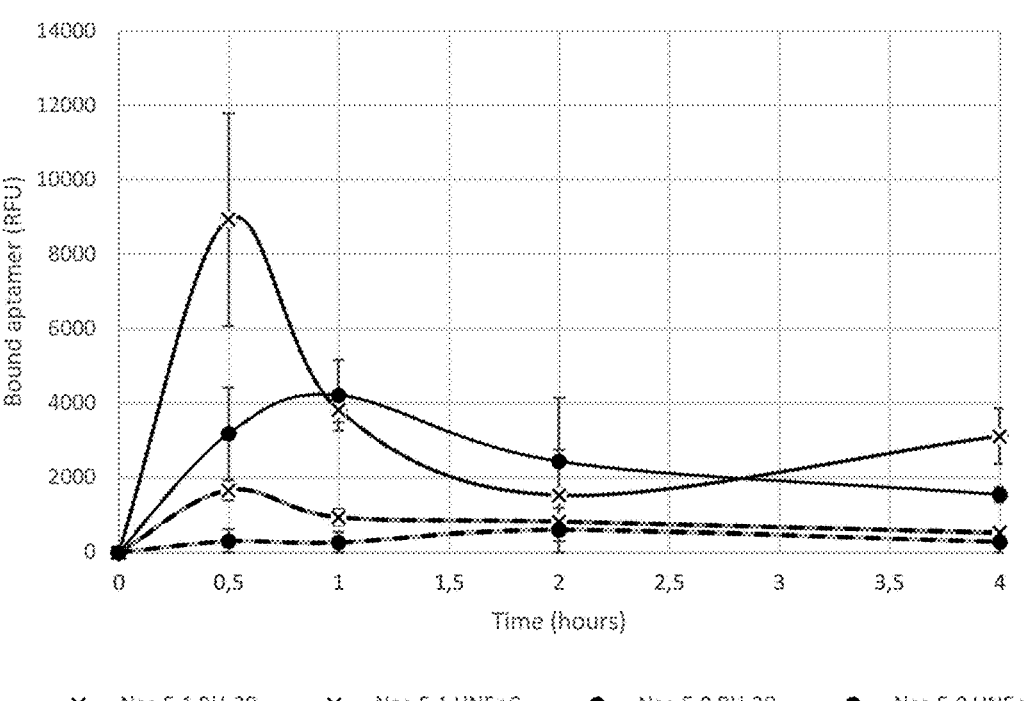
FIG. 25 shows the binding of truncated aptamer of SEQ ID NO. 245 (designated 5.1) compared to the parent aptamer sequence SEQ ID NO. 105 (designated 5.0).

Maximal binding of the truncated sequence Nas.D-5 (SEQ ID NO: 245) can be observed after 0.5 hours, wherein more than 2 times of the truncated aptamers bound to HNEpC compared to the parent aptamer. Binding to RH-30 cells was hardly detectable (FIG. 25).

Figure 26:
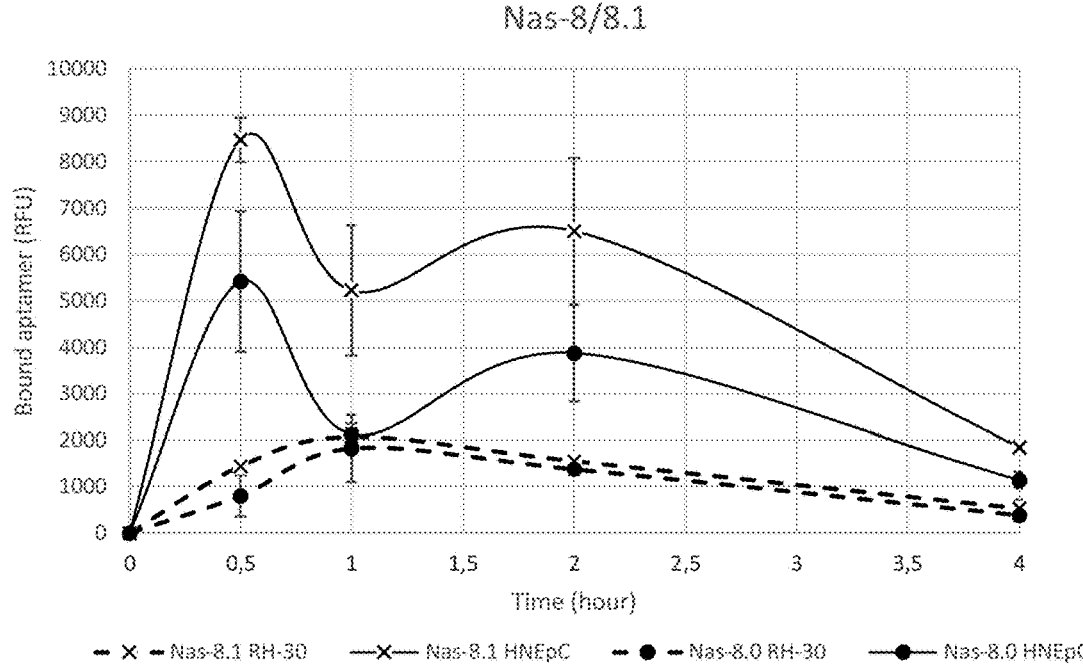
FIG. 26 shows the binding of truncated aptamer of SEQ ID NO. 246 (designated 8.1) compared to the parent aptamer sequence SEQ ID NO. 108 (designated 8.0.)

Binding profile of Nas.D-8.1 (SEQ ID NO: 246) to HNEpC shows again two peaks of maximal binding after 0.5 hours and 2 hours. The absolute number of bound oligonucleotides of the truncated aptamer (SEQ ID NO: 246) is again higher than the number of bound oligonucleotides of the parent sequence (SEQ ID NO: 108). Binding to RH-30 cells is worse and shows its maximum after 1 hour for both aptamers (FIG. 26).

B.1. Visualizing Aptamer Bound to ICAM-1 on HNEpC and HEK293 by Fluorescence

B.1.1. Preparation of Fluorescently Tagged RNA Aptamers

Modified RNA aptamer Nas.R-4 with a spacer (AAACAAACAAAC; SEQ ID No 235) and a sense binding sequence (GUAUGGCGGUCUCCAACAGG; SEQ ID No 236)

at the 3' end was synthesized, as previously described in section A.1.

(SEQ ID No 229)
5'-GGGUGCAUCGUUUACGCGCAACAUAAAAAUUUAAAGUGCUCAGUUGUCAAUCUAUGACUG
CUGCUGAGGAAGGAUAUGAG AAACAAACAAAC GUAUGGCGGUCUCCAACAGG-3'.

The sense binding sequence was added to anneal to a 6-FAM labelled fluorescent antisense oligonucleotide. Before each binding assay, the NAS-FAM antisense oligonucleotide (5' 6-FAM/CCTGTT GGAGACCGCCATAC-3' (SEQ ID No 230)) was mixed with the modified RNA aptamer at equimolar concentrations in 1× selection buffer, followed by incubation at 37° C. for 15 minutes.

B.1.2. HNepC and Hek293 Cell Preparation

HNepC and HEK293 cells were prepared following the procedure outlined in Section A.2 but were seeded at densities of about 50% one to two days before the assay, onto 12 mm glass coverslips (Fisher Scientific, Catalog #12-545-82) submersed in medium in wells of 24-well plates.

B.1.3. Binding of the Fluorescently Labelled Aptamers to Cells

Figures 6A, 6B, 6C, 6D:
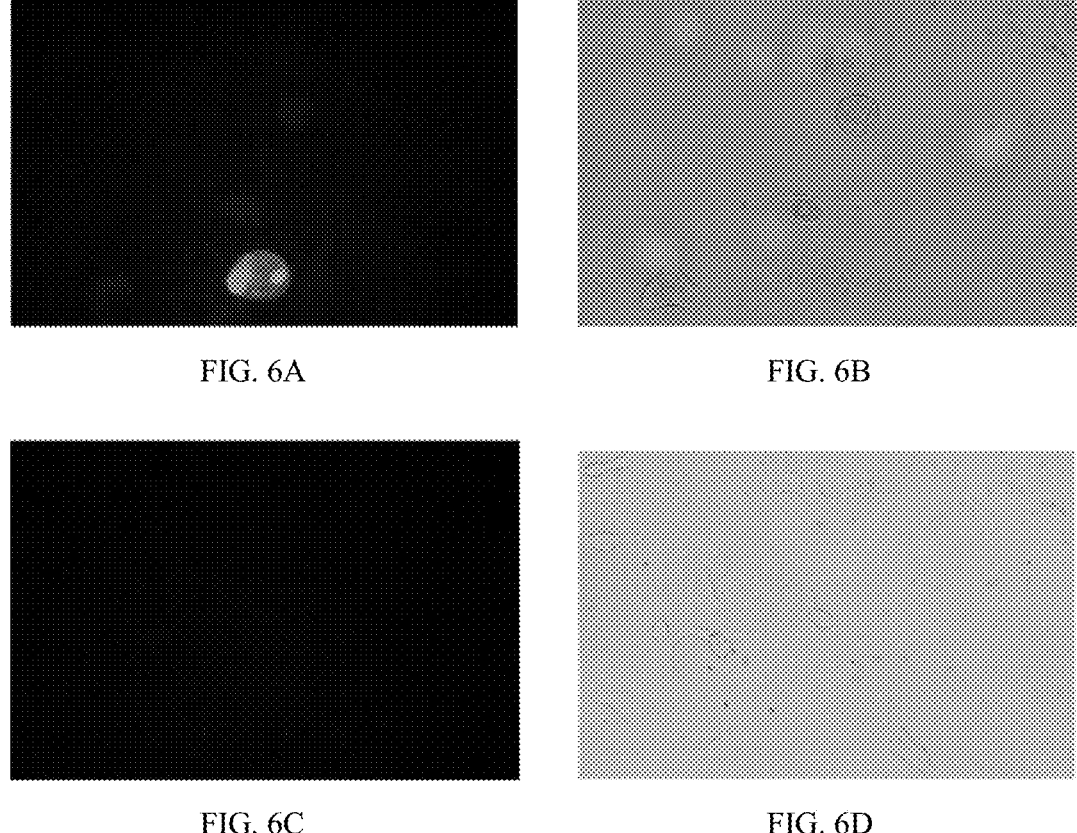

The medium was aspirated from the HNepC culture. Then, an aliquot of 150 μL of the aptamer/NAS-FAM antisense mixture, prepared as described in Section B.1, was applied to the cells, followed by incubation for 15 minutes at 37° C. and 5% $CO_2$ and with gentle agitation every 5 minutes. The unbound RNA aptamer was aspirated and the HNepC were washed three times with 150 μL of 1× selection buffer prewarmed at 37° C. The coverslip was removed and submersed into a drop of selection buffer on a glass microscope slide. Fluorescence of the cells was monitored for up to about 1 hour using a Nikon inverted fluorescent microscope and a FITC fluorescence filter. Images (see FIGS. 6A-6B) were taken using a Nikon D7500 camera at ⅓₀ sec exposure. The same process was followed using HEK293 cells (see FIGS. 6C and 6D). As illustrated in FIGS. 6A and 6B, significant fluorescence was observed when the labelled aptamers were incubated with HNepC, while no fluorescence was detected with HEK293 cells (FIGS. 6C and 6D), confirming the stronger binding affinity of the aptamers towards surface markers on the surface of HNepC (e.g. ICAM-1) compared to markers on HEK293 cells.

B.2. Visualizing Virus Inhibition on H1-HeLa Cells by a Viral Inhibition Assay Using Fluorescence RNA aptamers Nas.R-2 and Nas.R-8 that bind to ICAM-1 were tested in a viral inhibition assay compared to a negative control aptamer to demonstrate their efficacy in inhibiting Rhinovirus infection (FIGS. 7A-7H).

B.2.1. Aptamer Incubation and Viral Infection

H1-HeLa cells in RPMI+2% Fetal Bovine Serum were seeded onto 24-well plates at $1 \times 10^5$ cells/mL and 1.0 mL/well. The seed medium was aspirated, and 0.5 mL of each aptamer at 40 μM was added to the host cell wells. The host cells were incubated for 30±5 minutes at 33±2° C. with 5±3% $CO_2$. 0.5 mL of Rhinovirus Type 14 at $10^3$ $TCID_{50}$/well was added to the host cell wells without aspiration. The host cell wells were incubated 120±10 minutes at 33±2° C. with 5±3% $CO_2$. The host cells wells were aspirated and refed with 1.0 mL of each aptamer in cell culture medium and returned to incubation at 33±2° C. with 5±3% $CO_2$. After 18±1 hours, the cells were refed with 1.0 mL of a 2× concentration of aptamer in cell culture medium and incubated for 12±1 hours at 33±2° C. with 5±3% $CO_2$.

B.2.2. Quantification of Viral Inhibition

After the total incubation period the host cell plates were frozen at −60 to −90° C. overnight and then thawed at ambient temperature. The contents of each well were individually harvested and centrifuged at 2,000 rpm for 10 minutes. The supernatant of each harvest was collected, serially diluted in cell culture medium and inoculated onto fresh H1-HeLa cells to determine the quantity of infectious virus using a Tissue Culture Infectious Does 50% ($TCID_{50}$) assay. The average yield of virus from control wells with cells treated with cell culture medium only were used to calculate the viral inhibitory activity ($Log_{10}$ reduction) by each aptamer.

B.2.3. TABLE 1

| | Results | |
| --- | --- | --- |
| Aptamer | Log Viral Titer Reduction | Reduction (%) |
| Nas.R-2 | 2.08 | 99.2 |
| Nas.R-8 | 1.33 | 95.3 |

FIGS. 7A-7H shows the result as images. Red labelled cells can be seen in the fluorescent image, if the TRITC-labelled virus was able to infect the cells. The position of the cells in the fluorescent images was marked with an arrow based on the corresponding position in the brightfield image. No infection can be seen using the Nas.R-2 aptamer (FIG. 7A fluorescent image; FIG. 7B brightfield image). Nearly no infection can be seen using the Nas.R-8 aptamer (FIG. 7C fluorescent image; FIG. 7D brightfield image). The cells were infected and appear red (FIG. 7E) using the negative control aptamer (FIG. 7F brightfield image) and FIGS. 7G and H show the control cells which were not infected with the virus (FIG. 7G fluorescent image; FIG. 7H brightfield image).

C. Determination of Binding Affinity by Surface Plasmon Resonance (SPR)

C.1. Immobilization of RNA Aptamers in Gold Chips

RNA aptamers Nas.R-1, Nas.R-2, Nas.R-4, Nas.R-8, and a negative control were immobilized on the surface of gold chips. In brief, the RNA aptamer was dissolved in 1×PBS buffer supplemented with 10 mM EDTA. Then, an aliquot of 20 μL of this solution was added to 3.375 mg of 1-ethyl-3-(3-dimethylaminopropyl)carbodiimide (EDC) in a 1.5 mL tube. Next, an aliquot of 13.5 jut of cystamine-imidazole solution was added to the RNA aptamer and EDC solution, followed by mixing and centrifugation. The supernatant was removed and an additional aliquot of 54 μL of 100 μM imidazole (pH 6.0) was added. The solution was incubated at room temperature overnight. Finally, an RNA cleanup column was used to remove unincorporated cystamine and imidazole.

After conjugation of the cystamine moeities to phosphoramidate bonds at the 5' phosphate group, the aptamer was immobilized on a gold chip by depositing an aliquot of 10 nL of aptamer solution at a concentration of 10 μM onto the surface of the chip. The gold reduces the cystamine to a pair of thiols and then catalyzes the reduction reaction that results in the covalent bond between the gold surface and the thiol groups of the modified aptamers.

C.2. Surface Plasmon Resonance (SPR) Procedure

Solutions of 200 μL of ICAM-1 protein or human serum albumin were flown over the gold chip at a concentration of 250 nM and a flow rate of 50 μL/min using an Openplex Surface Plasmon Resonance System (Horiba, Kyoto, Kyoto, Japan). Thus, the association phase lasted for 4 minutes after injection and was immediately followed by the disassociation phase. The total resonance of the negative control aptamer was subtracted from the total resonance observed for each of the candidate aptamers. The result corresponds to the resonance contribution due to the binding of the protein to the aptamer. FIG. 8 shows the observed binding curves of 250 nM exogenous ICAM-1 binding to the parent aptamers Nas.R-1, Nas.R-2, Nas.R-4, and Nas.R-8. All aptamers show a binding peak after about 250 min, wherein strongest binding was observed for Nas.R-2. FIG. 9 shows the results from the comparative experiment using 250 nM human serum albumin which does not show any significant binding.

The kd (koff) value was calculated by fitting the curve to equation [1]:

$$x' \sim -kd^* x \qquad [1]$$

wherein x is the resonance due to binding and x' is the derivative of this value at each time point captured on the disassociation curve. The kd value is then used to determine the ka value by using equation [2]:

$$x' \sim ka^* Rmax^* c - (ka^* c + kd)^* x \qquad [2]$$

where Rmax is the maximum resonance due to binding observed, and c is the concentration of the injectant. Finally, the dissociation equilibrium constant kD was calculated as the ratio of kd over ka (see Table 2). The low nanomolar kD values obtained for the different aptamers confirm the strong binding affinity of such molecules towards ICAM-1 and validate the aptamer selection process described in Example 1. As used herein, "kd" refers to the dissociation rate, "ka" refers to the association rate, and "kD" refers to the dissociation equilibrium constant.

TABLE 2

| | Binding Coefficients of Nas.R-1, Nas.R-2, Nas.R-4, and Nas.R-8 on 250 nM Exogenous ICAM-1. | | | |
| --- | --- | --- | --- | --- |
| Aptamer | Nas.R-1 | Nas.R-2 | Nas.R-4 | Nas.R-8 |
| kd, [1/s] | 1.27E−02 | 1.42E−02 | 2.25E−02 | 2.63E−03 |
| ka, [1/M · s] | 1.97E+05 | 2.02E+05 | 5.08E+05 | 9.27E+04 |
| kD, [M] | 6.44E−08 | 7.02E−08 | 4.43E−08 | 2.84E−08 |

D. Aptamer Binding Specificity

As described in Example 1, in the selection process, a counter selection was performed against with HEK293 cells. HEK293 cells do not express the ICAM-1 receptor, but they do express the related receptor proteins ICAM-3 and ICAM-5. For certain sequences, for instance Nas.R-2 (SEQ ID NO: 2), substantially higher affinity to nasal cells compared to HEK293 cells was observed. Not wishing to be bound by theory, given the presence of ICAM-5 and ICAM-3 on the HEK293 cells, it stands to reason that the selected aptamers are binding to epitopes from regions of the ICAM-1 receptor protein that are different in sequence from those of the ICAM-5 or ICAM-3 receptors. FIG. 10 illustrates the sequence alignment of the extracellular domains of ICAM-1 (SEQ ID NO: 214), ICAM-3 (SEQ ID NO: 232), and ICAM-5 (SEQ ID NO: 263) and the regions that are likely to give rise to ICAM-1 specific binding are highlighted, wherein "*" marks positions that show complete conservation of amino acid identity, ":" means a high level of conservation of amino acid properties with a score greater than 0.5 on the PAM 250 matrix and "." means conservation of amino acid with weakly similar properties and a PAM 250 score less than 0.5 on the PAM matrix (Schwartz R M, Dayhoff M. Matrices for detecting distant relationships. In: Dayhoff M, editor. Atlas of Protein Sequence and Structure. supplement 3. volume 5. National Biomedical Research Foundation; Silver Spring, MD: 1978. pp. 353-358). The PAM score refers to the probability of the mutation occurring rather than a similarity of properties, so this definition is a combination of conservation of properties, and probability of occurrence. For binding of the aptamer to the proteins, clearly an epitope is completely conserved when there is complete amino acid identity in a region. However, an epitope may be also conserved when there are different amino acids but a maintenance of properties (positive or negative charge being the most important property) and an epitope is less likely to be conserved when there is only weak similarity or no similarity at all.

Rhinoviruses bind to the N-terminal Ig-like C2-type 1 domain of ICAM-1 receptor. Given the selection strategy, including elution with human rhinovirus particles, and counter selection against HEK293 cells, it is clear to one trained in the art that the mature selected aptamer library would be enriched in aptamer sequences that not only bind to the extracellular domain of the ICAM-1 receptor but do so specifically to the Ig-like C2-type 1 domain at the N-terminus.

Figure 11:
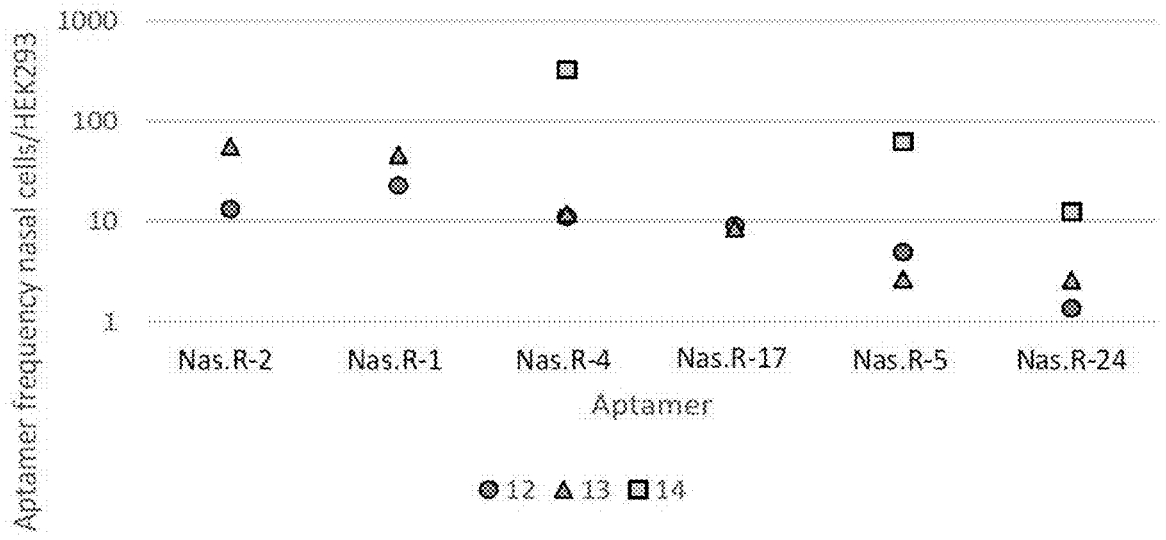
FIG. 11 illustrates examples of sequences that exhibited higher enrichment levels with nasal cells positive selection than with HEK293 cells positive selection. Data points are given after 12, 13 and 14 selections rounds.

FIG. 11 illustrates a fold comparison in aptamer frequency over the final three selection rounds applied in the aptamer selection process. The data is presented as the frequency of the individual aptamer sequence as selected against nasal cells divided by the frequency of the same sequence observed in selection against HEK293 cells. For aptamers Nas.R-2, Nas.R-1, and Nas.R-17, the sequences were not observed in the selections against HEK293 cells (the legend refers to the selection round). That is, at least in terms of the subsample of sequences observed in the next generation sequencing process, these sequences were observed at high frequency in selection round 14 against the nasal cells but not observed at all in the selections against HEK293 cells.

Figure 12:
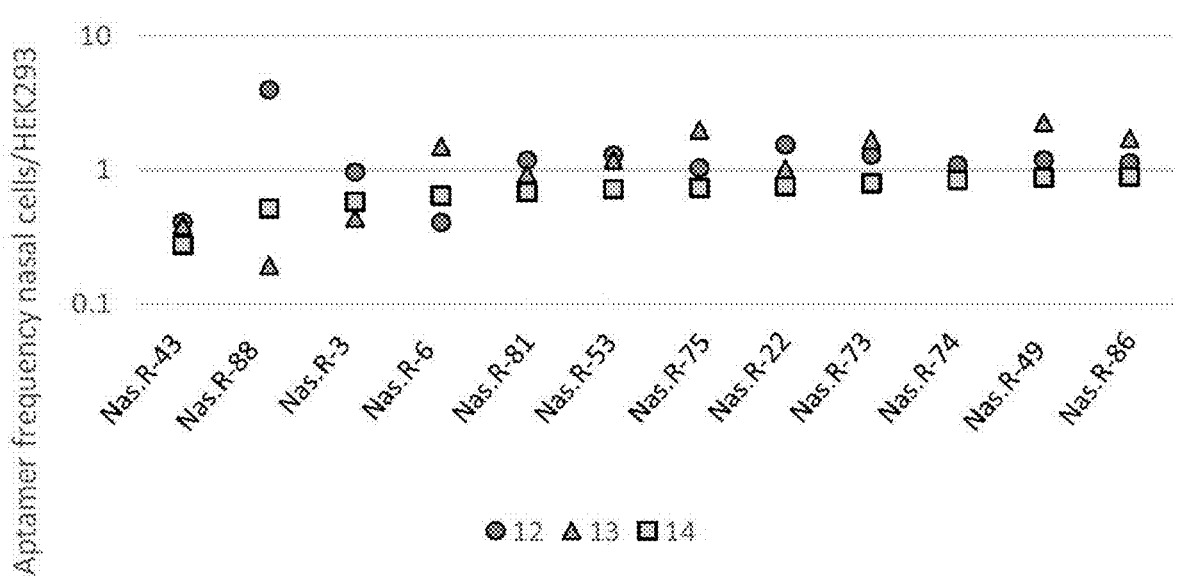
FIG. 12 illustrates examples of sequences in selection round 14 that exhibited higher enrichment levels with HEK293 positive selection than with positive selection against nasal cells. Data points are given after 12, 13 and 14 selections rounds.

Not wishing to be bound by theory, aptamers that did not exhibit enrichment in frequency when selected on nasal cells compared to HEK293 cells should be considered as aptamers that likely would not inhibit HRV binding. FIG. 12 depicts sequences that in selection round 14 all exhibited higher enrichment levels with HEK293 positive selection than with positive selection against nasal cells. These aptamers would be expected to bind to regions of the ICAM-1 receptor that are not in the N-terminus and that have considerable sequence identity with regions of ICAM-3 or ICAM-5.

B.2.4. Binding of Ribonucleotide Parent Aptamer compared to Truncated Aptamer

To compare binding specificity and affinity of the ribonucleotide aptamers, binding assays were performed with both full-length parent and truncated aptamers on Human Nasal Epithelial Cells (HNEpC) and a Rhabdomyosarcoma cell line (RH-30) as control cells. Fluorescein amidite (FAM)-conjugated RNA aptamers were incubated at 500 nM onto cells cultured in 24-well plates for 4 hours at 37° C. in 5% $CO_2$. At specific timepoints (0.5 h, 1 h, 2 h, 4 h), the cell media was aspirated, and the wells were washed three times with 1× selection buffer. To elute and lyse the cells, 200 ul of 6M urea was applied to the well and incubated at 37° C. for 5 minutes. The urea-aptamer solution was transferred and measured in a 96-well microplate reader at 495 nm absorbance. Samples were measured in triplicate and results are shown in Table 3.

B.2.3. TABLE 3

| Binding of truncated aptamers compared to corresponding full-length parent sequence. | |
| --- | --- |
| Aptamer | Surface Bound |
| Nas.R-2 | 17% |
| Nas.R-2.1a | 64% |
| Nas.R-4 | 11% |
| Nas.R-4.1 | 26% |
| Nas.R-8 | 12% |
| Nas.R-8.1 | 22% |

Table 3 shows the summary of maximum proportions bound to HNEp cells. The truncated aptamers (Nas-R.2.1/SEQ ID NO:237, Nas-R.4.1/SEQ ID NO:239 and Nas-R.8.1/SEQ ID NO:241) all exhibited significant improvement in binding versus their full-length parent sequence (SEQ ID NO:2; SEQ ID NO:4 and SEQ ID NO:8). The binding efficacy for the truncated aptamers Nas-R.4.1 (SEQ ID NO:239) and Nas-R.8.1 (SEQ ID NO:241) is more than 2 times better than that of the parent aptamers (SEQ ID NO:4; SEQ ID NO:8) and for truncated aptamer Nas-R.2.1a (SEQ ID NO:237) more than 3 times higher binding was observed compared to the parent aptamer (SEQ ID NO:2).

Example 3. Analysis of Sequences Similarity

Alignment of SEQ ID NO: 101 to SEQ ID NO: 200 was performed using the software Align X, a component of Vector NTI Advanced 11.5.4 by Invitrogen. Several groups of sequences have at least 90%, at least 70%, or at least 50% nucleotide sequence identity as illustrated in the example alignments of FIGS. 13, 14, and 15 showing the results for the DNA aptamer analysis. FIG. 13 shows the comparison of the central region of sequences of Nas.D-3 (SEQ ID NO: 103) and Nas.D-88 (SEQ ID No: 188). The shown sequences (SEQ ID No: 247 and SEQ ID No: 248) start at position 18 of the parent sequences, wherein alignment was shown in grey, non-alignment in white. FIG. 14 shows the comparison of the central region of sequences of Nas.D-45 (SEQ ID NO: 145) and Nas.D-8 (SEQ ID NO: 108) as well as the central region of sequences of Nas.D-47 (SEQ ID NO: 147) and Nas.D-78 (SEQ ID NO: 178). The shown sequences (SEQ ID NO: 249 and SEQ ID NO: 250 as well as SEQ ID NO: 251 and SEQ ID NO: 252) start at position 18 of the parent sequences, wherein alignment was shown in grey, non-alignment in white and free positions by "-". FIG. 15 shows the comparison of the central region of sequences of Nas.D-13 (SEQ ID NO: 113) and Nas.D-97 (SEQ ID NO: 197), of Nas.D-31 (SEQ ID NO: 131) and Nas.D-93 (SEQ ID NO: 193), of Nas.D-39 (SEQ ID NO: 139) and Nas.D-82 (SEQ ID NO: 182), of Nas.D-61 (Seq ID NO: 161) and Nas.D-91 (SEQ ID NO: 191), as well as the central region of sequences of Nas.D-87 (Seq ID NO: 187) and Nas.D-94 (SEQ ID NO: 194). The shown sequences (SEQ ID NO: 253 and SEQ ID NO: 254, SEQ ID NO: 255 and SEQ ID NO: 256, SEQ ID NO: 257 and SEQ ID NO: 258, SEQ ID NO: 259 and SEQ ID NO: 260 as well as SEQ ID NO: 261 and SEQ ID NO: 262) start at position 18 of the parent sequences, wherein alignment was shown in grey, non-alignment in white and free positions by "-". In these alignments, only the central variable region of the aptamers was included for simplicity. Thus, a similar binding effectivity, e.g. said of Nas.D-8 (SEQ ID NO:108), is expected for oligonucleotides with at least 50%, at least 70%, or at least 90% nucleotide sequence identity to sequences shown to bind effectively to ICAM-1.

Example 4. Motif Analysis and Predicted Secondary Structure

Aptamers bind to target molecules on the basis of the lowest free-energy shape that they form. The lowest free energy shape is a function of homology between regions within the single stranded sequence. These regions of homology fold back onto each other and thus create the secondary and tertiary shape of the aptamer that is crucial to enable binding. We characterized the core characteristics of these aptamers through a combined analysis of conserved motif sequences and their effect on the predicted structure of the whole aptamer. A motif in this context is defined as a contiguous sequence of nucleotides of a defined length. For this example, we considered each possible overlapping six nucleotide motif within the random region of each aptamer characterized.

The frequency of motifs of six nucleotides from the random regions of the top aptamers (Nas.R-1, Nas.R-2, Nas.R-4, and Nas.R-8) within all the sequences of selection round 14—Nasal Epithelial Cell Split library was determined. Then, the average motif frequency was subtracted from the frequency of each motif and this value was divided by the standard deviation of all the motifs frequencies in that selection round, resulting in a Z value for every motif. It stands to reason that sequences containing high frequency motifs also bind to the target molecule.

Figure 16:
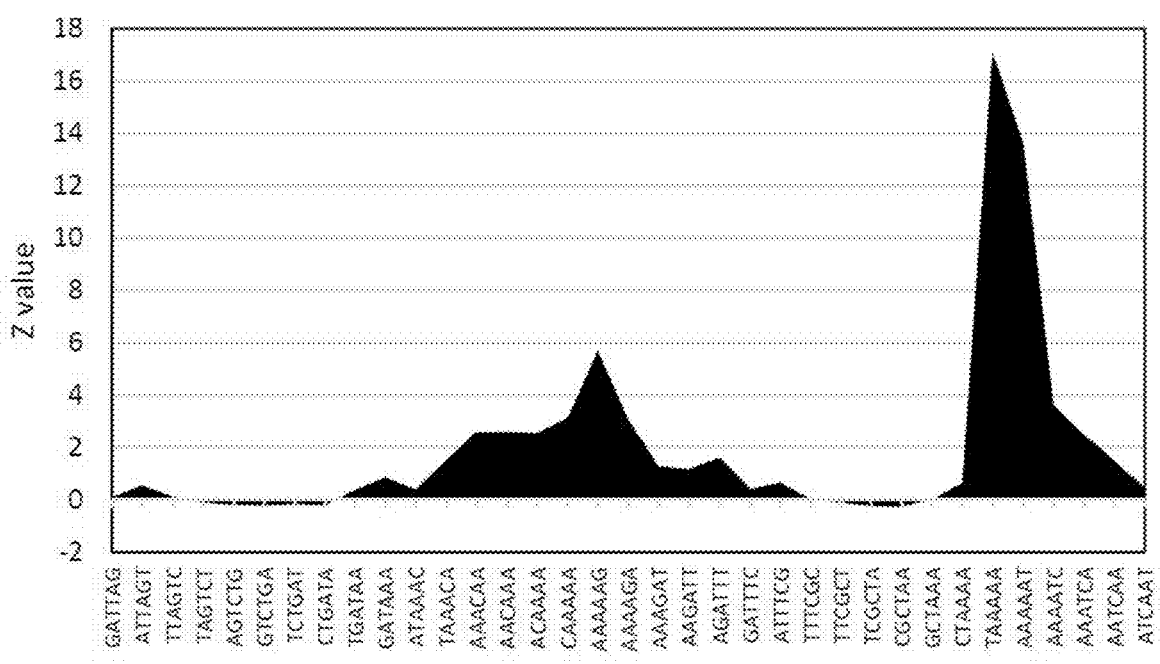
FIG. 16 illustrates the results of the motif analysis of random region of parent aptamer Nas.D-1 (SEQ ID NO: 101).

The prediction of the secondary structures of the aptamers was performed with The Vienna RNA Websuite. (http://rna.tbi.univie.ac.at//cgi-bin/RNAWebSuite/RNAfold.cgi. Gruber A R, Lorenz R, Bernhart S H, Neuböck R, Hofacker I L; Nucleic Acids Research, Volume 36, Issue suppl_2, 1 Jul. 2008, Pages W70-W74, DOI: 10.1093/nar/gkn188) and the motifs are highlighted within these structures.
A. Analysis of the Role of Conserved Motifs on Structure within the Aptamer Nas.R-1/Nas.D-1:

The results of motif analysis are presented in FIG. 16. The overlapping six nucleotide motifs comprising the random region of the aptamer are provided consecutively along the x axis in this figure. The y axis provides a statistical significance (Z value) for each motif in the library. The Z value was computed as the observed frequency of this motif in the library minus the average of the frequency for all motifs in the library and this subtractant was divided by the standard deviation of all motifs in the library to provide the Z value. Thus, a Z value of 2 represents a frequency of this motif in the library that is two standard deviations greater than the average value for all motifs.

Figure 17:
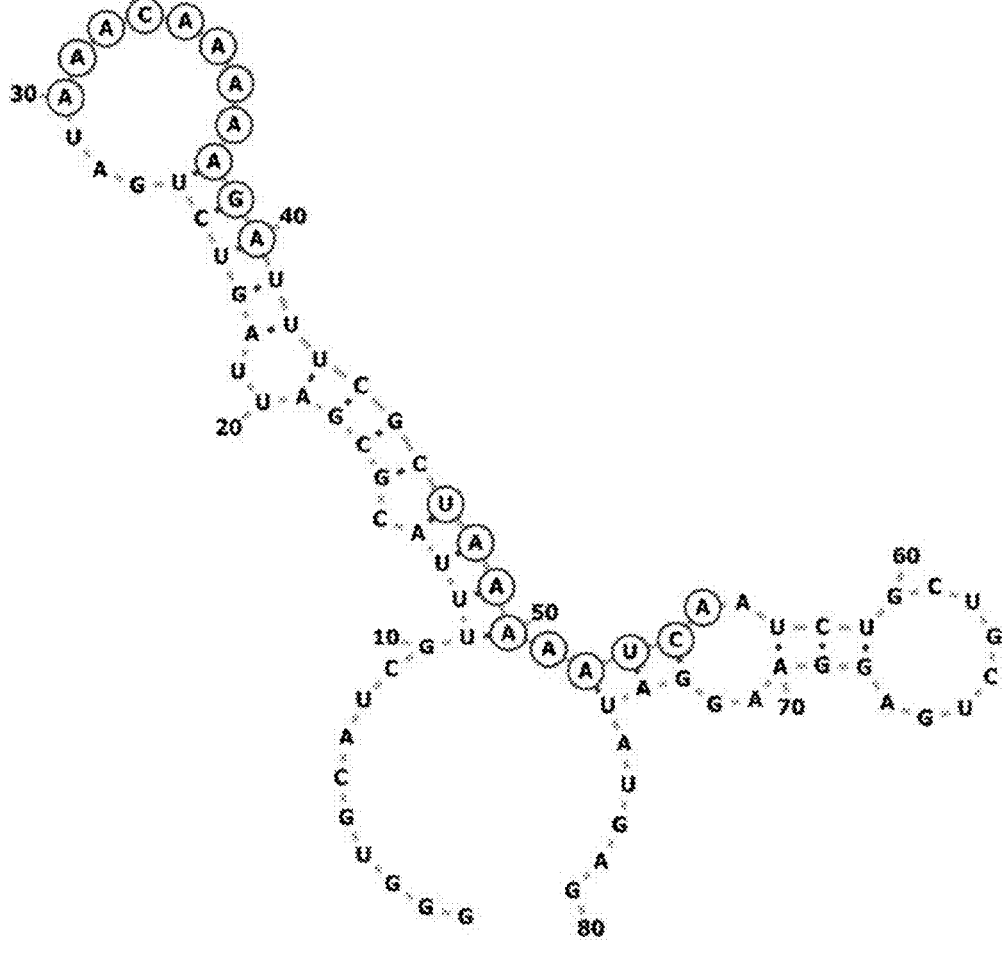
FIG. 17 illustrates the predicted secondary structures of parent aptamer Nas.R-1 (SEQ ID NO: 01) and its conserved motifs shown highlighted in circles.

The sequences AAACAAAAGA and UAAAAAUCA were conserved at a level that represented more than two standard deviations from the average. The lowest free energy predicted structure of the Nas.R-1 aptamer and the consensus sequences are shown in FIG. 17.

```
SEQ ID NO: 201:
5'-AAACAAAAGA-3'

SEQ ID NO: 202:
5'-UAAAAAUCA-3'
```

Sequences containing any of these motifs are also expected to bind to ICAM-1 and are included as parent embodiments of the present invention. The conclusions arrived at within this example regarding conserved motifs in the RNA sequence would apply to the DNA sequence as well (FIG. 16). Thus, any sequences containing the corresponding deoxyribonucleotide motif

```
SEQ ID NO: 203:
5'-AAACAAAAGA-3'

Figure 19:
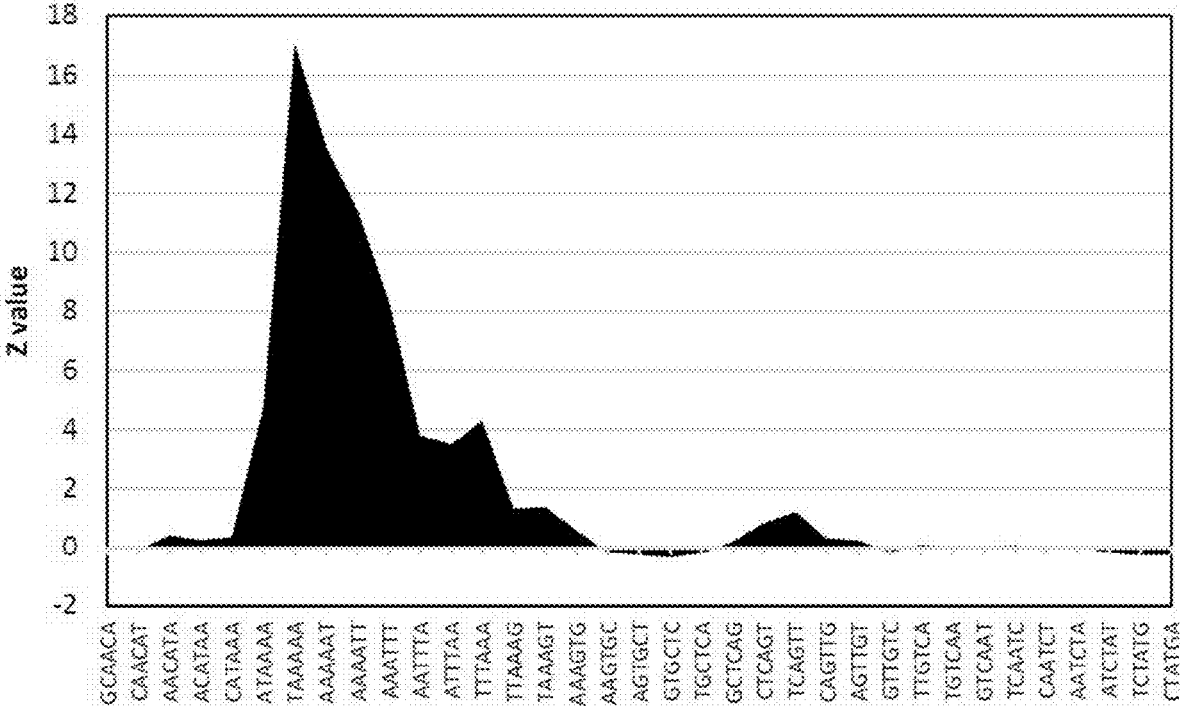
FIG. 19 illustrates the results of the motif analysis of random region of aptamer Nas.D-4 (SEQ ID NO: 104).

SEQ ID NO: 204:
5'-TAAAAATCA-3'
``` are also included as parent embodiments.
B. Analysis of the Role of Conserved Motifs on Structure within the Aptamer Nas.R-4/Nas.D-4:

The analysis of the role of conserved motifs on structure within aptamer Nas.R-4 was performed in a manner identical to that described for Nas.R-1 and the conclusions arrived at within this example regarding conserved motifs in the RNA sequence would apply to the DNA sequence as well. FIG. 19 provides a summary of the motif analysis for aptamer Nas.D-4. There is a thirteen-nucleotide motif present at a frequency that was more than two standard deviations from the overall average motif frequency in the selected libraries, namely SEQ ID NO 205: 5'-AUAAAAAUUUAAA-3' and the corresponding deoxyribonucleotide motif:

```
SEQ ID NO 206:
5'-ATAAAAATTTAAA-3'.
```

Figure 21:
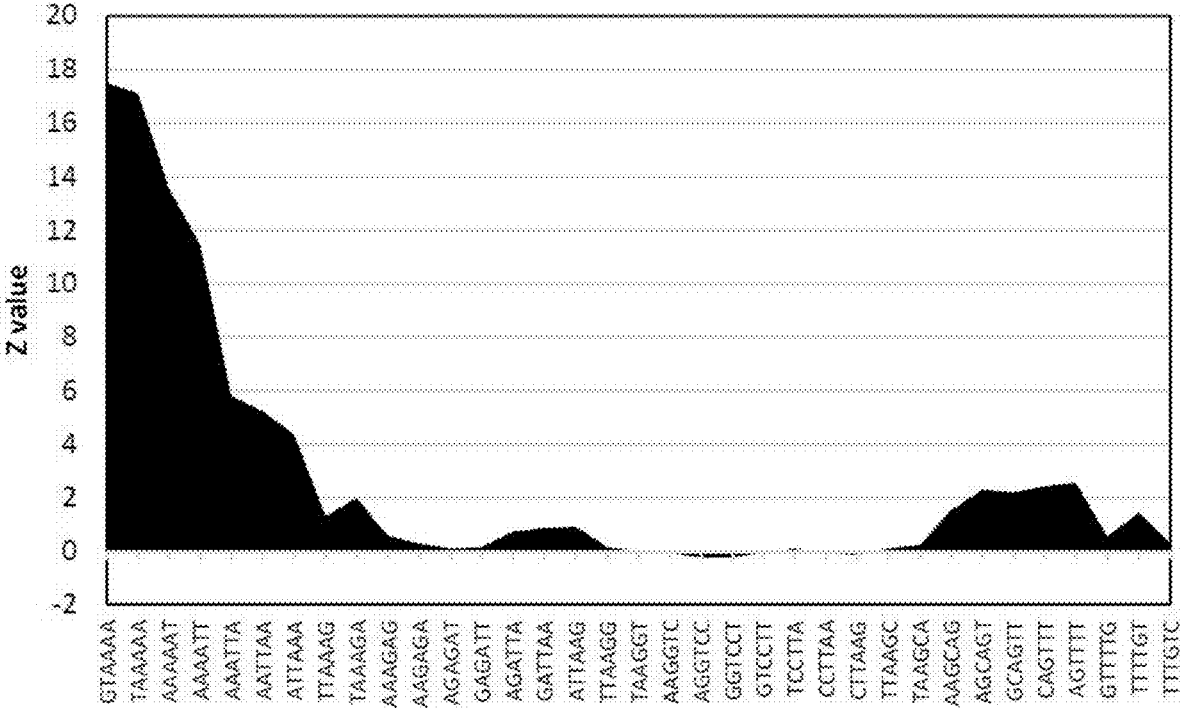
FIG. 21 illustrates the results of the motif analysis of random region of parent aptamer Nas.D-8 (SEQ ID NO: 108).

Sequences containing this motif are also expected to bind to ICAM-1 and are included as parent embodiments of the present invention.
C. Analysis of the Role of Conserved Motifs on Structure within the Aptamer Nas.R-8/Nas.D-8:

The analysis of the role of conserved motifs on structure within aptamer Nas.R-8 was performed in a manner identical to that described for Nas.R-1 and Nas.R-4. The conclusions arrived at within this example regarding conserved motifs in the RNA sequence would apply to the DNA sequence as well. FIG. 21 provides a summary of the motif analysis for aptamer Nas.D-8. There is a twelve-nucleotide motif present at a frequency that was more than two standard deviations from the overall average motif frequency in the selected libraries, namely

```
SEQ ID NO: 207:
5'-GUAAAAAUUAAA-3'
``` and the corresponding deoxyribonucleotide motif:

```
SEQ ID NO 208:
5'-GTAAAAATTAAA-3'
```

Sequences containing this motif are also expected to bind to ICAM-1 and are included as parent embodiments.

Figure 18:
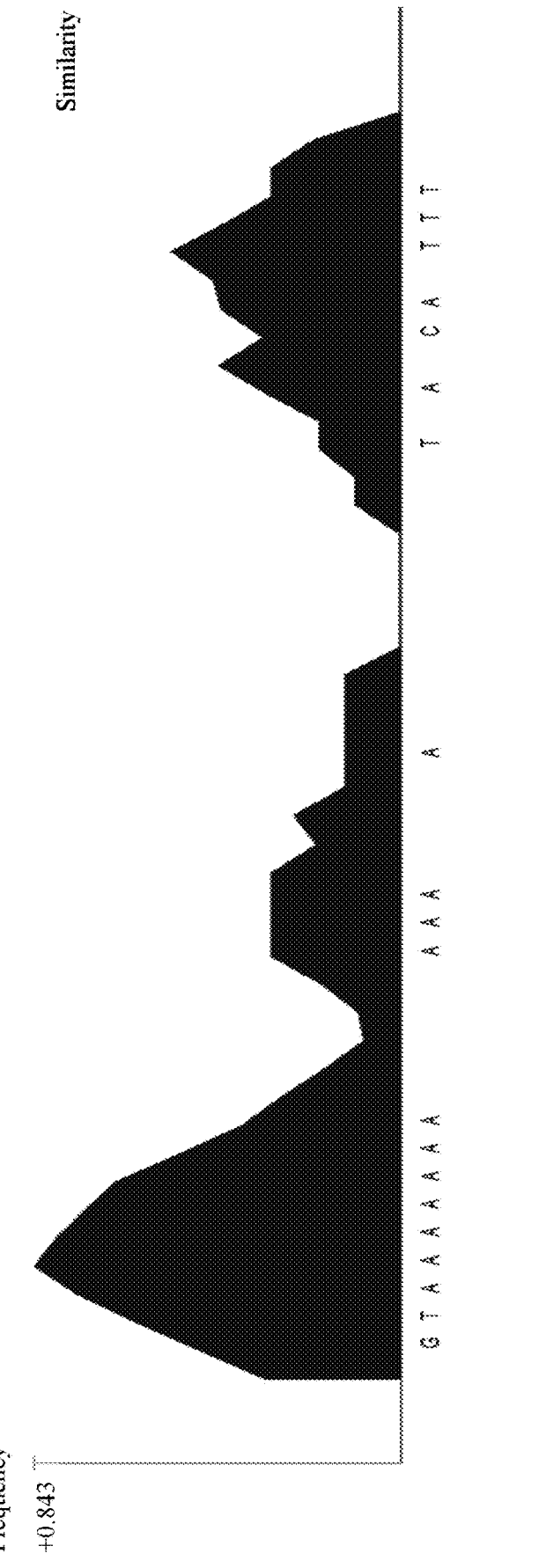
FIG. 18 illustrates the motif analysis based on motif frequency of the random region of the top 100 parent aptamers shown as DNA sequences.

D. Analysis of Common Motifs within Aptamer Library:

A search for common motifs within the top 100 sequences in terms of frequency was performed (see FIG. 18). The lead motifs identified in terms of significant deviation from random distribution were SEQ ID NO: 209 and SEQ IP NO: 210.

```
SEQ ID NO: 209:
5'-GUAAAAAAA-3'

SEQ ID NO: 210:
5'-UNAGCANUUU-3'
```

Oligonucleotides comprising the motifs SEQ ID NO: 209, SEQ ID NO: 210, or both are included as a parent embodiment of the current invention. Similarly, any sequences containing the corresponding deoxyribonucleotide motifs

```
SEQ ID NO: 211:
5'-GTAAAAAAA-3'

SEQ ID NO: 212:
5'-TNAGCANTTT-3'
``` are also expected to bind to ICAM-1 and are included as parent embodiments of the present invention.

E. Preparation of Truncated Aptamers

E.1.: Identification of Suitable Sequences for Truncation

In order to identify more effective aptamers, the oligonucleotides of SEQ ID NO: 1 to SEQ ID NO: 200 were truncated to the main effective regions which were determined by theoretical analysis. Full length parent aptamers are generally in flux among possible shapes at 37° C. The possible shapes that a single sequence can form were characterized therein and the relative proportion of each shape at a given temperature was determined with online software provided by ViennaRNA Web Services, created by the Theoretical Biology Group at the Institute for Theoretical Chemistry at the University of Vienna. Then truncated aptamers that exhibit certain of these shapes with as high a level of stability as possible were identified and synthesized as disclosed above in Example 2 A.1. If needed single nucleotide substitutions were introduced to stabilize the shape. These truncated, optimized aptamers were then all retested for binding, thus laying the basis for a hypothesis regarding the interaction between aptamer shape and function. The truncated aptamers were designed to keep all properties of the parent aptamers, in particular showing a binding affinity for intercellular adhesion molecule 1 (ICAM-1) and being able to reduce the binding of one or more human rhinoviruses to the intercellular adhesion molecule 1 (ICAM-1). Suitable truncated aptamer sequences comprised from about 30 to about 60 nucleotides from the parent aptamer sequence, and preferably comprised at least one of the conserved motifs as disclosed in SEQ ID NO: 201 to SEQ ID NO: 212. The resulting truncated sequences were preferably able to form a stable secondary structure as disclosed herein to act as aptamer able to reduce the binding of one or more human rhinoviruses to the intercellular adhesion molecule 1 (ICAM-1) over time.

Four of the top aptamer sequences Nas.D-2 (SEQ ID NO: 102), Nas.D-4 (SEQ ID NO: 104), Nas.D-5 (SEQ ID NO: 105), and Nas.D-8 (SEQ ID NO: 108)) that were identified to show high binding affinity to ICAM-1 in the binding specificity process above (Example 2) were used as example parent sequences, wherein deoxyribonucleotide aptamers were chosen for the experiments due to higher stability compared to ribonucleotide aptamers. The parent sequences were analyzed, and stable secondary structures based on the lowest free energy were visualized.

Figure 20A:
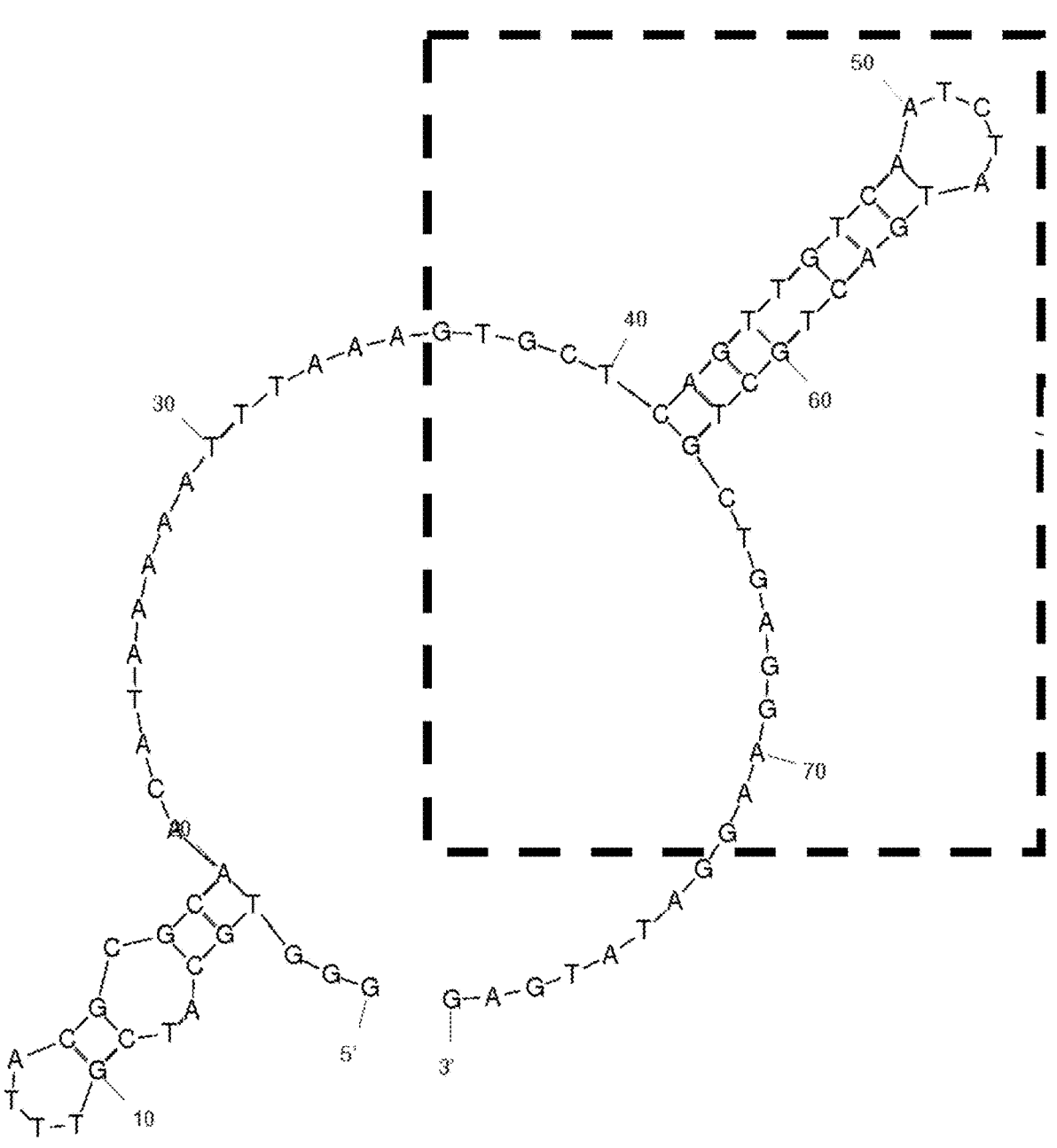
FIG. 20A illustrates the predicted secondary structure of parent aptamer Nas.D-4 (SEQ ID NO: 104).
Figures 20B, 20C:
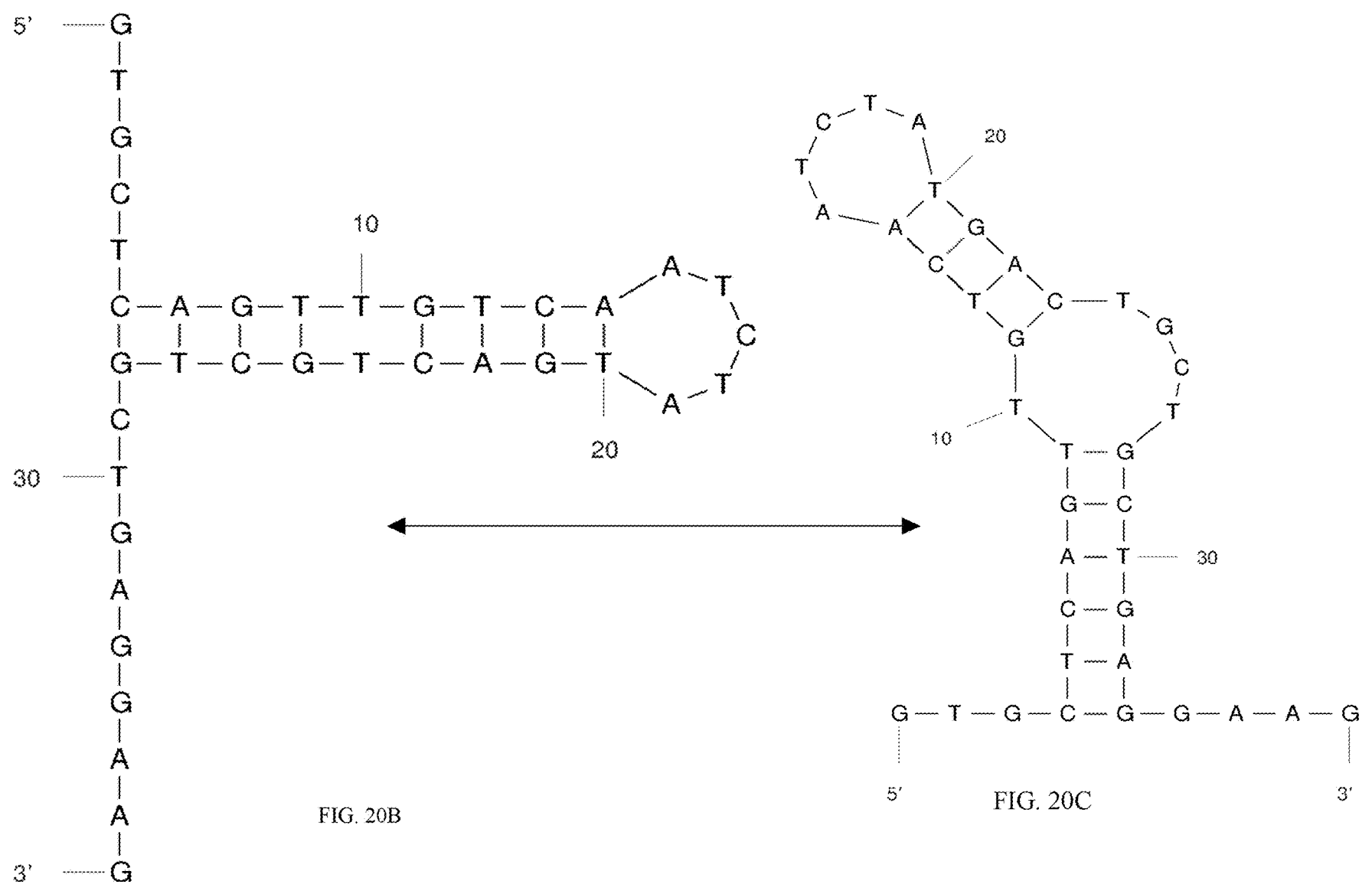

FIG. 20A shows a preferred secondary structure of the parent oligonucleotide of SEQ ID NO: 104. The central hairpin structure represents a promising binding candidate for binding to the ICAM-1 receptor. The nucleotides identified in the dashed box were identified to form the truncated aptamer sequence SEQ ID NO: 244. FIGS. 20B and 20C show that the truncated oligonucleotide of SEQ ID NO: 244 appears in two different stable secondary structures. Both secondary structures comprise a common structural concept forming a hairpin comprising a central loop of unpaired/unhybridized nucleotides 15 to 19 (counted from the 5'-end), followed by a double-stranded stem comprising 9 hybridized base pairs in the first secondary structure (FIG. 20B) and 9 hybridized base pairs divided into 4 base pairs, a second internal loop comprising 5 unpaired/unhybridized nucleotides and a second double-stranded stem comprising 6 hybridized base pairs in the second secondary structure (FIG. 20C). Both secondary structures show unpaired/unhybridized 3'- and 5-ends. Both variants of the secondary structure are stable and show a common structural concept.

Figure 22A:
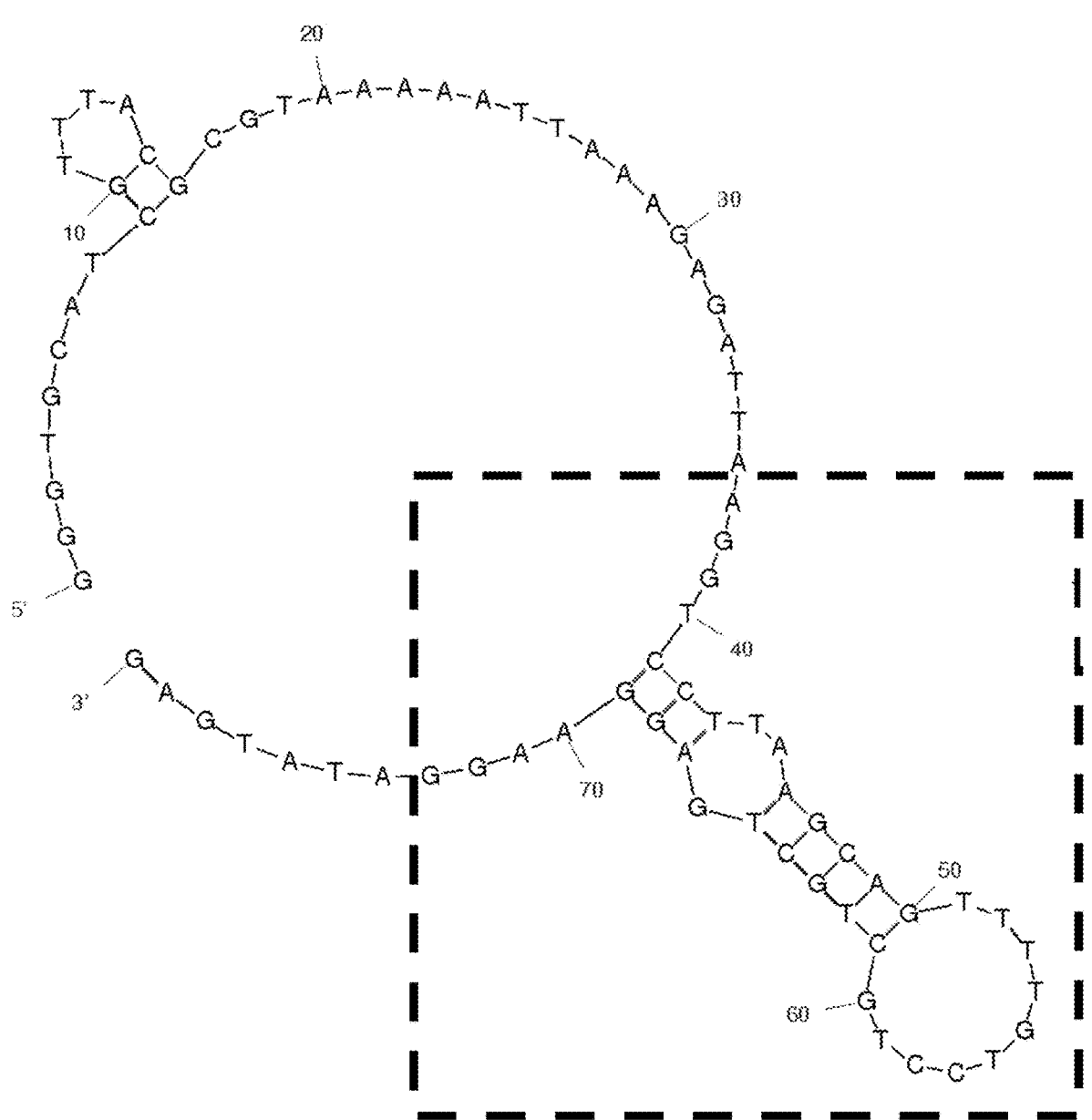
FIG. 22A illustrates the predicted secondary structure of parent aptamer Nas.D-8 (SEQ ID NO: 108).
Figure 22B:
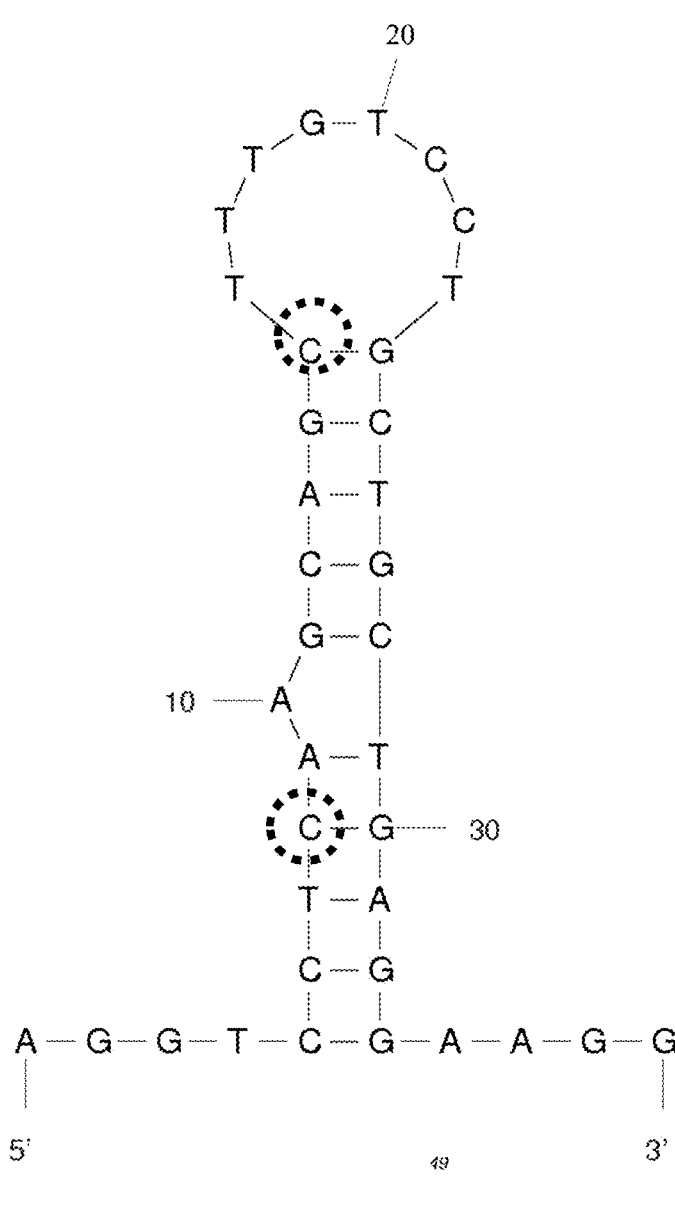
FIG. 22B shows the predicted secondary structure of an aptamer truncated from Nas.D-8 (shown within the dotted line in FIG. 22A) comprising two mutations shown in dotted circles (SEQ ID NO: 246).

FIG. 22A shows a preferred secondary structure of the parent aptamer of SEQ ID NO: 108. The hairpin structure formed near to the 3'-end (marked with the dashed box) represents a promising binding candidate for binding to the ICAM-1 receptor. The non-interesting parts of the parent sequence were truncated accordingly thereby forming the truncated aptamer of SEQ ID NO: 246. The hairpin comprises a central first loop comprising 10 unpaired/unhybridized nucleotides, a first double-stranded stem comprising 5 hybridized base pairs, a second internal loop comprising 3 unpaired/unhybridized nucleotides, a second double-stranded stem comprising 3 hybridized base pairs and an unpaired/unhybridized 3'-end and 5'-end (FIG. 22A). FIG. 22B shows the secondary structure which can be achieved with small mutations to the sequence. The central loop was diminished to 8 unpaired/unhybridized nucleotides by a T to C change at position 15 forming another G-C pair. The first double-stranded stem still comprises 5 hybridized base pairs and the second loop was diminished to only one unpaired/unhybridized nucleotide at position 10. Accordingly, a larger second double-stranded stem comprising 5 hybridized base pairs could be formed by another T to C mutation at position 8. The unpaired/unhybridized 3'-end and 5'-end remain unchanged (FIG. 22B).

F. Detailed Analysis of the Secondary Structure of Truncated Aptamers

F. 1.: Preparation of Mutated Aptamers Based on Truncated Aptamer NasD-4.1

A detailed analysis of the secondary structure motifs and their relevance for binding affinity to ICAM-1 as was performed using the NasD-4.1 truncated aptamer (SEQ ID NO: 244). The importance of the individual motifs and/or potential relevance of sequence identity was analyzed with four selection rounds against nasal cells and for binding to the ICAM-1 receptor as disclosed above under C.4.3 using the original aptamer and mutated aptamers with a mutation load of 9% on each nucleotide within the aptamer. For amplification between the selection rounds 9 nucleotides (ATCTAATAA) were added at the 5'-end and 8 nucleotides were added at the 3'-end (AAAAACCC) with a view to not disrupt the predicted secondary structure of the aptamer. The mutation events were limited to the Nas-4.1 aptamer (SEQ ID NO: 244) as shown in FIG. 20C. The libraries from all four selection rounds as well as the naïve, unselected library were analyzed by next generation sequencing (NGS). Lists of all possible single and double mutations within the 37 nucleotides were generated and the frequency of each of these mutated sequence through the selection process was extracted. The proportion of any given sequence in the library over selection rounds was considered as a measure of the efficacy of this sequence for binding to the ICAM-1 receptor. To minimize the potential effect of PCR error on the interpretation of these results the average frequency of each sequence in selection round 3 and 4 was also computed and divided by the respective frequency for that sequence in the naïve library (selection round 0). From this dividend one was subtracted to reduce this fraction to a direct indication of proportional change for each sequence ("proportion").

F.2.: Correlation of Aptamer Efficacy and Structural Motifs

It is possible to constrain the analysis of the effect of sequences on aptamer efficacy, but the reason that different sequences perform as they do is because of differences that they cause to the structure of the aptamer. These differences are manifested in the presence or absence of charge groups that interact with the ICAM-1 receptor and differences in the distance between these interactions. One can consider an analysis of all the sequences that make up a given mutation load as an examination of the sequence space at that level around the non-mutated sequence. Therefore the aptamer sequence is transferred into its structural motifs based on the code disclosed in P. Danaee et al. (*Nucleic Acids Research*, Volume 46, Issue 11, 20 Jun. 2018, Pages 5381-5394) and based on the predicted aptamer structure as disclosed herein. The transfer of the 4.1 aptamer sequence into the structural code allows comparison of the structure effects independent of aptamer nucleotide sequence.

The structural code for aptamer 4.1 is

```
5'-EEEEEEEEEESISSSSSSISSSSHHHHHSSSSIIIISSSSSSISEEE

EEEEEEE-3'
```

Figure 27A:
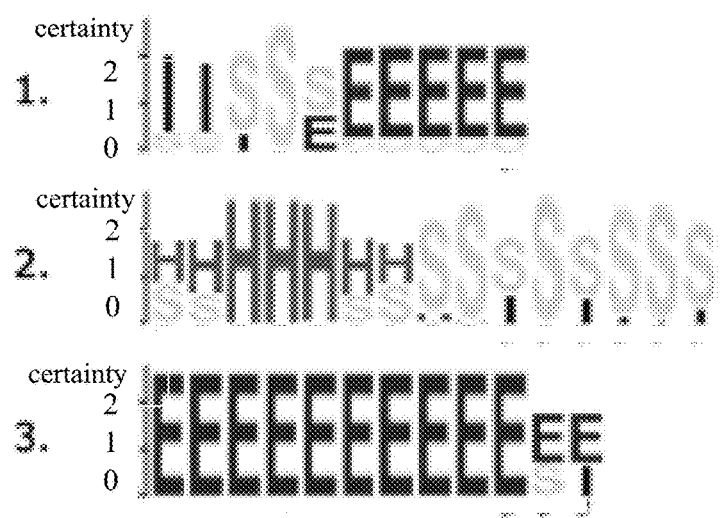
FIG. 27A shows the top three structural motifs formed in the secondary structure of the aptamers disclosed herein.
Figure 27B:
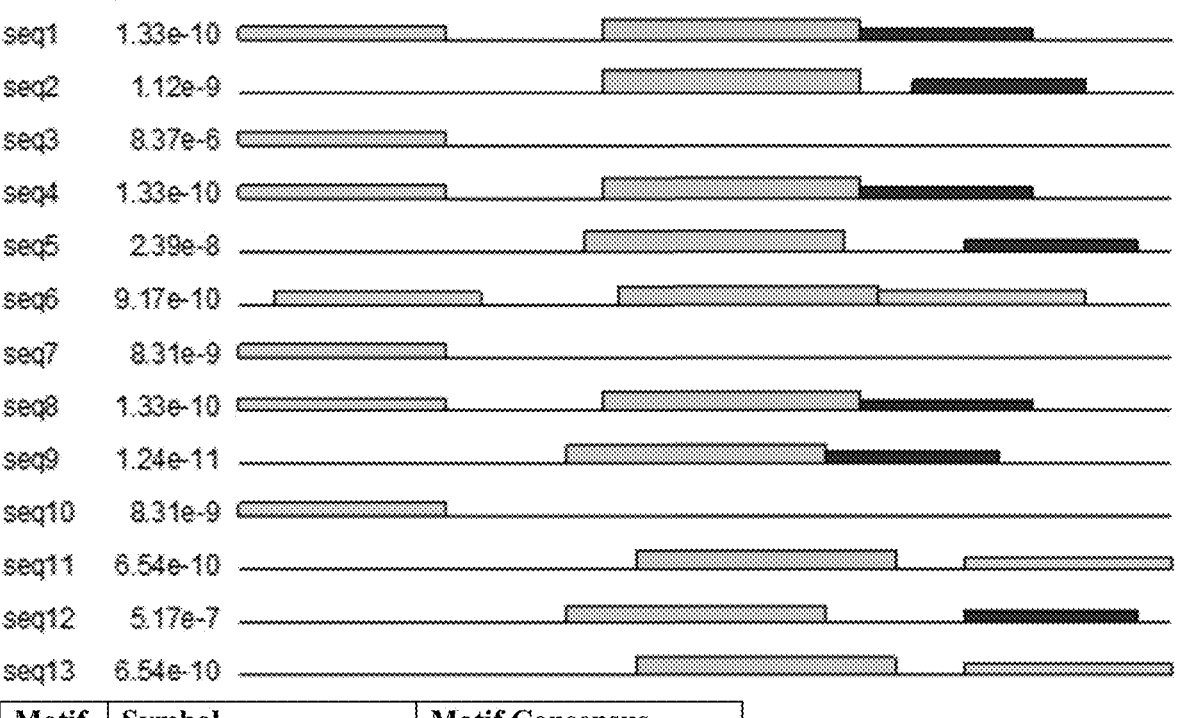
FIG. 27B shows the distribution of the motifs shown in FIG. 27A within example sequences.

Then the database of such structural information strings was evaluated for those motifs that exhibit the strongest statistical significance for favorable selection. The MEME suite of software (T. L. Bailey et al.; *Nucleic Acids Research*, 43(W1):W39-W49, 2015) was used to explore consensus motifs and their relationship to the structure codes as shown above. The top 500 double mutation sequences were compared to the bottom 500 double mutation sequences in terms of efficacy (proportion) sequences. Thereby, the structural motifs which were most consistently present in the top 500 sequences versus the bottom 500 sequences were determined. After three motifs were identified the analysis was stopped. FIG. 27A shows the results. The relative height of the structural codes is a measurement for certainty of the information, i.e. it shows how certain one is to observe a particular code at a particular position. The top motif by a large margin was $IISS^S/_EEEEEE$. This implicitly refers to a dangling end on the 3' end of the aptamer given that there is stem structure adjacent to the 5' side of the E's. Other motifs of interest are the hairpin turn at the bottom of the aptamer followed by stem structure on the 3' side, and a dangling 5' end with a length of 12 nucleotides. The distribution of these motifs within the aptamers is provided in the FIG. 27B showing examples of some of the sequences that were included in the statistically significant classes identified above. The presence of the second motif (large square grey) illustrates the need for hairpin/stem structures but that the position of these structures within the aptamer is not completely fixed. The first motif (black) is only observed on the 3' end, while the third motif (small square grey) is observed on both the 5' and 3' ends. The third motif has no implicit anchoring as it represents only a contiguous string of E's (dangling end). Where this motif ends prior to the end of the aptamer it still means that the aptamer has dangling ends all the way to the terminal nucleotide. This conclusion also applies to the first motif (black). If it appears all positions between it and the 3' end will also be dangling ends. In summary with the structural analysis three significant regions of interest in the aptamer were identified.

1.) A 3' dangling end that includes the junction between the dangling end and upstream stem structure.

2.) A stem hairpin structure whose position within the aptamer is not completely fixed 3.) A 5' dangling end.

F.3.: Correlation of Aptamer Efficacy and Structural Motifs

Figure 28:
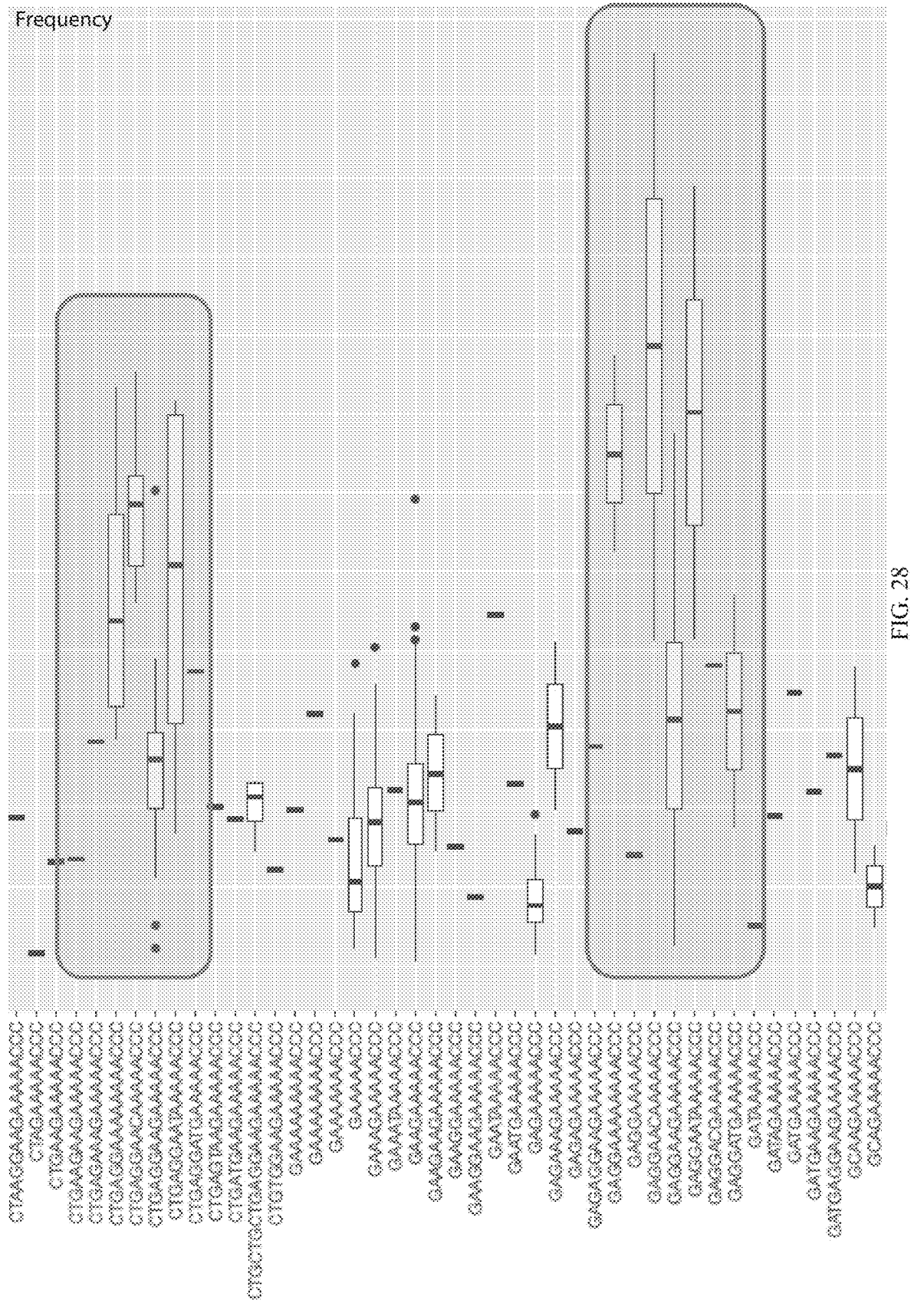
FIG. 28 shows the efficacy of aptamers comprising special sequence motifs in binding experiments.

As shown above the effective aptamers comprise both ends as dangling ends as well as an internal stem/hairpin structure. The sequences correlating to the identified motifs were analyzed and in the structural motif at the 3'-dangling end an interesting accumulation was found. In FIG. 28 a part of the graph is shown visualizing the frequency (average proportion) of the aptamers comprising said sequence. All aptamers which were found to be highly present which means highly effective comprised the motif GAGGYYZ, in the sequence at the 3'-dangling end. Aptamers having the sequence GAGGYYZ the average proportion observed was 0.23, wherein average proportion of −0.17 was observed for aptamers does not showing the motif at said location.

F.4.: Binding Analysis of Mutated Nas-4.1 Sequences

Aptamers as disclosed herein were selected to perform at 37° C. in the SELEX selection process. Further, all experiments relating to performance of aptamers executed on cells grown in culture were performed at 37° C. as well, as this was the appropriate temperature for optimal cell growth and corresponds to body temperature. However, the aptamers are intended to function on the inner surface of the nasal cavity in vivo and said nasal cells show a slightly lower average temperature of 33° C. As such it was important to ensure that the aptamers of the present invention perform at both temperatures. Accordingly, binding analysis was executed using isothermal titration calorimetry (ITC) using Nano ITC (Low Volume of TA Instruments) and following user instructions for the NasD-4.1 aptamer (SEQ ID NO: 244) at 37° C. as well as at 33° C. Specific mutations in sequence (SEQ ID NO: 264-270) were tested to analyze the impact of temperature and secondary structure. 600 nM concentration of the NasD-4.1 aptamer was injected in 11 injections of 4.88 uL each into a 100 nM concentration of ICAM-1 receptor protein in a volume of 193 uL. The same concentration of mutant aptamer was injected into buffer, as well as buffer was injected into the same amount of protein as controls. The ITC experiments were performed at 33° C. and 37° C. in potassium phosphate buffer.

The following aptamers were tested, wherein mutations are shown in bold:

NasD-4.1:

(SEQ ID NO. 244)

5'-GTG CTC AGT TGT CAA TCT ATG ACT GCT GCT GAG GAA

G-3

State 1:

(SEQ ID NO. 264)

5'-GTG GTC AGT TGT GAA TCT ATG ACT GCT GCT GAG GAA

G-3

57

```
                  -continued
State 2:
                              (SEQ ID NO. 265)
5'-GAG CTC AGT TGT CAA TCT ATG ACT GCT GCT GAG GAA G-3
State 3:
                              (SEQ ID NO. 266)
5'-GTG CTC ACT TGT CAA TCT ATG ACT GCT GCT CAG GAA G-3
State 4:
                              (SEQ ID NO. 267)
5'-GTG CTC ACT TGT CAA TCT ATG ACT GCT GCT GAG TAA G-3
State 5:
                              (SEQ ID NO. 268)
5'-GTG CTC TCT TGT CAA TCT ATG ACT GCT GGA GAG GAA G-3
State 6:
                              (SEQ ID NO. 269)
5'-GTG CTC AGT TGT CAA TCT AAG ACT GCT GCT GAG GAA G-3
State 7:
                              (SEQ ID NO. 270)
5'-GTG CTC AGT TGT CAA AGA ATG ACT GCT GCT GAG GAA

G-3
```

The measured values of the dissociation constant (kD) which represent a direct measure for the binding affinity of the mutant aptamers were compared to the original/unmutated Nas-D4.1 aptamer. The kD value is given in nM. Higher values than measured for the Nas-D 4.1 aptamer show a lower Binding Affinity of the mutant and vice versa. The results are shown in Table 4:

TABLE 4

|  | kD (nM) at 33° C. | kD (nM) at 37° C. |
|---|---|---|
| Original 4.1 | 8.86 | 11.2 |
| State 1 | 18.1 | 2.83 |
| State 2 | 10 | 102 |
| State 3 | 14.3 | 40.4 |
| State 4 | 37 | 6.39 |
| State 5 | 7.96 | 5.14 |
| State 6 | 1.27 | 18.6 |
| State 7 | 9.09 | 6.77 |

Figure 29:
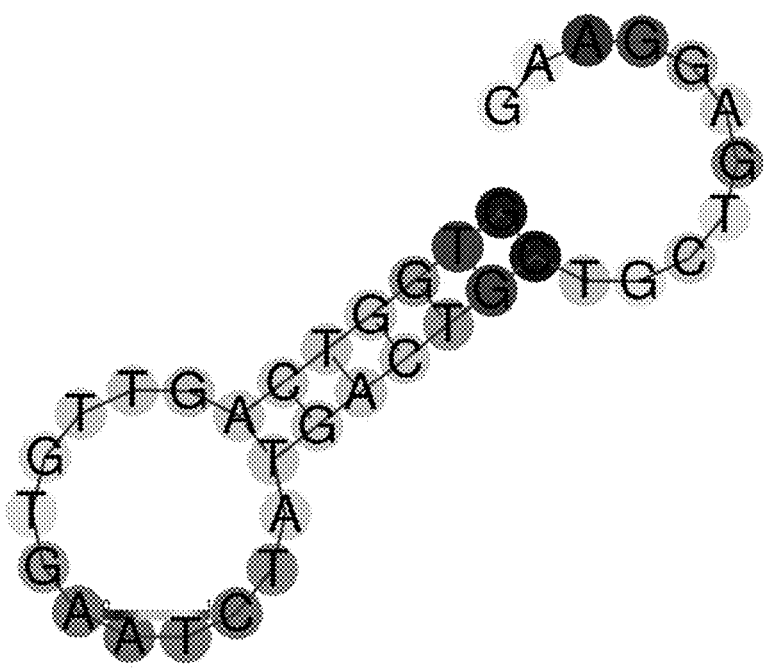
FIG. 29 shows the most likely secondary structure of mutant aptamer 4.1 of SEQ ID NO: 264 (designated State 1) at 33° C. and 37° C.
Figure 30:
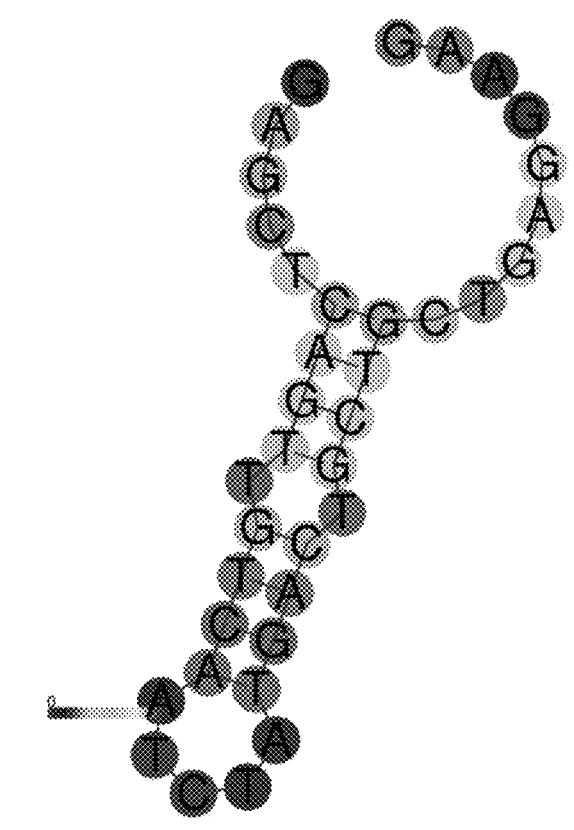
FIG. 30 shows the most likely secondary structure of mutant aptamer 4.1 of SEQ ID NO: 265 (designated State 2) at 33° C. and 37° C.

The mutation in aptamer of State 1 (SEQ ID NO. 264) is located close to the 5'-end. Structure prediction revealed that the structure is stable at both temperatures and that the GAAGYYZ motif is located at the dangling 3'-end. Predictive secondary structures were generated for all mutant aptamers at 33° C. and at 37° C. using RNAfold (http://rna.tbi.univie.ac.at/cgi-bin/RNAWebSuite/RNAfold.cgi). FIG. 29 shows the most likely secondary structure of mutant State 1, wherein the grey scale shows the likelihood of the nucleotide to be in the shown structure, with darker shades having a higher likelihood. Compared to the unmutated NasD-4.1 aptamer (SEQ ID NO. 244) no 5' dangling end was observed. This might explain the lower binding affinity of the mutant under in vivo conditions at 33° C. The mutation in aptamer of State 2 (SEQ ID NO. 265) is also located close to the 5'-end but is intended to amend the secondary structure of the aptamer compared to the control NasD-4.1 aptamer (SEQ ID NO. 244) by fixing the GAG-GYYZ motif halfway into the stem region. However, the predicted structure (FIG. 30) with maximum likelihood shows that the mutation did not alter the secondary structure

Figure 31C:
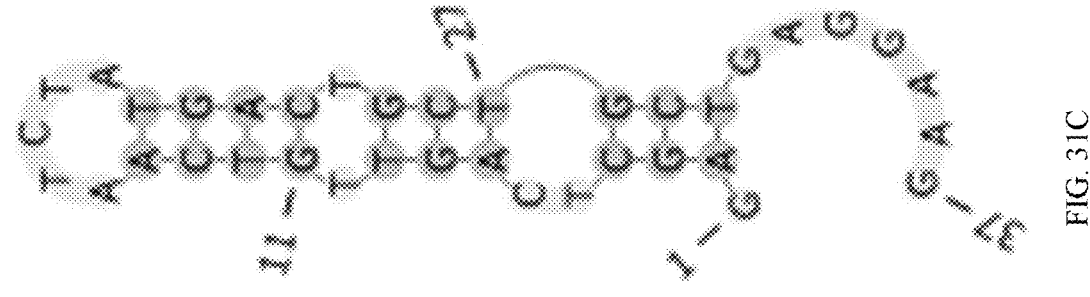
FIG. 31B shows the secondary structure formed with the secondary likelihood (designated Structure 2) and FIG. 31C shows the secondary structure formed with the third likelihood (designated Structure 3).
Figure 31B:
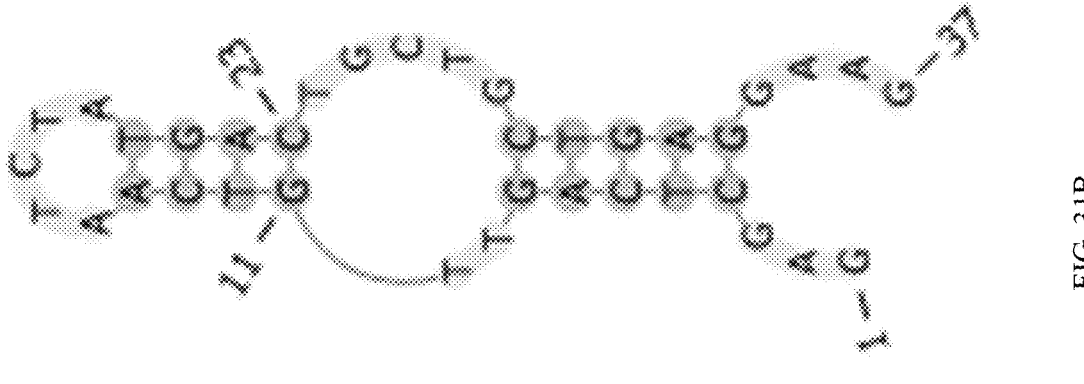
Figure 31A:
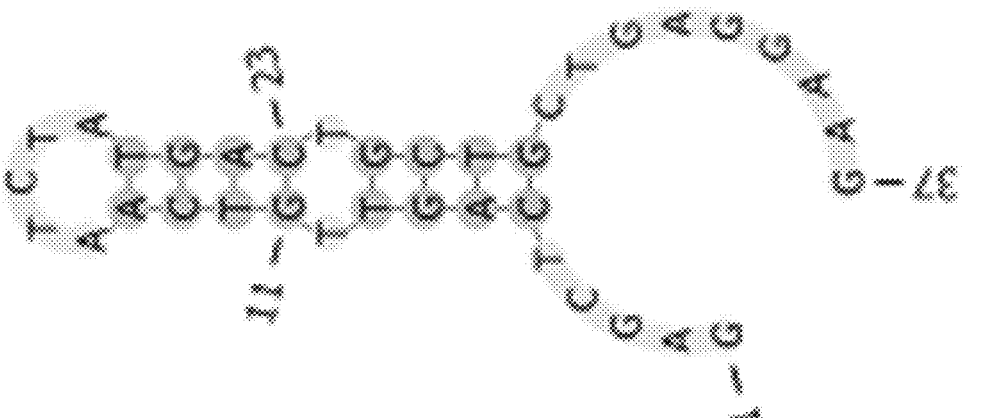
FIG. 31A shows the secondary structure formed with the maximum likelihood (designated Structure 1)
Figure 32A:
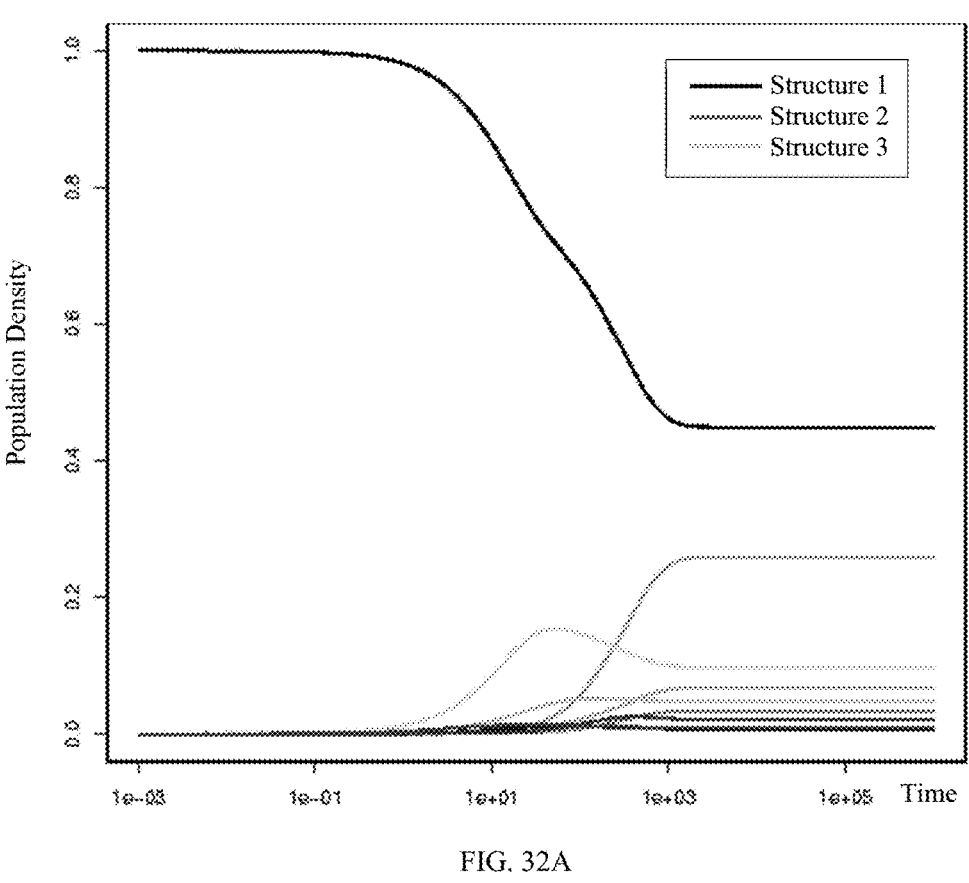
FIG. 32A shows the distribution at 33° C.
Figure 32B:
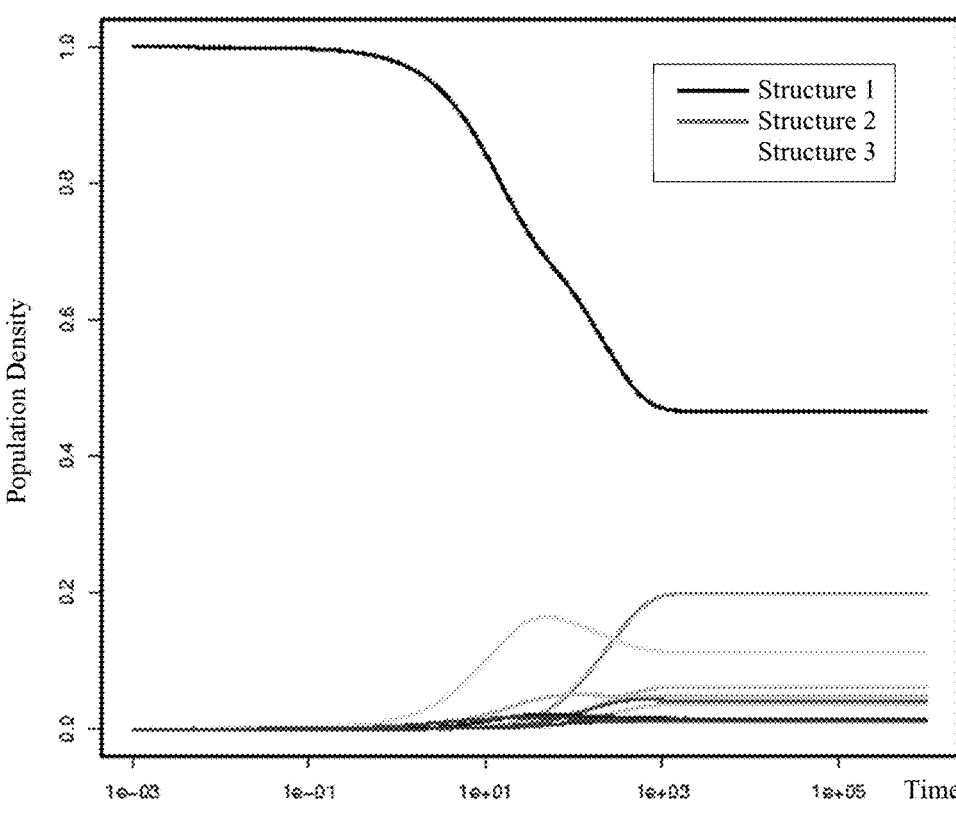
FIG. 32B shows the distribution at 37° C.

58 and the GAGGYYZ motif is still located in the dangling 3'-end which corresponds well to the nearly unchanged binding affinity under in vivo conditions. To understand the reduced binding affinity of the mutant aptamer State 2 at 37° C. the secondary and third preferred secondary structure which is formed in equilibrium was determined again with online software provided by ViennaRNA Web Services. FIG. 31 show the results, wherein hybridized nucleotides are shown in darker grey and unhybridized nucleotides are shown in lighter grey. The maximum likely structure 1 (FIG. 31A) is the structure also calculated in FIG. 30. The secondary likely structure 2 (FIG. 31B) differs in that a larger internal loop is formed and the second stem comprises a fifth base pair. Accordingly, the dangling ends were shortened and the GAGGYYZ motif is partially located in the stem region. In the third likely secondary structure (FIG. 31C) a second internal loop and a third stem is formed resulting in only one nucleotide dangling at the 5'-end, but the complete GAGGYYZ motif dangling at the 3'-end. FIG. 32 show the distribution of the three secondary structure variants shown in FIG. 31 at 33° C. (FIG. 32A) and 37° C. (FIG. 32B). At both temperatures Structure 1 (as shown in FIG. 31A) is dominantly present. However, at 37° C. the share of Structure 3 (as shown in FIG. 31C) is significant larger compared to the distribution at 33° C. Thereby, the share of Structure 2 (as shown in FIG. 31B) is significantly smaller at 37° C. compared to the distribution at 33° C. This difference in share distribution of the different secondary structure variants contributes to the loss in binding affinity for mutant aptamer State 2. Without wishing to be bound by theory it is believed that the missing dangling 5'-end shows negative impact on binding affinity of the whole aptamer as already observed similarly for mutant aptamer State 1.

Figure 33A:
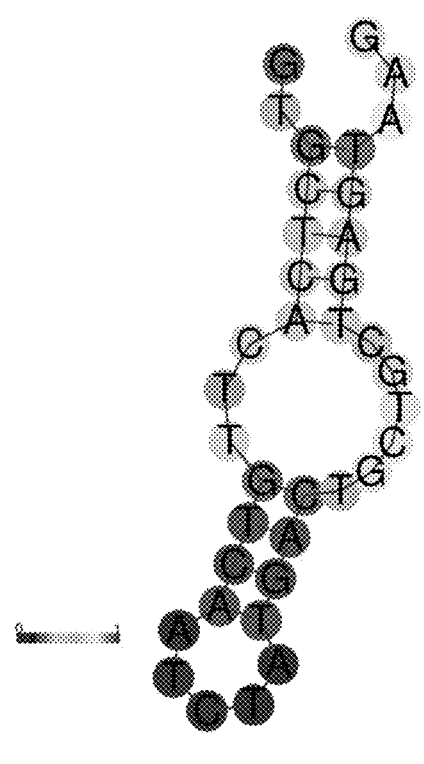
FIG. 33A shows the most likely secondary structure of mutant aptamer 4.1 of SEQ ID NO: 267 (designated State 4) at 33° C.
Figure 33B:
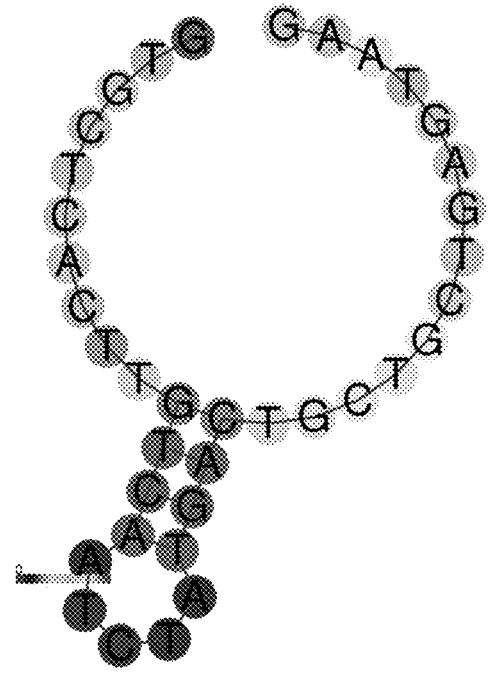
FIG. 33B shows the most likely secondary structure of mutant aptamer 4.1 of SEQ ID NO: 267 at 37° C. (designated State 4).

The mutation in aptamer of State 3 (SEQ ID NO. 266) is at the first position of the GAGGYYZ motif. Reduction in binding affinity was observed at both temperatures. It seems that the mutation has less effect on aptamer performance at the in vivo temperature. The mutation in mutant aptamer of State 4 (SEQ ID NO. 267) is at the 4th position of the GAGGYYZ motif. Surprisingly, the binding affinity of the mutant aptamer of State 4 was nearly not affected at 37° C., wherein a decrease in binding affinity was observed at 33° C. Secondary structure prediction revealed that four bases of the mutated GAGTAAG motif are hybridized,—as intended by the mutation—, and form a stem which results in the lower binding affinity (FIG. 33A) under in vivo conditions. However, at higher temperature (37° C.) the mutation in the motif sequence shifted the secondary structure into a shape having the GAGTAAG motif completely unhybridized and left dangling in the 3'-end (FIG. 31B), thereby being more similar to the NasD-4.1 structure, and full functionality of this mutant state was observed in the ITC binding experiment at higher temperature. The grey scale in FIG. 33 shows the likelihood of the nucleotide to be in the shown structure, with darker shades having a higher likelihood. Without wishing to be bound by theory it is believed that the freedom of the sequence dangling at the 3'-end compensated the potentially negative effect of the sequence motif mutation resulting in a slightly higher binding affinity.

The mutations in mutant aptamer of State 5 (SEQ ID NO. 268) are located in the stem region directly before the GAGGYYZ motif. General changes of the secondary structure of the mutant aptamer compared to the control NasD-4.1 aptamer (SEQ ID NO. 244) were not predicted by these mutations and a slight improvement of binding affinity was observed.

In mutant aptamers of States 6 (SEQ ID NO: 269) and 7 (SEQ ID NO: 270) the hairpin motif was mutated. In State 6 the hairpin loop was enlarged which decreases binding affinity at 37° C. and increases binding affinity at 33° C. Without wishing to be bound by theory it is believed that the size of the hairpin structure is less relevant at 33° C. than at 37° C. In mutant aptamer State 7 the hairpin loop is formed by different nucleotides compared to the original aptamer (SEQ ID NO: 244), but the impact on the binding affinity at both temperatures was noteworthy.

It was shown by the binding experiments that the aptamers of the present invention also function similarly at 33° C. and as such will function appropriately on nasal cells in vivo. The analysis of the performance of the mutated states, in particular at 33° C., further showed the impact of certain characteristics claimed herein regarding sequence and/or structure for performance in vivo. For example, nucleotide mutation(s) which do not influence the secondary structure do not show any significant change to binding affinity (State 5). Similar results were observed for an exchange in the sequence of the hairpin loop (State 7). Increasing the size of the hairpin loop (State 6) was considered to be advantageous under in vivo conditions as an increase in binding affinity was observed. Significant reduction in binding affinity could be observed with a mutation in the GAGGYYZ motif (State 3) or if the motif was halfway fixed in the stem region (State 4). Without wishing to be bound by theory, it is concluded therefrom that the binding affinity is higher in aptamers having the GAGGYYZ motif completely unhybridized such as located in a dangling 3'-end region compared to those which are still effective but include the GAGGYYZ motif partially hybridized in a stem region.

TABLE 5

List of top ribonucleotides parent sequences from selection experiment. All the pyrimidine nucleotides are fluorinated at the 2' position of the pentose group.

| SEQ ID NO | Name | Sequence |
|---|---|---|
| 1 | Nas.R-1 | GGGUGCAUCGUUUACGCGAUUAGUCUGAUAAACAAAAAGAUUUCGC UAAAAAUCAAUCUGCUGCUGAGGAAGGAUAUGAG |
| 2 | Nas.R-2 | GGGUGCAUCGUUUACGCAGAUAGCAGCAGGAAUCAAGCGGUAGGAG UCUAGCAGAAGCUGCUGCUGAGGAAGGAUAUGAG |
| 3 | Nas.R-3 | GGGUGCAUCGUUUACGCAUUUUCGUUUUAUUUCAGUUUAAUUGCGU UUAGUAUCUGGCUGCUGCUGAGGAAGGAUAUGAG |
| 4 | Nas.R-4 | GGGUGCAUCGUUUACGCGCAACAUAAAAAUUUAAAGUGCUCAGUUG UCAAUCUAUGACUGCUGCUGAGGAAGGAUAUGAG |
| 5 | Nas.R-5 | GGGUGCAUCGUUUACGCGUAAAUGGUCCGCUAUUAAAAGAAAAGAA UGAAGUCUCAGCUGCUGCUGAGGAAGGAUAUGAG |
| 6 | Nas.R-6 | GGGUGCAUCGUUUACGCUAUUUUCAUUUGUUUUUUUAAUUUACUAG UGUAAACAAUCCUGCUGCUGAGGAAGGAUAUGAG |
| 7 | Nas.R-7 | GGGUGCAUCGUUUACGCGUAAAUAAGUAGAUAAAGUGGCAGUUUG UUUUCCUUGGAACUGCUGCUGAGGAAGGAUAUGAG |
| 8 | Nas.R-8 | GGGUGCAUCGUUUACGCGUAAAAAUUAAAGAGAUUAAGGUCCUUAA GCAGUUUUGUCCUGCUGCUGAGGAAGGAUAUGAG |
| 9 | Nas.R-9 | GGGUGCAUCGUUUACGCGUAAAAAAAUCAAACUUCAGCAAAUUAU UUAUCAACGUCCUGCUGCUGAGGAAGGAUAUGAG |
| 10 | Nas.R-10 | GGGUGCAUCGUUUACGCGUAAAAUAAAUUAAAAAGAACUUCUUCAG CAAUCAAUAUCCUGCUGCUGAGGAAGGAUAUGAG |
| 11 | Nas.R-11 | GGGUGCAUCGUUUACGCGUAAAUAAAAAUGAAAAAUUGUCUCUCAG CUUUCAAAGUCCUGCUGCUGAGGAAGGAUAUGAG |
| 12 | Nas.R-12 | GGGUGCAUCGUUUACGCGUAAAAAAAAAAAUAUCUUCGGAGAAUUCA GCAAUUUUAUCCUGCUGCUGAGGAAGGAUAUGAG |
| 13 | Nas.R-13 | GGGUGCAUCGUUUACGCGUAAAAAAUUUUCAUCUCAGCAAUUAAAUC CAAAGAAUCCACUGCUGCUGAGGAAGGAUAUGAG |
| 14 | Nas.R-14 | GGGUGCAUCGUUUACGCGUAAAAUAUAUCAGCAAAGUAGUUUAAGC CUCCUCAGUUUCUGCUGCUGAGGAAGGAUAUGAG |
| 15 | Nas.R-15 | GGGUGCAUCGUUUACGCGUAAAAUUAUGAAAAAUACAGCAAGGAUUU AACCUCAGUUUCUGCUGCUGAGGAAGGAUAUGAG |
| 16 | Nas.R-16 | GGGUGCAUCGUUUACGCGUAAAAUAAAUAAAUCUUCAAAGUACAGA CCUCGAUUUUUCUGCUGCUGAGGAAGGAUAUGAG |
| 17 | Nas.R-17 | GGGUGCAUCGUUUACGCUUAUAGGUAUUAGACAUUUUCAAUUAAAG UGAAUUAGUGUCUGCUGCUGAGGAAGGAUAUGAG |
| 18 | Nas.R-18 | GGGUGCAUCGUUUACGCGUAAAAUGUGACAGCAGGAUAAUAAAAUA AGUACUCAGUACUGCUGCUGAGGAAGGAUAUGAG |

TABLE 5-continued

List of top ribonucleotides parent sequences from selection
experiment. All the pyrimidine nucleotides are
fluorinated at the 2' position of the pentose group.

| SEQ ID NO | Name | Sequence |
|---|---|---|
| 19 | Nas.R-19 | GGGUGCAUCGUUUACGCGUAAUUAAGAAAAAUAAAAGUACUCUGCA<br>GUUUUUAUCCACUGCUGCUGAGGAAGGAUAUGAG |
| 20 | Nas.R-20 | GGGUGCAUCGUUUACGCGUAAAAAUAAAAUUUUCCCAGACCAGUUA<br>UCUGCCUUAAACUGCUGCUGAGGAAGGAUAUGAG |
| 21 | Nas.R-21 | GGGUGCAUCGUUUACGCGUAAAGAAAAAAAUCAGCUUUUAGUCGCC<br>UUCCAUUUUGACUGCUGCUGAGGAAGGAUAUGAG |
| 22 | Nas.R-22 | GGGUGCAUCGUUUACGCGUAAAUAAAUAAUCAAAAUUACACUCAGU<br>GGCAAUUUCCUCUGCUGCUGAGGAAGGAUAUGAG |
| 23 | Nas.R-23 | GGGUGCAUCGUUUACGCGUAAAAUACAGGAUACGACAAUAACUCAG<br>CAGAUUUUAUCCUGCUGCUGAGGAAGGAUAUGAG |
| 24 | Nas.R-24 | GGGUGCAUCGUUUACGCGUUAAAAAUUGUGCACUGAGAUGACGCAG<br>CAUUAACUACACUGCUGCUGAGGAAGGAUAUGAG |
| 25 | Nas.R-25 | GGGUGCAUCGUUUACGCGUAAAUAAAAAUUAAUCAGCAAUUUUCCA<br>CUCAGUUGUACCUGCUGCUGAGGAAGGAUAUGAG |
| 26 | Nas.R-26 | GGGUGCAUCGUUUACGCGUAAAAAUAAAAAAUCUCGAUCACUGCAG<br>UUUUAUUCCGGCUGCUGCUGAGGAAGGAUAUGAG |
| 27 | Nas.R-27 | GGGUGCAUCGUUUACGCGUAAACAAAUAUCGAUUAAAAUAAAAUCU<br>CAGCAAGAAUCCUGCUGCUGAGGAAGGAUAUGAG |
| 28 | Nas.R-28 | GGGUGCAUCGUUUACGCGUAAAAAUAAAUAAAAUUAUCCCAGGAGCA<br>AAUUUUCUUCGCUGCUGCUGAGGAAGGAUAUGAG |
| 29 | Nas.R-29 | GGGUGCAUCGUUUACGCGUAGAAGAAUUAAUAGUGGACAUAUCAAU<br>AGCAGUUUAUCCUGCUGCUGAGGAAGGAUAUGAG |
| 30 | Nas.R-30 | GGGUGCAUCGUUUACGCGUAAACAUAUUCAGCAGUUAAAAUUUAGU<br>AGGUUCAGUAGCUGCUGCUGAGGAAGGAUAUGAG |
| 31 | Nas.R-31 | GGGUGCAUCGUUUACGCGUAAAAAAGAUAAAACUUAGUUGCAGAAU<br>UUGCCUUCAUUCUGCUGCUGAGGAAGGAUAUGAG |
| 32 | Nas.R-32 | GGGUGCAUCGUUUACGCGUAAAAAGUUUGAUGGAAGCAGAUUAGU<br>UUAGUCAAAUUUCUGCUGCUGAGGAAGGAUAUGAG |
| 33 | Nas.R-33 | GGGUGCAUCGUUUACGCGUAAAAUGAAAUAAGGAAUCCUUCAGCAG<br>UAUUUAUCCUUCUGCUGCUGAGGAAGGAUAUGAG |
| 34 | Nas.R-34 | GGGUGCAUCGUUUACGCGUAAAGAAUAAAAAUGACAAAAUUCUCAG<br>CUUUUGUCAACCUGCUGCUGAGGAAGGAUAUGAG |
| 35 | Nas.R-35 | GGGUGCAUCGUUUACGCGUAAAAAAUGAAAUGAAAAAAUUCUCAGC<br>UGUCUAUCUUCCUGCUGCUGAGGAAGGAUAUGAG |
| 36 | Nas.R-36 | GGGUGCAUCGUUUACGCGUAAAUAAGUAAAAAACUCAGUUUUCAGU<br>UAAGUAUCCAACUGCUGCUGAGGAAGGAUAUGAG |
| 37 | Nas.R-37 | GGGUGCAUCGUUUACGCGUAAAUUUCAGCAGAGUAAUAAUAACACU<br>UCUUCAGUUUGCUGCUGCUGAGGAAGGAUAUGAG |
| 38 | Nas.R-38 | GGGUGCAUCGUUUACGCGUAAAAAUUAAGAAGUAUUAUCAGUUAGCU<br>UUUUCUUCCAACUGCUGCUGAGGAAGGAUAUGAG |
| 39 | Nas.R-39 | GGGUGCAUCGUUUACGCGUAAAAUAAAAAGUUUUCCUAUCAGCAAA<br>CUCACAAAUUCCUGCUGCUGAGGAAGGAUAUGAG |
| 40 | Nas.R-40 | GGGUGCAUCGUUUACGCGUAAAAUGAAAUGUAAAAGAAUUGAACU<br>UGGCAGAUUUUCCUGCUGCUGAGGAAGGAUAUGAG |
| 41 | Nas.R-41 | GGGUGCAUCGUUUACGCGUAAAUUAAAGUAGCAGUAAUUUCAGCAG<br>UUUUUACCUCUCUGCUGCUGAGGAAGGAUAUGAG |
| 42 | Nas.R-42 | GGGUGCAUCGUUUACGCGUAAAUAAAGGAUAAAAUAAUUUCAGGGC<br>AGUUUCUCAUCCUGCUGCUGAGGAAGGAUAUGAG |

TABLE 5-continued

List of top ribonucleotides parent sequences from selection experiment. All the pyrimidine nucleotides are fluorinated at the 2' position of the pentose group.

| SEQ ID NO | Name | Sequence |
|---|---|---|
| 43 | Nas.R-43 | GGGUGCAUCGUUUACGCAGGAUCGUUUUAAGUAAAAUAAAAGAUU UCCUUGGUAAUCCUGCUGCUGAGGAAGGAUAUGAG |
| 44 | Nas.R-44 | GGGUGCAUCGUUUACGCGUAAAAUAAAGAUCAAUUAAAGGCUUUGA UCGAUUUUCCUCUGCUGCUGAGGAAGGAUAUGAG |
| 45 | Nas.R-45 | GGGUGCAUCGUUUACGCGUAAAAAUUAGAGAUUAAAAUAGUUCCUU UCAGUUUUGUCCUGCUGCUGAGGAAGGAUAUGAG |
| 46 | Nas.R-46 | GGGUGCAUCGUUUACGCGUAAAAUUGACAAUGUGAAAAGCAGACAG CAAAUAUUCCUCUGCUGCUGAGGAAGGAUAUGAG |
| 47 | Nas.R-47 | GGGUGCAUCGUUUACGCGUAAAUAACCAGUUAUACAGAAAGAUCUC AGCAAUUUAUCCUGCUGCUGAGGAAGGAUAUGAG |
| 48 | Nas.R-48 | GGGUGCAUCGUUUACGCUUACAGAAGGAUUGCACCACAUGCGUACU CGAUGAAACACCUGCUGCUGAGGAAGGAUAUGAG |
| 49 | Nas.R-49 | GGGUGCAUCGUUUACGCGUAAAAUAAUAAUUAAACUCAGCAAAUUC AAUCCAACUUUCUGCUGCUGAGGAAGGAUAUGAG |
| 50 | Nas.R-50 | GGGUGCAUCGUUUACGCGUAAACAAGAAUAAAUUCAGCAGUGGUUU UGAUCCUUUGACUGCUGCUGAGGAAGGAUAUGAG |
| 51 | Nas.R-51 | GGGUGCAUCGUUUACGCGUAAAUUAAUCAGAUUGAACAAAAGUUUU CCCUCAGUUUUCUGCUGCUGAGGAAGGAUAUGAG |
| 52 | Nas.R-52 | GGGUGCAUCGUUUACGCGUAAAGAAAAACAUCAGAGCAGUUAUAAU AGUCCUUUUUCCUGCUGCUGAGGAAGGAUAUGAG |
| 53 | Nas.R-53 | GGGUGCAUCGUUUACGCGUAAAGAAAAUAAACUUGAUCAAACUUAG CAGUUUUUAUCCUGCUGCUGAGGAAGGAUAUGAG |
| 54 | Nas.R-54 | GGGUGCAUCGUUUACGCAUUUUCGUUAUAUUUCUGGUUUUUAUGCG UGAGAAUCCUGCUGCUGAGGAAGGAUAUGAG |
| 55 | Nas.R-55 | GGGUGCAUCGUUUACGCGUAAAAAUAAGAUCUCACAGCGACAAAUU UUUCUUCCAGUCUGCUGCUGAGGAAGGAUAUGAG |
| 56 | Nas.R-56 | GGGUGCAUCGUUUACGCGUAAAUUUAAGACAUGACAGCAGACAUUU UAUCUUCAGACCUGCUGCUGAGGAAGGAUAUGAG |
| 57 | Nas.R-57 | GGGUGCAUCGUUUACGCGUAAUAACAGAAAUAUAACUCAGCUGAAU UAAUUUUUCCGCUGCUGCUGAGGAAGGAUAUGAG |
| 58 | Nas.R-58 | GGGUGCAUCGUUUACGCGUAAAAAUAAAUUCCAAAAUAUUCAGCAG AAAUCCUCGAACUGCUGCUGAGGAAGGAUAUGAG |
| 59 | Nas.R-59 | GGGUGCAUCGUUUACGCGUAAAAAUAAUAGGUUCCAAUCAAGCAGU ACAAAAUUCCUCUGCUGCUGAGGAAGGAUAUGAG |
| 60 | Nas.R-60 | GGGUGCAUCGUUUACGCGUAAAAAAUCUAAAAAGAUAUCAGCAGGC AAAUUUUCCUUCUGCUGCUGAGGAAGGAUAUGAG |
| 61 | Nas.R-61 | GGGUGCAUCGUUUACGCGUAAAAUAAAGAGGAUAACUACAAUCAUC AGCAAUCAUAUCUGCUGCUGAGGAAGGAUAUGAG |
| 62 | Nas.R-62 | GGGUGCAUCGUUUACGCGUAAAUUUAGUAGAAAGGAAAGACGAAG UUUCCUCAGUUUCUGCUGCUGAGGAAGGAUAUGAG |
| 63 | Nas.R-63 | GGGUGCAUCGUUUACGCGUAAAAAUAAUAGAUCUCAGAAUAUGAAA GCAGUUCUUUCCUGCUGCUGAGGAAGGAUAUGAG |
| 64 | Nas.R-64 | GGGUGCAUCGUUUACGCGUAACAAGAUAUUCACAGCAGAUUUUAAA AAAUUCCUCGUCUGCUGCUGAGGAAGGAUAUGAG |
| 65 | Nas.R-65 | GGGUGCAUCGUUUACGCGUAAAAAGUUGACAAUUAAUAAAAUCUUC UUAGCAUUUUCCUGCUGCUGAGGAAGGAUAUGAG |
| 66 | Nas.R-66 | GGGUGCAUCGUUUACGCGUAAAACAAAAUGAAACUUAUAGCUCAGC AUAUUUUGAUCCUGCUGCUGAGGAAGGAUAUGAG |

TABLE 5-continued

List of top ribonucleotides parent sequences from selection
experiment. All the pyrimidine nucleotides are
fluorinated at the 2' position of the pentose group.

| SEQ ID NO | Name | Sequence |
|---|---|---|
| 67 | Nas.R-67 | GGGUGCAUCGUUUACGCGUAAAUUAUCAAAAAAGCAGAUUUAAGUA<br>UACCUCAGUUACUGCUGCUGAGGAAGGAUAUGAG |
| 68 | Nas.R-68 | GGGUGCAUCGUUUACGCGUAAAUAAAAUAGCUCAGCAAGGAAGUUU<br>UUUUCCUCAAACUGCUGCUGAGGAAGGAUAUGAG |
| 69 | Nas.R-69 | GGGUGCAUCGUUUACGCGUAAAUUUGAGAAAAGAACAGCAGACUCA<br>AAUCUUUUUAACUGCUGCUGAGGAAGGAUAUGAG |
| 70 | Nas.R-70 | GGGUGCAUCGUUUACGCGUAACAGAAAAUUAAGCUCAGCAAUAGUA<br>AUUAUCCUAGUCUGCUGCUGAGGAAGGAUAUGAG |
| 71 | Nas.R-71 | GGGUGCAUCGUUUACGCGUAAUGAAAAUAAAUCAGUCUCACAGCAU<br>UUUAAAACUUCCUGCUGCUGAGGAAGGAUAUGAG |
| 72 | Nas.R-72 | GGGUGCAUCGUUUACGCGUAUUUACAAGCAACAAAGUUACAAUCAG<br>CAGAAUUUAUCCUGCUGCUGAGGAAGGAUAUGAG |
| 73 | Nas.R-73 | GGGUGCAUCGUUUACGCGUAAAAAAUUGUCUAUAGCACUUUUAGAU<br>UCCCAAACUAACUGCUGCUGAGGAAGGAUAUGAG |
| 74 | Nas.R-74 | GGGUGCAUCGUUUACGCGUAAAAAAAUCAGCAAAAUCGAAAACUCA<br>UGCAGUUUGUCCUGCUGCUGAGGAAGGAUAUGAG |
| 75 | Nas.R-75 | GGGUGCAUCGUUUACGCGUAAAAAAUUCCUUAAAAAUUUAACUAAC<br>UGGAUAGGUCUCUGCUGCUGAGGAAGGAUAUGAG |
| 76 | Nas.R-76 | GGGUGCAUCGUUUACGCGUAAAACAAAAUUUCUGACAGCAAUUCCU<br>UCGUUAAAAAUCUGCUGCUGAGGAAGGAUAUGAG |
| 77 | Nas.R-77 | GGGUGCAUCGUUUACGCGUAAAUUAUUAAAAAAAAUCAGCAAAGUUU<br>AUUUCCCACGGCUGCUGCUGAGGAAGGAUAUGAG |
| 78 | Nas.R-78 | GGGUGCAUCGUUUACGCGUAAUUAAUCAAACAAUAGCAGCAAAUCU<br>CAGCAAUUUUCCUGCUGCUGAGGAAGGAUAUGAG |
| 79 | Nas.R-79 | GGGUGCAUCGUUUACGCGUAAUUUGAAAGUCUCAUAAAUUUUUUUU<br>UUUUUUUCAAUCUGCUGCUGAGGAAGGAUAUGAG |
| 80 | Nas.R-80 | GGGUGCAUCGUUUACGCGUAAAAAUUCAGCAUGAUUUCAAUUACUC<br>CUUUCAUUGAUCUGCUGCUGAGGAAGGAUAUGAG |
| 81 | Nas.R-81 | GGGUGCAUCGUUUACGCGUAAAAUAAAUAAAAAUCAGUAGCAAUCU<br>UUCUCACAGUGCUGCUGCUGAGGAAGGAUAUGAG |
| 82 | Nas.R-82 | GGGUGCAUCGUUUACGCGUAAAUAAAAAGCAGAUCUCAGCAAAACU<br>CGUAAAUUCAACUGCUGCUGAGGAAGGAUAUGAG |
| 83 | Nas.R-83 | GGGUGCAUCGUUUACGCGUAAAUAAUGAAGGACUCAGACAGUUAAA<br>AGAUGCAUUAACUGCUGCUGAGGAAGGAUAUGAG |
| 84 | Nas.R-84 | GGGUGCAUCGUUUACGCGUAAAAAAGAUCAAUAUGAAAAUCAGCAG<br>UUAAUAUCUUCCUGCUGCUGAGGAAGGAUAUGAG |
| 85 | Nas.R-85 | GGGUGCAUCGUUUACGCGUAAAAAUAACAAACUUCUCAGCUGUUUA<br>AUAUCUCCUGACUGCUGCUGAGGAAGGAUAUGAG |
| 86 | Nas.R-86 | GGGUGCAUCGUUUACGCGUAAAAUUAAACAAAUAGCUCAGCACGAA<br>AAUUUGCGUAACUGCUGCUGAGGAAGGAUAUGAG |
| 87 | Nas.R-87 | GGGUGCAUCGUUUACGCGUAAUUAAAAAACCUUCACACAGAAAACA<br>UUCCUCAAUUUCUGCUGCUGAGGAAGGAUAUGAG |
| 88 | Nas.R-88 | GGGUGCAUCGUUUACGCAUUUUCGUUUUAUUUUAGUUUAAUUGCGU<br>UUAGUAUCUGGCUGCUGCUGAGGAAGGAUAUGAG |
| 89 | Nas.R-89 | GGGUGCAUCGUUUACGCGUAAAAAGUAUAAAGGUUAGAAAUUCAGC<br>AGUUUGAUAUCCUGCUGCUGAGGAAGGAUAUGAG |
| 90 | Nas.R-90 | GGGUGCAUCGUUUACGCGUAAAAAGGAGAAUUAGUACUCACCAGUC<br>GUUUAAAAUUUCUGCUGCUGAGGAAGGAUAUGAG |
| 91 | Nas.R-91 | GGGUGCAUCGUUUACGCGUAAAAAUAAAUAACUACGAGAUCUCAGC<br>AGAUCAUUAUCCUGCUGCUGAGGAAGGAUAUGAG |

TABLE 5-continued

List of top ribonucleotides parent sequences from selection
experiment. All the pyrimidine nucleotides are
fluorinated at the 2' position of the pentose group.

| SEQ ID NO | Name | Sequence |
| --- | --- | --- |
| 92 | Nas.R-92 | GGGUGCAUCGUUUACGCGUAAAAUGGUUUUUCAGCAGUUAACAUAA<br>UGCCUCAGUUUCUGCUGCUGAGGAAGGAUAUGAG |
| 93 | Nas.R-93 | GGGUGCAUCGUUUACGCGUAAAUAACAAAAAUCUCAGCUUUUGCAG<br>AAUUUAUCCACCUGCUGCUGAGGAAGGAUAUGAG |
| 94 | Nas.R-94 | GGGUGCAUCGUUUACGCGUAAAUAAACUCACAGCAGAAAAAAUUCC<br>UUCAACUUGUACUGCUGCUGAGGAAGGAUAUGAG |
| 95 | Nas.R-95 | GGGUGCAUCGUUUACGCGAGUAGUUAAUAACAAAUAGUCAGCAGUUU<br>UGUCCUUCAUUCUGCUGCUGAGGAAGGAUAUGAG |
| 96 | Nas.R-96 | GGGUGCAUCGUUUACGCGUAAAAAUAGCAGUAGAUAGCGGCAGUUU<br>UGUAUUUGUUACUGCUGCUGAGGAAGGAUAUGAG |
| 97 | Nas.R-97 | GGGUGCAUCGUUUACGCGUAAAAAUUUAAAUAACUCAGCAAUCAUA<br>GAUCCGACUGACUGCUGCUGAGGAAGGAUAUGAG |
| 98 | Nas.R-98 | GGGUGCAUCGUUUACGCGUAAAGAACAGCUGACAAGAAAUUCAAAC<br>CUUCAGAUUUUCUGCUGCUGAGGAAGGAUAUGAG |
| 99 | Nas.R-99 | GGGUGCAUCGUUUACGCGUAAAGAUAAUAAGCAGUAUUCAGCAGAU<br>UUGUAAGGUUUCUGCUGCUGAGGAAGGAUAUGAG |
| 100 | Nas.R-100 | GGGUGCAUCGUUUACGCGUAAAUAAGAGGCAGACAGUAUUACAAAU<br>AUCCUAAAAUACUGCUGCUGAGGAAGGAUAUGAG |

TABLE 6

List of deoxyribonucleotides parent aptamers based on the top
sequences from selection experiments.

| SEQ ID NO | Name | Sequence |
| --- | --- | --- |
| 101 | Nas.D-1 | GGGTGCATCGTTTACGCGATTAGTCTGATAAACAAAAAGATTTCGCTA<br>AAAATCAATCTGCTGCTGAGGAAGGATATGAG |
| 102 | Nas.D-2 | GGGTGCATCGTTTACGCAGATAGCAGCAGGAATCAAGCGGTAGGAGTC<br>TAGCAGAAGCTGCTGCTGAGGAAGGATATGAG |
| 103 | Nas.D-3 | GGGTGCATCGTTTACGCATTTTCGTTTTATTTCAGTTTAATTGCGTTT<br>AGTATCTGGCTGCTGCTGAGGAAGGATATGAG |
| 104 | Nas.D-4 | GGGTGCATCGTTTACGCGCAACATAAAAATTTAAAGTGCTCAGTTGTC<br>AATCTATGACTGCTGCTGAGGAAGGATATGAG |
| 105 | Nas.D-5 | GGGTGCATCGTTTACGCGTAAATGGTCCGCTATTAAAAGAAAAGAATG<br>AAGTCTCAGCTGCTGCTGAGGAAGGATATGAG |
| 106 | Nas.D-6 | GGGTGCATCGTTTACGCTATTTTCATTTGTTTTTTTAATTTACTAGTG<br>TAAACAATCCTGCTGCTGAGGAAGGATATGAG |
| 107 | Nas.D-7 | GGGTGCATCGTTTACGCGTAAATAAGTAGATAAAGTGGCAGTTTGTTT<br>TCCTTGGAACTGCTGCTGAGGAAGGATATGAG |
| 108 | Nas.D-8 | GGGTGCATCGTTTACGCGTAAAAATTAAAGAGATTAAGGTCCTTAAGC<br>AGTTTTGTCCTGCTGCTGAGGAAGGATATGAG |
| 109 | Nas.D-9 | GGGTGCATCGTTTACGCGTAAAAAAATCAAAACTTCAGCAAATTATTT<br>ATCAACGTCCTGCTGCTGAGGAAGGATATGAG |
| 110 | Nas.D-10 | GGGTGCATCGTTTACGCGTAAATAAATTAAAAAGAACTTCTTCAGCA<br>ATCAATATCCTGCTGCTGAGGAAGGATATGAG |
| 111 | Nas.D-11 | GGGTGCATCGTTTACGCGTAAATAAAAATGAAAAATTGTCTCTCAGCT<br>TTCAAAGTCCTGCTGCTGAGGAAGGATATGAG |
| 112 | Nas.D-12 | GGGTGCATCGTTTACGCGTAAAAAAAAAAATATCTTCGGAGAATTCAGC<br>AATTTTATCCTGCTGCTGAGGAAGGATATGAG |

TABLE 6-continued

List of deoxyribonucleotides parent aptamers based on the top
sequences from selection experiments.

| SEQ ID NO | Name | Sequence |
|---|---|---|
| 113 | Nas.D-13 | GGGTGCATCGTTTACGCGTAAAAATTTTCATCTCAGCAATTAAATCCA AAGAATCCACTGCTGCTGAGGAAGGATATGAG |
| 114 | Nas.D-14 | GGGTGCATCGTTTACGCGTAAAATATATCAGCAAAGTAGTTTAAGCCT CCTCAGTTTCTGCTGCTGAGGAAGGATATGAG |
| 115 | Nas.D-15 | GGGTGCATCGTTTACGCGTAAATTATGAAAAATACAGCAAGGATTTAA CCTCAGTTTCTGCTGCTGAGGAAGGATATGAG |
| 116 | Nas.D-16 | GGGTGCATCGTTTACGCGTAAAATAAATAAATCTTCAAAGTACAGACC TCGATTTTTCTGCTGCTGAGGAAGGATATGAG |
| 117 | Nas.D-17 | GGGTGCATCGTTTACGCTTATAGGTATTAGACATTTTCAATTAAAGTG AATTAGTGTCTGCTGCTGAGGAAGGATATGAG |
| 118 | Nas.D-18 | GGGTGCATCGTTTACGCGTAAAATGTGACAGCAGGATAATAAAATAAG TACTCAGTACTGCTGCTGAGGAAGGATATGAG |
| 119 | Nas.D-19 | GGGTGCATCGTTTACGCGTAATTAAGAAAAATAAAAGTACTCTGCAGT TTTTATCCACTGCTGCTGAGGAAGGATATGAG |
| 120 | Nas.D-20 | GGGTGCATCGTTTACGCGTAAAAATAAAATTTTCCCAGACCAGTTATC TGCCTTAAACTGCTGCTGAGGAAGGATATGAG |
| 121 | Nas.D-21 | GGGTGCATCGTTTACGCGTAAAGAAAAAAATCAGCTTTTAGTCGCCTT CCATTTTGACTGCTGCTGAGGAAGGATATGAG |
| 122 | Nas.D-22 | GGGTGCATCGTTTACGCGTAAATAAATAATCAAAATTACACTCAGTGG CAATTTCCTCTGCTGCTGAGGAAGGATATGAG |
| 123 | Nas.D-23 | GGGTGCATCGTTTACGCGTAAAATACAGGATACGACAATAACTCAGCA GATTTTATCCTGCTGCTGAGGAAGGATATGAG |
| 124 | Nas.D-24 | GGGTGCATCGTTTACGCGTTAAAAATTGTGCACTGAGATGACGCAGCA TTAACTACACTGCTGCTGAGGAAGGATATGAG |
| 125 | Nas.D-25 | GGGTGCATCGTTTACGCGTAAATAAAAATTAATCAGCAATTTTCCACT CAGTTGTACCTGCTGCTGAGGAAGGATATGAG |
| 126 | Nas.D-26 | GGGTGCATCGTTTACGCGTAAAAATAAAAAATCTCGATCACTGCAGTT TTATTCCGGCTGCTGCTGAGGAAGGATATGAG |
| 127 | Nas.D-27 | GGGTGCATCGTTTACGCGTAAACAAATATCGATTAAAATAAAATCTCA GCAAGAATCCTGCTGCTGAGGAAGGATATGAG |
| 128 | Nas.D-28 | GGGTGCATCGTTTACGCGTAAAATAAATAAAATTATCCCAGGAGCAAA TTTTCTTCGCTGCTGCTGAGGAAGGATATGAG |
| 129 | Nas.D-29 | GGGTGCATCGTTTACGCGTAGAAGAATTAATAGTGGACATATCAATAG CAGTTTATCCTGCTGCTGAGGAAGGATATGAG |
| 130 | Nas.D-30 | GGGTGCATCGTTTACGCGTAAACATATTCAGCAGTTAAAATTTAGTAG GTTCAGTAGCTGCTGCTGAGGAAGGATATGAG |
| 131 | Nas.D-31 | GGGTGCATCGTTTACGCGTAAAAAAGATAAAACTTAGTTGCAGAATTT GCCTTCATTCTGCTGCTGAGGAAGGATATGAG |
| 132 | Nas.D-32 | GGGTGCATCGTTTACGCGTAAAAAGTTTGATGGAAGCAGATTAGTTTA GTCAAATTTCTGCTGCTGAGGAAGGATATGAG |
| 133 | Nas.D-33 | GGGTGCATCGTTTACGCGTAAAATGAAATAAGGAATCCTTCAGCAGTA TTTATCCTTCTGCTGCTGAGGAAGGATATGAG |
| 134 | Nas.D-34 | GGGTGCATCGTTTACGCGTAAAGAATAAAAATGACAAAATTCTCAGCT TTTGTCAACCTGCTGCTGAGGAAGGATATGAG |
| 135 | Nas.D-35 | GGGTGCATCGTTTACGCGTAAAAAATGAAATGAAAAAATTCTCAGCTG TCTATCTTCCTGCTGCTGAGGAAGGATATGAG |
| 136 | Nas.D-36 | GGGTGCATCGTTTACGCGTAAATAAGTAAAAAACTCAGTTTTCAGTTA AGTATCCAACTGCTGCTGAGGAAGGATATGAG |
| 137 | Nas.D-37 | GGGTGCATCGTTTACGCGTAAATTTCAGCAGAGTAATAATAACACTTC TTCAGTTTGCTGCTGCTGAGGAAGGATATGAG |

TABLE 6-continued

List of deoxyribonucleotides parent aptamers based on the top
sequences from selection experiments.

| SEQ ID NO | Name | Sequence |
|---|---|---|
| 138 | Nas.D-38 | GGGTGCATCGTTTACGCGTAAAATTAAGAAGTATTATCAGTTAGCTTT<br>TTCTTCCAACTGCTGCTGAGGAAGGATATGAG |
| 139 | Nas.D-39 | GGGTGCATCGTTTACGCGTAAAATAAAAAGTTTTCCTATCAGCAAACT<br>CACAAATTCCTGCTGCTGAGGAAGGATATGAG |
| 140 | Nas.D-40 | GGGTGCATCGTTTACGCGTAAAATGAAATGTAAAAGAATTGAACTTGG<br>CAGATTTTCCTGCTGCTGAGGAAGGATATGAG |
| 141 | Nas.D-41 | GGGTGCATCGTTTACGCGTAAATTAAAGTAGCAGTAATTTCAGCAGTT<br>TTTACCTCTCTGCTGCTGAGGAAGGATATGAG |
| 142 | Nas.D-42 | GGGTGCATCGTTTACGCGTAAATAAAGGATAAAATAATTTCAGGGCAG<br>TTTCTCATCCTGCTGCTGAGGAAGGATATGAG |
| 143 | Nas.D-43 | GGGTGCATCGTTTACGCAGGATCGTTTTAAGTAAAATAAAAGATTTCC<br>TTGGTAATCCTGCTGCTGAGGAAGGATATGAG |
| 144 | Nas.D-44 | GGGTGCATCGTTTACGCGTAAAATAAAGATCAATTAAAGGCTTTGATC<br>GATTTTCCTCTGCTGCTGAGGAAGGATATGAG |
| 145 | Nas.D-45 | GGGTGCATCGTTTACGCGTAAAAATTAGAGATTAAAATAGTTCCTTTC<br>AGTTTTGTCCTGCTGCTGAGGAAGGATATGAG |
| 146 | Nas.D-46 | GGGTGCATCGTTTACGCGTAAAATTGACAATGTGAAAAGCAGACAGCA<br>AATATTCCTCTGCTGCTGAGGAAGGATATGAG |
| 147 | Nas.D-47 | GGGTGCATCGTTTACGCGTAAATAACCAGTTATACAGAAAGATCTCAG<br>CAATTTATCCTGCTGCTGAGGAAGGATATGAG |
| 148 | Nas.D-48 | GGGTGCATCGTTTACGCTTACAGAAGGATTGCACCACATGCGTACTCG<br>ATGAAACACCTGCTGCTGAGGAAGGATATGAG |
| 149 | Nas.D-49 | GGGTGCATCGTTTACGCGTAAAATAATAATTAAACTCAGCAAATTCAA<br>TCCAACTTTCTGCTGCTGAGGAAGGATATGAG |
| 150 | Nas.D-50 | GGGTGCATCGTTTACGCGTAAACAAGAATAAATTCAGCAGTGGTTTTG<br>ATCCTTTGACTGCTGCTGAGGAAGGATATGAG |
| 151 | Nas.D-51 | GGGTGCATCGTTTACGCGTAAATTAATCAGATTGAACAAAGTTTTCC<br>CTCAGTTTTCTGCTGCTGAGGAAGGATATGAG |
| 152 | Nas.D-52 | GGGTGCATCGTTTACGCGTAAAGAAAAACATCAGAGCAGTTATAATAG<br>TCCTTTTTCCTGCTGCTGAGGAAGGATATGAG |
| 153 | Nas.D-53 | GGGTGCATCGTTTACGCGTAAAGAAAATAAACTTGATCAAACTTAGCA<br>GTTTTTATCCTGCTGCTGAGGAAGGATATGAG |
| 154 | Nas.D-54 | GGGTGCATCGTTTACGCATTTTCGTTATATTTCTGGTTTTTATGCGTG<br>AGAATCCTGCTGCTGCTGAGGAAGGATATGAG |
| 155 | Nas.D-55 | GGGTGCATCGTTTACGCGTAAAAATAAGATCTCACAGCGACAAATTTT<br>TCTTCCAGTCTGCTGCTGAGGAAGGATATGAG |
| 156 | Nas.D-56 | GGGTGCATCGTTTACGCGTAAATTTAAGACATGACAGCAGACATTTTA<br>TCTTCAGACCTGCTGCTGAGGAAGGATATGAG |
| 157 | Nas.D-57 | GGGTGCATCGTTTACGCGTAATAACAGAAATATAACTCAGCTGAATTA<br>ATTTTTCCGCTGCTGCTGAGGAAGGATATGAG |
| 158 | Nas.D-58 | GGGTGCATCGTTTACGCGTAAAAATAAATTCCAAAATATTCAGCAGAA<br>ATCCTCGAACTGCTGCTGAGGAAGGATATGAG |
| 159 | Nas.D-59 | GGGTGCATCGTTTACGCGTAAAAATAATAGGTTCCAATCAAGCAGTAC<br>AAAATTCCTCTGCTGCTGAGGAAGGATATGAG |
| 160 | Nas.D-60 | GGGTGCATCGTTTACGCGTAAAAAATCTAAAAAGATATCAGCAGGCAA<br>ATTTTCCTTCTGCTGCTGAGGAAGGATATGAG |
| 161 | Nas.D-61 | GGGTGCATCGTTTACGCGTAAAATAAAGAGGATAACTACAATCATCAG<br>CAATCATATCTGCTGCTGAGGAAGGATATGAG |
| 162 | Nas.D-62 | GGGTGCATCGTTTACGCGTAAATTTAGTAGAAAGGAAAGACGAAGTTT<br>CCTCAGTTTCTGCTGCTGAGGAAGGATATGAG |

TABLE 6-continued

List of deoxyribonucleotides parent aptamers based on the top
sequences from selection experiments.

| SEQ ID NO | Name | Sequence |
| --- | --- | --- |
| 163 | Nas.D-63 | GGGTGCATCGTTTACGCGTAAAAATAATAGATCTCAGAATATGAAAGC AGTTCTTTCCTGCTGCTGAGGAAGGATATGAG |
| 164 | Nas.D-64 | GGGTGCATCGTTTACGCGTAACAAGATATTCACAGCAGATTTTAAAAA ATTCCTCGTCTGCTGCTGAGGAAGGATATGAG |
| 165 | Nas.D-65 | GGGTGCATCGTTTACGCGTAAAAAGTTGACAATTAATAAAATCTTCTT AGCATTTTCCTGCTGCTGAGGAAGGATATGAG |
| 166 | Nas.D-66 | GGGTGCATCGTTTACGCGTAAAACAAAATGAAACTTATAGCTCAGCAT ATTTTGATCCTGCTGCTGAGGAAGGATATGAG |
| 167 | Nas.D-67 | GGGTGCATCGTTTACGCGTAAATTATCAAAAAAGCAGATTTAAGTATA CCTCAGTTACTGCTGCTGAGGAAGGATATGAG |
| 168 | Nas.D-68 | GGGTGCATCGTTTACGCGTAAATAAAATAGCTCAGCAAGGAAGTTTTT TTCCTCAAACTGCTGCTGAGGAAGGATATGAG |
| 169 | Nas.D-69 | GGGTGCATCGTTTACGCGTAAATTTGAGAAAAGAACAGCAGACTCAAA TCTTTTTAACTGCTGCTGAGGAAGGATATGAG |
| 170 | Nas.D-70 | GGGTGCATCGTTTACGCGTAACAGAAAATTAAGCTCAGCAATAGTAAT TATCCTAGTCTGCTGCTGAGGAAGGATATGAG |
| 171 | Nas.D-71 | GGGTGCATCGTTTACGCGTAATGAAAATAAATCAGTCTCACAGCATTT TAAAACTTCCTGCTGCTGAGGAAGGATATGAG |
| 172 | Nas.D-72 | GGGTGCATCGTTTACGCGTATTTACAAGCAACAAAGTTACAATCAGCA GAATTTATCCTGCTGCTGAGGAAGGATATGAG |
| 173 | Nas.D-73 | GGGTGCATCGTTTACGCGTAAAAAATTGTCTATAGCACTTTTAGATTC CCAAACTAACTGCTGCTGAGGAAGGATATGAG |
| 174 | Nas.D-74 | GGGTGCATCGTTTACGCGTAAAAAAATCAGCAAAATCGAAAACTCATG CAGTTTGTCCTGCTGCTGAGGAAGGATATGAG |
| 175 | Nas.D-75 | GGGTGCATCGTTTACGCGTAAAAAATTCCTTAAAAATTTAACTAACTG GATAGGTCTCTGCTGCTGAGGAAGGATATGAG |
| 176 | Nas.D-76 | GGGTGCATCGTTTACGCGTAAAACAAAATTTCTGACAGCAATTCCTTC GTTAAAAATCTGCTGCTGAGGAAGGATATGAG |
| 177 | Nas.D-77 | GGGTGCATCGTTTACGCGTAAATTATTAAAAAAATCAGCAAAGTTTAT TTCCCACGGCTGCTGCTGAGGAAGGATATGAG |
| 178 | Nas.D-78 | GGGTGCATCGTTTACGCGTAATTAATCAAACAATAGCAGCAAATCTCA GCAATTTTCCTGCTGCTGAGGAAGGATATGAG |
| 179 | Nas.D-79 | GGGTGCATCGTTTACGCGTAATTTGAAAGTCTCATAAATTTTTTTTTT TTTTTCAATCTGCTGCTGAGGAAGGATATGAG |
| 180 | Nas.D-80 | GGGTGCATCGTTTACGCGTAAAAATTCAGCATGATTTCAATTACTCCT TTCATTGATCTGCTGCTGAGGAAGGATATGAG |
| 181 | Nas.D-81 | GGGTGCATCGTTTACGCGTAAAATAAATAAAAATCAGTAGCAATCTTT CTCACAGTGCTGCTGCTGAGGAAGGATATGAG |
| 182 | Nas.D-82 | GGGTGCATCGTTTACGCGTAAATAAAAAGCAGATCTCAGCAAAACTCG TAAATTCAACTGCTGCTGAGGAAGGATATGAG |
| 183 | Nas.D-83 | GGGTGCATCGTTTACGCGTAAATAATGAAGGACTCAGACAGTTAAAAG ATGCATTAACTGCTGCTGAGGAAGGATATGAG |
| 184 | Nas.D-84 | GGGTGCATCGTTTACGCGTAAAAAAGATCAATATGAAAATCAGCAGTT AATATCTTCCTGCTGCTGAGGAAGGATATGAG |
| 185 | Nas.D-85 | GGGTGCATCGTTTACGCGTAAAAATAACAAACTTCTCAGCTGTTTAAT ATCTCCTGACTGCTGCTGAGGAAGGATATGAG |
| 186 | Nas.D-86 | GGGTGCATCGTTTACGCGTAAAATTAAACAAATAGCTCAGCACGAAAA TTTGCGTAACTGCTGCTGAGGAAGGATATGAG |
| 187 | Nas.D-87 | GGGTGCATCGTTTACGCGTAATTAAAAAACCTTCACACAGAAAACATT CCTCAATTTCTGCTGCTGAGGAAGGATATGAG |

TABLE 6-continued

List of deoxyribonucleotides parent aptamers based on the top
sequences from selection experiments.

| SEQ ID NO | Name | Sequence |
|---|---|---|
| 188 | Nas.D-88 | GGGTGCATCGTTTACGCATTTTCGTTTTATTTTAGTTTAATTGCGTTT<br>AGTATCTGGCTGCTGCTGAGGAAGGATATGAG |
| 189 | Nas.D-89 | GGGTGCATCGTTTACGCGTAAAAAGTATAAAGGTTAGAAATTCAGCAG<br>TTTGATATCCTGCTGCTGAGGAAGGATATGAG |
| 190 | Nas.D-90 | GGGTGCATCGTTTACGCGTAAAAAGGAGAATTAGTACTCACCAGTCGT<br>TTAAAATTTCTGCTGCTGAGGAAGGATATGAG |
| 191 | Nas.D-91 | GGGTGCATCGTTTACGCGTAAAAATAAATAACTACGAGATCTCAGCAG<br>ATCATTATCCTGCTGCTGAGGAAGGATATGAG |
| 192 | Nas.D-92 | GGGTGCATCGTTTACGCGTAAAATGGTTTTTCAGCAGTTAACATAATG<br>CCTCAGTTTCTGCTGCTGAGGAAGGATATGAG |
| 193 | Nas.D-93 | GGGTGCATCGTTTACGCGTAAATAACAAAAATCTCAGCTTTTGCAGAA<br>TTTATCCACCTGCTGCTGAGGAAGGATATGAG |
| 194 | Nas.D-94 | GGGTGCATCGTTTACGCGTAAATAAACTCACAGCAGAAAAAATTCCTT<br>CAACTTGTACTGCTGCTGAGGAAGGATATGAG |
| 195 | Nas.D-95 | GGGTGCATCGTTTACGCAGTAGTTAATAACAAATAGTCAGCAGTTTTG<br>TCCTTCATTCTGCTGCTGAGGAAGGATATGAG |
| 196 | Nas.D-96 | GGGTGCATCGTTTACGCGTAAAAATAGCAGTAGATAGCGGCAGTTTTG<br>TATTTGTTACTGCTGCTGAGGAAGGATATGAG |
| 197 | Nas.D-97 | GGGTGCATCGTTTACGCGTAAAAATTTAAATAACTCAGCAATCATAGA<br>TCCGACTGACTGCTGCTGAGGAAGGATATGAG |
| 198 | Nas.D-98 | GGGTGCATCGTTTACGCGTAAAGAACAGCTGACAAGAAATTCAAACCT<br>TCAGATTTTCTGCTGCTGAGGAAGGATATGAG |
| 199 | Nas.D-99 | GGGTGCATCGTTTACGCGTAAAGATAATAAGCAGTATTCAGCAGATTT<br>GTAAGGTTTCTGCTGCTGAGGAAGGATATGAG |
| 200 | Nas.D-100 | GGGTGCATCGTTTACGCGTAAATAAGAGGCAGACAGTATTACAAATAT<br>CCTAAAATACTGCTGCTGAGGAAGGATATGAG |

TABLE 7

List of conserved motifs.

| SEQ ID NO | Sequence |
|---|---|
| 201 | AAACAAAAGA |
| 202 | UAAAAUCA |
| 203 | AAACAAAAGA |
| 204 | TAAAAATCA |
| 205 | AUAAAAAUUUAAA |
| 206 | ATAAAAATTTAAA |

TABLE 7-continued

List of conserved motifs.

| SEQ ID NO | Sequence |
|---|---|
| 207 | GUAAAAAUUAAA |
| 208 | GTAAAAATTAAA |
| 209 | GUAAAAAAA |
| 210 | UNAGCANUUU |
| 211 | GTAAAAAAA |
| 212 | TNAGCANTTT |

TABLE 8

List of truncated aptamers based on the top ribonucleotide and
deoxyribonucleotide parent aptamers.

| SEQ ID NO | Name | Sequence |
|---|---|---|
| 237 | Nas.R-2.1a | AGACAGCAGCAGGAAUCAAGCCGUAGGAGUCUAGCAGAAGCUGCUGCUGAGG |
| 238 | Nas.R-2.1b | AGACAGCAGCAGGAA-CCA-GCGCAGGAGUCUGGCAGGAGCUGCUGCUGAGG |
| 239 | Nas.R-4.1 | GUGCUCAGUUGUCAAUCUAUGACUGCUGCUGAGGAAG |

TABLE 8-continued

List of truncated aptamers based on the top ribonucleotide and
deoxyribonucleotide parent aptamers.

| SEQ ID NO | Name | Sequence |
| --- | --- | --- |
| 240 | Nas.R-5.1 | GGGCGCACCGUUUACGCGUAAAUCGGUCCGCUAUU |
| 241 | Nas.R-8.1 | AGGUCCUCAAGCAGCCUUUGUCCUGCUGCUGAGGAAGG |
| 242 | Nas.D-2.1a | AGACAGCAGCAGGAATCAAGCCGTAGGAGTCTAGCAGAAGCTGCTGCTGAGG |
| 243 | Nas.D-2.1b | AGACAGCAGCAGGAA-CCA-GCGCAGGAGTCTGGCAGGAGCTGCTGCTGAGG |
| 244 | Nas.D-4.1 | GTGCTCAGTTGTCAATCTATGACTGCTGCTGAGGAAG |
| 245 | Nas.D-5.1 | GGGCGCACCGTTTACGCGTAAATCGGTCCGCTATT |
| 246 | Nas.D-8-1 | AGGTCCTCAAGCAGCCTTTGTCCTGCTGCTGAGGAAGG |

TABLE 9

List of protein sequences

| SEQ ID NO | Description | Sequence |
| --- | --- | --- |
| 213 | ICAM-1 | MAPSSPRPALPALLVLLGALFPGPGNAQTSVSPSKVILPRGGSVLVTCS TSCDQPKLLGIETPLPKKELLLPGNNRKVYELSNVQEDSQPMCYSNCP DGQSTAKTFLTVYWTPERVELAPLPSWQPVGKNLTLRCQVEGGAPRA NLTVVLLRGEKELKREPAVGEPAEVTTTVLVRRDHHGANFSCRTELDL RPQGLELFENTSAPYQLQTFVLPATPPQLVSPRVLEVDTQGTVVCSLDG LFPVSEAQVHLALGDQRLNPTVTYGNDSFSAKASVSVTAEDEGTQRLT CAVILGNQSQETLQTVTIYSFPAPNVILTKPEVSEGTEVTVKCEAHPRA KVTLNGVPAQPLGPRAQLLLKATPEDNGRSFSCSATLEVAGQLIHKNQ TRELRVLYGPRLDERDCPGNWTWPENSQQTPMCQAWGNPLPELKCLK DGTFPLPIGESVTVTRDLEGTYLCRARSTQGEVTRKVTNVLSPRYEIVI ITVVAAAVIMGTAGLSTYLYNRQRKIKKYRLQQAQKGTPMKPNTQATPP |
| 214 | Extracellular domain of ICAM-1 | QTSVSPSKVILPRGGSVLVTCSTSCDQPKLLGIETPLPKKELLLPGNNRK VYELSNVQEDSQPMCYSNCPDGQSTAKTFLTVYWTPERVELAPLPSW QPVGKNLTLRCQVEGGAPRANLTVVLLRGEKELKREPAVGEPAEVTT TVLVRRDHHGANFSCRTELDLRPQGLELFENTSAPYQLQTFVLPATPPQ LVSPRVLEVDTQGTVVCSLDGLFPVSEAQVHLALGDQRLNPTVTYGN DSFSAKASVSVTAEDEGTQRLTCAVILGNQSQETLQTVTIYSFPAPNVIL TKPEVSEGTEVTVKCEAHPRAKVTLNGVPAQPLGPRAQLLLKATPEDN GRSFSCSATLEVAGQLIHKNQTRELRVLYGPRLDERDCPGNWTWPENS QQTPMCQAWGNPLPELKCLKDGTFPLPIGESVTVTRDLEGTYLCRARS TQGEVTRKVTNVLSPRYE |
| 215 | Ig-like C2- type 1 domain | GGSVLVTCSTSCDQPKLLFIETPLPKKELLLPGNNRKVYELSNVQEDSQ PMCYSNCPDGQSTA |
| 216 | Ig-like C2- type 2 domain | GKNLTLRCQVEGGAPRANLTVVLLRGEKELKREPAVGEPAEVTTTVL VRRDHHGANFSCRTELDLR |
| 217 | Ig-like C2- type 3 domain | DTQGTVVCSLDGLFPVSEAQVHLALGDQRLNPTVTYGNDSFSAKASVS VTAEDEGTQRLTCAVILGNQ |
| 218 | Ig-like C2- type 4 domain | GTEVTVKCEAHPRAKVTLNGVPAQPLGPRAQLLLKATPEDNGRSFSCS ATLEVA |
| 219 | Ig-like C2- type 5 domain | NSQQTPMCQAWGNPLPELKCLKDGTFPLPIGESVTVTRDLEGTYLCRA RSTQG |
| 220 | Fragment of ICAM-1 | QTSVSPSKVILPR |
| 221 | Fragment of ICAM-2 | SCDQPKLLGI |
| 222 | Fragment of ICAM-3 | PKKELLLPGNNRKVYE |
| 223 | Fragment of ICAM-4 | YSNCPDGQSTAKTFL |

TABLE 9-continued

List of protein sequences

| SEQ ID NO | Description | Sequence |
| --- | --- | --- |
| 231 | ICAM-3 | MATMVPSVLWPRACWTLLVCCLLTPGVQGQEFLLRVEPQNPVLSAGG<br>SLFVNCSTDCPSSEKIALETSLSKELVASGMGWAAFNLSNVTGNSRILC<br>SVYCNGSQITGSSNITVYRLPERVELAPLPPWQPVGQNFTLRCQVEDGS<br>PRTSLTVVLLRWEEELSRQPAVEEPAEVTATVLASRDDHGAPFSCRTEL<br>DMQPQGLGLFVNTSAPRQLRTFVLPVTPPRLVAPRFLEVETSWPVDCT<br>LDGLFPASEAQVYLALGDQMLNATVMNHGDTLTATATATARADQEG<br>AREIVCNVTLGGERREARENLTVFSFLGPIVNLSEPTAHEGSTVTVSCM<br>AGARVQVTLDGVPAAAPGQPAQLQLNATESDDGRSFFCSATLEVDGE<br>FLHRNSSVQLRVLYGPKIDRATCPQHLKWKDKTRHVLQCQARGNPYP<br>ELRCLKEGSSREVPVGIPFFVNVTHNGTYQCQASSSRGKYTLVVVMDI<br>EAGSSHFVPVFVAVLLTLGVVTIVLALMYVFREHQRSGSYHVREESTY<br>LPLTSMQPTEAMGEEPSRAE |
| 232 | Extracellular domain of ICAM-3 | QEFLLRVEPQNPVLSAGGSLFVNCSTDCPSSEKIALETSLSKELVASGM<br>GWAAFNLSNVTGNSRILCSVYCNGSQITGSSNITVYRLPERVELAPLPP<br>WQPVGQNFTLRCQVEDGSPRTSLTVVLLRWEEELSRQPAVEEPAEVTA<br>TVLASRDDHGAPFSCRTELDMQPQGLGLFVNTSAPRQLRTFVLPVTPP<br>RLVAPRFLEVETSWPVDCTLDGLFPASEAQVYLALGDQMLNATVMNH<br>GDTLTATATATARADQEGAREIVCNVTLGGERREARENLTVFSFLGPI<br>VNLSEPTAHEGSTVTVSCMAGARVQVTLDGVPAAAPGQPAQLQLNAT<br>ESDDGRSFFCSATLEVDGEFLHRNSSVQLRVLYGPKIDRATCPQHLKW<br>KDKTRHVLQCQARGNPYPELRCLKEGSSREVPVGIPFFVNVTHNGTYQ<br>CQASSSRGKYTLVVVMDIEAGSSH |
| 233 | ICAM-5 | MPGPSPGLRRALLGLWAALGLGLFGLSAVSQEPFWADLQPRVAFVER<br>GGSLWLNCSTNCPRPERGGLETSLRRNGTQRGLRWLARQLVDIREPET<br>QPVCFFRCARRTLQARGLIRFQRPDRVELMPLPPWQPVGENFTLSCRVP<br>GAGPRASLTLTLLRGAQELIRRSFAGEPPRARGAVLTATVLARREDHG<br>ANFSCRAELDLRPHGLGLFENSSAPRELRTFSLSPDAPRLAAPRLLEVG<br>SERPVSCTLDGLFPASEARVYLALGDQNLSPDVTLEGDAFVATATATA<br>SAEQEGARQLVCNVTLGGENRETRENVTIYSFPAPLLTLSEPSVSEGQM<br>VTVTCAAGAQALVTLEGVPAAVPGQPAQLQLNATENDDRRSFFCDAT<br>LDVDGETLIKNRSAELRVLYAPRLDDSDCPRSWTWPEGPEQTLRCEAR<br>GNPEPSVHCARSDGGAVLALGLLGPVTRALSGTYRCKAANDQGEAVK<br>DVTLTVEYAPALDSVGCPERITWLEGTEASLSCVAHGVPPPDVICVRSG<br>ELGAVIEGLLRVAREHAGTYRCEATNPRGSAAKNVAVTVEYGPRFEEP<br>SCPSNWTWVEGSGRLFSCEVDGKPQPSVKCVGSGGATEGVLLPLAPPD<br>PSPRAPRIPRVLAPGIYVCNATNRHGSVAKTVVVSAESPPEMDESTCPS<br>HQTWLEGAEASALACAARGRPSPGVRCSREGIPWPEQQRVSREDAGT<br>YHCVATNAHGTDSRTVTVGVEYRPVVAELAASPPGGVRPGGNFTLTC<br>RAEAWPPAQISWRAPPGALNIGLSSNNSTLSVAGAMGSHGGEYECAAT<br>NAHGRHARRITVRVAGPWLWVAVGGAAGGAALLAAGAGLAFYVQS<br>TACKKGEYNVQEAESSGEAVCLNGAGGGAGGAAGAEGGPEAAGGAA<br>ESPAEGEVFAIQLTSA |
| 234 | Extracellular domain of ICAM-5 | EPFWADLQPRVAFVERGGSLWLNCSTNCPRPERGGLETSLRRNGTQRG<br>LRWLARQLVDIREPETQPVCFFRCARRTLQARGLIRTFQRPDRVELMPL<br>PPWQPVGENFTLSCRVPGAGPRASLTLTLLRGAQELIRRSFAGEPPRAR<br>GAVLTATVLARREDHGANFSCRAELDLRPHGLGLFENSSAPRELRTFS<br>LSPDAPRLAAPRLLEVGSERPVSCTLDGLFPASEARVYLALGDQNLSPD<br>VTLEGDAFVATATATASAEQEGARQLVCNVTLGGENRETRENVTIYSF<br>PAPLLTLSEPSVSEGQMVTVTCAAGAQALVTLEGVPAAVPGQPAQLQL<br>NATENDDRRSFFCDATLDVDGETLIKNRSAELRVLYAPRLDDSDCPRS<br>WTWPEGPEQTLRCEARGNPEPSVHCARSDGGAVLALGLLGPVTRALS<br>GTYRCKAANDQGEAVKDVTLTVEYAPALDSVGCPERITWLEGTEASL<br>SCVAHGVPPPDVICVRSGELGAVIEGLLRVAREHAGTYRCEATNPRGS<br>AAKNVAVTVEYGPRFEEPSCPSNWTWVEGSGRLFSCEVDGKPQPSVK<br>CVGSGGATEGVLLPLAPPDPSPRAPRIPRVLAPGIYVCNATNRHGSVAK<br>TVVVSAESPPEMDESTCPSHQTWLEGAEASALACAARGRPSPGVRCSR<br>EGIPWPEQQRVSREDAGTYHCVATNAHGTDSRTVTVGVEYRPVVAEL<br>AASPPGGVRPGGNFTLTCRAEAWPPAQISWRAPPGALNIGLSSNNSTLS<br>VAGAMGSHGGEYECAATNAHGRHARRITVRVAGPW |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Aptamer composition comprising at least one oligonucleotide consisting of: deoxyribonucleotides, ribonucleotides, derivatives of deoxyribonucleotides, derivatives of ribonucleotides, or mixtures thereof, wherein the aptamer composition has a binding affinity for intercellular adhesion molecule 1 (ICAM-1) and wherein the aptamer composition is configured to reduce the binding of one or more human rhinoviruses to the intercellular adhesion molecule 1 (ICAM-1) and wherein the aptamer composition comprises at least one oligonucleotide forming a secondary structure from a 5'-end to a 3'-end comprising at least a 5'-dangling end, a stem, a hairpin loop, and a 3'-dangling end, wherein the stem is formed between the hairpin loop and the dangling end(s); and wherein the secondary structure comprises at least the structural sequence 5'-EEEYYSSSSYSSSSYHHHH-YYYYYYYYYSYYYYYEEEE-3' (Structure I), wherein H represents a nucleotide located in the hairpin loop, S represents a nucleotide located in the stem, E represents a nucleotide located in a dangling end, and Y represents a nucleotide being absent or H, S, E or I, wherein I represent an internal loop.

2. The aptamer composition of claim 1, wherein the hairpin loop comprises at least 5 nucleotides.

3. The aptamer composition of claim 2, wherein the hairpin loop comprises a purine base.

4. The aptamer composition of claim 2, wherein, the hairpin loop comprises at least three pyrimidine bases.

5. The aptamer composition of claim 1, wherein the last nucleotide in the stem adjacent to the hairpin loop is a purine base.

6. The aptamer composition of claim 1, wherein the last nucleotide in the stem adjacent to the 3'-dangling end is a purine base.

7. The aptamer composition of claim 1, wherein the last 4 nucleotides of the 3'-dangling end are purine bases.

8. The aptamer composition of claim 1, wherein the 5'-dangling end comprises from 4 to 15 nucleotides.

9. The aptamer composition of claim 1 comprising an internal loop, a $1^{st}$ stem and a $2^{nd}$ stem, wherein the internal loop comprises from 1 to 10 nucleotides and is located between the $1^{st}$ stem and the $2^{nd}$ stem.

10. The aptamer composition of claim 1 wherein the stem adjacent to the dangling ends comprises at least 3 base pairs.

11. The aptamer composition of claim 1, wherein the stem adjacent to the 3'-dangling end comprises the motif guanine-cytosine-thymine (GCT).

12. The aptamer composition of claim 1, wherein the stem adjacent to the 5'-dangling end comprises the motif thymine-cytosine-adenine (TCA).

13. The aptamer composition of claim 1, wherein the at least one oligonucleotide comprises a length from 30 to 60 nucleotides.

14. The aptamer composition of claim 1, wherein the at least one oligonucleotide is truncated from parent oligo-nucleotides selected from the group consisting of SEQ ID NO: 1 to SEQ ID NO: 200.

15. The aptamer composition of claim 14, wherein the at least one oligonucleotide is truncated from parent oligo-nucleotides comprising SEQ ID NO: 2, SEQ ID NO: 4, SEQ ID NO: 5 and SEQ ID NO: 8, or SEQ ID NO: 102, SEQ ID NO: 104, SEQ ID NO: 105, SEQ ID NO: 108, or mixtures thereof.

16. The aptamer composition of claim 1, wherein the at least one oligonucleotide comprises natural and non-natural nucleobases, wherein the non-natural nucleobases comprise hypoxanthine, xanthine, 7-methylguanine, 5,6-dihydroura-cil, 5-5-methylcytosine, 5-hydroxymethylcytosine, thioura-cil, 1-methylhypoxanthine, 6-methylisoquinoline-1-thione-2-yl, 3-methoxy-2-naphthyl, 5-propynyluracil-1-yl, 5-meth-ylcytosin-1-yl, 2-aminoadenin-9-yl, 7-deaza-7-iodoadenin-9-yl, 7-deaza-7-propynyl-2-aminoadenin-9-yl, phenoxazi-nyl, phenoxazinyl-G-clam, or mixtures thereof.

17. The aptamer composition of claim 1, where the derivatives of ribonucleotides or the derivatives of deoxy-ribonucleotides comprise locked oligonucleotides, peptide oligonucleotides, glycol oligonucleotides, threose oligo-nucleotides, hexitol oligonucleotides, altritol oligonucle-otides, butyl oligonucleotides, L-ribonucleotides, arabino oligonucleotides, 2'-fluoroarabino oligonucleotides, cyclo-hexene oligonucleotides, phosphorodiamidate morpholino oligonucleotides, or mixtures thereof.

18. The aptamer composition of claim 1, wherein at least one pyrimidine nucleotide of the at least one oligonucleotide is fluorinated at the 2' position of the pentose group.

19. Personal health care composition comprising an aptamer composition comprising at least one oligonucle-otide consisting of: deoxyribonucleotides, ribonucleotides, derivatives of deoxyribonucleotides, derivatives of ribo-nucleotides, and mixtures thereof, wherein the aptamer composition has a binding affinity for intercellular adhesion molecule 1 (ICAM-1) and wherein the aptamer is configured to reduce the binding of one or more human rhinoviruses to the intercellular adhesion molecule 1 (ICAM-1), and wherein the aptamer composition comprises at least one oligonucleotide forming a secondary structure from a 5'-end to a 3'-end comprising at least a 5'-dangling end, a stem, a hairpin loop, and a 3'-dangling end; and wherein the secondary structure comprises at least the structural sequence 5'-EEEYYSSSSYSSSSYHHHH YYYYYYYYYSYYYYYEEEE-3' (Structure I), wherein H represents a nucleotide located in the hairpin loop, S represents a nucleotide located in the stem, E represents a nucleotide located in a dangling end, and Y represents a nucleotide being absent or H, S, E or I, wherein I represent an internal loop.

20. The personal health care composition of claim 19 comprising at least one oligonucleotide showing at least 80% nucleotide identity to the sequences comprising SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, or mixtures thereof.

21. Method of inhibiting human rhinovirus infection by inhibiting binding of the human rhinovirus to the intercel-lular adhesion molecule 1 (ICAM-1) of epithelial cells comprising applying an aptamer composition comprising at least one oligonucleotide consisting of: deoxyribonucle-otides, ribonucleotides, derivatives of deoxyribonucleotides, derivatives of ribonucleotides, or mixtures thereof, wherein the aptamer composition has a binding affinity for intercellular adhesion molecule 1 (ICAM-1) and wherein the aptamer is configured to reduce the binding of one or more human rhinoviruses to the intercellular adhesion molecule 1 (ICAM-1), and wherein the aptamer composition comprises at least one oligonucleotide forming a secondary structure from a 5'-end to a 3'-end comprising at least a 5'-dangling end, a stem, a hairpin loop, and a 3'-dangling end; and wherein the secondary structure comprises at least the structural sequence 5'-EEEYYSSSSYSSSSYHHHH YYYYYYYYYSYYYYYEEEE-3' (Structure I), wherein H represents a nucleotide located in the hairpin loop, S represents a nucleotide located in the stem, E represents a nucleotide located in the dangling end, and Y represents a nucleotide being absent or H, S, E or I, wherein I represent an internal loop.

22. Method of claim 21, wherein the epithelial cells are cells of the upper respiratory tract and the aptamer compo-sition is delivered by spraying.

\* \* \* \* \*